(12) United States Patent
Ono et al.

(10) Patent No.: US 7,892,543 B2
(45) Date of Patent: Feb. 22, 2011

(54) RESHAPED HUMAN ANTI-HM 1.24 ANTIBODY

(75) Inventors: Koichiro Ono, Gotenba (JP); Toshihiko Ohtomo, Shizuoka (JP); Masayuki Tsuchiya, Shizuoka (JP); Yasushi Yoshimura, Gotenba (JP); Yasuo Koishihara, Gotenba (JP); Masaaki Kosaka, Tokushima (JP)

(73) Assignee: Chugai Seiyako Kabushiki Kaisha, Tokyo (JP)

( * ) Notice: Subject to any disclaimer, the term of this patent is extended or adjusted under 35 U.S.C. 154(b) by 991 days.

(21) Appl. No.: 10/218,253

(22) Filed: Aug. 13, 2002

(65) Prior Publication Data

US 2003/0129185 A1 Jul. 10, 2003

Related U.S. Application Data

(62) Division of application No. 09/269,921, filed as application No. PCT/JP97/03553 on Oct. 3, 1997, now Pat. No. 6,699,974.

(30) Foreign Application Priority Data

Oct. 4, 1996 (JP) .................................. 8-264756

(51) Int. Cl.
*A61K 38/00* (2006.01)
*C07K 16/18* (2006.01)
*C07K 16/30* (2006.01)

(52) U.S. Cl. .................. 424/133.1; 435/320.1; 435/328; 435/69.1; 530/387.3; 536/23.53

(58) Field of Classification Search .............. 424/133.1; 435/320.1, 328, 69.1; 536/23.53
See application file for complete search history.

(56) References Cited

U.S. PATENT DOCUMENTS

| | | | | |
|---|---|---|---|---|
| 5,530,101 | A * | 6/1996 | Queen et al. ............. | 530/387.3 |
| 6,503,510 | B2 * | 1/2003 | Koishihara et al. ........ | 424/156.1 |
| 7,052,873 | B2 * | 5/2006 | Tsuchiya ................... | 435/69.6 |
| 2002/0034507 | A1 * | 3/2002 | Koishihara ............... | 424/130.1 |
| 2003/0113334 | A1 * | 6/2003 | Koishihara et al. ........ | 424/156.1 |
| 2003/0175281 | A1 * | 9/2003 | Kosaka et al. ............ | 424/155.1 |
| 2006/0008456 | A1 * | 1/2006 | Tsuchiya ................. | 424/133.1 |

FOREIGN PATENT DOCUMENTS

| | | |
|---|---|---|
| EP | 0 255 694 | 2/1988 |
| EP | 0 628 639 | 12/1994 |
| WO | WO 90/07861 | 7/1990 |
| WO | PCT GB90/02017 | * 12/1990 |
| WO | WO92/01059 | * 1/1992 |
| WO | WO 92/19759 | 4/1992 |
| WO | WO-96/04925 | 2/1996 |
| WO | WO 2004/003019 | * 1/2004 |

OTHER PUBLICATIONS

Fundamental Immunology 242 (William E. Paul, M.D. ed., 3d ed. 1993).*
Search results from ATCC website for human antibodies HSGI, REI or HG3.*
Rudikoff et al (Proc Natl Acad Sci USA 79:1979-1983 (1982)).*
Panka et al. (Proc Natl Acad Sci USA 85:3080-3084 (May 1988)).*
Amit et al., Science 233 747-753 (1986)).*
Verhoeyen et al., Science 239: 1534-1536 (1988).*
Output for sequence search of SEQ ID No. 9.*
Output for sequence search of SEQ ID Nos. 1 and 2.*
Output for sequence search of SEQ ID Nos. 16-26, 28 and 102.*
Wu et al. J. Mol. Biol. (1999) 294, 151-162.*
Coleman (Research in Immunol. 145:33-36 (1994)).*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Smith-Gill et al. (J. Immunol. 139:4135-4144 (1987)).*
Ward et al. Nature 341:544-546 (1989); Abstract.*
Kumar et al. (J. Biol. Chem. 275:35129-35136 (2000)).*
Song et al. (Biochem Biophys Res Comm 268:390-394 (2000)).*
ATCC search output for REI (p. 1; Mar. 30, 2009).*
ATCC search output for HG3 (p. 1; Mar. 30, 2009).*
U.S. Appl. No. 09/367,833, filed Aug. 25, 1998, now abandoned, no PGPub.*
U.S. Appl. No. 09/509,530; abandoned; priority to Oct. 14, 1998; no PGPub.*
U.S. Appl. No. 09/622,646; priority to Feb. 25, 1999; no PGPub.*
Anderson, KC et al. "Antigens on Human Plasma Cells Identified by Monoclonal Antibodies" J. Immunol. 130:1132 (1983).
Anderson, KC et al. "A Monoclonal Antibody with Reactivity Restricted to Normal and Neoplastic Plasma Cells" J. Immunol. 132:3172 (1983).
Billadeau, D et al. "The Bone Marrow of Multiple Myeloma Patients Contains B Cell Populations at Different Stages of Differentiation That Are Clonally Related to the Malignant Plasma Cell" J. Exp. Med. 178:1023 (1993).
Carter, P et al. "Humanization of an Anti-p185$^{HER2}$ Antibody for Human Cancer Therapy" Proc. Natl. Acad. Sci. USA 89:4285-4289 (1992).

(Continued)

*Primary Examiner*—Lynn Bristol
(74) *Attorney, Agent, or Firm*—Morrison & Foerster LLP

(57) ABSTRACT

The invention provides a reshaped human anti-HM 1.24 antibody having: (A) an L chain having (1) the C region of a human L chain, and (2) the V region of an L chain having the FR of a human L chain and the CDR of the L chain of a mouse anti-HM 1.24 monoclonal antibody; and (B) an H chain having (1) the C region of a human H chain, and (2) the V region of an H chain having the FR of a human H chain and the CDR of the H chain of a mouse anti-HM 1.24 monoclonal antibody. This reshaped human antibody is derived from human antibody and the CDR has a low antigenicity, and the reshaped human antibody of the present invention has a low antigenicity and can be used for medical treatment.

46 Claims, 40 Drawing Sheets

OTHER PUBLICATIONS

Co, MS et al. "Humanized Antibodies for Antiviral Therapy" Proc. Natl. Acad. Sci. USA 88:2869-2873 (1991).

Co, MS et al. "Chimeric and Humanized Antibodies with Specificity for the CD33 Antigen" J. Immunol. 148:1149-1154 (1992).

Co et al. "Humanized Anti-Lewis Y Antibodies: In Vitro Properties and Pharmacokinetics in Rhesus Monkeys" Cancer Research 56:1118-1125 (1996).

Epstein, J et al. "Markers of Multiple Hematopoietic-Cell Lineages in Multiple Myeloma" N. Engl. J. Med. 322:664 (1990).

Goto, T et al. Jpn. J. Clin. Immun. 16:688-691 (1992).

Goto, T et al. "A Novel Membrane Antigen Selectively Expressed on Terminally Differentiated Human B Cells" Blood 84(4):1922-1930 (1994).

Gideon; R et al. "Evolutionary Aspects of Immunoglobulin Heavy Chain Variable Region (VH) Gene Subgroups" Proc. Natl. Acad. Sci. USA 80:855-859 (1983).

Gorman, SD et al. "Reshaping a Therapeutic CD4 Antibody" Proc. Natl. Acad. Sci. USA 88:4181-4185 (1991).

Harada, H et al. "Phenotypic Difference of Normal Plasma Cells from Mature Myeloma Cells" Blood 81:2658 (1993).

Hata, H et al. "Interleukin-6 Gene Expression in Multiple Myeloma: A Characteristic of Immature Tumor Cells" Blood 81:3357 (1993).

Jeffrey, VR et al. "Structure of the Human Immunoglobulin u Locus: Characterization of Embryonic and Rearranged J and D Genes" Cell 27:583-591 (1981).

Kettleborough, CA et al. "Humanization of a Mouse Monoclonal Antibody by CDR-Grafting: The Importance of Framework Residues on Loop Conformation" Protein Engng. 4:773-783 (1991).

Kosaka, M et al. "Advances in Biology and Pathogenesis of Multiple Myeloma" Nippon Rinsho 53:91-99 (1995).

Leo, R et al. "Multiparameter Analyses of Normal and Malignant Human Plasma Cells: CD38++, CD56+, CD54+, cIg+ Is the Common Phenotype of Myeloma Cells" Ann. Hematol. 64:132 (1992).

Ling, NR et al. "B-Cell and Plasma Cell Antigens: New and Previously Defined Clusters" Ch. 7 In Leucocyte Typing III Oxford, UK p. 302 (1986).

LoBuglio, AF et al. "Mouse/Human Chimeric Monoclonal Antibody in Man: Kinetics and Immune Response" Proc. Natl. Acad. Sci. USA 86:4220-4224 (1989).

Lutz, R et al. "Reshaping Human Antibodies for Therapy" Nature 322:323-327 (1988).

Meada, H et al. "Construction of Reshaped Human Antibodies with HIV-Neutralizing Activity" Human Antibodies and Hybridoma 2:124-134 (1991).

Ohtomo et al. "Humanization of Mouse ONS-M21 Antibody with the Aid of Hybrid Variable Regions" Molecular Immunology 32:407-416 (1995).

Ozaki, K et al. "Localization and Imaging of Human Plasmacytoma Xenografts in Severe Combined Immunodeficiency Mice by a New Murine Monoclonal Antibody, Anti-HM1.24" Tokushima J. Exp. Med. 43:7-15 (1996).

Queen et al. "A Humanized Antibody That Binds to the Interleukin 2 Receptor" Proc. Natl. Acad. Sci. USA 86: 10029-10033 (1989).

Riechmann, L et al. "Reshaping Human Antibodies for Therapy" Nature 332:323-327 (1988).

Sato, K et al. "Reshaping a Human Antibody to Inhibit the Interleukin 6-Dependent Tumor Cell Growth" Cancer Res. 53:851-856 (1993).

Shimazaki, C et al. "Immunophenotype and DNA Content of Myeloma Cells in Primary Plasma Cell Leukemia" Am. J. Hematol. 39:159 (1992).

Tempest, PR et al. "Reshaping a Human Monoclonal Antibody to Inhibit Human Respiratory Syncytial Virus Infection in Vivo" Bio/Technology 9:266-271 (1991).

Terstappen, L et al. "Identification and Characterization of Plasma Cells in Normal Human Bone Marrow by High-Resolution Flow Cytometry" Blood 76:1739 (1990).

Tong, AW et al. "Characterization of a Monoclonal Antibody Having Selective Reactivity with Normal and Neoplastic Plasma Cells" Blood 69:238 (1987).

Verhoeyen, M et al. "Reshaping Human Antibodies: Grafting an Antilysozyme Activity" Science 239:1534-1536 (1988).

Supplementary European Search Report for EP 97 94 2246, mailed on Dec. 3, 2004, 4 pages.

Takeda et al., Nature (1985) 314:452-454.

Chothia et al., Nature (1989) 342:877-883.

Chothia and Lesk, Journal of Molecular Biology (1987) 196:901-917.

* cited by examiner

Fig.6
V REGION OF THE MOUSE ANTI-HM 1.24 ANTIBODY
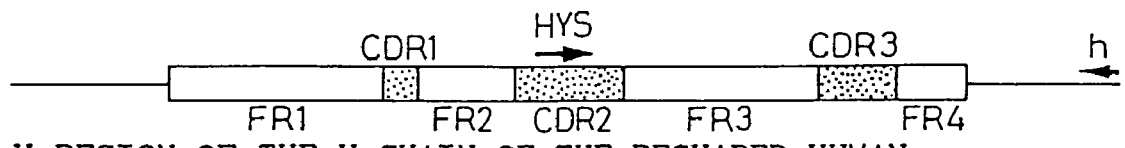
V REGION OF THE H CHAIN OF THE RESHAPED HUMAN ANTI-HM 1.24 ANTIBODY VERSION "a"
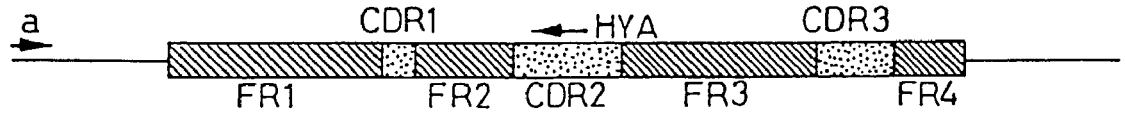
↓
FIRST PCR
↓
(a-HYA)
(HYS-h)
↓
ASSEMBLY
↓
SECOND PCR
a →
← h
↓
V REGION OF H CHAIN OF HUMAN MOUSE HYBRID
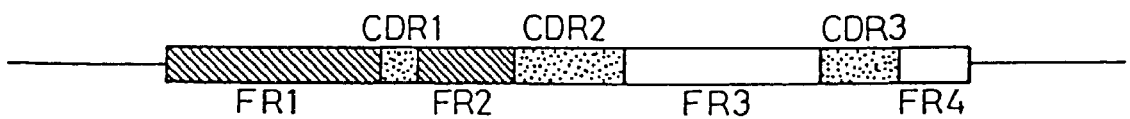

Fig. 7
V REGION OF THE MOUSE ANTI-HM 1.24 ANTIBODY
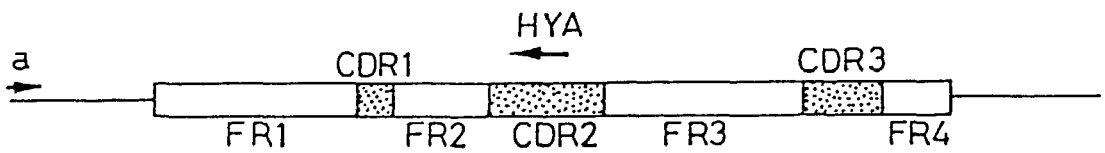
V REGION OF THE H CHAIN OF THE RESHAPED HUMAN ANTI-HM 1.24 ANTIBODY VERSION "a"
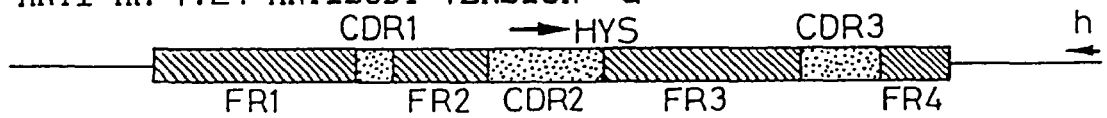
↓
FIRST PCR
↓
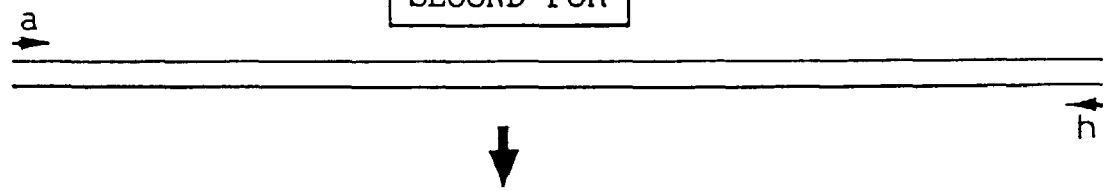
↓
ASSEMBLY
↓
SECOND PCR
↓
V REGION OF H CHAIN OF MOUSE HUMAN HYBRID

SEQUENCE LISTING

```
<160> NUMBER OF SEQ ID NOS: 137

<210> SEQ ID NO 1
<211> LENGTH: 394
<212> TYPE: DNA
<213> ORGANISM: murine
<220> FEATURE:
<221> NAME/KEY: CDS
<222> LOCATION: (1)..(393)
<220> FEATURE:
<221> NAME/KEY: sig_peptide
<222> LOCATION: (1)..(72)
<220> FEATURE:
<221> NAME/KEY: mat_peptide
<222> LOCATION: (73)..(393)
<220> FEATURE:
<223> OTHER INFORMATION: Nucleotide sequence coding for L chain V
      region of mouse anti-HM 1.24 antibody

<400> SEQUENCE: 1 atg ggc ttc aag atg gag tca cat ttt ctg gtc ttt gta ttc gtg ttt         48
Met Gly Phe Lys Met Glu Ser His Phe Leu Val Phe Val Phe Val Phe
        -20                 -15                 -10
```

```
ctc tgg ttg tct ggt gtt gac gga gac att gtg atg acc cag tct cac      96
Leu Trp Leu Ser Gly Val Asp Gly Asp Ile Val Met Thr Gln Ser His
         -5              -1  1                   5 aaa ttc atg tcc aca tca gta gga gac agg gtc agc atc acc tgc aag     144
Lys Phe Met Ser Thr Ser Val Gly Asp Arg Val Ser Ile Thr Cys Lys
     10              15                  20 gcc agt cag gat gtg aat act gct gta gcc tgg tat caa caa aaa cca     192
Ala Ser Gln Asp Val Asn Thr Ala Val Ala Trp Tyr Gln Gln Lys Pro
 25              30                  35                  40 gga caa tcg cct aaa cta ctg att tac tcg gca tcc aac cgg tac act     240
Gly Gln Ser Pro Lys Leu Leu Ile Tyr Ser Ala Ser Asn Arg Tyr Thr
                 45              50                  55 gga gtc cct gat cgc atc act ggc agt gga tct ggg acg gat ttc act     288
Gly Val Pro Asp Arg Ile Thr Gly Ser Gly Ser Gly Thr Asp Phe Thr
             60              65                  70 ttc acc atc agc agt gtg cag gcg gaa gac ctg gca ctt tat tac tgt     336
Phe Thr Ile Ser Ser Val Gln Ala Glu Asp Leu Ala Leu Tyr Tyr Cys
         75              80                  85 cag caa cat tat agt act cca ttc acg ttc ggc tcg ggg aca aag ttg     384
Gln Gln His Tyr Ser Thr Pro Phe Thr Phe Gly Ser Gly Thr Lys Leu
     90              95                 100 gaa ata aaa c                                                       394
Glu Ile Lys
105

<210> SEQ ID NO 2
<211> LENGTH: 418
<212> TYPE: DNA
<213> ORGANISM: murine
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)
<220> FEATURE:
<223> OTHER INFORMATION: Nucleotide sequence coding for H chain V
      region of mouse anti-HM 1.24 antibody

<400> SEQUENCE: 2 atg gaa tgt aac tgg ata ctt cct ttt att ctg tca gta act tca ggt      48
Met Glu Cys Asn Trp Ile Leu Pro Phe Ile Leu Ser Val Thr Ser Gly
             -15             -10                  -5 gcc tac tca cag gtt caa ctc cag cag tct ggg gct gag ctg gca aga      96
Ala Tyr Ser Gln Val Gln Leu Gln Gln Ser Gly Ala Glu Leu Ala Arg
         -1  1                   5                  10 cct ggg gct tca gtg aag ttg tcc tgc aag gct tct ggc tac acc ttt     144
Pro Gly Ala Ser Val Lys Leu Ser Cys Lys Ala Ser Gly Tyr Thr Phe
     15                  20                  25 act ccc tac tgg atg cag tgg gta aaa cag agg cct gga cag ggt ctg     192
Thr Pro Tyr Trp Met Gln Trp Val Lys Gln Arg Pro Gly Gln Gly Leu
 30                  35                  40                  45 gaa tgg att ggg tct att ttt cct gga gat ggt gat act agg tac agt     240
Glu Trp Ile Gly Ser Ile Phe Pro Gly Asp Gly Asp Thr Arg Tyr Ser
                 50                  55                  60 cag aag ttc aag ggc aag gcc aca ttg act gca gat aaa tcc tcc agt     288
Gln Lys Phe Lys Gly Lys Ala Thr Leu Thr Ala Asp Lys Ser Ser Ser
             65                  70                  75 aca gcc tac atg caa ctc agc atc ttg gca ttt gag gac tct gcg gtc     336
Thr Ala Tyr Met Gln Leu Ser Ile Leu Ala Phe Glu Asp Ser Ala Val
```

```
            80                  85                  90
tat tac tgt gca aga gga tta cga cga ggg ggg tac tac ttt gac tac    384
Tyr Tyr Cys Ala Arg Gly Leu Arg Arg Gly Gly Tyr Tyr Phe Asp Tyr
        95                  100                 105 tgg ggc caa ggc acc act ctc aca gtc tcc tca g                      418
Trp Gly Gln Gly Thr Thr Leu Thr Val Ser Ser
110                 115                 120
```

<210> SEQ ID NO 3
<211> LENGTH: 11
<212> TYPE: PRT
<213> ORGANISM: murine
<220> FEATURE:
<223> OTHER INFORMATION: Amino acid sequence of L chain V region
      CDR(1) of mouse anti-HM 1.24 antibody

<400> SEQUENCE: 3

```
Lys Ala Ser Gln Asp Val Asn Thr Ala Val Ala
 1               5                  10
```

<210> SEQ ID NO 4
<211> LENGTH: 7
<212> TYPE: PRT
<213> ORGANISM: murine
<220> FEATURE:
<223> OTHER INFORMATION: Amino acid sequence of CDR(2) of L chain V
      region of mouse anti-HM 1.24 antibody

<400> SEQUENCE: 4

```
Ser Ala Ser Asn Arg Tyr Thr
 1               5
```

<210> SEQ ID NO 5
<211> LENGTH: 9
<212> TYPE: PRT
<213> ORGANISM: murine
<220> FEATURE:
<223> OTHER INFORMATION: Amino acid sequence of CDR(3) of L chain V
      region of mouse anti-HM 1.24 antibody

<400> SEQUENCE: 5

```
Gln Gln His Tyr Ser Thr Pro Phe Thr
 1               5
```

<210> SEQ ID NO 6
<211> LENGTH: 5
<212> TYPE: PRT
<213> ORGANISM: murine
<220> FEATURE:
<223> OTHER INFORMATION: Amino acid sequence of CDR(1) of H chain V
      region of mouse anti-HM 1.24 antibody

<400> SEQUENCE: 6

```
Pro Tyr Trp Met Gln
 1               5
```

<210> SEQ ID NO 7
<211> LENGTH: 17
<212> TYPE: PRT
<213> ORGANISM: murine
<220> FEATURE:
<223> OTHER INFORMATION: Amino acid sequence of CDR(2) of H chain V
      region of mouse anti-HM 1.24 antibody

<400> SEQUENCE: 7

```
Ser Ile Phe Pro Gly Asp Gly Asp Thr Arg Tyr Ser Gln Lys Phe Lys
 1               5                  10                  15
```

Gly

<210> SEQ ID NO 8
<211> LENGTH: 11
<212> TYPE: PRT
<213> ORGANISM: murine
<220> FEATURE:
<223> OTHER INFORMATION: Amino acid sequence of CDR(3) of H chain V
      region of mouse anti-HM 1.24 antibody

<400> SEQUENCE: 8

Gly Leu Arg Arg Gly Gly Tyr Tyr Phe Asp Tyr
 1               5                  10

<210> SEQ ID NO 9
<211> LENGTH: 379
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody L chain
      V region version a
<220> FEATURE:
<221> NAME/KEY: CDS
<222> LOCATION: (1)..(378)
<220> FEATURE:
<221> NAME/KEY: sig_peptide
<222> LOCATION: (1)..(57)
<220> FEATURE:
<221> NAME/KEY: mat_peptide
<222> LOCATION: (58)..(378)

<400> SEQUENCE: 9

```
atg gga tgg agc tgt atc atc ctc tcc ttg gta gca aca gct aca ggt        48
Met Gly Trp Ser Cys Ile Ile Leu Ser Leu Val Ala Thr Ala Thr Gly
            -15                 -10                 -5 gtc cac tcc gac atc cag atg acc cag agc cca agc agc ctg agc gcc        96
Val His Ser Asp Ile Gln Met Thr Gln Ser Pro Ser Ser Leu Ser Ala
         -1  1               5                  10 agc gtg ggt gac aga gtg acc atc acc tgt aag gct agt cag gat gtg       144
Ser Val Gly Asp Arg Val Thr Ile Thr Cys Lys Ala Ser Gln Asp Val
         15                  20                  25 aat act gct gta gcc tgg tac cag cag aag cca gga aag gct cca aag       192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga       240
Leu Leu Ile Tyr Ser Ala Ser Asn Arg Tyr Thr Gly Val Pro Ser Arg
                 50                  55                  60 ttc agc ggt agc ggt agc ggt acc gac ttc acc ttc acc atc agc agc       288
Phe Ser Gly Ser Gly Ser Gly Thr Asp Phe Thr Phe Thr Ile Ser Ser
                 65                  70                  75 ctc cag cca gag gac atc gct acc tac tac tgc cag caa cat tat agt       336
Leu Gln Pro Glu Asp Ile Ala Thr Tyr Tyr Cys Gln Gln His Tyr Ser
             80                  85                  90 act cca ttc acg ttc ggc caa ggg acc aag gtg gaa atc aaa c              379
Thr Pro Phe Thr Phe Gly Gln Gly Thr Lys Val Glu Ile Lys
             95                 100                 105
```

<210> SEQ ID NO 10
<211> LENGTH: 379
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody L chain
      V region version b -continued

```
<220> FEATURE:
<221> NAME/KEY: CDS
<222> LOCATION: (1)..(378)
<220> FEATURE:
<221> NAME/KEY: sig_peptide
<222> LOCATION: (1)..(57)
<220> FEATURE:
<221> NAME/KEY: mat_peptide
<222> LOCATION: (58)..(378)

<400> SEQUENCE: 10 atg gga tgg agc tgt atc atc ctc tcc ttg gta gca aca gct aca ggt    48
Met Gly Trp Ser Cys Ile Ile Leu Ser Leu Val Ala Thr Ala Thr Gly
            -15                 -10                  -5 gtc cac tcc gac atc cag atg acc cag agc cca agc agc ctg agc gcc    96
Val His Ser Asp Ile Gln Met Thr Gln Ser Pro Ser Ser Leu Ser Ala
         -1   1                   5                  10 agc gtg ggt gac aga gtg acc atc acc tgt aag gct agt cag gat gtg   144
Ser Val Gly Asp Arg Val Thr Ile Thr Cys Lys Ala Ser Gln Asp Val
        15                  20                  25 aat act gct gta gcc tgg tac cag cag aag cca gga aag gct cca aag   192
Asn Thr Ala Val Ala Trp Tyr Gln Gln Lys Pro Gly Lys Ala Pro Lys
 30                  35                  40                  45 ctg ctg atc tac tcg gca tcc aac cgg tac act ggt gtg cca agc aga   240
Leu Leu Ile Tyr Ser Ala Ser Asn Arg Tyr Thr Gly Val Pro Ser Arg
                 50                  55                  60 ttc agc ggt agc ggt agt ggt acc gac tac acc ttc acc atc agc agc   288
Phe Ser Gly Ser Gly Ser Gly Thr Asp Tyr Thr Phe Thr Ile Ser Ser
             65                  70                  75 ctc cag cca gag gac atc gct acc tac tac tgc cag caa cat tat agt   336
Leu Gln Pro Glu Asp Ile Ala Thr Tyr Tyr Cys Gln Gln His Tyr Ser
         80                  85                  90 act cca ttc acg ttc ggc caa ggg acc aag gtg gaa atc aaa c         379
Thr Pro Phe Thr Phe Gly Gln Gly Thr Lys Val Glu Ile Lys
     95                 100                 105

<210> SEQ ID NO 11
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version a
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 11 atg gac tgg acc tgg agg gtc ttc ttc ttg ctg gct gta gct cca ggt    48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag    96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc   144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt   192
Thr Pro Tyr Trp Met Gln Trp Val Arg Gln Ala Pro Gly Gln Gly Leu
```

```
                 30                  35                  40                  45
gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aga gtc acc atg acc gca gac acg tcc acg agc        288
Gln Lys Phe Lys Gly Arg Val Thr Met Thr Ala Asp Thr Ser Thr Ser
             65                  70                  75 aca gtc tac atg gag ctg agc agc ctg aga tct gag gac acg gcc gtg        336
Thr Val Tyr Met Glu Leu Ser Ser Leu Arg Ser Glu Asp Thr Ala Val
                 80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
             95                  100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 12
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version b
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 12 atg gac tgg acc tgg agg gtc ttc ttc ttg ctg gct gta gct cca ggt         48
Met Asp Trp Thr Trp Arg Val Phe Phe Leu Leu Ala Val Ala Pro Gly
                 -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
         -1   1                   5                  10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc acg agc        288
Gln Lys Phe Lys Gly Lys Val Thr Met Thr Ala Asp Thr Ser Thr Ser
             65                  70                  75 aca gtc tac atg gag ctg agc agc ctg aga tct gag gac acg gcc gtg        336
Thr Val Tyr Met Glu Leu Ser Ser Leu Arg Ser Glu Asp Thr Ala Val
                 80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
             95                  100                 105 tgg ggg caa ggg acc acg gtc acc gtc tcc tca g                          418
Trp Gly Gln Gly Thr Thr Val Thr Val Ser Ser
110                 115                 120
```

<210> SEQ ID NO 13
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version c
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 13

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
     -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
             50                  55                  60 cag aag ttc aag ggc aga gtc act atg acc gca gac aag tcc acg agc     288
Gln Lys Phe Lys Gly Arg Val Thr Met Thr Ala Asp Lys Ser Thr Ser
 65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
 95                 100                 105 tgg ggg caa ggg acc acg gtc acc gtc tcc tca g                       418
Trp Gly Gln Gly Thr Thr Val Thr Val Ser Ser
110             115                 120
```

<210> SEQ ID NO 14
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version d
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 14

```
atg gac tgg acc tgg agg gtc ttc ttc ttg ctg gct gta gct cca ggt      48
```

```
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aaa gtc acc atg acc gca gac aag tcc acg agc     288
Gln Lys Phe Lys Gly Lys Val Thr Met Thr Ala Asp Lys Ser Thr Ser
                 65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
                 80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
                 95                 100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 15
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version e
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 15 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aga gcc acc ctg acc gca gac acg tcc acg agc     288
Gln Lys Phe Lys Gly Arg Ala Thr Leu Thr Ala Asp Thr Ser Thr Ser
                 65                  70                  75
```

```
aca gtc tac atg gag ctg agc agc ctg aga tct gag gac acg gcc gtg        336
Thr Val Tyr Met Glu Leu Ser Ser Leu Arg Ser Glu Asp Thr Ala Val
        80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
    95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 16
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version f
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 16 atg gac tgg acc tgg agg gtc ttc ttc ttg ctg gct gta gct cca ggt        48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag        96
Ala His Ser Gln Val Gln Leu Val Gln Ser Gly Ala Glu Val Lys Lys
    -1   1               5                  10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
        15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                50                  55                  60 cag aag ttc aag ggc aga gcc acc ctg act gca gac acg tcc tcg agc        288
Gln Lys Phe Lys Gly Arg Ala Thr Leu Thr Ala Asp Thr Ser Ser Ser
            65                  70                  75 aca gcc tac atg gag ctg agc agc ctg aga tct gag gac acg gcc gtg        336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
    95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 17
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version g
```

-continued

```
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 17 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
        -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
    -1   1               5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
         15                  20                  25 act ccc tac tgg atg cag tgg gtg cga cag cgc cct gga caa ggg ctt     192
Thr Pro Tyr Trp Met Gln Trp Val Arg Gln Arg Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aga gtc acc atg acc gca gac acg tcc acg agc     288
Gln Lys Phe Lys Gly Arg Val Thr Met Thr Ala Asp Thr Ser Thr Ser
             65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                       418
Trp Gly Gln Gly Thr Thr Val Thr Val Ser Ser
110                 115                 120

<210> SEQ ID NO 18
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version h
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 18 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
        -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
    -1   1               5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
```

```
act ccc tac tgg atg cag tgg gtg cga cag gcc cct gga caa ggg ctt      192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
             50                  55                  60 cag aag ttc aag ggc aaa gtc acc atg acc gca gac acg tcc tcg agc      288
Gln Lys Phe Lys Gly Lys Val Thr Met Thr Ala Asp Thr Ser Ser Ser
         65                  70                  75 aca gcc tac atg gag ctg agc agc ctg aga tct gag gac acg gcc gtg      336
Thr Ala Tyr Met Glu Leu Ser Ser Leu Arg Ser Glu Asp Thr Ala Val
     80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
 95                 100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 19
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version i
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 19 atg gac tgg acc tgg agg gtc ttc ttc ttg ctg gct gta gct cca ggt       48
Met Asp Trp Thr Trp Arg Val Phe Phe Leu Leu Ala Val Ala Pro Gly
                -15                 -10                 -5 gct cac tcc cag gtg cag ctg gtg cag tct ggg gct gag gtg aag aag       96
Ala His Ser Gln Val Gln Leu Val Gln Ser Gly Ala Glu Val Lys Lys
         -1  1                   5                  10 cct ggg gcc tca gtg aag gtt tcc tgc aag gca tct gga tac acc ttc      144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt      192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt      240
Glu Trp Met Gly Ser Ile Phe Pro Gly Asp Gly Asp Thr Arg Tyr Ser
             50                  55                  60 cag aag ttc aag ggc aaa gtc acc atg acc gca gac acg tcc tcg agc      288
Gln Lys Phe Lys Gly Lys Val Thr Met Thr Ala Asp Thr Ser Ser Ser
         65                  70                  75 aca gcc tac atg gag ctg agc agc ctg gca ttt gag gac acg gcc gtg      336
Thr Ala Tyr Met Glu Leu Ser Ser Leu Ala Phe Glu Asp Thr Ala Val
     80                  85                  90 tat tac tgt gcg aga gga tta cga cga ggg ggg tac tac ttt gac tac      384
Tyr Tyr Cys Ala Arg Gly Leu Arg Arg Gly Gly Tyr Tyr Phe Asp Tyr
 95                 100                 105
```

```
tgg ggg caa ggg acc acg gtc acc gtc tcc tca g                              418
Trp Gly Gln Gly Thr Thr Val Thr Val Ser Ser
110             115             120
```

<210> SEQ ID NO 20
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version j
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 20

```
atg gac tgg acc tgg agg gtc ttc ttc ttg ctg gct gta gct cca ggt          48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag          96
Ala His Ser Gln Val Gln Leu Val Gln Ser Gly Ala Glu Val Lys Lys
        -1  1               5                  10 cct ggg gcc tca gtg aag gtt tcc tgc aag gca tct gga tac acc ttc         144
Pro Gly Ala Ser Val Lys Val Ser Cys Lys Ala Ser Gly Tyr Thr Phe
    15                  20                  25 act ccc tac tgg atg cag tgg gtg cga cag gcc cct gga caa ggg ctt         192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt         240
Glu Trp Met Gly Ser Ile Phe Pro Gly Asp Gly Asp Thr Arg Tyr Ser
                50                  55                  60 cag aag ttc aag ggc aaa gcc acc ctg act gca gac acg tcc tcg agc         288
Gln Lys Phe Lys Gly Lys Ala Thr Leu Thr Ala Asp Thr Ser Ser Ser
            65                  70                  75 aca gcc tac atg gag ctg agc agc ctg aga tct gag gac acg gcc gtg         336
Thr Ala Tyr Met Glu Leu Ser Ser Leu Arg Ser Glu Asp Thr Ala Val
        80                  85                  90 tat tac tgt gcg aga gga tta cga cga ggg ggg tac tac ttt gac tac         384
Tyr Tyr Cys Ala Arg Gly Leu Arg Arg Gly Gly Tyr Tyr Phe Asp Tyr
    95                  100                 105 tgg ggg caa ggg acc acg gtc acc gtc tcc tca g                           418
Trp Gly Gln Gly Thr Thr Val Thr Val Ser Ser
110             115             120
```

<210> SEQ ID NO 21
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version k
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 21

```
atg gac tgg acc tgg agg gtc ttc ttc ttg ctg gct gta gct cca ggt         48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
        -1   1               5                   10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
     15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc        288
Gln Lys Phe Lys Gly Lys Val Thr Met Thr Ala Asp Thr Ser Ser Ser
             65                  70                  75 aca gcc tac atg cag ctg agc agc cta aga tct gag gac acg gcc gtg        336
Thr Ala Tyr Met Gln Leu Ser Ser Leu Arg Ser Glu Asp Thr Ala Val
         80                  85                  90 tat tac tgt gcg aga gga tta cga cga ggg ggc tac tac ttt gac tac        384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                          418
Trp Gly Gln Gly Thr Thr Val Thr Val Ser Ser
110                 115                 120
```

<210> SEQ ID NO 22
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version 1
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 22

```
atg gac tgg acc tgg agg gtc ttc ttc ttg ctg gct gta gct cca ggt         48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
        -1   1               5                   10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
     15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60
```

```
cag aag ttc aag ggc aaa gtc acc atg acc gca gac acg tcc tcg agc     288
Gln Lys Phe Lys Gly Lys Val Thr Met Thr Ala Asp Thr Ser Ser Ser
                65                  70                  75 aca gcc tac atg cag ctg agc atc ctg aga tct gag gac acg gcc gtg     336
Thr Ala Tyr Met Gln Leu Ser Ile Leu Arg Ser Glu Asp Thr Ala Val
            80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
        95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 23
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version m
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 23 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
                -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1  1                   5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
    15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                50                  55                  60 cag aag ttc aag ggc aaa gtc acc atg acc gca gac acg tcc tcg agc     288
Gln Lys Phe Lys Gly Lys Val Thr Met Thr Ala Asp Thr Ser Ser Ser
                65                  70                  75 aca gcc tac atg cag ctg agc atc ctg aga tct gag gac tcg gcc gtg     336
Thr Ala Tyr Met Gln Leu Ser Ile Leu Arg Ser Glu Asp Ser Ala Val
            80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
        95                  100                 105 tgg ggg caa ggg acc acg gtc acc gtc tcc tca g                        418
Trp Gly Gln Gly Thr Thr Val Thr Val Ser Ser
110                 115                 120

<210> SEQ ID NO 24
<211> LENGTH: 418
<212> TYPE: DNA
<213> ORGANISM: Artificial Sequence
```

<220> FEATURE:
<223> OTHER INFORMATION: Description of Artificial Sequence: Nucleotide
      sequence coding for reshaped human anti-HM 1.24 antibody H chain
      V region version n
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 24

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
         -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc     288
Gln Lys Phe Lys Gly Lys Val Thr Met Thr Ala Asp Thr Ser Ser Ser
             65                  70                  75 aca gcc tac atg gag ctg agc atc ctg aga tct gag gac acg gcc gtg     336
Thr Ala Tyr Met Glu Leu Ser Ile Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                       418
Trp Gly Gln Gly Thr Thr Val Thr Val Ser Ser
110                 115                 120
```

<210> SEQ ID NO 25
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version o
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 25

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
```

```
              -1    1                 5                      10
cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aaa gtc acc atg acc gca gac acg tcc tcg agc        288
Gln Lys Phe Lys Gly Lys Val Thr Met Thr Ala Asp Thr Ser Ser Ser
                 65                  70                  75 aca gcc tac atg gag ctg agc agc ctg aga tct gag gac tcg gcc gta        336
Thr Ala Tyr Met Glu Leu Ser Ser Leu Arg Ser Glu Asp Ser Ala Val
             80                  85                  90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
         95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 26
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version p
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 26 atg gac tgg acc tgg agg gtc ttc ttc ttg ctg gct gta gct cca ggt         48
Met Asp Trp Thr Trp Arg Val Phe Phe Leu Leu Ala Val Ala Pro Gly
                 -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
         -1    1                 5                      10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
         15                  20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30              35                  40                  45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                  55                  60 cag aag ttc aag ggc aga gtc acc atg acc gca gac acg tcc acg agc        288
Gln Lys Phe Lys Gly Arg Val Thr Met Thr Ala Asp Thr Ser Thr Ser
                 65                  70                  75 aca gcc tac atg gag ctg agc agc ctg aga tct gag gac acg gcc gtg        336
Thr Ala Tyr Met Glu Leu Ser Ser Leu Arg Ser Glu Asp Thr Ala Val
             80                  85                  90
```

```
tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
         95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 27
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version q
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 27 atg gac tgg acc tgg agg gtc ttc ttc ttg ctg gct gta gct cca ggt         48
Met Asp Trp Thr Trp Arg Val Phe Phe Leu Leu Ala Val Ala Pro Gly
                -15                 -10                 -5 gct cac tcc cag gtg cag ctg gtg cag tct ggg gct gag gtg aag aag         96
Ala His Ser Gln Val Gln Leu Val Gln Ser Gly Ala Glu Val Lys Lys
        -1   1               5                  10 cct ggg gcc tca gtg aag gtt tcc tgc aag gca tct gga tac acc ttc        144
Pro Gly Ala Ser Val Lys Val Ser Cys Lys Ala Ser Gly Tyr Thr Phe
         15                 20                  25 act ccc tac tgg atg cag tgg gtg cga cag gcc cct gga caa ggg ctt        192
Thr Pro Tyr Trp Met Gln Trp Val Arg Gln Ala Pro Gly Gln Gly Leu
 30                 35                 40                 45 gag tgg atg gga tct att ttt cct gga gat ggt gat act agg tac agt        240
Glu Trp Met Gly Ser Ile Phe Pro Gly Asp Gly Asp Thr Arg Tyr Ser
                 50                 55                  60 cag aag ttc aag ggc aga gtc acc atg acc gca gac acg tcc tcg agc        288
Gln Lys Phe Lys Gly Arg Val Thr Met Thr Ala Asp Thr Ser Ser Ser
             65                 70                 75 aca gtc tac atg gag ctg agc agc ctg aga tct gag gac acg gcc gtg        336
Thr Val Tyr Met Glu Leu Ser Ser Leu Arg Ser Glu Asp Thr Ala Val
         80                 85                 90 tat tac tgt gcg aga gga tta cga cga ggg ggg tac tac ttt gac tac        384
Tyr Tyr Cys Ala Arg Gly Leu Arg Arg Gly Gly Tyr Tyr Phe Asp Tyr
         95                 100                 105 tgg ggg caa ggg acc acg gtc acc gtc tcc tca g                          418
Trp Gly Gln Gly Thr Thr Val Thr Val Ser Ser
110                 115                 120

<210> SEQ ID NO 28
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version r
<220> FEATURE:
<221> NAME/KEY: CDS
<222> LOCATION: (1)..(417)
<220> FEATURE:
<221> NAME/KEY: sig_peptide
```

<222> LOCATION: (1)..(57)
<220> FEATURE:
<221> NAME/KEY: mat_peptide
<222> LOCATION: (58)..(417)

<400> SEQUENCE: 28

```
atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
     -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60 cag aag ttc aag ggc aga gtc acc atg acc gca gac aag tcc acg agc     288
Gln Lys Phe Lys Gly Arg Val Thr Met Thr Ala Asp Lys Ser Thr Ser
             65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                        418
Trp Gly Gln Gly Thr Thr Val Thr Val Ser Ser
110                 115                 120
```

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 29
actagtcgac atgaagttgc ctgttaggct gttggtgctg      40

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 30
actagtcgac atggagwcag acacactcct gytatgggt      39

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 31
actagtcgac atgagtgtgc tcactcaggt cctggsgttg      40

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 32
actagtcgac atgaggrccc ctgctcagwt tyttggmwtc ttg            43

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 33
actagtcgac atggatttwc aggtgcagat twtcagcttc                40

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 34
actagtcgac atgaggtkcy ytgytsagyt yctgrgg                   37

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 35
actagtcgac atgggcwtca agatggagtc acakwyycwg g              41

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 36
actagtcgac atgtggggay ctktttycmm ttttcaatt g               41

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 37
actagtcgac atggtrtccw casctcagtt ccttg                     35

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: primer

```
<400> SEQUENCE: 38
actagtcgac atgtatatat gtttgttgtc tatttct                              37

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 39
actagtcgac atggaagccc cagctcagct tctcttcc                             38

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 40
ggatcccggg tggatggtgg gaagatg                                         27

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 41
tagagtcacc gaggagccag ttgta                                           25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 42
ggatcccggg agtggataga ccgatg                                          26

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 43
gataagcttc caccatgggc ttcaagatgg agtc                                 34

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 44
gataagcttc caccatggaa tgtaactgga tact                                 34

<210> SEQ ID NO 45
```

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 45
ggcggatcca ctcacgtttt atttccaact ttgt                               34

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 46
ggcggatcca ctcacctgag gagactgtga gagt                               34

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 47
cagacagtgg ttcaaagt                                                 18

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 48
gaattcggat ccactcacgt ttgatt                                        26

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 49
agtcaggatg tgaatactgc tgtagcctgg taccagcaga agccagga                48

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 50
gcatccaacc ggtacactgg tgtgccaagc agattcagc                          39

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 51

```
caacattata gtactccatt cacgttcggc caagggacca aggtg              45
```

<210> SEQ ID NO 52
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 52

```
gcagtattca catcctgact ggccttacag gtgatggtca ctctgtc            47
```

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 53

```
acaccagtgt accggttgga tgccgagtag atcagcag                      38
```

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 54

```
gtgaatggag tactataatg ttgctggcag tagtaggtag c                   41
```

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 55

```
ggtaccgact acaccttcac catcagcagc c                             31
```

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 56

```
ggtgaaggtg tagtcggtac cgctaccgct a                             31
```

<210> SEQ ID NO 57
<211> LENGTH: 144
<212> TYPE: DNA
<213> ORGANISM: Artificial Sequence
<220> FEATURE:
<223> OTHER INFORMATION: Description of Artificial Sequence: DNA
      fragment for construction of H chain V region

<400> SEQUENCE: 57

```
atgccttgca ggaaaccttc actgaggccc caggcttctt cacctcagcc ccagactgca    60
ccagctgcac ctgggagtga gcacctggag ctacagccag caagaagaag accctccagg   120
tccagtccat ggtggaagct tatc                                          144
```

<210> SEQ ID NO 58
<211> LENGTH: 130
<212> TYPE: DNA
<213> ORGANISM: Artificial Sequence
<220> FEATURE:
<223> OTHER INFORMATION: Description of Artificial Sequence: DNA
      fragment for construction of H chain V region

<400> SEQUENCE: 58
tcagtgaagg tttcctgcaa ggcatctgga tacaccttca ctccctactg gatgcagtgg      60
gtgcgacagg cccctggaca agggcttgag tggatgggat ctattttttcc tggagatggt    120 gatactaggt                                                            130

<210> SEQ ID NO 59
<211> LENGTH: 131
<212> TYPE: DNA
<213> ORGANISM: Artificial Sequence
<220> FEATURE:
<223> OTHER INFORMATION: Description of Artificial Sequence: DNA
      fragment for construction of H chain V region

<400> SEQUENCE: 59
aatacacggc cgtgtcctca gatctcaggc tgctcagctc catgtagact gtgctcgtgg      60
acgtgtctgc ggtcatggtg actctgccct tgaacttctg actgtaccta gtatcaccat    120
ctccaggaaa a                                                          131

<210> SEQ ID NO 60
<211> LENGTH: 119
<212> TYPE: DNA
<213> ORGANISM: Artificial Sequence
<220> FEATURE:
<223> OTHER INFORMATION: Description of Artificial Sequence: DNA
      fragment for construction of H chain V region

<400> SEQUENCE: 60
gagatctgag gacacggccg tgtattactg tgcgagagga ttacgacgag gggggtacta     60
ctttgactac tgggggcaag ggaccacggt caccgtctcc tcaggtgagt ggatccgac    119

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 61
gataagcttc caccatggac tggac                                           25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 62
gtcggatcca ctcacctgag gagac                                           25

<210> SEQ ID NO 63
<211> LENGTH: 26
<212> TYPE: DNA
<213> ORGANISM: Artificial Sequence

```
-continued

<220> FEATURE:
<223> OTHER INFORMATION: Description of Artificial Sequence: primer

<400> SEQUENCE: 63
aagttcaagg gcaaagtcac catgac                                          26

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 64
gtcatggtga ctttgccctt gaactt                                          26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 65
atgaccgcag acaagtccac gagcac                                          26

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 66
gtgctcgtgg acttgtctgc ggtcat                                          26

<210> SEQ ID NO 67
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 67
aagttcaagg gcaaagtcac catgaccgca gacaagtcca cgagcac                   47

<210> SEQ ID NO 68
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 68
gtgctcgtgg acttgtctgc ggtcatggtg actttgccct tgaactt                   47

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 69
aagttcaagg gcagagccac cctgaccgca gacacgtc                             38
```

```
<210> SEQ ID NO 70
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 70
gacgtgtctg cggtcagggt ggctctgccc ttgaactt                              38

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 71
cagacagtgg ttcaaagt                                                    18

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 72
gccccaaagc caaggtc                                                     17

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 73
atttttcctg gagatggtga tac                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 74
gtatcaccat ctccaggaaa tat                                              23

<210> SEQ ID NO 75
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region (mouse-human hybrid)
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)
```

```
<400> SEQUENCE: 75 atg gaa tgt aac tgg ata ctt cct ttt att ctg tca gta act tca ggt      48
Met Glu Cys Asn Trp Ile Leu Pro Phe Ile Leu Ser Val Thr Ser Gly
            -15                 -10                 -5 gcc tac tca cag gtt caa ctc cag cag tct ggg gct gag ctg gca aga      96
Ala Tyr Ser Gln Val Gln Leu Gln Gln Ser Gly Ala Glu Leu Ala Arg
        -1   1               5                   10 cct ggg gct tca gtg aag ttg tcc tgc aag gct tct ggc tac acc ttt     144
Pro Gly Ala Ser Val Lys Leu Ser Cys Lys Ala Ser Gly Tyr Thr Phe
     15                  20                  25 act ccc tac tgg atg cag tgg gta aaa cag agg cct gga cag ggt ctg     192
Thr Pro Tyr Trp Met Gln Trp Val Lys Gln Arg Pro Gly Gln Gly Leu
 30                  35                  40                  45 gaa tgg att ggg tct att ttt cct gga gat ggt gat act agg tac agt     240
Glu Trp Ile Gly Ser Ile Phe Pro Gly Asp Gly Asp Thr Arg Tyr Ser
                 50                  55                  60 cag aag ttc aag ggc aga gtc acc atg acc gca gac acg tcc acg agc     288
Gln Lys Phe Lys Gly Arg Val Thr Met Thr Ala Asp Thr Ser Thr Ser
             65                  70                  75 aca gtc tac atg gag ctg agc agc ctg aga tct gag gac acg gcc gtg     336
Thr Val Tyr Met Glu Leu Ser Ser Leu Arg Ser Glu Asp Thr Ala Val
         80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
     95                 100                 105 tgg ggg caa ggg acc acg gtc acc gtc tcc tca g                       418
Trp Gly Gln Gly Thr Thr Val Thr Val Ser Ser
110                 115                 120

<210> SEQ ID NO 76
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region (human-mouse hybrid)
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 76 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                 -5 gct cac tcc cag gtg cag ctg gtg cag tct ggg gct gag gtg aag aag      96
Ala His Ser Gln Val Gln Leu Val Gln Ser Gly Ala Glu Val Lys Lys
        -1   1               5                   10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
     15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
                 50                  55                  60
```

-continued

```
cag aag ttc aag ggc aag gcc aca ttg act gca gat aaa tcc tcc agt      288
Gln Lys Phe Lys Gly Lys Ala Thr Leu Thr Ala Asp Lys Ser Ser Ser
            65                  70                  75 aca gcc tac atg caa ctc agc atc ttg gca ttt gag gac tct gcg gtc      336
Thr Ala Tyr Met Gln Leu Ser Ile Leu Ala Phe Glu Asp Ser Ala Val
        80                  85                  90 tat tac tgt gca aga gga tta cga cga ggg ggg tac tac ttt gac tac      384
Tyr Tyr Cys Ala Arg Gly Leu Arg Arg Gly Gly Tyr Tyr Phe Asp Tyr
    95                  100                 105 tgg ggc caa ggc acc act ctc aca gtc tcc tca g                        418
Trp Gly Gln Gly Thr Thr Leu Thr Val Ser Ser
110                 115                 120

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 77
ctggttcggc ccacctctga aggttccaga atcgatag                            38

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 78
gcagacacgt cctcgagcac agcctacatg gagct                               35

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 79
agctccatgt aggctgtgct cgaggacgtg tctgc                               35

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 80
tgggtgcgac agcgccctgg acaagg                                         26

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 81
ccttgtccag ggcgctgtcg caccca                                         26

<210> SEQ ID NO 82
<211> LENGTH: 41
```

```
<210> SEQ ID NO 82
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 82
tacatggagc tgagcagcct ggcatttgag gacacggccg t                               41

<210> SEQ ID NO 83
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 83
acggccgtgt cctcaaatgc caggctgctc agctccatgt a                               41

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 84
aagttcaagg gcaaagccac cctgac                                                26

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 85
gtcaggGtgg ctttgccctt gaactt                                                26

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 86
gcctacatgc agctgagcag cct                                                   23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 87
aggctgctca gctgcatgta ggc                                                   23

<210> SEQ ID NO 88
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 88
```

```
gcctacatgc agctgagcat cctgagatct gaggacac                              38

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 89
gatctcagga tgctcagctg catgtaggct gtgct                                 35

<210> SEQ ID NO 90
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 90
gcctacatgc agctgagcat cctgagatct gaggactcgg ccgtgtatta                 50

<210> SEQ ID NO 91
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 91
acggccgagt cctcagatct caggatgctc agctgcatgt aggctgtgct                 50

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 92
gagctgagca tcctgagatc                                                  20

<210> SEQ ID NO 93
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 93
gatctcagga tgctcagctc catgta                                           26

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 94
agatctgagg actcggccgt                                                  20

<210> SEQ ID NO 95
<211> LENGTH: 20
<212> TYPE: DNA
<213> ORGANISM: Artificial Sequence
```

```
<220> FEATURE:
<223> OTHER INFORMATION: Description of Artificial Sequence: primer

<400> SEQUENCE: 95
acggccgagt cctcagatct                                              20

<210> SEQ ID NO 96
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 96
gcagacacgt ccacgagcac agcctacatg gagct                             35

<210> SEQ ID NO 97
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 97
agctccatgt aggctgtgct cgtggacgtg tctgc                             35

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 98
gcagacacgt cctcgagcac agtctacatg gagct                             35

<210> SEQ ID NO 99
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 99
agctccatgt agactgtgct cgaggacgtg tctgc                             35

<210> SEQ ID NO 100
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 100
agagtcacca tcaccgcaga caagtc                                       26

<210> SEQ ID NO 101
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 101
gacttgtctg cggtgatggt gactct                                       26
```

```
<210> SEQ ID NO 102
<211> LENGTH: 418
<212> TYPE: DNA
<213> ORGANISM: Artificial Sequence
<220> FEATURE:
<223> OTHER INFORMATION: Description of Artificial Sequence: Nucleotide
      sequence coding for reshaped human anti-HM 1.24 antibody H chain
      V region version s inserted into HEF-RVHs-AHM-g(y)l
<220> FEATURE:
<221> NAME/KEY: CDS
<222> LOCATION: (1)..(417)
<220> FEATURE:
<221> NAME/KEY: sig_peptide
<222> LOCATION: (1)..(57)
<220> FEATURE:
<221> NAME/KEY: mat_peptide
<222> LOCATION: (58)..(417)

<400> SEQUENCE: 102 atg gac tgg acc tgg agg gtc ttc ttc ttg ctg gct gta gct cca ggt      48
Met Asp Trp Thr Trp Arg Val Phe Phe Leu Leu Ala Val Ala Pro Gly
            -15                 -10                  -5 gct cac tcc cag gtg cag ctg gtg cag tct ggg gct gag gtg aag aag      96
Ala His Ser Gln Val Gln Leu Val Gln Ser Gly Ala Glu Val Lys Lys
     -1   1               5                  10 cct ggg gcc tca gtg aag gtt tcc tgc aag gca tct gga tac acc ttc     144
Pro Gly Ala Ser Val Lys Val Ser Cys Lys Ala Ser Gly Tyr Thr Phe
 15                  20                  25 act ccc tac tgg atg cag tgg gtg cga cag gcc cct gga caa ggg ctt     192
Thr Pro Tyr Trp Met Gln Trp Val Arg Gln Ala Pro Gly Gln Gly Leu
 30                  35                  40                  45 gag tgg atg gga tct att ttt cct gga gat ggt gat act agg tac agt     240
Glu Trp Met Gly Ser Ile Phe Pro Gly Asp Gly Asp Thr Arg Tyr Ser
             50                  55                  60 cag aag ttc aag ggc aga gtc acc atc acc gca gac aag tcc acg agc     288
Gln Lys Phe Lys Gly Arg Val Thr Ile Thr Ala Asp Lys Ser Thr Ser
         65                  70                  75 aca gcc tac atg gag ctg agc agc ctg aga tct gag gac acg gcc gtg     336
Thr Ala Tyr Met Glu Leu Ser Ser Leu Arg Ser Glu Asp Thr Ala Val
     80                  85                  90 tat tac tgt gcg aga gga tta cga cga ggg ggg tac tac ttt gac tac     384
Tyr Tyr Cys Ala Arg Gly Leu Arg Arg Gly Gly Tyr Tyr Phe Asp Tyr
 95                 100                 105 tgg ggg caa ggg acc acg gtc acc gtc tcc tca g                       418
Trp Gly Gln Gly Thr Thr Val Thr Val Ser Ser
110                 115                 120

<210> SEQ ID NO 103
<211> LENGTH: 1013
<212> TYPE: DNA
<213> ORGANISM: Artificial Sequence
<220> FEATURE:
<223> OTHER INFORMATION: Description of Artificial Sequence: Nucleotide
      sequence coding for HM 1.24 antigen
<220> FEATURE:
<221> NAME/KEY: CDS
<222> LOCATION: (23)..(562)

<400> SEQUENCE: 103
gaattcggca cgagggatct gg atg gca tct act tcg tat gac tat tgc aga     52
                         Met Ala Ser Thr Ser Tyr Asp Tyr Cys Arg
                           1               5                  10 gtg ccc atg gaa gac ggg gat aag cgc tgt aag ctt ctg ctg ggg ata     100
Val Pro Met Glu Asp Gly Asp Lys Arg Cys Lys Leu Leu Leu Gly Ile
             15                  20                  25
```

```
gga att ctg gtg ctc ctg atc atc gtg att ctg ggg gtg ccc ttg att    148
Gly Ile Leu Val Leu Leu Ile Ile Val Ile Leu Gly Val Pro Leu Ile
             30                  35                  40 atc ttc acc atc aag gcc aac agc gag gcc tgc cgg gac ggc ctt cgg    196
Ile Phe Thr Ile Lys Ala Asn Ser Glu Ala Cys Arg Asp Gly Leu Arg
     45                  50                  55 gca gtg atg gag tgt cgc aat gtc acc cat ctc ctg caa caa gag ctg    244
Ala Val Met Glu Cys Arg Asn Val Thr His Leu Leu Gln Gln Glu Leu
 60                  65                  70 acc gag gcc cag aag ggc ttt cag gat gtg gag gcc cag gcc gcc acc    292
Thr Glu Ala Gln Lys Gly Phe Gln Asp Val Glu Ala Gln Ala Ala Thr
 75                  80                  85                  90 tgc aac cac act gtg atg gcc cta atg gct tcc ctg gat gca gag aag    340
Cys Asn His Thr Val Met Ala Leu Met Ala Ser Leu Asp Ala Glu Lys
                 95                 100                 105 gcc caa gga caa aag aaa gtg gag gag ctt gag gga gag atc act aca    388
Ala Gln Gly Gln Lys Lys Val Glu Glu Leu Glu Gly Glu Ile Thr Thr
            110                 115                 120 tta aac cat aag ctt cag gac gcg tct gca gag gtg gag cga ctg aga    436
Leu Asn His Lys Leu Gln Asp Ala Ser Ala Glu Val Glu Arg Leu Arg
        125                 130                 135 aga gaa aac cag gtc tta agc gtg aga atc gcg gac aag aag tac tac    484
Arg Glu Asn Gln Val Leu Ser Val Arg Ile Ala Asp Lys Lys Tyr Tyr
140                 145                 150 ccc agc tcc cag gac tcc agc tcc gct gcg gcg ccc cag ctg ctg att    532
Pro Ser Ser Gln Asp Ser Ser Ser Ala Ala Ala Pro Gln Leu Leu Ile
155                 160                 165                 170 gtg ctg ctg ggc ctc agc gct ctg ctg cag tgagatccca ggaagctggc      582
Val Leu Leu Gly Leu Ser Ala Leu Leu Gln
                175                 180 acatcttgga aggtccgtcc tgctcggctt tcgcttgaa cattcccttg atctcatcag   642
ttctgagcgg gtcatggggc aacacggtta gcggggagag cacggggtag ccggagaagg  702
gcctctggag caggtctgga ggggccatgg ggcagtcctg ggtctgggga cacagtcggg  762
ttgacccagg gctgtctccc tccagagcct ccctccggac aatgagtccc cctcttgtc   822 tcccaccctg agattgggca tggggtgcgg tgtggggggc atgtgctgcc tgttgttatg  882
ggtttttttt gcgggggggg ttgctttttt ctggggtctt tgagctccaa aaaaataaac  942
acttcctttg agggagagca caccttaaaa aaaaaaaaa aaaaaaaaa aaaaaattc    1002 gggcggccgc c                                                     1013
```

<210> SEQ ID NO 104
<211> LENGTH: 131
<212> TYPE: PRT
<213> ORGANISM: murine
<220> FEATURE:
<222> LOCATION:
<223> OTHER INFORMATION: Amino acid sequence of anti-HM 1.24 antibody
      L chain V region

<400> SEQUENCE: 104

```
Met Gly Phe Lys Met Glu Ser His Phe Leu Val Phe Val Phe
                -20                 -15                 -10

Leu Trp Leu Ser Gly Val Asp Gly Asp Ile Val Met Thr Gln Ser His
             -5                  -1   1               5

Lys Phe Met Ser Thr Ser Val Gly Asp Arg Val Ser Ile Thr Cys Lys
         10                  15                  20

Ala Ser Gln Asp Val Asn Thr Ala Val Ala Trp Tyr Gln Gln Lys Pro
 25                  30                  35                  40
```

-continued

Gly Gln Ser Pro Lys Leu Leu Ile Tyr Ser Ala Ser Asn Arg Tyr Thr
                45                  50                  55

Gly Val Pro Asp Arg Ile Thr Gly Ser Gly Ser Gly Thr Asp Phe Thr
            60                  65                  70

Phe Thr Ile Ser Ser Val Gln Ala Glu Asp Leu Ala Leu Tyr Tyr Cys
        75                  80                  85

Gln Gln His Tyr Ser Thr Pro Phe Thr Phe Gly Ser Gly Thr Lys Leu
    90                  95                  100

Glu Ile Lys
105

<210> SEQ ID NO 105
<211> LENGTH: 139
<212> TYPE: PRT
<213> ORGANISM: murine
<220> FEATURE:
<222> LOCATION:
<223> OTHER INFORMATION: Amino acid sequence of anti-HM 1.24 antibody
      H chain V region

<400> SEQUENCE: 105

Met Glu Cys Asn Trp Ile Leu Pro Phe Ile Leu Ser Val Thr Ser Gly
                -15                 -10                 -5

Ala Tyr Ser Gln Val Gln Leu Gln Gln Ser Gly Ala Glu Leu Ala Arg
        -1   1               5                   10

Pro Gly Ala Ser Val Lys Leu Ser Cys Lys Ala Ser Gly Tyr Thr Phe
    15                  20                  25

Thr Pro Tyr Trp Met Gln Trp Val Lys Gln Arg Pro Gly Gln Gly Leu
30                  35                  40                  45

Glu Trp Ile Gly Ser Ile Phe Pro Gly Asp Gly Asp Thr Arg Tyr Ser
                50                  55                  60

Gln Lys Phe Lys Gly Lys Ala Thr Leu Thr Ala Asp Lys Ser Ser Ser
            65                  70                  75

Thr Ala Tyr Met Gln Leu Ser Ile Leu Ala Phe Glu Asp Ser Ala Val
        80                  85                  90

Tyr Tyr Cys Ala Arg Gly Leu Arg Arg Gly Gly Tyr Tyr Phe Asp Tyr
    95                  100                 105

Trp Gly Gln Gly Thr Thr Leu Thr Val Ser Ser
110                 115                 120

<210> SEQ ID NO 106
<211> LENGTH: 126
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody L chain V region
      version a

<400> SEQUENCE: 106

Met Gly Trp Ser Cys Ile Ile Leu Ser Leu Val Ala Thr Ala Thr Gly
                -15                 -10                 -5

Val His Ser Asp Ile Gln Met Thr Gln Ser Pro Ser Ser Leu Ser Ala
        -1   1               5                   10

Ser Val Gly Asp Arg Val Thr Ile Thr Cys Lys Ala Ser Gln Asp Val
    15                  20                  25

Asn Thr Ala Val Ala Trp Tyr Gln Gln Lys Pro Gly Lys Ala Pro Lys
30                  35                  40                  45

```
Leu Leu Ile Tyr Ser Ala Ser Asn Arg Tyr Thr Gly Val Pro Ser Arg
            50                  55                  60

Phe Ser Gly Ser Gly Ser Gly Thr Asp Phe Thr Phe Thr Ile Ser Ser
        65                  70                  75

Leu Gln Pro Glu Asp Ile Ala Thr Tyr Tyr Cys Gln Gln His Tyr Ser
    80                  85                  90

Thr Pro Phe Thr Phe Gly Gln Gly Thr Lys Val Glu Ile Lys
    95                 100                 105

<210> SEQ ID NO 107
<211> LENGTH: 126
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody L chain V region
      version b

<400> SEQUENCE: 107

Met Gly Trp Ser Cys Ile Ile Leu Ser Leu Val Ala Thr Ala Thr Gly
                -15                 -10                  -5

Val His Ser Asp Ile Gln Met Thr Gln Ser Pro Ser Ser Leu Ser Ala
         -1   1               5                  10

Ser Val Gly Asp Arg Val Thr Ile Thr Cys Lys Ala Ser Gln Asp Val
    15                  20                  25

Asn Thr Ala Val Ala Trp Tyr Gln Gln Lys Pro Gly Lys Ala Pro Lys
30                  35                  40                  45

Leu Leu Ile Tyr Ser Ala Ser Asn Arg Tyr Thr Gly Val Pro Ser Arg
            50                  55                  60

Phe Ser Gly Ser Gly Ser Gly Thr Asp Tyr Thr Phe Thr Ile Ser Ser
        65                  70                  75

Leu Gln Pro Glu Asp Ile Ala Thr Tyr Tyr Cys Gln Gln His Tyr Ser
    80                  85                  90

Thr Pro Phe Thr Phe Gly Gln Gly Thr Lys Val Glu Ile Lys
    95                 100                 105

<210> SEQ ID NO 108
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version a

<400> SEQUENCE: 108

Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
            50                  55                  60

Gln Lys Phe Lys Gly Arg Val Thr Met Thr Ala Asp Thr Ser Thr Ser
        65                  70                  75

Thr Val Tyr Met Glu Leu Ser Ser Leu Arg Ser Glu Asp Thr Ala Val
```

```
                80              85              90
Tyr Tyr Cys Ala Arg Gly Leu Arg Arg Gly Gly Tyr Tyr Phe Asp Tyr
        95              100             105

Trp Gly Gln Gly Thr Thr Val Thr Val Ser Ser
110             115             120

<210> SEQ ID NO 109
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version b

<400> SEQUENCE: 109

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Val Thr Met Thr Ala Asp Thr Ser Thr Ser
            65                  70                  75

Thr Val Tyr Met Glu Leu Ser Ser Leu Arg Ser Glu Asp Thr Ala Val
        80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110             115             120

<210> SEQ ID NO 110
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version c

<400> SEQUENCE: 110

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Met Thr Ala Asp Lys Ser Thr Ser
            65                  70                  75

Thr Val Tyr Met Glu Leu Ser Ser Leu Arg Ser Glu Asp Thr Ala Val
        80                  85                  90
```

```
Tyr Tyr Cys Ala Arg Gly Leu Arg Arg Gly Tyr Tyr Phe Asp Tyr
        95                 100                 105

Trp Gly Gln Gly Thr Thr Val Thr Val Ser Ser
110             115                 120

<210> SEQ ID NO 111
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version d

<400> SEQUENCE: 111

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Val Thr Met Thr Ala Asp Lys Ser Thr Ser
                65                  70                  75

Thr Val Tyr Met Glu Leu Ser Ser Leu Arg Ser Glu Asp Thr Ala Val
        80                  85                  90

Tyr Tyr Cys Ala Arg Gly Leu Arg Arg Gly Tyr Tyr Phe Asp Tyr
        95                 100                 105

Trp Gly Gln Gly Thr Thr Val Thr Val Ser Ser
110             115                 120

<210> SEQ ID NO 112
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version e

<400> SEQUENCE: 112

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
        15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Arg Ala Thr Leu Thr Ala Asp Ser Thr Ser
                65                  70                  75

Thr Val Tyr Met Glu Leu Ser Ser Leu Arg Ser Glu Asp Thr Ala Val
        80                  85                  90
```

```
Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110                 115                 120

<210> SEQ ID NO 113
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version f

<400> SEQUENCE: 113

Met Asp Trp Thr Trp Arg Val Phe Phe Leu Leu Ala Val Ala Pro Gly
             -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Ala Thr Leu Thr Ala Asp Thr Ser Ser Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110                 115                 120

<210> SEQ ID NO 114
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version g

<400> SEQUENCE: 114

Met Asp Trp Thr Trp Arg Val Phe Phe Leu Leu Ala Val Ala Pro Gly
             -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Arg Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Val Thr Met Thr Ala Asp Thr Ser Thr Ser
             65                  70                  75

Thr Val Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
```

```
                 95                  100                 105

Trp Gly Gln Gly Thr Thr Val Thr Val Ser Ser
110                 115                 120

<210> SEQ ID NO 115
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version h

<400> SEQUENCE: 115

Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
             65                  70                  75

Thr Ala Tyr Met Glu Leu Ser Ser Leu Arg Ser Glu Asp Thr Ala Val
             80                  85                  90

Tyr Tyr Cys Ala Arg Gly Leu Arg Arg Gly Gly Tyr Tyr Phe Asp Tyr
         95                  100                 105

Trp Gly Gln Gly Thr Thr Val Thr Val Ser Ser
110                 115                 120

<210> SEQ ID NO 116
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version i

<400> SEQUENCE: 116

Met Asp Trp Thr Trp Arg Val Phe Phe Leu Leu Ala Val Ala Pro Gly
                -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
             65                  70                  75

Thr Ala Tyr Met Glu Leu Ser Ser Leu Ala Phe Glu Asp Thr Ala Val
             80                  85                  90

Tyr Tyr Cys Ala Arg Gly Leu Arg Arg Gly Gly Tyr Tyr Phe Asp Tyr
         95                  100                 105
```

Trp Gly Gln Gly Thr Thr Val Thr Val Ser Ser
110                 115                 120

<210> SEQ ID NO 117
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version j

<400> SEQUENCE: 117

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Ala Thr Leu Thr Ala Asp Thr Ser Ser Ser
            65                  70                  75

Thr Ala Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
            95                  100                 105

Trp Gly Gln Gly Thr Thr Val Thr Val Ser Ser
110                 115                 120

<210> SEQ ID NO 118
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version k

<400> SEQUENCE: 118

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Lys Val Thr Met Thr Ala Asp Thr Ser Ser Ser
            65                  70                  75

Thr Ala Tyr Met Gln Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
            95                  100                 105

Trp Gly Gln Gly Thr Thr Val Thr Val Ser Ser
110                 115                 120

<210> SEQ ID NO 119
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version l

<400> SEQUENCE: 119

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
             15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
                 65                  70                  75

Thr Ala Tyr Met Gln Leu Ser Ile Leu Arg Ser Glu Asp Thr Ala Val
             80                  85                  90

Tyr Tyr Cys Ala Arg Gly Leu Arg Arg Gly Gly Tyr Tyr Phe Asp Tyr
         95                  100                 105

Trp Gly Gln Gly Thr Thr Val Thr Val Ser Ser
110                 115                 120

<210> SEQ ID NO 120
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version m

<400> SEQUENCE: 120

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
             15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Lys Val Thr Met Thr Ala Asp Thr Ser Ser Ser
                 65                  70                  75

Thr Ala Tyr Met Gln Leu Ser Ile Leu Arg Ser Glu Asp Ser Ala Val
             80                  85                  90

Tyr Tyr Cys Ala Arg Gly Leu Arg Arg Gly Gly Tyr Tyr Phe Asp Tyr
         95                  100                 105

Trp Gly Gln Gly Thr Thr Val Thr Val Ser Ser

<210> SEQ ID NO 121
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version n

<400> SEQUENCE: 121

Met Asp Trp Thr Trp Arg Val Phe Phe Leu Leu Ala Val Ala Pro Gly
              -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                  50                  55                  60

Gln Lys Phe Lys Gly Lys Val Thr Met Thr Ala Asp Thr Ser Ser Ser
                 65                  70                  75

Thr Ala Tyr Met Glu Leu Ser Ile Leu Arg Ser Glu Asp Thr Ala Val
             80                  85                  90

Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110                 115                 120

<210> SEQ ID NO 122
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version o

<400> SEQUENCE: 122

Met Asp Trp Thr Trp Arg Val Phe Phe Leu Leu Ala Val Ala Pro Gly
              -15                 -10                  -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                  50                  55                  60

Gln Lys Phe Lys Gly Lys Val Thr Met Thr Ala Asp Thr Ser Ser Ser
                 65                  70                  75

Thr Ala Tyr Met Glu Leu Ser Ser Leu Arg Ser Glu Asp Ser Ala Val
             80                  85                  90

Tyr Tyr Cys Ala Arg Gly Leu Arg Arg Gly Gly Tyr Tyr Phe Asp Tyr
         95                 100                 105

Trp Gly Gln Gly Thr Thr Val Thr Val Ser Ser
110                 115                 120

<210> SEQ ID NO 123
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version p

<400> SEQUENCE: 123

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Met Thr Ala Asp Thr Ser Thr Ser
            65                  70                  75

Thr Ala Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110                 115                 120

<210> SEQ ID NO 124
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version q

<400> SEQUENCE: 124

Met Asp Trp Thr Trp Arg Val Phe Phe Leu Leu Ala Val Ala Pro Gly
            -15                 -10                 -5

Ala His Ser Gln Val Gln Leu Val Gln Ser Gly Ala Glu Val Lys Lys
        -1   1               5                  10

Pro Gly Ala Ser Val Lys Val Ser Cys Lys Ala Ser Gly Tyr Thr Phe
    15                  20                  25

Thr Pro Tyr Trp Met Gln Trp Val Arg Gln Ala Pro Gly Gln Gly Leu
30                  35                  40                  45

Glu Trp Met Gly Ser Ile Phe Pro Gly Asp Gly Asp Thr Arg Tyr Ser
                50                  55                  60

Gln Lys Phe Lys Gly Arg Val Thr Met Thr Ala Asp Thr Ser Ser Ser
            65                  70                  75

Thr Val Tyr Met Glu Leu Ser Ser Leu Arg Ser Glu Asp Thr Ala Val
            80                  85                  90

Tyr Tyr Cys Ala Arg Gly Leu Arg Arg Gly Gly Tyr Tyr Phe Asp Tyr
        95                  100                 105

Trp Gly Gln Gly Thr Thr Val Thr Val Ser Ser
110                 115                 120

```
<210> SEQ ID NO 125
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version r

<400> SEQUENCE: 125

Met Asp Trp Thr Trp Arg Val Phe Phe Leu Leu Ala Val Ala Pro Gly
                -15                 -10                 -5

Ala His Ser Gln Val Gln Leu Val Gln Ser Gly Ala Glu Val Lys Lys
         -1   1               5                  10

Pro Gly Ala Ser Val Lys Val Ser Cys Lys Ala Ser Gly Tyr Thr Phe
         15                  20                  25

Thr Pro Tyr Trp Met Gln Trp Val Arg Gln Ala Pro Gly Gln Gly Leu
 30                  35                  40                  45

Glu Trp Met Gly Ser Ile Phe Pro Gly Asp Gly Asp Thr Arg Tyr Ser
                 50                  55                  60

Gln Lys Phe Lys Gly Arg Val Thr Met Thr Ala Asp Lys Ser Thr Ser
             65                  70                  75

Thr Ala Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                  100                 105

Trp Gly Gln Gly Thr Thr Val Thr Val Ser Ser
110                 115                 120

<210> SEQ ID NO 126
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      (mouse-human hybrid)

<400> SEQUENCE: 126

Met Glu Cys Asn Trp Ile Leu Pro Phe Ile Leu Ser Val Thr Ser Gly
                -15                 -10                 -5

Ala Tyr Ser Gln Val Gln Leu Gln Gln Ser Gly Ala Glu Leu Ala Arg
         -1   1               5                  10

Pro Gly Ala Ser Val Lys Leu Ser Cys Lys Ala Ser Gly Tyr Thr Phe
         15                  20                  25

Thr Pro Tyr Trp Met Gln Trp Val Lys Gln Arg Pro Gly Gln Gly Leu
 30                  35                  40                  45

Glu Trp Ile Gly Ser Ile Phe Pro Gly Asp Gly Asp Thr Arg Tyr Ser
                 50                  55                  60

Gln Lys Phe Lys Gly Arg Val Thr Met Thr Ala Asp Thr Ser Thr Ser
             65                  70                  75

Thr Val Tyr Met Glu Leu Ser Ser Leu Arg Ser Glu Asp Thr Ala Val
         80                  85                  90

Tyr Tyr Cys Ala Arg Gly Leu Arg Arg Gly Gly Tyr Tyr Phe Asp Tyr
         95                  100                 105

Trp Gly Gln Gly Thr Thr Val Thr Val Ser Ser
110                 115                 120
```

```
<210> SEQ ID NO 127
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      (human-mouse hybrid)

<400> SEQUENCE: 127

Met Asp Trp Thr Trp Arg Val Phe Phe Leu Leu Ala Val Ala Pro Gly
                -15                 -10                 -5
Ala His Ser Gln Val Gln Leu Val Gln Ser Gly Ala Glu Val Lys Lys
         -1   1               5                  10
Pro Gly Ala Ser Val Lys Val Ser Cys Lys Ala Ser Gly Tyr Thr Phe
         15                  20                  25
Thr Pro Tyr Trp Met Gln Trp Val Arg Gln Ala Pro Gly Gln Gly Leu
     30                  35                  40                  45
Glu Trp Met Gly Ser Ile Phe Pro Gly Asp Gly Asp Thr Arg Tyr Ser
                 50                  55                  60
Gln Lys Phe Lys Gly Lys Ala Thr Leu Thr Ala Asp Lys Ser Ser Ser
                 65                  70                  75
Thr Ala Tyr Met Gln Leu Ser Ile Leu Ala Phe Glu Asp Ser Ala Val
             80                  85                  90
Tyr Tyr Cys Ala Arg Gly Leu Arg Arg Gly Gly Tyr Tyr Phe Asp Tyr
         95                 100                 105
Trp Gly Gln Gly Thr Thr Leu Thr Val Ser Ser
110                 115                 120

<210> SEQ ID NO 128
<211> LENGTH: 139
<212> TYPE: PRT
<213> ORGANISM: Artificial Sequence
<220> FEATURE:
<223> OTHER INFORMATION: Description of Artificial Sequence: Amino acid
      sequence of reshaped human anti-HM 1.24 antibody H chain V region
      version s

<400> SEQUENCE: 128

Met Asp Trp Thr Trp Arg Val Phe Phe Leu Leu Ala Val Ala Pro Gly
                -15                 -10                 -5
Ala His Ser Gln Val Gln Leu Val Gln Ser Gly Ala Glu Val Lys Lys
         -1   1               5                  10
Pro Gly Ala Ser Val Lys Val Ser Cys Lys Ala Ser Gly Tyr Thr Phe
         15                  20                  25
Thr Pro Tyr Trp Met Gln Trp Val Arg Gln Ala Pro Gly Gln Gly Leu
     30                  35                  40                  45
Glu Trp Met Gly Ser Ile Phe Pro Gly Asp Gly Asp Thr Arg Tyr Ser
                 50                  55                  60
Gln Lys Phe Lys Gly Arg Val Thr Ile Thr Ala Asp Lys Ser Thr Ser
                 65                  70                  75
Thr Ala Tyr Met Glu Leu Ser Ser Leu Arg Ser Glu Asp Thr Ala Val
             80                  85                  90
Tyr Tyr Cys Ala Arg Gly Leu Arg Arg Gly Gly Tyr Tyr Phe Asp Tyr
         95                 100                 105
Trp Gly Gln Gly Thr Thr Val Thr Val Ser Ser
110                 115                 120

<210> SEQ ID NO 129
```

```
<211> LENGTH: 180
<212> TYPE: PRT
<213> ORGANISM: Artificial Sequence
<220> FEATURE:
<223> OTHER INFORMATION: Description of Artificial Sequence: Amino acid
      sequence of HM 1.24 antigen

<400> SEQUENCE: 129

Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 130
<211> LENGTH: 80
<212> TYPE: PRT
<213> ORGANISM: Unknown
<220> FEATURE:
<223> OTHER INFORMATION: Description of Unknown Organism: HuSGI
<300> PUBLICATION INFORMATION:
<301> AUTHORS: Kabat, E.A. et al.
<303> JOURNAL: SEQUENCE OF PROTEINS OF IMMUNOLOGICAL INTEREST, U.S.
      DEPT. HEALTH AND HUMAN SERVICES
<307> DATE: 1991

<400> SEQUENCE: 130

Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Val Glu Ile Lys
65                  70                  75                  80

<210> SEQ ID NO 131
<211> LENGTH: 80
<212> TYPE: PRT
```

```
<213> ORGANISM: Unknown
<220> FEATURE:
<223> OTHER INFORMATION: Description of Unknown Organism: REI
<300> PUBLICATION INFORMATION:
<301> AUTHORS: Recchmann, L. et al.
<303> JOURNAL: NATURE
<304> VOLUME: 322
<306> PAGES: 21-25
<307> DATE: 1998

<400> SEQUENCE: 131

Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Phe Thr Ile Ser Ser Leu Gln Pro Glu Asp
    50                  55                  60

Ile Ala Thr Tyr Tyr Cys Phe Gly Gln Gly Thr Lys Val Glu Ile Lys
65                  70                  75                  80

<210> SEQ ID NO 132
<211> LENGTH: 44
<212> TYPE: PRT
<213> ORGANISM: Unknown
<220> FEATURE:
<223> OTHER INFORMATION: Description of Unknown Organism: HuSGI
<220> FEATURE:
<221> NAME/KEY: VARIANT
<222> LOCATION: 16,19,38
<223> OTHER INFORMATION: Xaa residues throughout the sequence may be
      any, other or uknown amino acid
<300> PUBLICATION INFORMATION:
<301> AUTHORS: Kabat, E.A. et al.
<303> JOURNAL: SEQUENCE OF PROTEINS OF IMMUNOLOGICAL INTEREST, U.S.
      DEPT. HEALTH AND HUMAN SERVICES
<307> DATE: 1991

<400> SEQUENCE: 132

Glu Val Gln Leu Val Gln Ser Gly Ala Asp Val Lys Lys Pro Gly Xaa
 1               5                  10                  15

Ser Val Xaa Val Ser Cys Lys Ala Ser Gly Tyr Thr Phe Ser Trp Val
            20                  25                  30

Arg Gln Ala Pro Gly Xaa Gly Leu Asp Trp Val Gly
        35                  40

<210> SEQ ID NO 133
<211> LENGTH: 44
<212> TYPE: PRT
<213> ORGANISM: Unknown
<220> FEATURE:
<223> OTHER INFORMATION: Description of Unknown Organism: HG3
<300> PUBLICATION INFORMATION:
<301> AUTHORS: Rechavi, G. et al.
<303> JOURNAL: PROC. NATL. ACAD. SCI. USA
<304> VOLUME: 80
<306> PAGES: 855-859
<307> DATE: 1983

<400> SEQUENCE: 133

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Trp Val
            20                  25                  30

Arg Gln Ala Pro Gly Gln Gly Leu Glu Trp Met Gly
```

```
                    35                  40

<210> SEQ ID NO 134
<211> LENGTH: 32
<212> TYPE: PRT
<213> ORGANISM: Unknown
<220> FEATURE:
<223> OTHER INFORMATION: Description of Unknown Organism: HuSGI
<220> FEATURE:
<221> NAME/KEY: VARIANT
<222> LOCATION: 4,6,8,10
<223> OTHER INFORMATION: Xaa residues throughout the sequence may be
      any, other or uknown amino acid
<300> PUBLICATION INFORMATION:
<301> AUTHORS: Kabat, E.A. et al.
<303> JOURNAL: SEQUENCE OF PROTEINS OF IMMUNOLOGICAL INTEREST, U.S.
      DEPT. HEALTH AND HUMAN SERVICES
<307> DATE: 1991

<400> SEQUENCE: 134

Arg Val Thr Xaa Thr Xaa Asp Xaa Ser Xaa Asn Thr Ala Tyr Met Glu
 1               5                  10                  15

Leu Ser Ser Leu Arg Ser Glu Asp Thr Ala Val Tyr Tyr Cys Ala Arg
            20                  25                  30

<210> SEQ ID NO 135
<211> LENGTH: 32
<212> TYPE: PRT
<213> ORGANISM: Unknown
<220> FEATURE:
<223> OTHER INFORMATION: Description of Unknown Organism: HG3
<300> PUBLICATION INFORMATION:
<301> AUTHORS: Rechavi, G. et al.
<303> JOURNAL: PROC. NATL. ACAD. SCI. USA
<304> VOLUME: 80
<306> PAGES: 855-859
<307> DATE: 1983

<400> SEQUENCE: 135

Arg Val Thr Met Thr Arg Asp Thr Ser Thr Ser Thr Val Tyr Met Glu
 1               5                  10                  15

Leu Ser Ser Leu Arg Ser Glu Asp Thr Ala Val Tyr Tyr Cys Ala Arg
            20                  25                  30

<210> SEQ ID NO 136
<211> LENGTH: 11
<212> TYPE: PRT
<213> ORGANISM: Unknown
<220> FEATURE:
<223> OTHER INFORMATION: Description of Unknown Organism: HuSGI
<300> PUBLICATION INFORMATION:
<301> AUTHORS: Kabat, E.A. et al.
<303> JOURNAL: SEQUENCE OF PROTEINS OF IMMUNOLOGICAL INTEREST, U.S.
      DEPT. HEALTH AND HUMAN SERVICES
<307> DATE: 1991

<400> SEQUENCE: 136

Trp Gly Gln Gly Thr Leu Val Thr Val Ser Ser
 1               5                  10

<210> SEQ ID NO 137
<211> LENGTH: 11
<212> TYPE: PRT
<213> ORGANISM: Unknown
<220> FEATURE:
<223> OTHER INFORMATION: Description of Unknown Organism: JH6
<300> PUBLICATION INFORMATION:
<301> AUTHORS: Ravetch, J. et al.
<303> JOURNAL: CELL
<304> VOLUME: 27
```

```
-continued
<306> PAGES: 583-591
<307> DATE: 1981

<400> SEQUENCE: 137

Trp Gly Gln Gly Thr Thr Val Thr Val Ser Ser
 1               5                   10
```

— ● — RESHAPED HUMAN ANTI-HM 1.24 ANTIBODY 1 μg/ml
— ▲ — RESHAPED HUMAN ANTI-HM 1.24 ANTIBODY 0.1 μg/ml
— ◆ — RESHAPED HUMAN ANTI-HM 1.24 ANTIBODY 0.01 μg/ml
— ■ — RESHAPED HUMAN ANTI-HM 1.24 ANTIBODY 0.001 μg/ml
----+---- CONTROL HUMAN IgG1 1 μg/ml
----○---- MOUSE ANTI-HM 1.24 ANTIBODY 1 μg/ml
----△---- MOUSE ANTI-HM 1.24 ANTIBODY 0.1 μg/ml
----◇---- MOUSE ANTI-HM 1.24 ANTIBODY 0.01 μg/ml
----◊---- CONTROL MOUSE IgG2a 1 μg/ml

—●— RESHAPED HUMAN ANTI-HM 1.24 ANTIBODY 1 μg/ml
—▲— RESHAPED HUMAN ANTI-HM 1.24 ANTIBODY 0.1 μg/ml
—◆— RESHAPED HUMAN ANTI-HM 1.24 ANTIBODY 0.01 μg/ml
—■— RESHAPED HUMAN ANTI-HM 1.24 ANTIBODY 0.001 μg/ml
---○--- CONTROL HUMAN IgG1 1 μg/ml

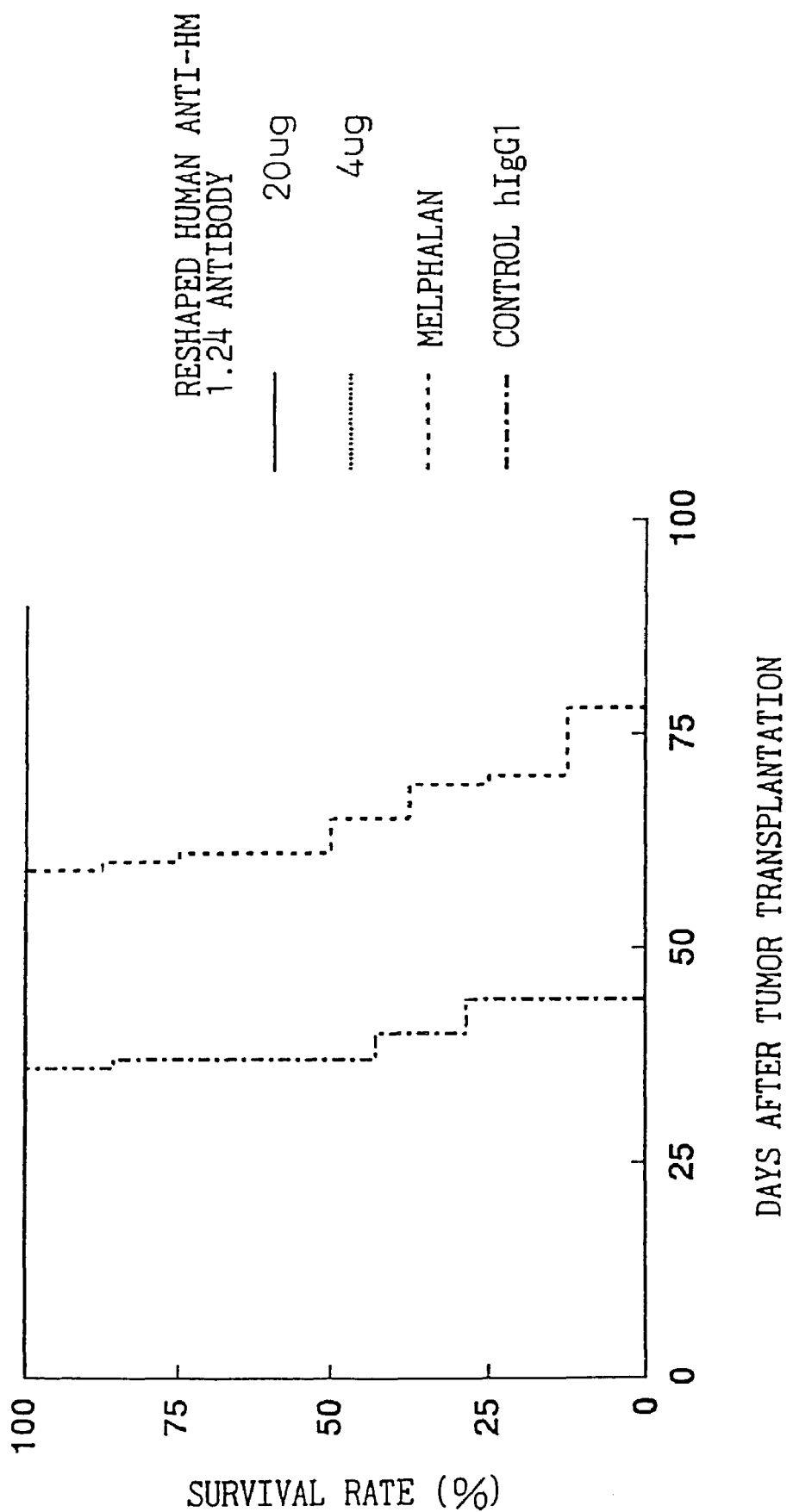

RESHAPED HUMAN ANTI-HM 1.24 ANTIBODY

RELATED APPLICATIONS

This application is a divisional of U.S. patent application Ser. No. 09/269,921, filed Apr. 1, 1999, which issued as U.S. Pat. No. 6,699,974, on Mar. 2, 2004, which was a national phase application claiming benefit of priority under 35 U.S.C. §371 to Patent Convention Treaty (PCT) International Application Serial No: PCT/JP97/03553, filed Oct. 3, 1997, and published as WO 98/14580, on Apr. 9, 1998, which claims benefit of priority to JP 8-264756, filed on Oct. 4, 1996. The aforementioned applications are explicitly incorporated herein by reference in their entirety and for all purposes.

FIELD OF THE INVENTION

The present invention relates to reshaped human anti-HM 1.24 antibodies and chimeric anti-HM 1.24 antibodies, genes encoding them, methods for producing said antibodies, and the use of said antibodies. The reshaped human antibodies and the chimeric antibodies of the present invention are useful as a therapeutic agent, etc. for myeloma.

BACKGROUND ART

Human B cells go through a variety of processes that are classified based on the kind of surface antigens being expressed, and finally mature into antibody-producing plasma cells. At the final stage of their differentiation, B cells, on one hand, acquire the ability of producing cytoplasmic immunoglobulins and, on the other, B cell-associated antigens such as cell surface immunoglobulins, HLA-DR, CD20, Fc receptors, complement C3 receptors and the like disappear (Ling, N. R. et al., Leucocyte Typing III (1986) p320, Oxford, UK, Oxford).

So far, there have been reports on monoclonal antiboies such as anti-PCA-1 (Anderson, K. C. et al., J. Immunol. (1983) 130, 1132), anti-PC-1 (Anderson, K. C. et al., J. Immunol. (1983) 132, 3172), anti-MM4 (Tong, A. W. et al., Blood (1987) 69, 238) and the like that recognize antigens on the cell membrane of the plasma cells. However, anti-CD38 monoclonal antibody is still being used for detection of plasma cells and myeloma cells (Epstein, J. et al., N. Engl. J. Med. (1990) 322, 664, Terstappen, L. W. M. M. et al., Blood (1990) 76, 1739, Leo, R. et al., Ann. Hematol. (1992) 64, 132, Shimazaki, C. et al., Am J. Hematol. (1992) 39, 159, Hata, H. et al., Blood (1993) 81, 3357, Harada, H. et al., Blood (1993) 81, 2658, Billadeau, D. et al., J. Exp. Med. (1993) 178, 1023).

However, anti-CD38 monoclonal antibody is an antigen associated with activation of T cells rather than an antigen associated with differentiation of B cells, and is expressed on various cells in addition to B cells. Furthermore, although CD38 is not expressed on some of the lymphoplasmacytoid, it is strongly expressed on the hemopoietic precursor cells. For these reasons, it is believed that anti-CD38 monoclonal antibody is not suitable for research on differentiation and maturation of human B cells or for treatment of diseases of plasma cells.

Goto, T. et al. have reported mouse anti-HM 1.24 monoclonal antibody that recognizes an antigen having a molecular weight of 29 to 33 kDa which is specifically expressed on B cell lines (Blood (1994) 84, 1922-1930). From the fact that the antigen recognized by anti-HM 1.24 monoclonal antibody is believed to be associated with the terminal differentiation of B cells (Goto, T. et al., Jpn. J. Clin. Immun. (1992) 16, 688-691) and that the administration of anti-HM 1.24 monoclonal antibody to a plasmacytoma-transplanted mouse resulted in specific accumulation of the antibody at the tumor (Shuji Ozaki et al., The Program of General Assembly of the 19th Japan Myeloma Study Meeting, general presentation 3), it has been suggested that anti-HM 1.24 monoclonal antibody, by labelling with a radioisotope, may be used for diagnosis of tumor localization, the missile therapy such as radioimmunotherapy, and the like.

Furthermore, the above-mentioned Blood describes that the anti-HM 1.24 monoclonal antibody has the complement-dependent cytotoxicity activity to the human myeloma cell line RPMI8226.

Myeloma is a neoplastic disease characterized by the accumulation of monoclonal plasma cells (myeloma cells) in the bone marrow. Myeloma is a disease in which terminally differentiated B cells that produce and secrete immunoglobulins, or plasma cells, are monoclonally increased mainly in the bone marrow, and accordingly monoclonal immunoglobulins or the constituting components thereof, L chains or H chains, are detected in the serum (Masaaki Kosaka et al., Nippon Rinsho (1995) 53, 91-99).

Conventionally chemotherapeutic agents have been used for treatment of myeloma, but there have been found no effective therapeutic agents that can lead to remission of myeloma and elongation of the survival period of patients with myeloma. There is, therefore, a long-awaited need for the advent of drugs that have a therapeutic effect on myeloma.

Mouse monoclonal antiboies have high immunogenicity (sometimes referred to as "antigenicity") in humans. Accordingly, the medical therapeutic value of mouse monoclonal antibodies in humans is limited. For example, a mouse antibody administered into a human may be metabolized as a foreign substance so that the half life of the mouse antibody in the human is relatively short and thereby it cannot fully exhibit its expected effects. Furthermore, human anti-mouse antibodies that are raised against the administered mouse antibody may trigger immunological responses that are unfavorable and dangerous to the patients, such as serum disease, other allergic reactions, or the like. Therefore, mouse monoclonal antibody cannot be frequently administered into humans.

In order to resolve these problems, a method was developed for reducing the immunogenicity of non-human-derived antibodies such as mouse-derived monoclonal antibodies. As one such example, there is a method of producing a chimeric antibody in which the variable region (V region) of the antibody is derived from the original mouse and the constant region (C region) thereof is derived from an appropriate human antibody.

Since the chimeric antibody thus obtained contains the variable region of the original mouse antibody in the intact form, it is expected to bind to the antigen with a specificity identical to that of the original mouse antibody. Furthermore, in a chimeric antibody the ratio of the amino acid sequences derived from non-humans is substantially reduced, and so the antibody is expected to have a low immunogenicity compared to the original mouse antibody. A chimeric antibody may bind to the antigen in an equal manner to the original mouse monoclonal antibody, and may include immunological responses against the mouse variable region though the immunogenicity is reduced (LoBuglio, A. F. et al., Proc. Natl. Acad. Sci. USA, 86, 4220-4224, 1989).

The second method for reducing the immunogenicity of mouse antibody, though much more complicated, can reduce the potential immunogenicity of mouse antibody further greatly. In this method, only the complementarity determining region (CDR) of the variable region of a mouse antibody is grafted to the variable region of a human antibody to prepare a "reshaped" human antibody variable region.

However, In order to make the structure of the CDR of a reshaped human antibody variable region as much close as possible to that of the original mouse antibody, if necessary, part of the amino acid sequence of the framework region (FR) that supports the CDR may be grafted from the variable region of the mouse antibody to the variable region of the human antibody. Subsequently, this V region of the humanized reshaped human antibody is linked to the constant region of a human antibody. The part that is derived from the non-human amino acid sequence in the finally reshaped humanized antibody is the CDR, and only part of the FR. A CDR is composed of hypervariable amino acid sequences which do not exhibit species-specific sequences. Therefore, the humanized antibody carrying the mouse CDR should not have an immunogenicity stronger than the natural human antibody having the human antibody CDR.

For the humanized antibody, see Riechmann, L. et al., Nature, 332, 323-327, 1988; Verhoeye, M. et al., Science, 239, 1534-1536, 1988; Kettleborough, C. A. et al., Protein Engng., 4, 773-783, 1991; Meada, H. et al.; Human Antibodies and Hybridoma, 2, 124-134, 1991; Groman, S. D. et al., Proc. Natl. Acad. Sci. USA, 88, 4181-4185, 1991; Tempest, P. R. et al., Bio/Technology, 9, 266-271; 1991; Co, M. S. et al., Proc. Natl. Acad. Sci. USA, 88, 2869-2873, 1991; Carter, P. et al., Proc. Natl. Acad. Sci. USA, 89, 4285-4289, 1992; Co, M. S. et al., J. Immunol., 148, 1149-1154, 1992; and Sato, K. et al, Cancer Res., 53, 851-856, 1993.

Queen et al. (International Application Publication No. WO 90-07861) describes a method for producing a humanized antibody of an anti-IL-2 receptor antibody Anti-Tac. However, it is difficult to completely humanize all antibodies even following the method as set forth in WO 90-07861. Thus, WO 90-07861 does not describe a general method for humanizing of antibodies, but merely describes a method for humanizing of Anti-Tac antibody which is one of anti-IL-2 receptor antibodies. Furthermore, even when the method of WO 90-07861 is completely followed, it is difficult to make a humanized antibody that has an activity completely identical to the original mouse antibody.

In general, the amino acid sequences of CDR/FR of individual antibodies are different. Accordingly, the determination of the amino acid residue to be replaced for the construction of a humanized antibody and the selection of the amino acid residue that replaces said amino acid residue vary with individual antibodies. Therefore, the method for preparing humanized antibodies as set forth in WO 90-07861 cannot be applied to humanization of all antibodies.

Queen et al. Proc. Natl. Acad. Sci. USA, (1989) 86, 10029-10033 has a similar disclosure to that of WO 90-07861. This reference describes that only one third of the activity of the original mouse antibody was obtained for a humanized antibody produced according to the method as set forth in WO 90-07861. In other words, this shows that the method of WO 90-07861 itself cannot produce a complete humanized antibody that has an activity equal to that of the original mouse antibody Co et al., Cancer Research (1996) 56, 1118-1125 was published by the group of the above-mentioned Queen et al. This reference describes that a humanized antibody having an activity equal to that of the original mouse antibody could not be constructed even by the method for making humanized antibody as set forth in WO 90-07861. Thus, the fact not only reveals that the method of WO 90-07861 itself cannot produce a complete humanized antibody having an activity equal to the original mouse antibody, but that the method for constructing humanized antibody as set forth in WO 90-07861 cannot be applied to humanization of all antibodies.

Ohtomo et al., Molecular Immunology (1995) 32, 407-416 describes humanization of mouse ONS-M21 antibody. This reference reveals that the amino acid residue which was suggested for humanization of the Anti-Tac antibody in WO 90-07861 has no relation with the activity and the method as set forth in WO 90-07861 cannot be applied.

Kettleborough et al, Protein Eng. (1991) 4, 773-783 discloses that several humanized antibodies were constructed from mouse antibody by substituting amino acid residues. However, the substitution of more amino acid residues than were suggested in the method of humanization of the Anti-Tac antibody as described in WO 90-07861 was required.

The foregoing references indicate that the method of producing humanized antibodies as set forth in WO 90-07861 is a technique applicable only to the Anti-Tac antibody described therein and that even the use of said technology does not lead to the activity equal to that of the original mouse antibody.

The original mouse antibodies described in these references have different amino acid sequences from that of the Anti-Tac antibody described in WO 90-07861. Accordingly, the method of constructing humanized antibody which was able to be applied to the Anti-Tac antibody could not be applied to other antibodies. Similarly, since the mouse anti-HM 1.24 antibody of the present invention has an amino acid sequence different from that of the Anti-Tac antibody, the method of constructing humanized antibody for the Anti-Tac antibody cannot be applied. Furthermore, the successfully constructed humanized antibody of the present invention has an amino acid sequence different from that of the humanized Anti-Tac antibody described in WO 90-07861. This fact also indicates that the same method cannot be applied for humanization of antibodies having different CDR-FR sequences.

Thus, even if the original mouse antibody for humanization is known, the identity of the CDR-FR sequence of a humanized antibody having an activity is confirmed only after trial and error experiments. WO 90-07861 makes no mention of the FR sequence which is combined in the humanized antibody constructed in the present invention and of the fact that an active humanized antibody could be obtained from the combination with FR, much less the sequence of the CDR.

As hereinabove mentioned, humanized antibodies are expected to be useful for therapeutic purposes, but humanized anti-HM 1.24 antibody is not known or not even suggested. Furthermore, there is no standardized method available that could be generally applied to any antibody for production of a humanized antibody, and a variety of contrivances are needed for constructing a humanized antibody that exhibits sufficient binding activity, binding inhibition activity, and neutralizing activity (for example, Sato, K. et al., Cancer Res., 53, 851-856, 1993).

DISCLOSURE OF THE INVENTION

The present invention provides reshaped antibodies of anti-HM 1.24 antibody. The present invention further provides human/mouse chimeric antibodies that are useful in the process of constructing said reshaped antibodies. The present invention further provides fragments of the reshaped antibodies. Furthermore, the present invention provides an expression system for production of chimeric antibodies, reshaped antibodies and the fragments thereof. The present invention further provides methods for producing chimeric antibodies of anti-HM 1.24 antibody and fragments thereof, as well as reshaped antibodies of anti-HM 1.24 antibody and fragments thereof.

More specifically, the present invention provides chimeric antibodies and reshaped antibodies that specifically recognize a polypeptide having the amino acid sequence as set forth in SEQ ID NO: 103. cDNA that encodes said polypeptide has been inserted between the XbaI cleavage sites of pUC19 vector, and thereby been prepared as plasmid pRS38-pUC19. *Escherichia coli* that contains this plasmid pRS38-pUC19 has been internationally deposited on Oct. 5, 1993, with the National Institute of Bioscience and Human-Technology, Agency of Industrial Science and Technology, MITI (Higashi 1-Chome 1-3, Tsukuba city, Ibalaki prefecture, Japan) as *Escherichia coli* DH5α (pRS38-pUC19) under the accession number FERM BP-4434 under the provisions of the Budapest Treaty (see Japanese Unexamined Patent Publication (Kokai) No. 7-196694).

As one embodiment of such chimeric antibodies or reshaped antibodies, there is mentioned a chimeric anti-HM 1.24 antibody or a reshaped human anti-HM 1.24 antibody. A detailed description of a chimeric anti-HM 1.24 antibody or a reshaped human anti-HM 1.24 antibody will be given hereinbelow.

Thus, the present invention also provides chimeric L chains comprising the constant region (C region) of a human light (L) chain and the variable (V) region of the L chain of an anti-HM 1.24 antibody, and a chimeric H chain comprising the constant region of a human heavy (H) chain and the V region of anti-HM 1.24 antibody heavy (H) chain.

The present invention further provides chimeric antibodies comprising:

(1) an L chain comprising the C region of a human L chain and the V region of the L chain of an anti-HM 1.24 antibody; and (2) an H chain comprising the C region of a human-H chain and the V region of the H chain of an anti-HM 1.24 antibody.

The present invention further provides the V region of the reshaped human L chain of anti-HM 1.24 antibody comprising:

(1) the framework region (FR) of the V region of a human L chain, and (2) the CDR of the V region of the L chain of an anti-HM 1.24 antibody; and the V region of the reshaped human H chain of anti-HM 1.24 antibody comprising (1) the FR of the V region of a human H chain, and (2) the CDR of the V region of the H chain of an anti-HM 1.24 antibody.

The present invention further provides the reshaped human L chain of anti-HM 1.24 antibody comprising (1) the C region of a human L chain, and (2) the V region of an L chain comprising the FR of a human L chain and the CDR of the L chain of an anti-HM 1.24 antibody; and the reshaped human H chain of anti-HM 1.24 antibody comprising (1) the C region of a human H chain, and (2) the V region of an H chain comprising the FR of a human H chain and the CDR of the H chain of an anti-HM 1.24 antibody.

The present invention further provides the reshaped human antibody of anti-HM 1.24 antibody comprising:

(A) an L chain comprising (1) the C region of a human L chain, and (2) the V region of an L chain comprising the FR of a human L chain and the CDR of the L chain of an anti-HM 1.24 antibody; and (B) an H chain comprising (1) the C region of a human H chain, and (2) the V region of an H chain comprising the FR of a human H chain and the CDR of the H chain of an anti-HM 1.24 antibody.

The present invention further provides DNA encoding the V region of the L chain of an anti-HM 1.24 antibody, and DNA encoding the V region of the H chain of an anti-HM 1.24 antibody.

The present invention further provides

DNA encoding a chimeric L chain comprising (1) the C region of a human L chain; and (2) the V region of the L chain of an anti-HM 1.24 antibody, and DNA encoding a chimeric H chain comprising (1) the C region of a human H chain; and (2) the V region of the H chain of an anti-HM 1.24 antibody.

The present invention further provides

DNA encoding the V region of the reshaped human L chain of anti-HM 1.24 antibody comprising:

(1) the FR of the V region of a human L chain; and (2) the CDR of the V region of the L chain of an anti-HM 1.24 antibody; and DNA encoding the V region of the reshaped human H chain of anti-HM 1.24 antibody comprising:

(1) the FR of the V region of a human H chain; and (2) the CDR of the V region of the H chain of an anti-HM 1.24 antibody.

The present invention further provides

DNA encoding the reshaped human L chain of an anti-HM 1.24 antibody comprising:

(1) the C region of a human L chain; and (2) the V region of an L chain comprising the FR of a human L chain and the CDR of the L chain of an anti-HM 1.24 antibody; and DNA encoding the reshaped human H chain of an anti-HM 1.24 antibody comprising:

(1) the C region of a human H chain; and (2) the V region of an H chain comprising the FR of a human H chain and the CDR of the H chain of an anti-HM 1.24 antibody.

The present invention further provides a vector comprising any of the various DNAs mentioned above.

The present invention further provides a host cell transformed with the above vector.

The present invention also provides methods for producing the chimeric antibody of an anti-HM 1.24 antibody comprising the steps of culturing a host cell which was cotransformed with an expression vector comprising DNA encoding said chimeric L chain and an expression vector comprising DNA encoding said H chain, and of recovering the desired antibody.

The present invention further provides methods for producing the reshaped human antibody of an anti-HM 1.24 antibody comprising the steps of culturing a host cell which was cotransformed with an expression vector comprising DNA encoding said reshaped human L chain and an expression vector comprising DNA encoding said reshaped human H chain, and of recovering the desired antibody.

The present invention further provides pharmaceutical compositions, especially therapeutic agents for myeloma, comprising said chimeric antibody or the reshaped human antibody.

The present invention further provides pharmaceutical compositions which contain as an active ingredient a chimeric antibody specifically recognizing a polypeptide having the amino acid sequence as set forth in SEQ ID NO: 103, and pharmaceutical compositions which contain as an active ingredient a reshaped human antibody specifically recognizing a polypeptide having the amino acid sequence as set forth in SEQ ID NO: 103. As a pharmaceutical composition, there is specifically provided a therapeutic agent for myeloma.

BRIEF EXPLANATION OF THE DRAWINGS

FIG. 6 is a diagramatic representation of a method for constructing the V region of the H chain of a human mouse hybrid anti-HM 1.24 antibody by the PCR method.

FIG. 7 is a diagramatic representation of a method for constructing the V region of the H chain of a mouse human hybrid anti-HM 1.24 antibody by the PCR method.

FIG. 40 is a graph showing that in a human myeloma cells-transplanted mouse the administration of a reshaped human anti-HM 1.24 antibody causes prolongation of the survival period as compared to the administration of melphalan or the control human IgG1.

MODE FOR CARRYING OUT THE INVENTION

Figure 1:
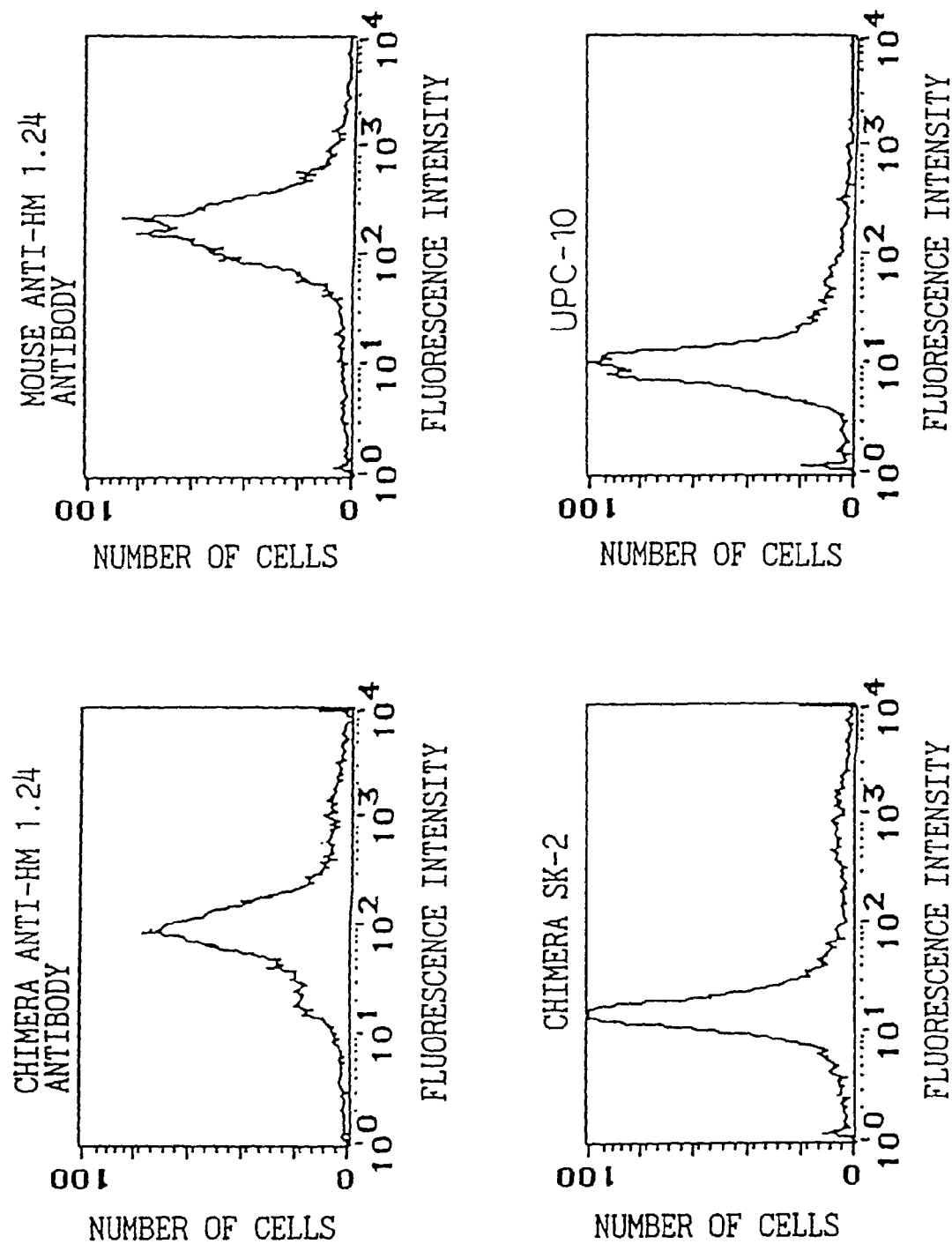
FIG. 1 is a graph showing that, in the FCM analysis using the human myeloma cell line KPMM2, the fluorescence intensity of a chimeric anti-HM 1.24 antibody is shifted in a similar manner to that of a mouse anti-HM 1.24 antibody as compared to the control antibody.

1. Construction of a Chimeric Antibody (1) Cloning of DNA Encoding the V Region of a Mouse Anti-HM 1.24 Monoclonal Antibody Preparation of mRNA In order to clone DNA encoding the V region of a mouse anti-HM 1.24 monoclonal antibody, the total RNA is prepared from a recovered hybridoma using a known method such as a guanidine-ultracentrifuge method (Chirgwin, J. M. et al., Biochemistry (1979), 18, 5294-5299), the AGPC method (Chomczynski, P. et al. (1987), 162, 156-159), etc. and mRNA is prepared using the Oligo(dT)-cellulose spun column etc. attached with the mRNA Purification Kit (manufactured by Pharmacia), etc. Furthermore, by using the QuickPrep mRNA Purification Kit (manufactured by Pharmacia) mRNA can be prepared without the extraction step of the total RNA.

Preparation and Amplification of cDNA

From the mRNA obtained in the above-mentioned Preparation of mRNA, each cDNA for the V regions of an L chain and an H chain is synthesized using a reverse transcriptase. The cDNA of the V region of the L chain is synthesized using the AMV Reverse Transcriptase First-Strand cDNA Synthesis Kit. For the amplification of the synthesized cDNA, an appropriate primer that hybridizes with the leader sequence and the C region of the antibody gene (for example, the MKV primer having the base sequences represented by the SEQ ID NO: 29 to 39, and the MKC primer having the base sequence represented by the SEQ ID NO: 40).

The synthesis and amplification of the cDNA of the v region of an H chain can be carried out by PCR (polymerase chain reaction) by the 5'-RACE method (Frohman, M. A. et al., Proc. Natl. Acad. Sci. USA, 85, 8998-9002, 1988, Belyavsky, A. et al., Nucleic Acids Res. 17, 2919-2932, 1989) using the 5'-Ampli FINDER RACE kit (CLONTECH). To the 5'-end of the cDNA synthesized as above, the Ampli FINDER Anchor is ligated, and as a primer for amplification of the V region of the H chain, a primer that specifically hybridizes with the Anchor primer (SEQ ID NO: 77) and the constant region (Cγ region) of a mouse H chain (for example, the MHC2a primer having the base sequence represented by SEQ ID NO: 42) can be used.

Purification of DNA and the Determination of the Base Sequence Thereof

An agarose gel electrophoresis is conducted on the PCR product using a known method to excise the desired DNA fragment, and DNA is recovered and purified therefrom, which is then ligated to a vector DNA.

DNA can be purified using a commercial kit (for example, GENECLEAN II; BIO101). A known vector DNA (for example, pUC19, Bluescript, etc.) can be used to retain DNA fragments.

The above DNA and the above DNA vector are ligated using a known ligation kit (manufactured by Takara Shuzo) to obtain a recombinant vector. The obtained recombinant vector is then introduced into *Escherichia coli* JM109, after which ampicillin resistant colonies are selected and a vector DNA is prepared based on a known method (J. Sambrook, et al., "Molecular Cloning", Cold Spring Harbor Laboratory Press, 1989). After digesting the above vector DNA with restriction enzymes, the base sequence of the desired DNA is determined by a known method (for example, the dideoxy method) (J. Sambrook, et al., "Molecular Cloning", Cold Spring Harbor Laboratory Press, 1989). In accordance with the present invention, an automatic sequencing system (DNA Sequencer 373A; manufactured by ABI Co. Ltd.) can be used.

Complementarity Determining Region

The V region of an H chain and the V region of an L chain form an antigen binding site, of which overall structures have similar properties. Thus, each of four framework regions (FR) has been ligated by three hypervariable regions, i.e. complementarity determining regions (CDRs). The amino acid sequences of FRs have been relatively well conserved whereas variation is extremely high among the amino acid sequences of CDR regions (Kabat, E. A. et al., "Sequence of Proteins of Immunological Interest", US Dept. Health and Human Services, 1983).

Many portions of the above four FRs take the β-sheet structure with a result that three CDRs form loops. CDRs may sometimes form part of the β-sheet structure. The three CDRs are retained sterically in close proximity with one another and form an antigen binding site with three CDRs of the pairing region.

Based on these facts, the amino acid sequence of the variable region of a mouse anti-HM 1.24 antibody is fitted to the data base of the amino acid sequences of antibodies prepared by Kabat et al. ("Sequence of Proteins of Immunological Interest", US Dept. Health and Human Services, 1983) to investigate homology and thereby to find CDR regions.

(2) Construction of Expression Vectors for a Chimeric Antibody

Once a DNA fragment encoding the V regions of the mouse L chain and H chain of a mouse monoclonal antibody is cloned, a chimeric anti-HM 1.24 antibody can be obtained by linking these mouse V regions to a DNA encoding the constant region of a human antibody and then by expressing them.

A basic method for constructing a chimeric antibody comprises linking the mouse leader sequence and the V region sequence present in the cloned cDNA to a sequence encoding the C region of a human antibody already present in an expression vector for mammalian cells. Alternatively it comprises linking the mouse leader sequence and the V region sequence present in the cloned cDNA to a sequence encoding the C region of a human antibody, which is then linked to an expression vector for mammalian cells.

The C region of a human antibody can be the C region of any H chain and the C region of any L chain. There can be mentioned, for example, Cγ1, Cγ2, Cγ3, or Cγ4 of a human H chain, or Cλ or Cκ of an L chain.

For production of a chimeric antibody two kinds of expression vectors are constructed: they are an expression vector comprising DNA encoding the V region of a mouse L chain and the C region of a human L chain under the control of an expression regulatory region such as the enhancer/promoter system, and an expression vector comprising DNA encoding the V region of a mouse H chain and the C region of a human H chain under the control of an expression regulatory region such as the enhancer/promoter system. Subsequently, using these expression vectors a host cell such as a mammalian cell is cotransformed, and the transformed cells are cultured in vitro or in vivo to produce a chimeric antibody (for example, WO 91-16928).

Alternatively, DNA encoding the mouse leader sequence and the V region of an L chain and the C region of a human L chain and DNA encoding the mouse leader sequence and the V region of an H chain and the C region of a human H chain present in the cloned cDNA are introduced into a single expression vector (see, International Application Publication No. WO 94-11523), and a host cell is transformed using said vector. The transformed host is then cultured in vitro or in vivo to produce the desired chimeric antibody.

1) Construction of a Chimeric H Chain

An expression vector for the H chain of the chimeric antibody can be obtained by introducing cDNA encoding the V region of a mouse H chain into an appropriate expression vector containing genomic DNA or cDNA encoding the C region of the H chain of a human antibody. As the C region of an H chain there can be mentioned, for example, Cγ1, Cγ2, Cγ3, or Cγ4.

Construction of an Expression Vector for a Chimeric H Chain Containing Cγ1 Genomic DNA As an expression vector having genomic DNA for Cγ1 as the C region of an H chain, there can be used, for example HFE-PMh-gγ1 (International Application Publication No. WO 92/19759) or DHFR-ΔE-RVh-PM1f (International Application Publication No. WO 92/19759).

In order to insert cDNA encoding the V region of a mouse H chain into these expression vectors, suitable base sequences may be introduced using the PCR method. These suitable base sequences can be introduced by the PCR method using a PCR primer designed to have a recognition sequence for a suitable restriction enzyme at the 5'-end and a Kozak consensus sequence immediately before the start codon, and a PCR primer designed to have at the 3'-end a recognition sequence for a suitable restriction enzyme and a splice donor site where a primary transcript of genomic DNA is properly spliced to become an mRNA.

The cDNA thus constructed encoding the V region of a mouse H chain is treated with suitable restriction enzymes, inserted into the above-mentioned expression vector, and a chimeric H chain-expression vector comprising the Cγ1 DNA can be constructed.

Construction of an Expression Vector for the cDNA Chimeric H Chain

An expression vector having the cDNA of Cγ1 as the C region of an H chain may be constructed as follows. Thus, it can be constructed by preparing mRNA from a CHO cell in which the expression vector DHFR-ΔE-RVh-PM1f (International Application Publication No. WO 92/19759) encoding genomic DNA of the V region of the H chain of a humanized PM1 antibody and the C region Cγ1 of the H chain of a human antibody (N. Takahashi, et al., Cell 29, 671-679, 1982) and the expression vector RV1-PM1a (International Application Publication No. WO 92/19759) encoding genomic DNA of the V region of the L chain of a humanized PM1 antibody and the C region of the κ chain of a human antibody L chain have been integrated; cloning cDNA comprising the V region of the H chain of the humanized PM1 antibody and the C region Cγ1 of the H chain of the human antibody by the RT-PCR method, and; ligating to a suitable expression vector for animal cells using suitable restriction enzyme sites.

In order to directly ligate cDNA encoding the V region of a mouse H chain to cDNA containing the C region Cγ1 of the H chain of a human antibody, suitable base sequences can be introduced by the PCR method. For example, these suitable base sequences can be introduced by the PCR method using a PCR primer designed to have a recognition sequence for a suitable restriction enzyme at the 5'-end and a Kozak consensus sequence immediately before the start codon, and a PCR primer designed to have a recognition sequence for a suitable restriction enzyme used for direct ligation of the C region Cγ1 of an H chain at the 3'-end.

An expression vector containing a cDNA chimeric H chain can be constructed by treating the cDNA thus constructed encoding the V region of a mouse H chain with a suitable restriction enzyme, ligating to the above-mentioned cDNA containing the C region Cγ1 of the H chain, and inserting to an expression vector such as pCOS1 or pCHO1.

2) Construction of the L Chain of a Chimeric Antibody

An expression vector for the L chain of a chimeric antibody may be obtained by linking cDNA encoding the V region of a mouse L chain to genomic DNA or cDNA encoding the C region of the L chain of a human antibody, and then introducing it into a suitable expression vector. As the C region of an L chain there can be mentioned, for example a κ chain or a λ chain.

Construction of an expression vector for the κ chain of a cDNA chimeric L chain

In order to construct an expression vector containing cDNA encoding the V region of a mouse L chain, suitable base sequences can be introduced using the PCR method. For example, these suitable base sequences can be introduced by the PCR method using a PCR primer designed to have a recognition sequence for a suitable restriction enzyme and a Kozak consensus sequence at the 5'-end, and a PCR primer designed to have a recognition sequence for a suitable restriction enzyme at the 3'-end.

The κ chain C region of a human L chain for linking to the V region of a mouse L chain can be constructed from, for example HEF-PM1k-gk (see International Application Publication No. WO 92/19759) containing genomic DNA. An expression vector for the κ chain of the L chain of a cDNA chimeric antibody can be constructed by introducing recognition sequences of suitable restriction enzymes at the 5'-end or 3'-end of DNA encoding the κ chain C region of L chain by the PCR method, ligating the thus constructed V region of the mouse L chain to the κ chain C region of L chain, and then inserting into an expression vector such as pCOS1 or pCHO1.

2. Construction of a Reshaped Human Antibody (1) Designing of the V Region of a Reshaped Human Anti-HM 1.24 Antibody In order to construct a reshaped human antibody in which the CDR of a mouse monoclonal antibody has been grafted to a human antibody, it is desirable that there is a high homology between the FR of the mouse monoclonal antibody and the FR of the human antibody. Thus, the V regions of the L chain and the H chain of the mouse anti-HM 1.24 antibody are compared to the V regions of all known antibodies of which structures have been elucidated, using the Protein Data Bank.

The V region of the L chain of a mouse anti-HM 1.24 antibody is most similar to the consensus sequence of the subgroup IV of the V region of the L chain of a human antibody (HSGIV) with a homology of 66.4%. On the other hand, it shows a homology of 56.9%, 55.8%, and 61.5% with HSGI, HSGII, and HSGIII, respectively.

The V region of L chain of a mouse anti-HM 1.24 antibody, when compared to the V region of the L chain of known human antibodies, shows a homology of 67.0% with the V region of the L chain of the human antibody REI, one of subgroup I of the V region of the L chain of the human antibody. Therefore, the FR of the REI was used as the starting material for construction of the V region of the L chain of the reshaped human anti-HM 1.24 antibody.

Version a of the V region of the L chain of the reshaped human anti-HM 1.24 antibody was designed. In this version, the FR of the human antibody was made identical with the REI-based FR present in the reshaped human CAMPATH-1H antibody (see Riechmann, L. et al., Nature 322, 21-25, (1988), the FR contained in version a of the V region of the L chain of a reshaped human PM-1 antibody described in International Application Publication No. WO 92-19759), and the mouse CDR was made identical with the CDR in the V region of the L chain of the mouse anti-HM 1.24 antibody.

The V region of the H chain of a mouse anti-HM 1.24 antibody is most similar to the consensus sequence of the V region of the H chain of a human antibody (HSGI) with a homology of 54.7%. On the other hand, it shows a homology of 34.6% and 48.1% with HSGII and HSGIII, respectively.

When the V region of the H chain of a mouse anti-HM 1.24 antibody is compared to the V region of the H chain of known human antibodies, FR1 to FR3 were most similar to the V region of the H chain of the human antibody HG3, one of subgroup I of the V region of a human H chain (Rechavi, G. et al., Proc. Natl. Acad. Sci. USA, 80, 855-859), with a homology of 67.3%.

Therefore, the FR of the human antibody HG3 was used as the starting material for construction of the V region of the H chain of a reshaped human anti-HM 1.24 antibody.

However, since the amino acid sequence of the FR4 of the human antibody HG3 has not been described, the amino acid sequence of the FR4 of the human antibody JH6 (Ravetch, J. V. et al., Cell, 27, 583-591) that shows the highest homology with the FR4 of a mouse anti-HM 1.24 antibody was used as FR4. The FR4 of JR6 has the same amino acid sequence as the FR4 of the H chain of a mouse anti-HM 1.24 antibody except only one amino acid.

In the first version a of the V region of the H chain of a reshaped human anti-HM 1.24 antibody, FR1 to FR3 were made identical with the FR1 to FR3 of the human antibody HG3, except that the amino acids at position 30 in the human FR1 and position 71 in the human FR3 were made identical with the amino acids of the mouse anti-HM 1.24 antibody, and the CDR was made identical with the CDR in the V region of the H chain of a mouse anti-HM 1.24 antibody.

Figure 4:
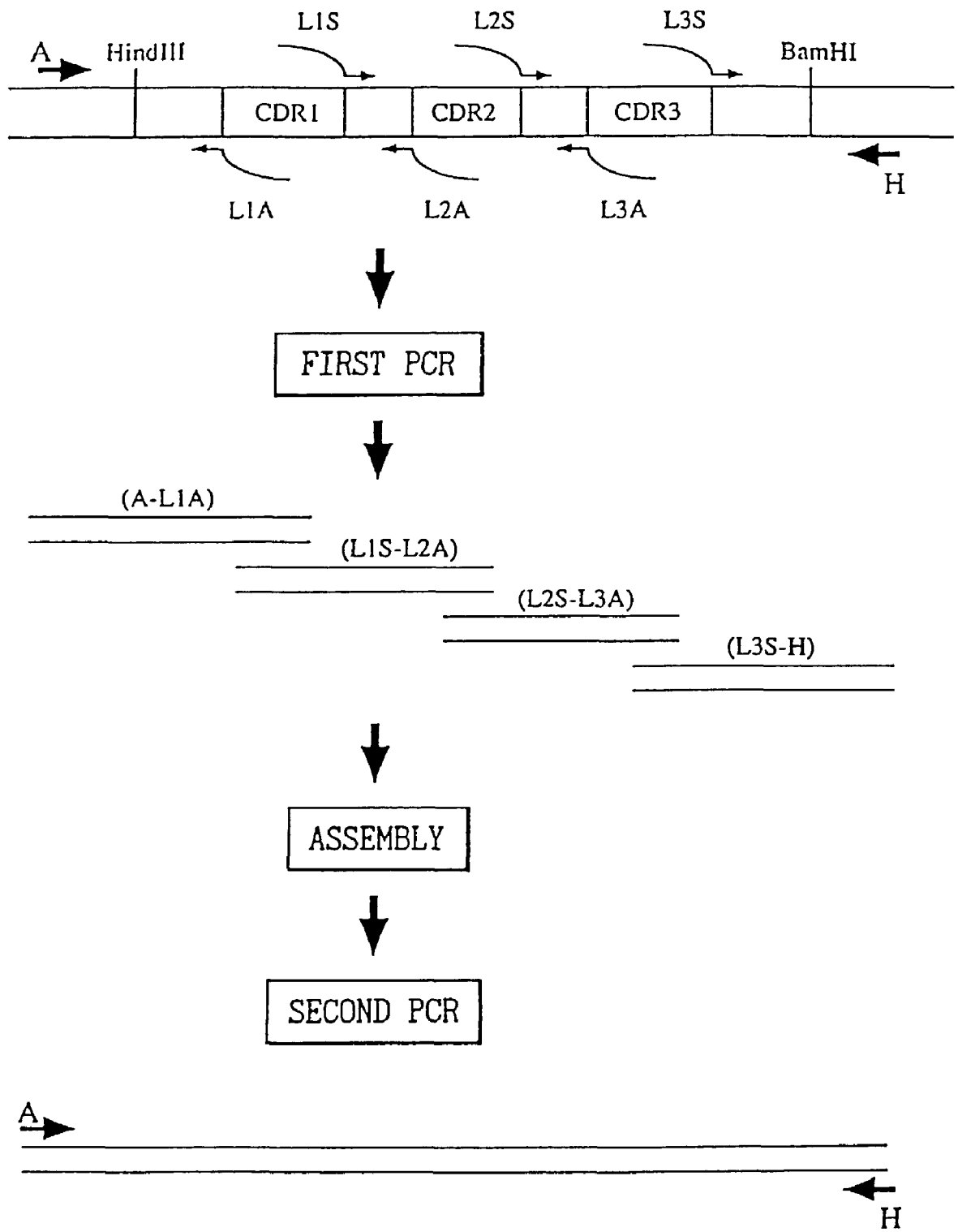
FIG. 4 is a diagramatic representation of a method for constructing the L chain of a reshaped human anti-HM 1.24 antibody by CDR grafting in the PCR method.

(2) Construction of the V Region of the L Chain of a Reshaped Human Anti-HM 1.24 Antibody The L chain of a reshaped human anti-HM 1.24 antibody is constructed by the CDR grafting in the PCR method. The method is schematically shown in FIG. 4. Eight PCR primers are used for construction of a reshaped human anti-HM 1.24 antibody (version a) having the FR derived from the human antibody REI. The external primers A (SEQ ID NO: 47) and H (SEQ ID NO: 48) are designed to hybridize with the DNA sequence of the HEF expression vector HEF-VL-gκ.

The CDR grafting primers L1S (SEQ ID NO: 49), L2S (SEQ ID NO: 50), and L3S (SEQ ID NO: 51) have a sense DNA sequence. The CDR grafting primers L1A (SEQ ID NO: 52), L2A (SEQ ID NO: 53), and L3A (SEQ ID NO: 54) have an antisense DNA sequence, each having a complementary DNA sequence (20 to 23 bp) to the DNA sequence at the 5'-end of the primers L1S, L2S, and L3S, respectively.

In the first stage of PCR, the four reactions A-L1A, L1S-L2A, L2S-L3A, and L3S-H are conducted and each PCR product purities. The four PCR products from the first PCR are allowed to assemble with one another by their own complementarity (see WO 92-19759). Then, the external primers A and H are added to amplify the full-length DNA encoding the V region of the L chain of a reshaped human anti-HM 1.24 antibody (the second PCR). In the above-mentioned PCR, the plasmid HEF-RVL-M21a (see International Application Publication No. WO 95-14041) encoding the version a of the V region of the L chain of a reshaped human ONS-M21 antibody based on the human antibody REI-derived FR can be employed as a template.

In the first stage of PCR, template DNA and each of primers were used.

PCR products A-L1A (215 bp), L1S-L2A (98 bp), L2S-L3A (140 bp), and L3S-H (151 bp) are purified using 1.5% low melting point agarose gel and are assembled in the second PCR. In the second PCR, each product from the first PCR and each external primer (A and H) are used.

A 516 bp DNA fragment resulting from the second PCR is purified using 1.5% low melting point agarose gel, digested with BamHI and HindIII, and the DNA fragments thus obtained are cloned into the HEF expression vector HEF-VL-gκ. After determining the DNA sequence, the plasmid containing the DNA fragment having the correct amino acid sequence of the V region of the L chain of a reshaped human anti-HM 1.24 antibody was termed the plasmid HEF-RVLa-AHM-gκ. The amino acid sequence and the base sequence of the V region of the L chain contained in this plasmid HEF-RVLa-AHM-gκ are shown in SEQ ID NO: 9.

The version b of the V region of the L chain of a reshaped human anti-HM 1.24 antibody can be constructed by mutagenesis using PCR. Mutagen primers FTY-1 (SEQ ID NO: 55) and FTY-2 (SEQ ID NO: 56) are so designed as to mutate phenylalanine at position 71 to tyrosine.

After the above primers are amplified using the plasmid HEF-RVLa-AHM-gκ as a template, the final product is purified. By digesting with BamHI and HindIII, the DNA fragments obtained are cloned into the HEF expression vector HEF-VL-gκ to obtain plasmid HEF-RVLb-AHM-gκ. The amino acid sequence and the base sequence of the V region of the L chain contained in this plasmid HEF-RVLb-AHM-gκ are shown in SEQ ID NO: 10.

(3) Construction of the V Region of the H Chain of a Reshaped Human Anti-HM 1.24 Antibody 3-1. Construction of Versions a to e of the V Region of the H Chain of a Reshaped Human Anti-HM 1.24 Antibody DNA encoding the V region of the H chain of a reshaped human anti-HM 1.24 antibody can be designed as follows. By linking the DNA sequence encoding the FRs 1 to 3 of the human antibody HG3 and the FR4 of the human antibody JH6 to the DNA sequence encoding the CDR of the V region of the H chain of a mouse anti-HM 1.24 antibody, a full length DNA encoding the V region of the H chain of a reshaped human anti-HM 1.24 antibody may be designed.

Then, the HindIII recognition site/KOZAK consensus sequence and the BamHI recognition site/splice donor sequence, respectively, are attached to the 5'-end and the 3'-end of this DNA sequence so as to allow insertion of the HEF expression vector.

The DNA sequence thus designed is divided into four oligonucleotides. Subsequently, oligonucleotides which potentially hinder the assembly of these oligonucleotides are subjected to computer analysis for the secondary structure.

Figure 5:
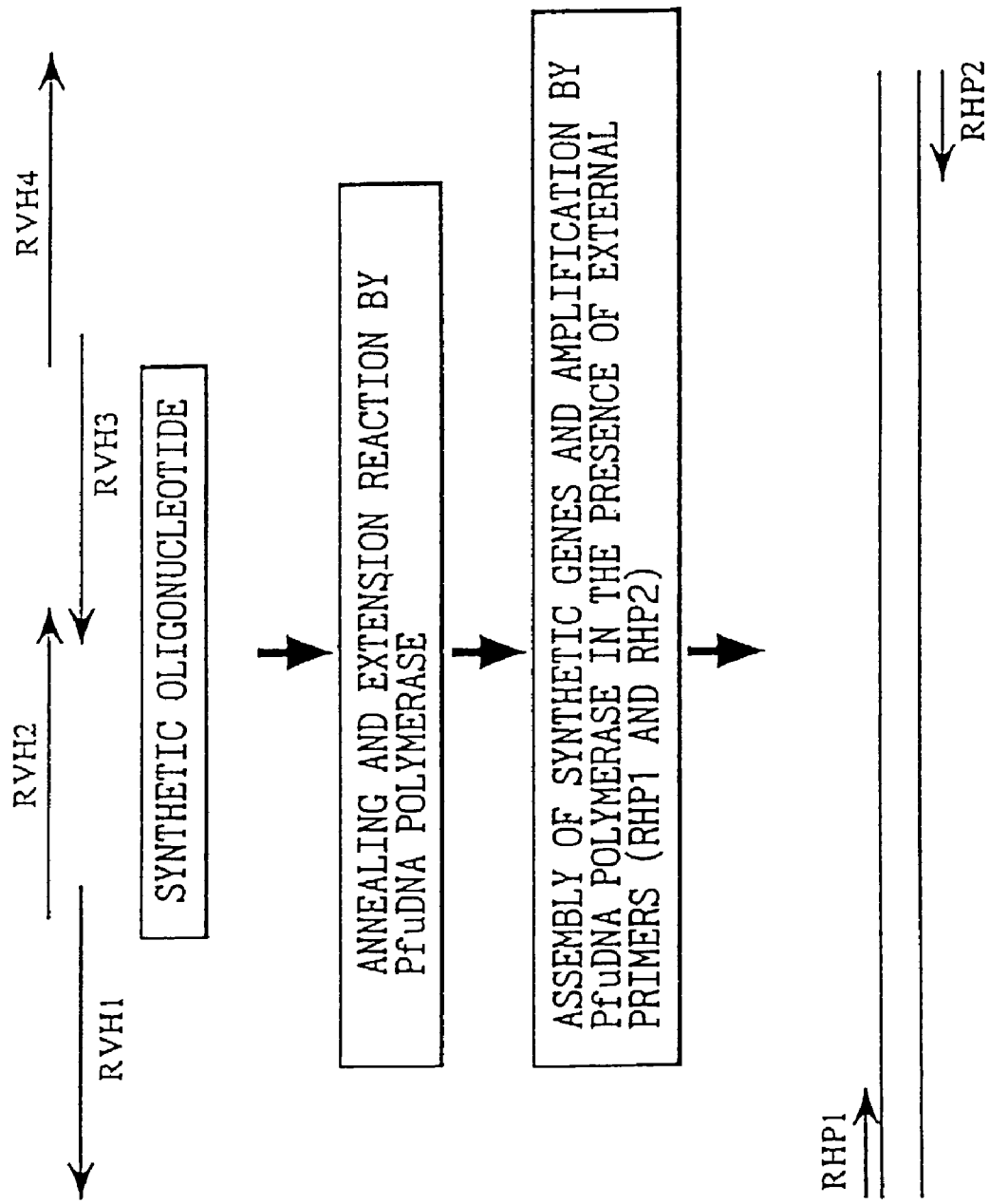
FIG. 5 is a diagramatic representation of a method for assemblying the oligonucleotides of RVH1, RVH2, RVH3, and RVH4 by the PCR method in the preparation of the H chain of the reshaped human anti-HM 1.24 antibody.

The sequences of the four oligonucleotides RVH1 to RVH4 are set forth in SEQ ID NO: 57 to 60. These oligonucleotides have a length of 119 to 144 bases and have a 25 to 26 bp overlapping region. Among the oligonucleotides, RVH2 (SEQ ID NO: 58) and RVH4 (SEQ ID NO: 60) have a sense DNA sequence, and RVH1 (SEQ ID NO: 57) and RVH3 (SEQ ID NO: 59) have an antisense DNA sequence. The method for assembling these four oligonucleotides by the PCR method is shown in the figure (see FIG. 5).

PCR is carried out using the four oligonucleotides and RHP1 (SEQ ID NO: 60) and RHP2 (SEQ ID NO: 62) as the external primers.

The amplified 438 bp DNA fragment is purified, digested with HindIII and BamHI, and then cloned into the HEF expression vector HEF-VH-gγ1. After determination of the base sequence, the plasmid that contains the DNA fragment encoding the correct amino acid sequence of the V region of the H chain was termed HEF-RVHa-AHM-gγ1. The amino acid sequence and the base sequence of the V region of the H chain contained in this plasmid HEF-RVHa-AHM-gγ1 are shown in SEQ ID NO: 11.

Each of versions b, c, d, and e of the V region of the H chain of a reshaped human anti-HM 1.24 antibody is constructed as follows. In constructing each of version b and after of the V region of the H chain of a reshaped human anti-HM 1.24 antibody, a three-dimensional structural model of the V region of a mouse anti-HM 1.24 antibody can be constructed in order to predict the position of the amino acid residue to be substituted in the antibody molecule.

Using as the mutagen primer BS (sequence 63) and BA (SEQ ID NO: 64) designed to mutate arginine at position 66 to lysine and as a template DNA the plasmid HEF-RVHa-AHM-gγ1 by the PCR method, version b is amplified to obtain plasmid HEF-RVHb-AHM-gγ1. The amino acid sequence and the base sequence of the V region of the H chain contained in this plasmid HEF-RVHb-AHM-gγ1 are shown in SEQ ID NO: 12.

Using as the mutagen primer CS (sequence 65) and CA (SEQ ID NO: 66) designed to mutate threonine at position 73 to lysine and as a template DNA the plasmid HEF-RVHa-AHM-gγ1 by the PCR method, version c is amplified to obtain plasmid HEF-RVHc-AHM-gγ1. The amino acid sequence and the base sequence of the V region of the H chain contained in this plasmid HEF-RVHc-AHM-gγ1 are shown in SEQ ID NO: 13.

Using as the mutagen primer DS (sequence 67) and DA (SEQ ID NO: 68) designed to mutate arginine at position 66 to lysine and threonine at position 73 to lysine and as a template DNA the plasmid HEF-RVHa-AHM-gγ1 by the PCR method, version d is amplified to obtain plasmid HEF-RVHd-AHM-gγ1. The amino acid sequence and the base sequence of the V region of the H chain contained in this plasmid HEF-RVHd-AHM-gγ1 are shown in SEQ ID NO: 14.

Using as the mutagen primer ES (sequence 69) and EA (SEQ ID NO: 70) designed to mutate valine at position 67 to alanine and methionine at position 69 to leucine and as, a template DNA the plasmid HEF-RVHa-AHM-gγ1, version e is amplified to obtain plasmid HEF-RVHe-AHM-gγ1. The amino acid sequence and the base sequence of the V region of the H chain contained in this plasmid HEF-RVHe-AHM-gγ1 are shown in SEQ ID NO: 15.

3-2. Construction of the H Chain Hybrid V Region

By constructing a H chain hybrid V region, it is possible to investigate which FR of the V region of a humanized antibody contributes to the binding activity and the binding inhibition activity. Among the two that were constructed, the amino acid sequences of FR1 and FR2 are derived from a mouse anti-HM 1.24 antibody and those of FR3 and FR4 are from version a of the V region of the H chain of a reshaped human anti-HM 1.24 antibody (mouse human hybrid anti-HM 1.24 antibody) in one, and the amino acid sequences of FR1 and FR2 are derived from version a of the V region of the H chain of a reshaped human anti-HM 1.24 antibody and those of FR3 and FR4 are from a mouse anti-HM 1.24 antibody (human mouse hybrid anti-HM 1.24 antibody) in the other. The amino acid sequences of the CDR regions are all derived from a mouse anti-HM 1.24 antibody.

Two H chain hybrid V regions are constructed by the PCR method. The method is schematically shown in FIGS. 6 and 7. For the construction of two H chain hybrid V regions four primers can be used. The external primers a (SEQ ID NO: 71) and h (SEQ ID NO: 72) are designed to hybridize with the DNA sequence of the HEF expression vector HEF-VH-gγ1. The H chain hybrid construction primer HYS (SEQ ID NO: 73) is designed to have the sense DNA sequence and the H chain hybrid primer HYA (SEQ ID NO: 74) to have the antisense DNA sequence so that the DNA sequences are complementary to each other.

For the construction of the H chain hybrid V region in which the amino acid sequences of FR1 and FR2 are derived from a mouse anti-HM 1.24 antibody and those of FR3 and FR4 are from version a of the V region of the H chain of a reshaped human anti-HM 1.24 antibody, PCR using the plasmid HEF-1.24H-gγ1 as a template, the external primer a, and the H chain hybrid primer HYA, and PCR using the plasmid HEF-RVHa-AHM-gγ1 as a template, the H chain hybrid primer HYA, and the external primer h are carried out in the first stage of PCR and each PCR product is purified.

The two PCR products from the first PCR are allowed to assemble by their own complementarity (see International Application Publication No. WO 92-19759). Then, by adding the external primers a and h, a full-length DNA encoding the H chain hybrid V region in which the amino acid sequences of FR1 and FR2 are derived from a mouse anti-HM 1.24 antibody and those of FR3 and FR4 are from version a of the V region of the H chain of a reshaped human anti-HM 1.24 antibody is amplified in the second PCR stage.

For the construction of the H chain hybrid V region in which the amino acid sequences of FR1 and FR2 are derived from version a of the V region of the H chain of a reshaped human anti-HM 1.24 antibody and those of FR3 and FR4 are from a mouse anti-HM 1.24 antibody, PCR, using the plasmid HEF-RVHa-AHM-gγ1 as a template, the external primer a, and the H chain hybrid primer HYA, and PCR using the plasmid HEF-1.24H-gγ1 as a template, the H chain hybrid primer HYS, and the external primer h are carried out in the first stage of PCR and each PCR product is purified.

The two PCR purified products from the first PCR are allowed to assemble by their own complementarity (see International Application Publication No. WO 97-19759). Then, by adding the external primers a and h, a full-length DNA encoding the H chain hybrid V region in which the amino acid sequences of FR1 and FR2 are derived from version a of the V region of the H chain of a reshaped human anti-HM 1.24 antibody and those of FR3 and FR4 are from a mouse anti-HM 1.24 antibody is amplified in the second PCR stage.

The methods of the first PCR, purification of PCR products, assembling, the second PCR, and cloning into the HEF expression vector HEF-VH-gγ1 are carried out according to the method shown in "Example 9. Construction of the V region of the L chain of a reshaped human anti-HM 1.24 antibody". After determination of the DNA sequence, the plasmid that contains the DNA fragment encoding the correct amino acid sequence of the H chain hybrid V region in which the amino acid sequences of FR1 and FR2 are derived from a mouse anti-HM 1.24 antibody and those of FR3 and FR4 are from version a of the V region of the H chain of a reshaped human anti-HM 1.24 antibody was termed HEF-MH-RVH-AHM-gγ1.

The amino acid sequence and the base sequence of the V region of the H chain contained in this plasmid HEF-MH-RVH-AHM-gγ1 are shown in SEQ ID NO: 75. Also, the plasmid that contains the DNA fragment encoding the correct amino acid sequence of the H chain hybrid V region in which the amino acid sequences of FR1 and FR2 are derived from a version a reshaped human anti-HM 1.24 antibody and those of FR3 and FR4 are from the V region of the H chain of a mouse anti-HM 1.24 antibody was termed HEF-HM-RVH-AHM-gγ1. The amino acid sequence and the base sequence of the V region of the H chain contained in this plasmid HEF-HM-RVH-AHM-gγ1 are shown in SEQ ID NO: 76.

3-3. Construction of Versions f to s of the V Region of the H Chain of a Reshaped Human Anti-HM 1.24 Antibody Each of versions f, g, h, i, j, k, l, m, n, o, p, q, r, and s of the V region of the H chain of a reshaped human anti-HM 1.24 antibody is constructed as follows. In constructing each of versions f and after of the V region of the H chain of a reshaped human anti-HM 1.24 antibody, a three-dimensional structural model of the V region of a mouse anti-HM 1.24 antibody can be constructed, as mentioned above, in order to predict the position of the amino acid residue to be substituted in the antibody molecule.

Using as the mutagen primer FS (sequence 78) and FA (SEQ ID NO: 79) designed to mutate threonine at position 75 to serine and valine at position 78 to alanine and as a template DNA the plasmid HEF-RVHe-AHM-gγ1 by the PCR method, version f is amplified to obtain plasmid HEF-RVHf-AHM-gγ1. The amino acid sequence and the base sequence of the V region of the H chain contained in this plasmid HEF-RVHf-AHM-gγ1 are shown in SEQ ID NO: 16.

Using as the mutagen primer GS (sequence 80) and GA (SEQ ID NO: 81) designed to mutate alanine at position 40 to arginine and as a template DNA the plasmid HEF-RVHa-AHM-gγ1, version g is amplified to obtain plasmid HEF-RVHg-AHM-gγ1. The amino acid sequence and the base sequence of the V region of the H chain contained in this plasmid HEF-RVHg-AHM-gγ1 are shown in SEQ ID NO: 17.

Using as the mutagen primer FS and FA and as a template DNA the plasmid HEF-RVHb-AHM-gγ1, version h is amplified to obtain the plasmid HEF-RVHh-AHM-gγ1. The amino acid sequence and the base sequence of the V region of the H chain contained in this plasmid HEF-RVHh-AHM-gγ1 are shown in SEQ ID NO: 18.

Using as the mutagen primer IS (sequence 82) and IA (SEQ ID NO: 83) designed to mutate arginine at position 83 to alanine and serine at position 84 to phenylalanine and as a template DNA the plasmid HEF-RVHh-AHM-gγ1, version i is amplified to obtain plasmid HEF-RVHi-AHM-gγ1. The amino acid sequence and the base sequence of the V region of the H chain contained in this plasmid HEF-RVHi-AHM-gγ1 are shown in SEQ ID NO: 19.

Using as the mutagen primer JS (SEQ ID NO: 84) and JA (SEQ ID NO: 85) designed to mutate arginine at position 66 to lysine and as a template DNA the plasmid HEF-RVHf-AHM-gγ1, version j is amplified to obtain plasmid HEF-RVHj-AHM-gγ1. The amino acid sequence and the base sequence of the V region of the H chain contained in this plasmid HEF-RVHj-AHM-gγ1 are shown in SEQ ID NO: 20.

Using as the mutagen primer KS (SEQ ID NO: 86) and KA (SEQ ID NO: 87) designed to mutate glutamic acid at position 81 to glutamine and as a template DNA the plasmid HEF-RVHh-AHM-gγ1, version k is amplified to obtain plasmid HEF-RVHk-AHM-gγ1. The amino acid sequence and the base sequence of the V region of the H chain contained in this plasmid HEF-RVHk-AHM-gγ1 are shown in SEQ ID NO: 21.

Using as the mutagen primer LS (SEQ ID NO: 88) and LA (SEQ ID NO: 89) designed to mutate glutamic acid at position 81 to glutamine and serine at position 82B to isoleucine and as a template DNA the plasmid HEF-RVHh-AHM-gγ1, version l is amplified to obtain plasmid HEF-RVHl-AHM-gγ1. The amino acid sequence and the base sequence of the V region of the H chain contained in this plasmid HEF-RVHl-AHM-gγ1 are shown in SEQ ID NO: 22.

Using as the mutagen primer MS (SEQ ID NO: 90) and MA (SEQ ID NO: 91) designed to mutate glutamic acid at position 81 to glutamine, serine at position 82b to isoleucine, and threonine at position 87 to serine and as a template DNA the plasmid HEF-RVHh-AHM-gγ1, version m is amplified to obtain plasmid HEF-RVHm-AHM-gγ1. The amino acid sequence and the base sequence of the V region of the H chain contained in this plasmid HEF-RVHm-AHM-gγ1 are shown in SEQ ID NO: 23.

Using as the mutagen primer NS (SEQ ID NO: 92) and NA (SEQ ID NO: 93) designed to mutate serine at position 82B to isoleucine and as a template DNA the plasmid HEF-RVHh-AHM-gγ1, version n is amplified to obtain plasmid HEF-RVHn-AHM-gγ1. The amino acid sequence and the base sequence of the V region of the H chain contained in this plasmid HEF-RVHn-AHM-gγ1 are shown in SEQ ID NO: 24.

Using as the mutagen primer OS (SEQ ID NO: 94) and OA (SEQ ID NO: 95) designed to mutate threonine at position 87 to serine and as a template DNA the plasmid HEF-RVHh-AHM-gγ1, version o is amplified to obtain plasmid HEF-RVHo-AHM-gγ1. The amino acid sequence and the base sequence of the V region of the H chain contained in this plasmid HEF-RVHo-AHM-gγ1 are shown in SEQ ID NO: 25.

Using as the mutagen primer PS (SEQ ID NO: 96) and PA (SEQ ID NO: 97) designed to mutate valine at position 78 to alanine and as a template DNA the plasmid HEF-RVHa-AHM-gγ1, version p is amplified by the PCR method to obtain plasmid HEF-RVHp-AHM-gγ1. The amino acid sequence and the base sequence of the V region of the H chain contained in this plasmid HEF-RVHp-AHM-gγ1 are shown in SEQ ID NO: 26.

Using as the mutagen primer QS (SEQ ID NO: 98) and QA (SEQ ID NO: 99) designed to mutate threonine at position 75 to serine and as a template DNA the plasmid HEF-RVHa-AHM-gγ1, version q is amplified by the PCR method to obtain plasmid HEF-RVHq-AHM-gγ1. The amino acid sequence and the base sequence of the V region of the H chain contained in this plasmid HEF-RVHq-AHM-gγ1 are shown in SEQ ID NO: 27.

Using as the mutagen primer CS (SEQ ID NO: 65) and CA (SEQ ID NO: 66) and as a template DNA the plasmid HEF-RVHp-AHM-gγ1, version r is amplified by the PCR method to obtain plasmid HEF-RVHr-AHM-gγ1. The amino acid sequence and the base sequence of the V region of the H chain contained in this plasmid HEF-RVHr-AHM-gγ1 are shown in SEQ ID NO: 28.

Using as the mutagen primer SS (SEQ ID NO: 100) and SA (SEQ ID NO: 101) designed to mutate methionine at position 69 to isoleucine and as a template DNA the plasmid HEF-RVHr-AHM-gγ1, version s is amplified to obtain plasmid HEF-RVHs-AHM-gγ1. The amino acid sequence and the base sequence of the V region of the H chain contained in this plasmid HEF-RVHs-AHM-gγ1 are shown in SEQ ID NO: 102.

The amino acid sequences of the V region of the L chain constructed are shown in Table 1, and the amino acid sequences of the V region of the H chain are shown in Tables 2 to 4.

TABLE 1

The amino acid sequence of the V region of the L chain

```
                    FR1                          CDR1
                 1          2          3
           12345678901234567890123 45678901234
AHM        DIVMTQSHKFMSTSVGDRVSITC KASQDVNTAVA           (a region of SEQ. ID NO: 1)
                FR2           CDR2         FR3
              4          5         6          7         8
           567890123456789 0123456 78901234567890123456789012345678
AHM        WYQQKPGQSPKLLIY SASNRYT GVPDRITGSGSGTDFTFTISSVQAEDLALYYC
               CDR3        FR4
              9          10
           901234567 8901234567
AHM        QQHYSTPFT FGSGTKLEIK
                    FR1                          CDR1
                 1          2          3
           12345678901234567890123 45678901234
HuSGI      DIQMTQSPSSLSASVGDRVTITC                       (SEQ ID NO: 130)
                FR2           CDR2         FR3
              4          5         6          7         8
           567890123456789 0123456 78901234567890123456789012345678
HuSGI      WYQQKPGKAPKLLIY         GVPSRFSGSGSGTDFTLTISSLQPEDFATYYC
               CDR3        FR4
              9          10
           901234567 8901234567
HuSGI                FGQGTKVEIK
                    FR1                          CDR1
                 1          2          3
           12345678901234567890123 45678901234
REI        DIQMTQSPSSLSASVGDRVTITC                       (SEQ ID NO: 131)
                FR2           CDR2         FR3
              4          5         6          7         8
           567890123456789 0123456 78901234567890123456789012345678
REI        WYQQKPGKAPKLLIY         GVPSRFSGSGSGTDFTFTISSLQPEDIATYYC
               CDR3        FR4
              9          10
           901234567 8901234567
REI                  FGQGTKVEIK
                    FR1                          CDR1
                 1          2          3
           12345678901234567890123 45678901234
RVLa       ----------------------- -----------           (a region of SEQ ID NO: 9
                                                         and SEQ ID NO: 106)
                FR2           CDR2         FR3
              4          5         6          7         8
```

TABLE 1-continued

The amino acid sequence of the V region of the L chain

```
            567890123456789 0123456 789012345678901234567890123456789
RVLa        --------------- ------- ---------------------------------
               CDR3          FR4
                 9             10
            901234567 8901234567
RVLa        --------- ----------
               FR1                          CDR1
                 1         2         3
            12345678901234567890123 45678901234
RVLb        ----------------------- -----------                   (a region of SEQ ID NO: 10)
               FR2       CDR2        FR3
                 4         5          6         7         8
            567890123456789 0123456 789012345678901234567890123456789
RVLb        --------------- ------- -------------Y-------------------
               CDR3          FR4
                 9             10
            901234567 8901234567
RVLb        --------- ----------
```

TABLE 2

The amino acid sequence of the V region of the H chain (1)

```
          FR1
             1         2         3
          12345678901234567890123456789
AHM       QVQLQQSGAELARPGASVKLSCKASGYTFT   (a region of SEQ ID NO: 3)

CDR1   FR2
                  4
          12345 67890123456789
AHM       PYWMQ WVKQRPGQGLEWIG

FR1
             1         2         3
          12345678901234567890123456789
HuSGI     EVQLVQSGADVKKPGXSVXVSCKASGYTFS   (SEQ ID NO: 132)

CDR1   FR2
                  4
          12345 67890123456789
HuSGI           WVRQAPGXGLDWVG

FR1
             1         2         3
          12345678901234567890123456789
HG3       QVQLVQSGAEVKKPGASVKVSCKASGYTFN   (SEQ ID NO: 133)

CDR1   FR2
                  4
          12345 67890123456789
HG3             WVRQAPGQGLEWMG

FR1
             1         2         3
          12345678901234567890123456789
RVHa      -----------------------------T   (a region of SEQ ID NO: 11)

CDR1   FR2
                  4
          12345 67890123456789
RVHa      ----- --------------

FR1
             1         2         3
          123456789012345678901234567890T
RVHb      ------------------------------   (a region of SEQ ID NO: 12)

CDR1   FR2
                  4
          12345 67890123456789
RVHb      ----- --------------

FR1
```

TABLE 2-continued

The amino acid sequence of the V region of the H chain (1)

```
                1         2         3
        12345678901234567890123456789 0
RVHc    -----------------------------T (a region of SEQ ID NO: 13)

CDR1  FR2
              4
        12345 67890123456789
RVHc    ----- -------------

FRI
                1         2         3
        12345678901234567890123456789 0
RVHd    -----------------------------T (a region of SEQ ID NO: 14)

CDR1  FR2
              4
        12345 67890123456789
RVHd    ----- -------------

FRI
                1         2         3
        12345678901234567890123456789 0
RVHe    -----------------------------T (a region of SEQ ID NO: 15)

CDR1  FR2
              4
        12345 67890123456789
RVHe    ----- -------------

FRI
                1         2         3
        12345678901234567890123456789 0
RVHf    -----------------------------T (a region of SEQ ID NO: 16)

CDR1  FR2
              4
        12345 67890123456789
RVHf    ----- -------------

FRI
                1         2         3
        12345678901234567890123456789 0
RVHg    -----------------------------T (a region of SEQ ID NO: 17)

CDR1  FR2
              4
        12345 67890123456789
RVHg    ----- ----R--------

FRI
                1         2         3
        12345678901234567890123456789 0
RVHh    -----------------------------T (a region of SEQ ID NO: 17)

CDR1  FR2
              4
        12345 67890123456789
RVHh    ----- -------------

FRI
                1         2         3
        12345678901234567890123456789 0
RVHi    -----------------------------T (a region of SEQ ID NO: 19)

CDR1  FR2
              4
        12345 67890123456789
RVHi    ----- -------------

FRI
                1         2         3
        12345678901234567890123456789 0
RVHi    -----------------------------T (a region of SEQ ID NO: 20)

CDR1  FR2
              4
        12345 67890123456789
```

TABLE 2-continued

The amino acid sequence of the V region of the H chain (1)

```
RVHi    -----  --------------

FR1
                  1         2         3
        12345678901234567890123456789 0
RVHk    ---------------------------T    (a region of SEQ ID NO: 21)

CDR1   FR2
                     4
        12345  67890123456789
RVHk    -----  --------------

FR1
                  1         2         3
        12345678901234567890123456789 0
RVHl    ---------------------------T    (a region of SEQ ID NO: 22)

CDR1   FR2
                     4
        12345  67890123456789
RVHl    -----  --------------

FR1
                  1         2         3
        12345678901234567890123456789 0
RVHm    ---------------------------T    (a region of SEQ ID NO: 23)

CDR1   FR2
                     4
        12345  67890123456789
RVHm    -----  --------------

FR1
                  1         2         3
        12345678901234567890123456789 0
RVHn    ---------------------------T    (a region of SEQ ID NO: 24)

CDR1   FR2
                     4
        12345  67890123456789
RVHn    -----  --------------

FR1
                  1         2         3
        12345678901234567890123456789 0
RVHo    ---------------------------T    (a region of SEQ ID NO: 25)

CDR1   FR2
                     4
        12345  67890123456789
RVHo    -----  --------------

FR1
                  1         2         3
        12345678901234567890123456789 0
RVHp    ---------------------------T    (a region of SEQ ID NO: 26)

CDR1   FR2
                     4
        12345  67890123456789
RVHp    -----  --------------

FR1
                  1         2         3
        12345678901234567890123456789 0
RVHq    ---------------------------T    (a region of SEQ ID NO: 27)

CDR1   FR2
                     4
        12345  67890123456789
RVHq    -----  --------------

FR1
                  1         2         3
        12345678901234567890123456789 0
RVHr    ---------------------------T    (a region of SEQ ID NO: 28
                                         and SEQ ID NO: 125)
```

TABLE 2-continued

The amino acid sequence of the V region of the H chain (1)

```
       CDR1  FR2
                4
       12345 67890123456789
RVHr   ----- --------------

FR1
               1         2         3
       1234567890123456789012234567890
RVHs   --------------------------T    (a region of SEQ ID NO: 102
                                       and SEQ ID NO: 128)

CDR1  FR2
                4
       12345 67890123456789
RVHs   ----- --------------
```

TABLE 3

The amino acid sequence of the V region of the H chain

```
        CDR2
        5              6
        012A3456789012345
AHM     SIFPGDGDTRYSQKFKG              (a region of SEQ ID NO: 3)

FR3
            7         8         9
        67890123456789012ABC345678901234
AHM     KATLTADKSSSTAYMQLSILAFEDSAVYYCAR

CDR2
        5              6
        012A3456789012345
HuSGI                                   (SEQ ID NO: 134)

FR3
            7         8         9
        67890123456789012ABC345678901234
HuSGI   RVTXTXDXSXNTAYMELSSLRSEDTAVYYCAR

CDR2
        5              6
        012A3456789012345
HG3                                     (SEQ ID NO: 135)

FR3
            7
        67890123456789012ABC345678901234
HG3     RVTMTRDTSTSTVYMELSSLRSEDTAVYYCAR

CDR2
        5              6
        012A3456789012345
RVHa    ----------------                (a region of SEQ ID NO: 11)

FR3
            7
        67890123456789012ABC345678901234
RVHa    -----A--------------------------

CDR2
        5              6
        012A3456789012345
RVHb    ----------------                (a region of SEQ ID NO: 12)

FR3
            7
        67890123456789012ABC345678901234
RVHb    K----A--------------------------

CDR2
        5              6
        012A3456789012345
```

TABLE 3-continued

| | The amino acid sequence of the V region of the H chain | |
|---|---|---|
| RVHc | ---------------- | (a region of SEQ ID NO: 13) |
| | FR3 |
| | 7 |
| | 67890123456789012ABC345678901234 |
| RVHc | -----A-K----------------------- |
| | CDR2 |
| | 5            6 |
| | 012A3456789012345 |
| RVHd | ---------------- | (a region of SEQ ID NO: 14) |
| | FR3 |
| | 7 |
| | 67890123456789012ABC345678901234 |
| RVHd | K----A-K----------------------- |
| | CDR2 |
| | 5            6 |
| | 012A3456789012345 |
| RVHe | ---------------- | (a region of SEQ ID NO: 15) |
| | FR3 |
| | 7 |
| | 67890123456789012ABC345678901234 |
| RVHe | -A-L-A------------------------- |
| | CDR2 |
| | 5            6 |
| | 012A3456789012345 |
| RVHf | ---------------- | (a region of SEQ ID NO: 16) |
| | FR3 |
| | 7 |
| | 67890123456789012ABC345678901234 |
| RVHf | -A-L-A---S--A------------------ |
| | CDR2 |
| | 5            6 |
| | 012A3456789012345 |
| RVHg | ---------------- | (a region of SEQ ID NO: 17) |
| | FR3 |
| | 7 |
| | 67890123456789012ABC345678901234 |
| RVHg | -----A------------------------- |
| | CDR2 |
| | 5            6 |
| | 012A3456789012345 |
| RVHh | ---------------- | (a region of SEQ ID NO: 18) |
| | FR3 |
| | 7 |
| | 67890123456789012ABC345678901234 |
| RVHh | K----A---S--A------------------ |
| | CDR2 |
| | 5            6 |
| | 012A3456789012345 |
| RVHi | ---------------- | (a region of SEQ ID NO: 19) |
| | FR3 |
| | 7 |
| | 67890123456789012ABC345678901234 |
| RVHi | K----A---S--A-------AF--------- |
| | CDR2 |
| | 5            6 |
| | 012A3456789012345 |
| RVHj | ---------------- | (a region of SEQ ID NO: 20) |
| | FR3 |
| | 7 |
| | 67890123456789012ABC345678901234 |
| RVHj | KA-L-A---S--A------------------ |

TABLE 3-continued

| | The amino acid sequence of the V region of the H chain | |
|---|---|---|
| | CDR2 | |
| | 5          6 | |
| | 012A3456789012345 | |
| RVHk | ---------------- | (a region of SEQ ID NO: 21) |
| | FR3 | |
| | 7 | |
| | 67890123456789012ABC345678901234 | |
| RVHk | K----A---S--A--Q-------------- | |
| | CDR2 | |
| | 5          6 | |
| | 012A3456789012345 | |
| RVHl | ---------------- | (a region of SEQ ID NO: 22) |
| | FR3 | |
| | 7 | |
| | 67890123456789012ABC345678901234 | |
| RVHl | K----A---S--A--Q--I------------ | |
| | CDR2 | |
| | 5          6 | |
| | 012A3456789012345 | |
| RVHm | ---------------- | (a region of SEQ ID NO: 23) |
| | FR3 | |
| | 7 | |
| | 67890123456789012ABC345678901234 | |
| RVHm | K----A---S--A--Q--I-----S------- | |
| | CDR2 | |
| | 5          6 | |
| | 012A3456789012345 | |
| RVHn | ---------------- | (a region of SEQ ID NO: 24) |
| | FR3 | |
| | 7 | |
| | 67890123456789012ABC345678901234 | |
| RVHn | K----A---S--A-----I------------ | |
| | CDR2 | |
| | 5          6 | |
| | 012A3456789012345 | |
| RVHo | ---------------- | (a region of SEQ ID NO: 25) |
| | FR3 | |
| | 7 | |
| | 67890123456789012ABC345678901234 | |
| RVHo | K----A---S--A-----------S------- | |
| | CDR2 | |
| | 5          6 | |
| | 012A3456789012345 | |
| RVHp | ---------------- | (a region of SEQ ID NO: 26) |
| | FR3 | |
| | 7 | |
| | 67890123456789012ABC345678901234 | |
| RVHp | -----A------A------------------ | |
| | CDR2 | |
| | 5          6 | |
| | 012A3456789012345 | |
| RVHq | ---------------- | (a region of SEQ ID NO: 27) |
| | FR3 | |
| | 7 | |
| | 67890123456789012ABC345678901234 | |
| RVHq | -----A---S--------------------- | |
| | CDR2 | |
| | 5          6 | |
| | 012A3456789012345 | |
| RVHr | ---------------- | (a region of SEQ ID NO: 28 and SEQ ID NO: 125) |
| | FR3 | |

TABLE 3-continued

The amino acid sequence of the V region of the H chain

```
              7
      67890123456789012ABC345678901234
RVHr  -----A-K----A------------------

CDR2
         5         6
         012A3456789012345
RVHs     ----------------     (a region of SEQ ID NO: 102
                               and SEQ ID NO: 128)

FR3
              7
      67890123456789012ABC345678901234
RVHs  ---I-A-K----A------------------
```

TABLE 4

The amino acid sequence of the V region
of the H chain (3)

```
       CDR3         FR4
       10           11
       57890ABJK12  34567890123
AHM    GLRRGGYYFDY  WGQGTTLYVSS   (a region of SEQ ID NO:3)

CDR3         FR4
       10           11
       57890ABJK12  34567890123
HuSGI               WGQGTLVTVSS   (SEQ ID NO: 136)

CDR3         FR4
       10           11
       57890ABJK12  34567890123
JH6                 WGQGTTVTVSS   (SEQ ID NO: 137)

CDR3         FR4
       10           11
       57890ABJK12  34567890123
RVHa   -----------  -----------   (a region of SEQ ID NO: 11)

CDR3         FR4
       10           11
       57890ABJK12  34567890123
RVHb   -----------  -----------   (a region of SEQ ID NO: 12)

CDR3         FR4
       10           11
       57890ABJK12  34567890123
RVHC   -----------  -----------   (a region of SEQ ID NO: 13)

CDR3         FR4
       10           11
       57890A3JK12  34567890123
RVHd   -----------  -----------   (a region of SEQ ID NO: 14)

CDR3         FR4
       10           11
       57890ABJK12  34567890123
RVHe   -----------  -----------   (a region of SEQ ID NO: 15)

CDR3         FR4
       10           11
       57890ABJK12  34567890123
RVHf   -----------  -----------   (a region of SEQ ID NO: 16)

CDR3         FR4
       10           11
       57890ABJK12  34567890123
RVHg   -----------  -----------   (a region of SEQ ID NO: 17)

CDR3         FR4
       10           11
       57890ABJK12  34567890123
RVHh   -----------  -----------   (a region of SEQ ID NO: 18)
```

TABLE 4-continued

The amino acid sequence of the V region
of the H chain (3)

```
         CDR3         FR4
          10           11
       57890ABJK12  34567890123
RVHi   -----------  -----------   (a region of SEQ ID NO: 19)

CDR3         FR4
          10           11
       57890ABJK12  34567890123
RVHj   -----------  -----------   (a region of SEQ ID NO: 20)

CDR3         FR4
          10           11
       57890ABJK12  34567890123
RVHk   -----------  -----------   (a region of SEQ ID NO: 21)

CDR3         FR4
          10           11
       57890ABJK12  34567890123
RVHl   -----------  -----------   (a region of SEQ ID NO: 22)

CDR3         FR4
          10           11
       57890ABJK12  34567890123
RVHm   -----------  -----------   (a region of SEQ ID NO: 23)

CDR3         FR4
          10           11
       57890ABJK12  34567890123
RVHn   -----------  -----------   (a region of SEQ ID NO: 24)

CDR3         FR4
          10           11
       57890ABJK12  34567890123
RVHo   -----------  -----------   (a region of SEQ ID NO: 25)

CDR3         FR4
          10           11
       57890ABJK12  34567890123
RVHp   -----------  -----------   (a region of SEQ ID NO: 26)

CDR3         FR4
          10           11
       57890ABJK12  34567890123
RVHq   -----------  -----------   (a region of SEQ ID NO: 27)

CDR3         FR4
          10           11
       57890ABJK12  34567890123
RVHr   -----------  -----------   (a region of SEQ ID NO: 28 and SEQ
                                    ID NO: 128)
         CDR3         FR4
          10           11
       57890ABJK12  34567890123
RVHs   -----------  -----------   (a region of SEQ ID NO: 102 and SEQ
                                    ID NO: 128)
```

3. Production of a Chimeric Antibody and a Reshaped Human Antibody

For the production of a chimeric antibody or a reshaped human antibody, two expression vectors for each are constructed, which comprises an expression vector comprising DNA encoding the V region of a mouse H chain and the C region of a human H chain under the control of an expression regulatory region such as the enhancer/promoter system and DNA encoding the V region of a mouse L chain and the C region of a human L chain under the control of an expression regulatory region such as the enhancer/promoter system, or an expression vector comprising DNA encoding the V region of a humanized H chain and the C region of a human H chain under the control of an expression regulatory region such as the enhancer/promoter system and DNA encoding the V region of a humanized L chain and the C region of a human L chain under the control of an expression regulatory region such as the enhancer/promoter system.

Subsequently, a host cell such as the mammalian cell is cotransformed using these vectors, and the transformed cells are cultured in vitro or in vivo to produce a chimeric antibody or a reshaped human antibody (for example, International Application Publication No. WO 91-16928). Furthermore, an antibody gene is introduced into mammals such as goat to produce a transgenic animal, from the milk of which a chimeric antibody or a reshaped human antibody can be obtained.

Also, the V region of an H chain and the C region of an H chain, and the V region of an L chain and the C region of an L chain are ligated to a single vector to transform a suitable host cell and thereby to produce antibodies. Thus, for the expression of chimeric antibodies, DNA encoding the mouse leader sequence and the V region of the H chain and human H chain C region present in the cloned cDNA, and DNA encoding the mouse leader sequence and L chain V region and human L chain C region are introduced into a single expression vector (see International Application Publication No. WO 94-11523).

For the expression of a reshaped human antibody, DNA encoding the V region of a humanized H chain and C region of a human H chain, and DNA encoding the V region of a humanized L chain and the C region of a human L chain are introduced into a single expression vector (see International Application Publication No. WO 94-11523). Using said vector a host cells are transformed, and the transformed host cells are cultured in vivo or in vitro to produce the desired chimeric antibody or the reshaped human antibody.

A transformant that was transformed, as mentioned above, by a gene encoding the desired chimeric antibody or a reshaped human antibody is cultured, and the chimeric antibody or the reshaped human antibody produced can be isolated from the inside or the outside of the cells and purified to homogeneity.

The isolation and purification of the desired protein of the present invention, a chimeric antibody or a reshaped human antibody, may be carried out using an affinity column. As a column that employs protein A, for example, there is mentioned HyperD, POROS, Sepharose F. F, etc. Alternatively, the conventional isolation and purification methods used for proteins can be used and the method is not limited in any way. For example, combinations of various chromatographic methods, ultrafiltration, salting-out, dialysis, and the like, as appropriate, would permit the isolation and purification of the chimeric antibody of the reshaped human antibody.

For the production of the chimeric anti-HM 1.24 antibody or the reshaped human anti, HM 1.24 antibody of the present invention, any expression method can be used including, for example, the eukaryotic cells such as animal cells, an established mammalian cell-line system, an insect cell system, a fungal cell system, and a yeast cell system, and the procaryotic cells such as bacterial cells such as *Escherichia coli* cells, and the like. Preferably, the chimeric antibody or the reshaped human antibody of the present invention may be expressed in the COS cells, the CHO cells, the Hela cells, the Vero cells, the myeloma cells or the BHK cells.

In these cases, common promoters that are useful for the expression of mammalian cells can be used. For example, preferably the human cytomegalovirus immediate early (HCMV) promoter may be used. Examples of the expression vectors containing the HCMV promoter include those which are HCMV-VH-HCγ1, HCMV-VL-HCκ, etc. and which are derived from pSV2neo (International Application Publication No. WO 92-19759).

Furthermore, as a promoter for gene expression in the mammalian cells for use in the present invention, there can be used viral promoters such as retrovirus, polyoma virus, adenovirus, simian virus 40 (SV40), etc., and promoters derived from mammalian cells such as human polypeptide chain elongation factor 1α (HEF-1α), etc. For example, when the promoter of SV40 is used, expression can be easily carried out using the method of Mulligan et al. (Nature 277, 108 (1979)), and when HEF-1α promoter is used the method of Mizushima, S. et al. (Nucleic Acids Research, 18, 5322, 1990) can be used.

As a source of replication, there can be used those derived from SV40, polyoma virus, adenovirus, bovine papilloma virus (BPV) and the like, and for the amplification of the copy number of the gene in a host cell system, the expression vector can include, as a selective marker, aminoglycoside phosphotransferase (APH) gene, thymidine kinase (TK) gene, *E. coli* xanthine-guanine phosphoribosyl transferase (Ecogpt) gene, dihydrofolate reductase (DHRF) gene, and the like.

4. The Binding Inhibition Activity of a Chimeric Antibody or a Reshaped Human Antibody (1) Measurement of Antibody Concentration The concentration of purified antibody may be measured by ELISA or the measurement of absorbance.

ELISA plates for measurement of antibody concentration may be prepared as follows. Each well of a 96-well ELISA plate (for example Maxisorp, manufactured by NUNC) is immobilized with 100 µl of goat anti-human IgG antibody at a concentration of 1 µg/ml.

After blocking with 100 µg/ml of a dilution buffer (for example 50 mM Tris-HCl, 1 mM $MgCl_2$, 0.15 M NaCl, 0.05% Tween 20, 0.02% $NaN_3$, 1% bovine serum albumin (BSA), pH 8.1), serial dilutions of culture supernatant of cells in which the chimeric antibody, the hybrid antibody, or the reshaped human antibody was expressed, for example the culture supernatant of COS cells or CHO-cels, or the purified chimeric antibody, hybrid antibody, or reshaped human antibody is added to each well. Then 100 µl of alkaline phosphatase conjugated goat anti-human IgG antibody is added, 1 mg/ml of the substrate solution (Sigma104, p-nitrophenyl phosphate, manufactured by SIGMA) is added, and then the absorbance at 405 nm is measured using a microplate reader (Bio Rad). As the standard for the measurement of concentration, a human IgG1κ (manufactured by The BInding Site) can be used. The concentration of the purified antibody is obtained by measuring absorbance at 280 nm and calculating with 1 mg/ml as 1.35 OD.

(2) Binding Activity

Binding activity can be measured by the Cell-ELISA using the human amniotic cell line WISH (ATCC CCL25). The Cell-ELISA plate may be prepared as follows. WISH cells prepared at an appropriate concentration with PRMI 1640 medium supplemented with 10% fetal bovine serum are added to a 96-well plate, incubated overnight, and after washing twice with PBS(–), are fixed with 0.1% glutaraldehyde (manufactured by Nakalai tesque).

After blocking, 100 µl of serial dilutions of the culture supernatant of cells in which the chimeric anti-HM 1.24 antibody, the hybrid anti-HM 1.24 antibody or the reshaped human anti-HM 1.24 antibody was expressed, for example the culture supernatant of COS cells or CHO cells, or the purified chimeric anti-HM 1.24 antibody, hybrid anti-HM 1.24 antibody or reshaped human anti-HM1.24 antibody is added to each well, incubated at room temperature for two hours, and then peroxidase-labelled rabbit anti-human IgG antibody (manufactured by DAKO) is added.

After icubating at room temperature for one hour, the substrate solution is added and then incubated. Subsequently, the reaction is stopped by 50 µl of 6N sulfuric acid, and then absorbance at 490 nm is measured using the MICROPLATE READER Model 3550 (manufactured by Bio-Rad).

(3) Measurement of Binding Inhibition Activity

Binding inhibition activity by the biotinylated mouse anti-HM 1.24 antibody is measured by the Cell-ELISA using the human amniotic cell line WISH (ATCC CCL25). The Cell-ELISA plate may be prepared according to the above-mentioned (2). WISH cells prepared at an appropriate concentration with PRMI 1640 medium supplemented with 10% fetal bovine serum are added to a 96-well plate, incubated overnight, and after washing twice with PBS(−), are fixed with 0.1% glutaraldehyde (manufactured by Nakalai tesque).

After blocking, 50 µl of serial dilutions of the culture supernatant of cells in which the chimeric anti-HM 1.24 antibody, the hybrid anti-HM 1.24 antibody or the reshaped human anti-HM 1.24 antibody was expressed, for example the culture supernatant of COS cells or CHO cells, or the purified chimeric anti-HM 1.24 antibody, hybrid anti-HM 1.24 antibody or reshaped human anti-HM 1.24 antibody is added to each well, and simultaneously 50 µl of 2 µg/ml biotinylated mouse anti-HM 1.24 antibody is added, and then incubated at room temperature for two hours, and after washing, peroxidase-labelled streptavidin (manufactured by DAKO) is added.

After icubating at room temperature for one hour and after washing, the substrate solution is added and then incubated. Subsequently, the reaction is stopped by 50 µl of 6N sulfuric acid, and then absorbance at 490 nm is measured using the MICROPLATE READER Model 3550 (manufactured by Bio-Rad).

Measurement of ADCC Activity

The ADCC activity of the chimeric antibody or the reshaped human antibody of the present invention can be measured as follows. First, mononuclear cells are separated from human peripheral blood or bone marrow by the density centrifugation method and prepared as the effector cell. Human myeloma cells are prepared as the target cell by labelling the RPMI 8226 cells (ATCC CCL 155) with $^{51}$Cr. Then, the chimeric antibody or the reshaped human antibody to be measured for ADCC activity is added to the labelled target cells and incubated, and then a suitable ratio of the effector cell is added to the target cell and incubated.

After incubation the supernatant is taken to be measured for radioactivity using a gamma counter. At this time, 1% NP-40 can be used for measurement of the maximum released radioactivity. Cytotoxicity (%) can be calculated as (A−C)/(B−C)×100, wherein A is radioactivity (cpm) released in the presence of antibody, B is radioactivity (cpm) released by NP-40, and C is radioactivity (cpm) released by the culture liquid alone without antibody.

When ADCC activity or CDC activity is expected for the C region of antibody, human Cγ1 or human Cγ3 can be used as the C region of antibody. Furthermore, by adding, altering, or modifying part of the amino acid of the C region of antibody, a higher ADCC activity or CDC activity can be induced.

For example, there are the IgM-like polymerization of IgG by amino acid substitution (Smith, R. I. F. & Morrison, S. L, BIO/TECHNOLOGY (1994) 12, 683-688), the IgM-like polymerization of IgG by amino acid addition (Smith, R. I. F. et al., J. Immunol. (1995) 154, 2226-2236), expression by tandem linking of genes encoding an L chain (Shuford, W. et al., Science (1991) 252, 724-727), dimerization of IgG by amino acid substitution (Caron, P. C. et al., J. Exp. Med. (1992) 176, 1191-1195, Shopes, B. J. Immunology (1992) 148, 2918-2922, dimerization of IgG by chemical modification (Wolff, E. A. et al., Cancer Res. (1993) 53, 2560-2565), and the introduction of the effector function by amino acid alteration at the hinge region of antibodies (Norderhaug, L. et al., Eur. J. Immunol (1991) 21, 2379-2384). They can be accomplished by the oligomer site directed mutagenesis using primers, addition of base sequences using restriction enzyme cleavage sites, and chemical modifiers that induces covalent bonding.

in vivo diagnostics for Myeloma

The chimeric anti-HM 1.24 antibody or the reshaped human anti-HM 1.24 antibody of the present invention can be used as an in vivo diagnostics for myeloma by linking it to a labelled compound such as radioisotope and the like.

Furthermore, fragments of the chimeric anti-HM 1.24 antibody or the reshaped human anti-HM 1.24 antibody, such as Fab, F(ab')2, Fv, or single chain Fv (scFv) wherein the Fv or the Fv of an H chain and an L chain are linked by a suitable linker that has been bound to a label compound such as radioisotope etc. can be used as an in vivo diagnostics for myeloma.

Specifically these antibody fragments can be obtained by constructing the gene encoding these antibody fragments, introducing them into an expression vector, and then expressing in a suitable host cells, or digesting the chimeric anti-HM 1.24 antibody or the reshaped human anti-HM 1.24 antibody with a suitable enzyme.

The above-mentioned in vivo diagnostics for myeloma can be systematically administered in a parenteral manner.

A Pharmaceutical Composition and a Therapeutic Agent for Myeloma

In order to confirm the therapeutic effects of the chimeric anti-HM 1.24 antibody or the humanized anti-HM 1.24 antibody of the present invention, said antibodies are administered to a myeloma cells-transplanted animal and the anti-tumor effects are evaluated.

As myeloma cells to be transplanted to animals, human myeloma cells are preferred, and there can be mentioned, for example, KPMM2 (Japanese Unexamined Patent Publication (Kokai) No. 7-236475), RPMI8226 (ATCC CCL 155), ARH-77 (ATCC CRL 1621), and S6B45 (Suzuki, H. et al., Eur. J. Immunol. (1992) 22, 1989-1993). As the animals to which said cells are transplanted, animals in which immunological functions are decreased or lacking are preferred, and there can be mentioned nude mouse, SCID mouse, beige mouse, and nude rat.

Furthermore, the anti-tumor effects to be evaluated can be confirmed by variation in the amount of human immunoglobulins in the serum, measurement of tumor volume and/or weight, variation in the weight of human Bence Jones proteins in the urine, the survival period of animals, or the like.

Pharmaceutical compositions or therapeutic agents for myeloma that contain as an active ingredient the chimeric anti-HM 1.24 antibody or the reshaped human anti-HM 1.24 antibody of the present invention can be systematically or locally administered in a parenteral manner. For example, intravenous injection such as drip infusion, intramuscular injection, intraperitoneal injection, or subcutaneous injection can be selected and the dosage regimen may be selected as appropriate depending on the age and the medical conditions of the patients.

Effective dosage is selected from the range of 0.01 mg to 1000 mg/kg body weight/dose. Alternatively, the dosage of 5 mg/body, preferably 50 to 100 mg/body, may be selected.

Pharmaceutical compositions or therapeutic agents for myeloma that contain as an active ingredient the chimeric anti-HM 1.24 antibody or the reshaped human anti-HM 1.24 antibody of the present invention may contain pharmaceutically acceptable carriers or additives depending on the route of administration.

As examples of such carriers and additives, there may be mentioned water, pharmaceutically acceptable organic solvents, collagen, polyvinyl alcohol, polyvinylpyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, arabic gum, casein, gelatin, agar, diglycerin, glycerin, propylene glycol, polyethylene glycol, vaseline, paraffin, stearyl alcohol, stearic acid, human serum albumin (HSA), mannitol, sorbitol, lactose, pharmaceutically acceptable surfactants, and the like. Additives to be used may be selected from, but not limited to, the above or combinations thereof.

EXAMPLES

Next, the present invention will be explained more specifically.

Example 1

Cloning of cDNA Encoding the V Region of a Mouse Anti-HM 1.24 Antibody

1. Isolation of Messenger RNA (mRNA)

Using Fast Track mRNA Isolation Kit Version 3.2 (manufactured by Invitrogen) according to the instruction attached thereto, mRNA was isolated from $2 \times 10^8$ hybridoma cells (FERM BP-5233) that produce a mouse anti-HM 1.24 antibody.

2. Amplification of the Gene Encoding the Variable Region of Antibody by the PCR Method PCR was carried out using the amplification Thermal Cycler (manufactured by Perkin Elmer Cetus).

2-1. Amplification and Fragmentation of the Gene Encoding the V Region of a Mouse L Chain From the mRNA thus isolated, single stranded cDNA was synthesized using the AMV Reverse Transcriptase First-strand cDNA Synthesis Kit (manufactured by Life Science) and used for PCR. As primers used for PCR, MKV (Mouse Kappa Variable) primers (Jones, S. T. et al, Bio/Technology, 9, 88-89, (1991)) shown in SEQ ID NO: 29 to 39 that hybridize with the leader sequence of a mouse kappa type L chain was used.

100 µl of the PCR solution containing 10 mM Tris-HCl (pH 8.3), 50 mM KCl, 0.1 mM dNTPs (DATP, dGTP, dCTP, dTTP), 1.5 mM $MgCl_2$, 5 units of DNA polymerase Ampli Taq (manufactured by Perkin Elmer Cetus), 0.25 mM of the MKV primers shown in SEQ ID NO: 29 to 39, 3 mM of the MKC primer shown in SEQ ID NO: 40, and 100 ng of single stranded cDNA was covered with 50 µl of mineral oil, and then heated at an initial temperature of 94° C. for 3 minutes, and then at 94° C. for 1 minute, at 55° C. for 1 minute and at 72° C. for 1 minute in this order. After repeating this cycle for 30 times, the reaction mixture was incubated at 72° C. for 10 minutes. The amplified DNA fragment was purified by the low melting point agarose (manufactured by Sigma), and digested with XmaI (manufactured by New England Biolabs) and SalI (manufactured by Takara Shuzo) at 37° C.

2-2. Amplification and Fragmentation of cDNA Encoding the V Region of a Mouse H Chain The gene encoding the V region of a mouse H chain was amplified by the 5'-RACE method (Rapid Amplification of cDNA ends; Frohman, M. A. et al., Proc. Natl. Acad. Sci. USA, 85, 8998-9002, (1988), Edwards, J. B. D. M., et al., Nucleic Acids Res., 19, 5227-5232, (1991)). After cDNA was synthesized using primer P1 (SEQ ID NO: 41) that specifically hybridizes with the constant region of mouse IgG2a, cDNA encoding the V region of a mouse H chain was amplified by the 5'-AmpliFINDER RACE KIT (manufactured by CLONTECH) using the primer MHC2a (SEQ ID NO: 42) that specifically hybridizes with the constant region of mouse IgG2a and the anchor primer (SEQ ID NO: 77) attached to the kit. The amplified DNA fragment was purified with the low melting point agarose (manufactured by Sigma) and digested with EcoRI (manufactured by Takara Shuzo) and XmaI (manufactured by New England Biolabs) at 37° C.

3. Linking and Transformation

The DNA fragment comprising the gene encoding the V region of the mouse kappa type L chain prepared as above was ligated to the pUC19 vector prepared by digesting with SalI and XmaI by reacting in a reaction mixture containing 50 mM Tris-HCl (pH 7.6), 10 mM $MgCl_2$, 10 mM dithiothreitol, 1 mM ATP, 50 mg/ml of polyethylene glycol (8000) and one unit of T4 DNA ligase (manufactured by GIBCO-BRL) at 16° C. for 2.5 hours. Similarly, the DNA fragment comprising the gene encoding the V region of the mouse H chain was reacted and ligated to pUC19 vector prepared by digesting with EcoRI and XmaI at 16° C. for three hours.

Then 10 µl of the above ligation mixture was added to 50 µl of the competent cells of *Escherichia coli* DH5α, which was left on ice for 30 minutes, at 42° C. for one minute, and again on ice for one minute. Subsequently 400 µl of 2×YT medium (Molecular Cloning: A Laboratory Manual, Sambrook et al., Cold Spring Harbor Laboratory Press, (1989)) was added thereto, incubated at 37° C. for one hour, and then the *E. coli* was plated on the 2×YT agar medium (Molecular Cloning: A Laboratory Manual, Sambrook et al., Cold Spring Harbor Laboratory Press, (1989)) containing 50 µg/ml of ampicillin, and then incubated overnight at 37° C. to obtain the *E. coli* transformant.

The transformant was cultured overnight at 37° C. in 10 ml of the 2×YT medium containing 50 µg/ml of ampicillin, and then from this culture plasmid DNA was prepared using the alkali method (Molecular Cloning: A Laboratory Manual, Sambrook et al., Cold Spring Harbor Laboratory Press, (1989)).

The plasmid thus obtained containing the gene encoding the V region of the mouse kappa type L chain derived from the hybridoma that produces the anti-HM 1.24 antibody was termed pUCHMVL9. The plasmid obtained in the above-mentioned method containing the gene encoding the V region of the mouse H chain derived from the hybridoma that produces the anti-HM 1.24 antibody was termed pUCHM-VHR16.

Example 2

Determination of the Base Sequence of DNA

The base sequence of the cDNA coding region in the above-mentioned plasmid was determined using the automatic DNA sequencer (manufactured by Applied Biosystem Inc.) and Taq Dye Deoxy Terminator Cycle Sequencing Kit (manufactured by Applied Biosystem Inc.) in the protocol indicated by the manufacturer.

The base sequence of the gene encoding the V region of the L chain of the mouse anti-HM 1.24 antibody contained in the plasmid pUCHMVL9 is shown in SEQ ID NO: 1. The base sequence of the gene encoding the V region of the H chain of the mouse anti-HM 1.24 antibody contained in the plasmid pUCHMVHR16 is shown in SEQ ID NO: 2.

Example 3

Determination of CDR

The overall structures of the V regions of an L chain and an H chain have similarity with each other, in which four framework portions are linked by three hypervariable regions, i.e.

complementarity determining regions (CDR). The amino acid sequence of the framework are relatively well conserved but variation in the amino acid sequence is extremely high (Kabat, E. A., et al., "Sequences of Proteins of Immunological Interest", US Dept. Health and Human Services, 1983).

Based on these facts, the amino acid sequence of the variable region of the anti-HM 1.24 antibody was compared the amino acid sequences of antibodies in the database to investigate homology, and the CDR region was determined as shown in Table 5.

TABLE 5

| Plasmid | Sequence No. | CDR(1) | CDR(2) | CDR(3) |
| --- | --- | --- | --- | --- |
| pUCHMVL9 | 3–5 | 24–34 | 50–56 | 89–97 |
| pUCHMVHR16 | 6–8 | 31–35 | 50–66 | 99–109 |

Example 4

Confirmation of Expression of the Cloned cDNA (Construction of the Chimeric Anti-HM 1.24 Antibody)

1. Construction of an Expression Vector

In order to construct the expression vector that expresses a chimeric anti-HM 1.24 antibody, cDNA clones pUCHMVL9 and pUCHMVHR16 encoding the V regions of the L chain and the H chain of the mouse anti-HM 1.24 antibody, respectively, were modified by the PCR method, and then introduced into the HEF expression vector (International Application Publication No. WO 92-19759).

The backward primer ONS-L722S (SEQ ID NO: 43) for the V region of an L chain and the backward primer VHR16S (SEQ ID NO: 44) for the V region of an H chain were designed so that they hybridize to the DNA encoding the start of the leader sequence of the V region of each and they have the Kozak consensus sequence (Kozak, M. et al., J. Mol. Biol., 196, 947-950, (1987)) and the recognition site for HindIII restriction enzyme. The forward primer VL9A (SEQ ID NO: 45) for the V region of an L chain and the forward primer VHR16A (SEQ ID NO: 46) for the V region of an H chain were designed so that they hybridize to the DNA sequence encoding the end of the J region and they have a splice donor sequence and the recognition site for BamHI restriction enzyme.

100 μl of the PCR reaction mixture containing 10 mM Tris-HCl (pH 8.3), 50 mM KCl, 0.1 mM dNTPs, 1.5mM $MgCl_2$, 100 pmole each of each primer, 100 ng of template DNA (pUCHMVL9 or pUCHMVHR16), and 5 units of Ampli Taq enzyme was covered with 50 μl of mineral oil, and then after the initial denaturation at 94° C., heated at 94° C. for 1 minute, at 55° C. for 1 minute and at 72° C. for 1 minute for 30 cycles and finally incubated at 72° C. for 10 minutes.

The PCR product was purified by the 1.5% low melting point agarose gel, and digested with HindIII and BamHI, and then cloned to HEF-VL-gκ for the V region of the L chain and to HEF-VH-gγ1 for the V region of the H chain. After determination of the DNA sequence, the plasmids containing the DNA fragment that contains the correct DNA sequence were termed HEF-1.24L-gκ and HEF-1.24H-gγ1, respectively.

The regions encoding the respective variable region from the above plasmids HEF-1.24L-gκ and HEF-1.24H-gγ1 were digested with restriction enzymes HindIII and BamHI to make restriction fragments, which were inserted to the HindIII site and the BamHI sites of plasmid vector pUC19 and they were termed pUC19-1.24L-gκ and pUC19-1.24H-gγ1, respectively.

Escherichia coli containing respective plasmids pUC19-1.24L-gκ and pUC19-1.24H-gγ1 were termed Escherichia coli DH5α (pUC19-1.24L-gκ) and Escherichia coli DH5α (pUC19-1.24H-gγ1), and were internationally deposited on Aug. 29, 1996, with the National Institute of Bioscience and Human-Technology, Agency of Industrial Science and Technology, MITI (Higashi 1-Chome 1-3, Tsukuba city, Ibalaki prefecture, Japan) under the accession numbers FERM BP-5646 and FERM BP-5644, respectively, under the provisions of the Budapest Treaty.

2. Transfection into COS-7 Cells

In order to observe the transient expression of the chimeric anti-HM 1.24 antibody, the above expression vectors were tested in the COS-7 (ATCC CRL-1651) cells. HEF-1.24L-gκ and HEF-1.24H-gγ1 were cotransformed into COS-7 cells by electroporation using the Gene Pulser instrument (manufactured by BioRad). Each DNA (10 μg) was added to 0.8 ml aliquots of $1×10^7$-cells/ml in PBS, and was subjected to pulses at 1500 V and a capacity of 25 μF.

After the recovery period of 10 minutes at room temperature, the electroporated cells were added to 30 ml of the DMEM culture liquid (manufactured by GIBCO) containing 10% γ-globulin free bovine fetal serum. After incubation of 72 hours in the $CO_2$ incubator BNA120D (manufactured by TABAI), the culture supernatant was collected, and the cell debris were removed by centrifugation, which were used for the following experiment.

3. FCM Analysis

The antigen binding activity of the chimeric anti-HM 1.24 antibody was investigated by FCM (flow cytometry) analysis using the KPMM2 cells. After $4.7×10^5$ KPMM2 cells (Japanese Unexamined Patent Publication (Kokai) No. 7-236475) were washed with PBS(−), 50 μl of the culture of COS-7 cells that produces the above-mentioned chimeric anti-HM 1.24 antibody and 50 μl of FACS buffer (PBS(−) containing 2% bovine fetal serum and 0.1% sodium azide), or 5 μl of 500 μg/ml purified mouse anti-HM 1.24 antibody and 95 μl of the FACS buffer were added, and incubated on ice for one hour.

As a control, 50 μl of 2 μg/ml chimeric SK2 (International Application Publication No. WO 94-28159) and 50 μl of the FACS buffer, or 5 μl of 500 μg/ml purified mouse IgG2aκ (UPC10) (manufactured by CAPPEL in stead of purified mouse anti-HM 1.24 antibody, and 95 μl of FACS buffer were added, and similarly incubated. After washing with the FACS buffer, 100 μl of 25 μg/ml FITC conjugated goat anti-human antibody (GAH) (manufactured by CAPPEL) or 10 μg/ml FITC conjugated goat anti-mouse antibody (GAM) (manufactured by Becton Dickinson) were added, and incubated at a temperature of ice for 30 minutes. After washing with the FACS buffer, it was suspended in one ml of the FACS buffer, and fluorescence intensity of each cell was measured by the FACScan (manufactured by Becton Dickinson).

As shown in FIG. 1, it was revealed that the chimeric anti-HM 1.24 antibody bound to the KPMM2 cell because the peak of fluorescence intensity shifted to the right in the chimeric anti-HM 1.24 antibody-added cells as compared to the control similarly to the case where mouse anti-HM 1.24 antibody was added. This confirmed that the cloned cDNA encodes the variable region of the mouse anti-HM 1.24 antibody.

Example 5

Establishment of the CHO Cell Line that Stably Produces a Chimeric Anti-HM 1.24 Antibody 1. Construction of an Expression Vector for the Chimeric H Chain After digesting the above plasmid HEF-1.24H-gγ1 with the restriction enzymes PvuI and BamHI, an about 2.8 kbp fragment containing the EF1 promoter and the DNA encoding the V region of the H chain of the mouse anti-HM 1.24 antibody was purified using 1.5% low melting point agarose gel. Then, the above DNA fragment was inserted into an about 6 kbp fragment prepared by digesting the expression vector used for a human H chain expression vector, DHFR-ΔE-Rvh-PM1f (see International Application Publication No. WO 92/19759), containing the DHFR gene and the gene encoding the constant region of a human H chain with PvuI and BamHI to construct an expression vector, DHFR-ΔE-HEF-1.24H-gγ1, for the H chain of the chimeric anti-HM 1.24 antibody.

2. Gene Introduction into CHO Cells

In order to establish a stable production system of the chimeric anti-HM 1.24 antibody, the genes of the above-mentioned expression vectors, HEF-1.24L-gκ and DHFR-ΔE-HEF-1.24H-gγ1, that were linearized by digestion with PvuI were simultaneously introduced into the CHO cell DXB11 (donated from the Medical Research Council Collaboration Center) by the electroporation method under the condition similar to the above-mentioned one (the above-mentioned transfection into the COS-7 cells).

3. Gene Amplification by MTX

Among the gene-introduced CHO cells, only those CHO cells in which both of the L chain and the H chain expression vectors have been introduced can survive in the nucleoside-free α-MEM culture liquid (manufactured by GIBCO-BRL) to which 500 μg/ml G418 (manufactured by GIBCO-BRL) and 10% bovine fetal serum were added, and so they were selected. Subsequently, 10 nM MTX (manufactured by Sigma) was added to the above culture liquid. Among the clones that propagated, those that produce the chimeric anti-HM 1.24 antibody in large amounts were selected. As a result, clones #8-13 that exhibit a production efficiency of about 20 μg/ml of the chimeric antibody were obtained and termed the chimeric anti-HM 1.24 antibody-producing cell lines.

Example 6

Construction of the Chimeric Anti-HM 1.24 Antibody

The chimeric anti-HM 1.24 antibody was constructed in the following method. The above chimeric anti-HM 1.24 antibody-producing CHO cells were subjected to continuous culture for 30 days using as the medium Iscove's Modified Dulbecco's Medium (manufactured by GIBCO-BRL) containing 5% γ-globulin free newborn bovine serum (manufactured by GIBCO-BRL) by the high-density cell culture instrument Verax system 20 (manufactured by CELLEX BIOSCIENCE Inc.).

On day 13, 20, 23, 26, and 30 after starting the culture, the culture liquid was recovered using a pressurized filter unit SARTOBRAN (manufactured by Sartorius), and then the chimeric anti-HM 1.24 antibody was affinity-purified using a large-volume antibody collection system Afi-Prep System (manufactured by Nippon Gaishi) and Super Protein A column (bed volume: 100 ml, manufactured by Nippon Gaishi) using PBS as the absorption/wash buffer and 0.1 M sodium citrate buffer (pH 3) as the elution buffer according to the attached instructions. The eluted fractions were adjusted to about pH 7.4 by immediately adding 1 M Tris-HCl (pH 8.0). Antibody concentration was measured by absorbance at 280 nm and calculated with 1 μg/ml as 1.35 OD.

Example 7

Determination of Activity of the Chimeric Anti-HM 1.24 Antibody

Chimeric anti-HM 1.24 antibody was evaluated by the following binding inhibition activity.

1. Measurement of Binding Inhibition Activity 1-1. Construction of a Biotinylated Anti-HM 1.24 Antibody After the mouse anti-HM 1.24 antibody was diluted with 0.1 M bicarbonate buffer to 4 mg/ml, 4 μl of 50 mg/ml Biotin-N-hydroxy succinimide (manufactured by EY LABS Inc.) was added and reacted at room temperature for 3 hours. Thereafter, 1.5 ml of 0.2 M glycine solution was added thereto, incubated at room temperature for 30 minutes to stop the reaction, and then the biotinylated IgG fractions were collected using the PD-10 column (manufactured by Pharmacia Biotech).

1-2. Measurement of Binding Inhibition Activity

The binding inhibition activity by the biotinylated mouse anti-HM 1.24 antibody was measured by the Cell-ELISA using the human amniotic membrane cell line WISH cells (ATCC CCL 25). The Cell-ELISA plates were prepared as follows. To a 96-well plate was added $4 \times 10^5$ cells/ml prepared with PRMI 1640 medium supplemented with 10% fetal bovine serum, incubated overnight, and after washing twice with PBS(-), were immobilized with 0.1% glutaraldehyde (manufactured by Nakalai tesque).

After blocking, 50 μl of serial dilutions of the chimeric anti-HM 1.24 antibody or the mouse anti-HM 1.24 antibody obtained by affinity-purification was added to each well and simultaneously 50 μl of 2 μg/ml biotinylated mouse anti-HM 1.24 antibody was added, incubated at room temperature for two hours, and then the peroxidase-labelled streptavidin (manufactured by DAKO) was added. After incubating at room temperature for one hour and then washing, the substrate solution was added. After stopping the reaction by adding 50 μl of 6N sulfuric acid, absorbance at 490 nm was measured using the MICROPLATE READER Model 3550 (manufactured by Bio-Rad).

Figure 2:
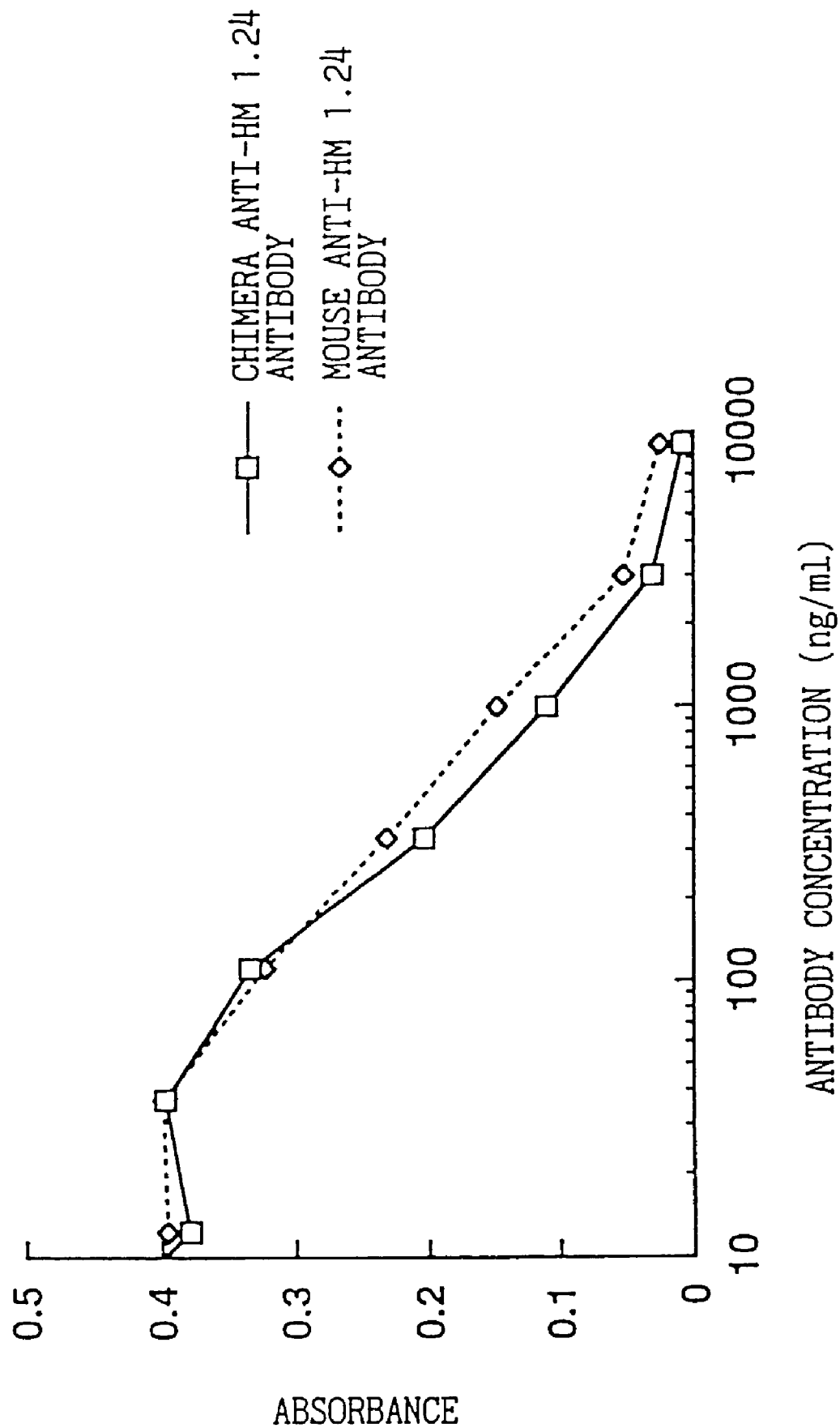
FIG. 2 is a graph showing that, in the Cell-ELISA using the WISH cell, the chimeric anti-HM 1.24 antibody similarly to the mouse anti-HM 1.24 antibody inhibits the binding of the biotinylated mouse anti-HM 1.24 antibody to the WISH cells in a dose dependent manner.

The result, as shown in FIG. 2, revealed that the chimeric anti-HM 1.24 antibody has the identical binding inhibition activity with the mouse anti-HM 1.24 antibody to the biotinylated mouse anti-HM 1.24 antibody. This indicates that the chimeric antibody had the same V region as the mouse anti-HM 1.24 antibody.

Example 8

Measurement of the ADCC Activity of the Chimeric Anti-HM 1.24 Antibody

ADCC (Antibody-dependent Cellular Cytotoxicity) activity was measured according to the method as set forth in Current Protocols in Immunology, Chapter 7. Immunologic studies in humans, Editor, John E, Coligan et al., John Wiley & Sons, Inc., 1993.

1. Preparation of Effector Cells

Monocytes were separated from the peripheral blood or bone marrow of healthy humans and patients with multiple myeloma by the density centrifugation method. Thus, an equal amount of PBS(-) was added to the peripheral blood and the bone marrow of healthy humans and patients with multiple myeloma, which was layered on Ficoll (manufactured by Pharmacia)-Conrey (manufactured by Daiichi Pharmaceutical Co. Ltd.) (specific gravity, 1.077), and was centrifuged at 400 g for 30 minutes. The monocyte layer was collected, and washed twice with RPMI 1640 (manufactured by Sigma) supplemented with 10% fetal bovine serum (manufactured by Witaker), and prepared at a cell density of $5\times10^6$/ml with the same culture liquid.

2. Preparation of Target Cells

The human myeloma cell line RPMI 8226 (ATCC CCL 155) was radiolabelled by incubating in the RPMI 1640 (manufactured by Sigma) supplemented with 10% fetal bovine serum (manufactured by Witaker) together with 0.1 mCi of 51Cr-sodium chromate at 37° C. for 60 minutes. After radiolabelling, cells were washed three times with Hanks balanced salt solution (HBSS) and adjusted to a concentration of $2\times10^5$/ml.

3. ADCC Assay

Into a 96-well U-bottomed plate (manufactured by Corning) were added 50 µl of $2\times10^5$ target cells/ml, 1 µg/ml of affinity-purified chimeric anti-HM 1.24 antibody and mouse anti-HM 1.24 antibody, or control human IgG (manufactured by Serotec), and reacted at 4° C. for 15 minutes.

Then, 100 µl of $5\times10^6$ effector cells/ml was added thereto, and cultured in the $CO_2$ incubator for 4 hours, when the ratio (E:T) of the effector cells (E) to the target cells (T) was set at 0:1, 5:1, 20:1, or 50:1.

One hundred µl of the supernatant was taken and the radioactivity released into the culture supernatant was measured by the gamma counter (ARC361, manufactured by Aloka). For measurement of the maximum radioactivity, 1% NP-40 (manufactured by BRL) was used. Cytotoxicity (%) was calculated by (A−C)/(B−C)×100, wherein A is radioactivity (cpm) released in the presence of antibody, B is radioactivity (cpm) released by NP-40, and C is radioactivity (cpm) released by the culture liquid alone without antibody.

Figure 3:
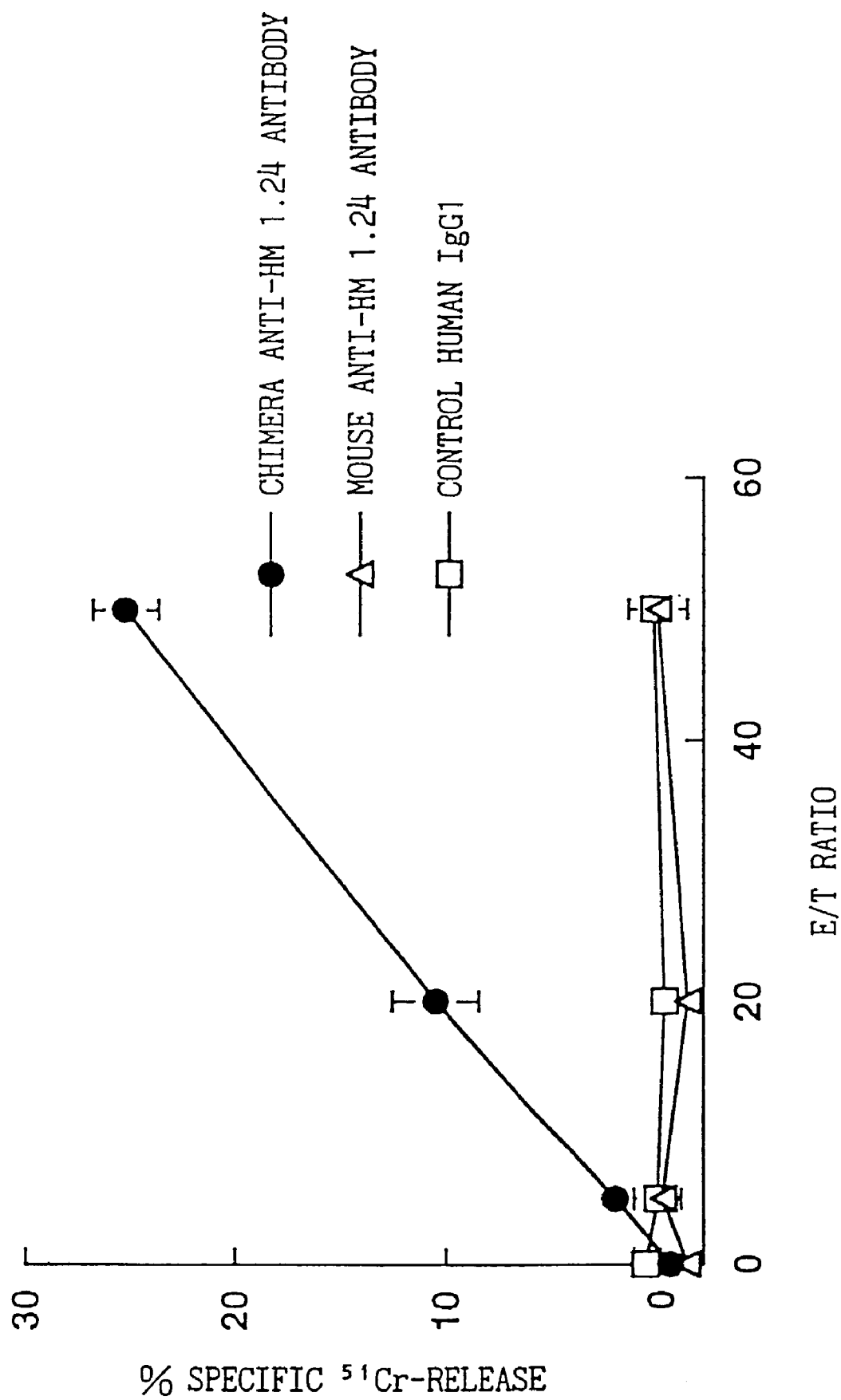
FIG. 3 is a graph showing that the control human IgG1 or the mouse anti-HM 1.24 antibody has no cytotoxicity whereas the chimeric anti-HM 1.24 antibody exhibits increased cytotoxicity to the RPMI 8226 cell with the increased ratio of E/T.

As shown in FIG. 3, when the chimeric anti-HM 1.24 antibody was added as compared to the control IgG1, cytotoxicity increased with the increase in the E:T ratio, which indicated that this chimeric anti-HM 1.24 antibody has ADCC activity. Furthermore, since there was no cytotoxicity observed even when the mouse anti-HM 1.24 antibody was added, it was shown that the Fc portion of human antibody is required to obtain ADCC activity when the effector cell is a human-derived cell.

Example 9

Construction of the Reshaped Human Anti-HM 1.24 Antibody

1. Designing of the V Region of the Reshaped Human Anti-HM 1.24 Antibody.

In order to construct the reshaped human antibody in which the CDR of mouse monoclonal antibody has been grafted to a human antibody, it is preferred that there is a high homology between the FR of the mouse antibody and the FR of the human antibody. Thus, the V regions of the L chain and the H chain of the mouse anti-HM 1.24 antibody were compared to the V regions of all known antibodies whose structure has been elucidated using the Protein Data Bank.

The V region of the L chain of the mouse anti-HM 1.24 antibody is most similar to the consensus sequence of the subgroup IV (HSGIV) of the V region of a human L chain with a homology of 66.4%. On the other hand, It has shown a homology of 56.9%, 55.8%, and 61.5% with HSGI, HSGII and HSG III, respectively.

When the V region of the L chain of the mouse anti-FDI 1.24 antibody is compared to the V region of the L chain of known human antibodies, it has shown a homology of 67.0% with the V region REI of a human L chain, one of the subgroup I of the V region of a human L chain. Thus, the FR of REI was used as the starting material for construction of the V region of the L chain of the reshaped human anti-HM 1.24 antibody.

Version a of the V region of the L chain of the reshaped human anti-HM 1.24 antibody was designed. In this version, human FR was made identical with the REI-based FR present in the reshaped human CAMPATH-1H antibody (see Riechmann, L. et al., Nature 322, 21-25, (1988), the FR contained in version a of the V region of the L chain of the reshaped human PM-1 described in International Application Publication No. WO 92-19759), and the mouse CDR was made identical with the CDR in the V region of the L chain of the mouse anti-HM 1.24 antibody.

The H chain v region of the mouse anti-HM 1.24 antibody is most similar to the consensus sequence of HSGI of the V region of a human H chain with a homology of 54.7%. On the other hand, it shows a homology of 34.6% and 48.1% with HSGII and HSGIII, respectively. When the V region of the H chain of the mouse anti-HM 1.24 antibody is compared to the V region of the H chain of known human antibodies, FR1 to FR3 were most similar to the V region of the H chain of the human antibody HG3, one of subgroup I of the V region of a human H chain (Rechavi, G. et al., Proc. Natl. Acad. Sci. USA, 80, 855-859), with a homology of 67.3%.

Therefore, the FR of the human antibody HG3 was used as the starting material for construction of the V region of the H chain of the reshaped human anti-HM 1.24 antibody. However, since the amino acid sequence of the FR4 of human HG3 has not been described, the amino acid sequence of the FR4 of the human antibody JH6 (Ravetch, J. V. et al., Cell, 27, 583-591) that shows the highest homology with the FR4 of the H chain of the mouse anti-HM 1.24 antibody was used. The FR4 of JH6 has the same amino acid sequence as that of the FR4 of the H chain of the mouse anti-HM 1.24 antibody except one amino acid.

In the first version a of the V region of the H chain of the reshaped human anti-HM 1.24 antibody, FR1 to FR3 were made identical with the FR1 to FR3 of human HG3, and the CDR was made identical with the CDR of the V region of the H chain of the mouse anti-HM 1.24 antibody, except that the amino acids at position 30 in the human FR1 and position 71 in the human FR3 were made identical with the amino acids in the mouse anti-HM 1.24 antibody.

2. Construction of the V Region of the L Chain of the Reshaped Human Anti-HM 1.24 Antibody The L chain of the reshaped human anti-HM 1.24 antibody was constructed by the CDR grafting in the PCR method. The method is shown in FIG. 4. Eight PCR primers were used for construction of the reshaped human anti-HM 1.24 antibody (version a) having the FR derived from the human antibody REI. The external primers A (SEQ ID NO: 47) and H (SEQ ID NO: 48) were designed to hybridize with the DNA sequence of the expression vector HEF-VL-gκ.

The CDR grafting primers L1S (SEQ ID NO: 49), L2S (SEQ ID NO: 50), and L3S (SEQ ID NO: 51) have the sense DNA sequence. The CDR grafting primers L1A (SEQ ID NO: 52), L2A (SEQ ID NO: 53), and L3A (SEQ ID NO: 54) have the antisense DNA sequence, each having a complementary DNA sequence (20 to 23 bp) to the DNA sequence at the 5'-end of the primers L1S, L2S, and L3S, respectively.

In the first stage of PCR, the four reactions A-L1A, L1S-L2A, L2S-L3A, and L3S-H were conducted to purify each PCR product. The four PCR products from the first PCR were allowed to assemble with one another by their own complementarity (see International Application Publication No. WO 92-19759). Then, external primers A and H were added to amplify the full-length DNA encoding the V region of the L chain of the reshaped human anti-HM 1.24 antibody (the second PCR). In the above-mentioned PCR, the plasmid HEF-RVL-M21a (see International Application Publication No. WO 95-14041) encoding the version a of the V region of the L chain of the reshaped human ONS-M21 antibody based on the human antibody REI-derived FR was employed as a template.

In the first stage of PCR, the PCR mixture containing 10 mM Tris-HCl (pH 8.3), 50 mM KCl, 0.1 mM dNTPs, 1.5 mM $MgCl_2$, 100 ng of template DNA, 100 pmole of each primer, and 5 u of Ampli Taq was used. Each PCR tube was covered with 50 μl of mineral oil. Then after it was first denatured by heating at 94° C., it was subjected to a reaction cycle of 94° C. for 1 minute, 55° C. for 1 minute and 72° C. for 1 minute, and then was incubated at 72° C. for 10 minutes.

PCR products A-L1A (215 bp), L1S-L2A (98 bp), L2S-L3A (140 bp), and L3S-H (151 bp) were purified using 1.5% low melting point agarose gel and were assembled in the second PCR. In the second PCR, 98 μl of PCR mixture containing 1 μg each of the first stage PCR products and 5 u of Ampli Taq was incubated for 2 cycles of 94° C. for 2 minutes, 55° C. for 2 minutes, and 72° C. for 2 minutes, and then 100 pmole each of the external primers (A and H) was added. The PCR tube was coated with 50 μl of mineral oil and 30 cycles of PCR were conducted under the same condition as above.

A 516 bp DNA fragment resulting from the second PCR was purified using 1.5% low melting point agarose gel, digested with BamHI and HindIII, and the DNA fragments thus obtained were cloned into the HEF expression vector HEF-VL-gκ. After determining the DNA sequence, the plasmid containing the DNA fragment having the correct amino acid sequence of the V region of the L chain of the reshaped human anti-HM 1.24 antibody was termed plasmid HEF-RVLa-AHM-gκ. The amino acid sequence and the base sequence of the V region of L chain contained in this plasmid HEF-RVLa-AHM-gκ are shown in SEQ ID NO: 9.

The version b of the V region of the L chain of the reshaped human anti-HM 1.24 antibody was constructed by mutagenesis using PCR. Mutagen primers FTY-1 (SEQ ID NO: 55) and FTY-2 (SEQ ID NO: 56) were so designed as to mutate phenylalanine at position 71 to tyrosine.

After the above primers were amplified using the plasmid HEF-RVLa-AHM-gκ as a template, the final product was purified and digested with BamHI and HindIII. The DNA fragments obtained were cloned into the HEF expression vector HEF-VL-gκ to obtain plasmid HEF-RVLb-AHM-gκ. The amino acid sequence and the base sequence of the V region of the L chain contained in this plasmid HEF-RVLb-AHM-gκ are shown in SEQ ID NO: 10.

3. Construction of the V Region of the H Chain of the Reshaped Human Anti-HM 1.24 Antibody 3-1. Construction of Versions a to e of the V Region of the H Chain of the Reshaped Human Anti-HM 1.24 Antibody DNA encoding the V region of the H chain of the reshaped human anti-HM 1.24 antibody was designed as follows. By linking the DNA sequence encoding the FR1 to 3 of the human antibody HG3 and the FR4 of the human antibody JH6 to the DNA sequence encoding the CDR of the V region of the H chain of the mouse anti-HM 1.24 antibody, the full length DNA encoding the V region of the H chain of the reshaped human anti-HM 1.24 antibody was designed.

Then, to the 5'-end and the 3'-end of this DNA sequence the HindIII recognition site/KOZAK consensus sequence and BamHI recognition site/splice donor sequence, respectively, were attached so as to enable insertion of the HEF expression vector.

The DNA sequence thus designed was divided into four oligonucleotides. Subsequently, oligonucleotides which potentially hinder assembly of these oligonucleotides were subjected to computer analysis for the secondary structure. The sequences of the four oligonucleotides RVH1 to RVH4 are shown in SEQ ID NO: 57 to 60. These oligonucleotides have a length of 119 to 144 bases and have the 25 to 26 bp overlapping region. Among the oligonucleotides, RVH2 (SEQ ID NO: 58) and RVH4 (SEQ ID NO: 60) have the sense DNA sequence, and RVH1 (SEQ ID NO: 57) and RVH3 (SEQ ID NO: 59) have the antisense DNA sequence. The method for assembling these four oligonucleotides by the PCR method is shown in the figure (see FIG. 5).

The PCR mixture (98 μl) containing 100 ng each of the four oligonucleotides and 5 u of Ampli Taq was first denatured by heating at 94° C. for 2 minutes, and was subjected to two cycles of incubation comprising 94° C. for 2 minutes, 55° C. for 2 minutes and 72° C. for 2 minutes. After 100 pmole each of RHP1 (SEQ ID NO: 61) and RHP2 (SEQ ID NO: 62) were added as the external primer, the PCR tube was coated with 50 μl of mineral oil. Then it was first denatured by heating at 94° C. for 1 minute, and then was subjected to 38 cycles of 94° C. for 1 minute, 55° C. for 1 minute and 72° C. for 1 minute, and then was incubated at 72° C. for 10 minutes.

The 438 bp DNA fragment was purified using 1.5% low melting point agarose gel, digested with HindIII and BamHI, and then cloned into the HEF expression vector HEF-VH-gγ1. After determination of the base sequence, the plasmid that contains the DNA fragment encoding the amino acid sequence of the correct V region of the H chain was termed HEF-RVHa-AHM-gγ1. The amino acid sequence and the base sequence of the V region of the H chain contained in this plasmid HEF-RVHa-AHM-gγ1 are shown in SEQ ID NO: 11.

Each of versions b, c, d, and e of the V region of the H chain of the reshaped human anti-HM 1.24 antibody was constructed as follows.

Using as the mutagen primer BS (SEQ ID NO: 63) and BA (SEQ ID NO: 64) designed to mutate arginine at position 66 to lysine and as a template DNA the plasmid HEF-RVHa-AHM-gγ1 by the PCR method, version b was amplified to obtain plasmid HEF-RVHb-AHM-gγ1. The amino acid sequence and the base sequence of the V region of the H chain contained in this plasmid HEF-RVHb-AHM-gγ1 are shown in SEQ ID NO: 12.

Using as the mutagen primer CS (SEQ ID NO: 65) and CA (SEQ ID NO: 66) designed to mutate threonine at position 73 to lysine and as a template DNA the plasmid HEF-RVHa-AHM-gγ1 by the PCR method, version c was amplified to obtain plasmid HEF-RVHc-AHM-gγ1. The amino acid sequence and the base sequence of the V region of the H chain contained in this plasmid HEF-RVHc-AHM-gγ1 are shown in SEQ ID NO: 13.

Using as the mutagen primer DS (SEQ ID NO: 67) and DA (SEQ ID NO: 68) designed to mutate arginine at position 66 to lysine and threonine at position 73 to lysine and as a template DNA the plasmid HEF-RVHa-AHM-gγ1 by the PCR method, version d was amplified to obtain plasmid HEF-RVHd-AHM-gγ1. The amino acid sequence and the base sequence of the V region of the H chain contained in this plasmid HEF-RVHd-AHM-gγ1 are shown in SEQ ID NO: 14.

Using as the mutagen primer ES (SEQ ID NO: 69) and EA (SEQ ID NO: 70) designed to mutate valine at position 67 to alanine and methionine at position 69 to leucine and as a template DNA the plasmid HEF-RVHa-AHM-gγ1, version e was amplified to obtain plasmid HEF-RVHe-AHM-gγ1. The amino acid sequence and the base sequence of the V region of the H chain contained in this plasmid HEF-RVHe-AHM-gγ1 are shown in SEQ ID NO: 15.

3-2. Construction of the H Chain Hybrid V Region

Two H chain hybrid V regions were constructed. One is a mouse human hybrid anti-HM 1.24 antibody in which the amino acid sequences of FR1 and FR2 are derived from the mouse anti-HM 1.24 antibody and those of FR3 and FR4 are from version a of the V region of the H chain of the reshaped human anti-HM 1.24 antibody, and the other is human mouse hybrid anti-HM 1.24 antibody in which the amino acid sequences of FR1 and FR2 are derived from version a of the V region of the H chain of the reshaped human anti-HM 1.24 antibody and those of FR3 and FR4 are from the mouse anti-HM 1.24 antibody. The amino acid sequences of the CDR regions are all derived from mouse anti-HM 1.24 antibody.

Two H chain hybrid V regions were constructed by the PCR method. The method is schematically shown in FIGS. 6 and 7. For the construction of two H chain hybrid V regions, four primers were used. The external primers a (SEQ ID NO: 71) and h (SEQ ID NO: 72) were designed to hybridize with the DNA sequence of the HEF expression vector HEF-VH-gγ1. The H chain hybrid construction primer HYS (SEQ ID NO: 73) was designed to have the sense DNA sequence and the H chain hybrid primer HYA (SEQ ID NO: 74) to have the antisense DNA sequence so that the DNA sequence are complementary to each other.

For the construction of the H chain hybrid V region in which the amino acid sequences of FR1 and FR2 are derived from the mouse anti-HM 1.24 antibody and those of FR3 and FR4 are from version a of the V region of the H chain of the reshaped human anti-HM 1.24 antibody, PCR using the plasmid HEF-1.24H-gyl as a template, the external primer a, and the H chain hybrid primer HYA, and PCR using the plasmid HEF-RVHa-AHM-gγ1 as a template, the H chain hybrid primer HYS (SEQ ID NO: 73), and the external primer h (SEQ ID NO: 72) were carried out in the first stage of PCR and each PCR product was purified. The two PCR products from the first PCR were allowed to assemble by their own complementarity (see International Application Publication No. WO 92-19759).

Then, by adding the external primers a (SEQ ID NO: 71) and h (SEQ ID NO: 72) a full-length DNA encoding the H chain hybrid V region in which the amino acid sequences of FR1 and FR2 are derived from the mouse anti-HM 1.24 antibody and those of FR3 and FR4 are from version a of the V region of the H chain of the reshaped human anti-HM 1.24 antibody was amplified in the second PCR stage.

For the construction of the H chain hybrid V region in which the amino acid sequences of FR1 and FR2 are derived from version a of the V region of the H chain of the reshaped human anti-HM 1.24 antibody and those of FR3 and FR4 are from the mouse anti-HM 1.24 antibody, PCR using the plasmid HEF-RVHa-AHM-gγ1 as a template, the external primer a, and the H chain hybrid primer HYA, and PCR using the plasmid HEF-1.24H-gγ1 as a template, the H chain hybrid primer HYS, and the external primer h were carried out in the first stage of PCR and each PCR product was purified. The two PCR purified products from the first PCR were allowed to assemble by their own complementarity (see International Application Publication No. WO 92-19759).

Then, by adding the external primers a and h, a full-length DNA encoding the H chain hybrid V region in which the amino acid sequences of FR1 and FR2 are derived from version a of the V region of the H chain of the reshaped human anti-HM 1.24 antibody and those of FR3 and FR4 are from the mouse anti-HM 1.24 antibody was amplified in the second PCR stage.

The methods of the first PCR, purification of PCR products, assembling, the second PCR, and cloning into the HEF expression vector HEF-VH-gγ1 were carried out according to the methods shown in "Example 9. Construction of the V region of the L chain of the reshaped human anti-HM 1.24 antibody".

After determination of the DNA sequence, the plasmid that contains the DNA fragment encoding the correct amino acid sequence of the H chain hybrid V region in which the amino acid sequences of FR1 and FR2 are derived from the mouse anti-HM 1.24 antibody and those of FR3 and FR4 are from version a of the V region of the H chain of the reshaped human anti-HM 1.24 antibody was termed HEF-MH-RVH-AHM-gγ1. The jamino acid sequence and the base sequence of the V region of the H chain contained in this plasmid HEF-MH-RVH-AHM-gγ1 are shown in SEQ ID NO: 75. Also, the plasmid that contains the DNA fragment encoding the correct amino acid sequence of the H chain hybrid V region in which the amino acid sequences of FR1 and FR2 are derived from version a of the V region of the H chain of the reshaped human anti-HM 1.24 antibody and those of FR3 and FR4 are from the mouse anti-HM 1.24 antibody was termed HEF-HM-RVH-AHM-gγ1. The amino acid sequence and the base sequence of the V region of the H chain contained in this plasmid HEF-HM-RVH-AHM-gγ1 are shown in SEQ ID NO: 76.

3-3. Construction of Versions f to s of the V Region of the H Chain of the Reshaped Human Anti-HM 1.24 Antibody Each of versions f, g, h, i, j, k, l, m, n, o, p, q, r, and s of the v region of the H chain of the reshaped human anti-HM 1.24 antibody were constructed as follows.

Using as the mutagen primer FS (SEQ ID NO: 78) and FA (SEQ ID NO: 79) designed to mutate threonine at position 75 to serine and valine at position 78 to alanine and as a template DNA the plasmid HEF-RVHe-AHM-gγ1 by the PCR method, version f was amplified to obtain plasmid HEF-RVHf-AHM-gγ1. The amino acid sequence and the base sequence of the V region of the H chain contained in this plasmid HEF-RVHf-AHM-gγ1 are shown in SEQ ID NO: 16.

Using as the mutagen primer GS (SEQ ID NO: 80) and GA (SEQ ID NO: 81) designed to mutate alanine at position 40 to arginine and as a template DNA the plasmid HEF-RVHa-AHM-gγ1, version g was amplified to obtain plasmid HEF-RVHg-AHM-gγ1. The amino acid sequence and the base sequence of the V region of the H chain contained in this plasmid HEF-RVHg-AHM-gγ1 are shown in SEQ ID NO: 17.

Using as the mutagen primer FS (SEQ ID NO: 78) and FA (SEQ ID NO: 79) and as a template DNA the plasmid HEF-RVHb-AHM-gγ1, version h was amplified to obtain plasmid HEF-RVHh-AHM-gγ1. The amino acid sequence and the base sequence of the V region of the H chain contained in this plasmid HEF-RVHh-AHM-gγ1 are shown in SEQ ID NO: 18.

Using as the mutagen primer IS (SEQ ID NO: 82) and IA (SEQ ID NO: 83) designed to mutate arginine at position 83 to alanine and serine at position 84 to phenylalanine as a template DNA the plasmid HEF-RVHh-AHM-gγ1, version i was amplified to obtain plasmid HEF-RVHi-AHM-gγ1. The amino acid sequence and the base sequence of the V region of the H chain contained in this plasmid HEF-RVHi-AHM-gγ1 are shown in SEQ ID NO: 19.

Using as the mutagen primer JS (SEQ ID NO: 84) and JA (SEQ ID NO: 85) designed to mutate arginine at position 66 to lysine and as a template DNA the plasmid HEF-RVHf-AHM-gγ1, version j was amplified to obtain plasmid HEF-RVHj-AHM-gγ1. The amino acid sequence and the base sequence of the V region of the H chain contained in this plasmid HEF-RVHj-AHM-gγ1 are shown in SEQ ID NO: 20.

Using as the mutagen primer KS (SEQ ID NO: 86) and KA (SEQ ID NO: 87) designed to mutate glutamic acid at position 81 to glutamine and as a template DNA the plasmid HEF-RVHh-AHM-gγ1, version k was amplified to obtain plasmid HEF-RVHk-AHM-gγ1. The amino acid sequence and the base sequence of the V region of the H chain contained in this plasmid HEF-RVHk-AHM-gγ1 are shown in SEQ ID NO: 21.

Using as the mutagen primer LS (SEQ ID NO: 88) and LA (SEQ ID NO: 89) designed to mutate glutamic acid at position 81 to glutamine and serine at position 82B to isoleucine and as a template DNA the plasmid HEF-RVHh-AHM-gγ1, version l was amplified to obtain plasmid HEF-RVHl-AHM-gγ1. The amino acid sequence and the base sequence of the V region of the H chain contained in this plasmid HEF-RVHl-AHM-gγ1 are shown in SEQ ID NO: 22.

Using as the mutagen primer MS (SEQ ID NO: 90) and MA (SEQ ID NO: 91) designed to mutate glutamic acid at position 81 to glutamine, serine at position 82b to isoleucine, and threonine at position 87 to serine and as a template DNA the plasmid HEF-RVHh-AHM-gγ1, version m was amplified to obtain plasmid HEF-RVHm-AHM-gγ1. The amino acid sequence and the base sequence of the V region of the H chain contained in this plasmid HEF-RVHm-AHM-gγ1 are shown in SEQ ID NO: 23.

Using as the mutagen primer NS (SEQ ID NO: 92) and NA (SEQ ID NO: 93) designed to mutate serine at position 82B to isoleucine and as a template DNA the plasmid HEF-RVHh-AHM-gγ1, version n was amplified to obtain plasmid HEF-RVHn-AHM-gγ1. The amino acid sequence and the base sequence of the V region of the H chain contained in this plasmid HEF-RVHn-AHM-gγ1 are shown in SEQ ID NO: 24.

Using as the mutagen primer OS (SEQ ID NO: 94) and OA (SEQ ID NO: 95) designed to mutate threonine at position 87 to serine and as a template DNA the plasmid HEF-RVHh-AHM-gγ1, version o was amplified to obtain plasmid HEF-RVHo-AHM-gγ1. The amino acid sequence and the base sequence of the V region of the H chain contained in this plasmid HEF-RVHo-AHM-gγ1 are shown in SEQ ID NO: 25.

Using as the mutagen primer PS (SEQ ID NO: 96) and PA (SEQ ID NO: 97) designed to mutate valine at position 78 to alanine and as a template DNA the plasmid HEF-RVHa-AHM-gγ1, version p was amplified by the PCR method to obtain plasmid HEF-RVHp-AHM-gγ1. The amino acid sequence and the base sequence of the V region of the H chain contained in this plasmid HEF-RVHp-AHM-gγ1 are shown in SEQ ID NO: 26.

Using as the mutagen primer QS (SEQ ID NO: 98) and QA (SEQ ID NO: 99) designed to mutate threonine at position 75 to serine and as a template DNA the plasmid HEF-RVHa-AHM-gγ1, version q was amplified by the PCR method to obtain plasmid HEF-RVHq-AHM-gγ1. The amino acid sequence and the base sequence of the V region of the H chain contained in this plasmid HEF-RVHq-AHM-gγ1 are shown in SEQ ID NO: 27.

Using as the mutagen primer CS (SEQ ID NO: 65) and CA (SEQ ID NO: 66) and as a template DNA the plasmid HEF-RVHp-AHM-gγ1, version r was amplified by the PCR method to obtain plasmid HEF-RVHr-AHM-gγ1. The amino acid sequence and the base sequence of the V region of the H chain contained in this plasmid HEF-RVHr-AHM-gγ1 are shown in SEQ ID NO: 28.

Version s of the V region of the H chain of the reshaped human anti-HM 1.24 antibody was constructed by mutagenesis using PCR. The mutagen primers SS (SEQ ID NO: 100) and SA (SEQ ID NO: 101) were designed to mutate methionine at position 69 to isoleucine.

After the above primer was amplified using plasmid HEF-RVHr-AHM-gγ1 as a template, the final product was purified, digested with BamHI and HindIII, and the DNA fragment obtained was cloned into the HEF expression vector HEF-VH-gγ1 to obtain plasmid HEF-RVHs-AHM-gγ1. The amino acid sequence and the base sequence of the V region of the H chain contained in this plasmid HEF-RVHs-AHM-gγ1 are shown in SEQ ID NO: 102.

The regions encoding the variable region of each of the above-mentioned plasmids HEF-RVLa-AHM-gκ and HEF-RVHr-AHM-gγ1 were digested to make restriction fragments with restriction enzymes HindIII and BamHI. They were inserted into the HindIII and BamHI sites of pIrsmid vector pUC19. Each plasmid was termed pUC19-RVLa-AHM-gκ and pUC19-RVHr-AHM-gγ1.

The *Escherichia coli* that contains each of the plasmids pUC19-RVLa-AHM-gκ and pUC19-RVHr-AHM-gγ1 was termed *Escherichia coli* DH5α (pUC19-RVLa-AHM-gκ) and *Escherichia coli* DH5α (pUC19-RVHr-AHM-gγ1), respectively, and has been internationally deposited on Aug. 29, 1996, with the National Institute of Bioscience and Human-Technology, Agency of Industrial Science and Technology, MITI (Higashi 1-Chome 1-3, Tsukuba city, Ibalaki prefecture, Japan) under the accession number FERM BP-5645 and FERM BP-5643, respectively, under the provisions of the Budapest Treaty.

The regions encoding the variable region of the above-mentioned plasmid HEF-RVHs-AHM-gγ1 were digested to make a restriction fragment with restriction enzymes HindIII and BamHI. They were inserted into the HindIII and BamHI sites of plasmid vector pUC19. The plasmid obtained was termed pUC19-RVHs-AHM-gγ1.

The *Escherichia coli* that contains the plasmid pUC19-RVHs-AHM-gγ1 was termed *Escherichia coli* DH5α (pUC19-RVHs-AHM-gγ1), and has been internationally deposited on Sep. 29, 1997, with the National Institute of Bioscience and Human-Technology, Agency of Industrial Science and Technology, MITI (Higashi 1-Chome 1-3, Tsukuba city, Ibalaki prefecture, Japan) under the accession number FERM BP-6127 under the provisions of the Budapest Treaty.

4. Construction of the Reshaped Human Anti-HM 1.24 Antibody, the Chimeric Anti-HM 1.24 Antibody, and the H chain Hybrid Antibody In order to evaluate each chain of the reshaped human anti-HM 1.24 antibody, the reshaped human anti-HM 1.24 antibody and the chimeric anti-HM 1.24 antibody as a positive control antibody were allowed to express. In constructing each of version b and after of the V region of the H chain of the reshaped human anti-HM 1.24 antibody, the H chain hybrid antibody was allowed to express in order to investigate which amino acid sequence in the FR should be substituted. Furthermore, it was expressed in combination with the chimeric H chain in order to evaluate version a of L chain of the reshaped human anti-HM 1.24 antibody.

4-1. Expression of the Reshaped Human Anti-HM 1.24 Antibody (1)

Ten μg each of the expression vector (HEF-RVHa-AHM-gγ1 to HEF-RVHr-AHM-gγ1) for the H chain of the reshaped human anti-HM 1.24 antibody and the expression vector (HEF-RVLa-AHM-gκ or HEF-RVLb-AHM-gκ) for the L chain of the reshaped human anti-HM 1.24 antibody were cotransformed into COS-7 cells by electroporation using the Gene Pulser instrument (manufactured by BioRad). Each DNA (10 μg) was added to 0.8 ml aliquots of $1 \times 10^7$ cells/ml in PBS, and was subjected to pulses at 1500 V and a capacity of 25 μF.

After the recovery period of 10 minutes at room temperature, the electroporated cells were added to 30 ml of DMEM culture medium (manufactured by GIBCO) containing 10% γ-globulin free fetal bovine serum. After incubation of 72 hours in the $CO_2$ incubator BNA120D (manufactured by TABAI) under the condition of 37° C. and 5% $CO_2$, the culture supernatant was collected, the cell debris were removed by centrifugation at 1000 rpm for 5 minutes in a centrifuge 15PR-22 (manufactured by HITACHI) equipped with a centrifuge rotor 03 (manufactured by HITACHI), and the microconcentrator (Centricon 100, manufactured by Amicon) was ultrafiltrated using a centrifuge J2-21 (manufactured by BECKMAN) equipped with a centrifuge rotor JA-20.1 (manufactured by BECKMAN), and was used for Cell-ELISA.

Expression of the Reshaped Human Anti-HM 1.24 Antibody (2)

Ten μg each of the expression vector (HEF-RVHs-AHM-gγ1) for version "s" of the H chain of the reshaped human anti-HM 1.24 antibody and the expression vector (HEF-RVLa-AHM-gκ) for the L chain of the reshaped human anti-HM 1.24 antibody were cotransformed into COS-7 cells by electroporation using the Gene Pulser instrument (manufactured by BioRad). Each DNA (10 μg) was added to 0.8 ml aliquots of $1 \times 10^7$ cells/ml in PBS, and was subjected to pulses at 1500 V and a capacity of 25 μF.

After the recovery period of 10 minutes at room temperature, the electroporated cells were added to 30 ml of DMEM culture medium (manufactured by GIBCO) containing 10% γ-globulin free fetal bovine serum. After incubation of 72 hours in the $CO_2$ incubator BNA120D (manufactured by TABAI) under the condition of 37° C. and 5% $CO_2$, the culture supernatant was collected, the cell debris were removed by centrifugation at 1000 rpm for 5 minutes in a centrifuge 05PR-22 (manufactured by HITACHI) equipped with a centrifuge rotor 03 (manufactured by HITACHI), and the microconcentrator (Centricon 100, manufactured by Amicon) was concentrated by ultrafiltration using a centrifuge J2-21 (manufactured by BECKYAN) equipped with a centrifuge rotor JA-20.1 (manufactured by BECKMAN), and was filtration-sterilized using a filter, Millex GV13mm (manufactured by Millipore), which was used for Cell-ELISA.

4-2. Expression of the Chimeric Anti-HM 1.24 Antibody

Using Ten μg each of the expression vector HEF-1.24H-gγ1 for the H chain of the chimeric anti-HM 1.24 antibody and the expression vector HEF-1.24L-gκ for the L chain of the chimeric anti-HM 1.24 antibody, the chimeric anti-HM 1.24 antibody to be used for Cell-ELISA was prepared according to the above-mentioned method for expression of the reshaped human anti-HM 1.24 antibody.

4-3. Expression of the Anti-HM 1.24 Antibody Comprising Version a of the Humanized L Chain and the Chimeric H Chain Using Ten μg each of the expression vector HEF-1.24H-gγ1 for the H chain of the chimeric anti-HM 1.24 antibody and the expression vector HEF-RVLa-AHM-gκ for version a of the L chain of the reshaped human anti-HM 1.24 antibody, the anti-HM 1.24 antibody comprising version a of the humanized L chain and the chimeric H chain to be used for Cell-ELISA was prepared according to the above-mentioned method for expression of the reshaped human anti-HM 1.24 antibody.

4-4. Expression of the H Chain Hybrid Antibody

Using Ten μg each of the expression vector (HEF-MH-RVH-AHM-gγ1 or HEF-HM-RVH-AHM-gγ1) for the V region of the H chain hybrid and the expression vector HEF-RVLa-AHM-gκ for the L chain of the reshaped human anti-HM 1.24 antibody, the H chain hybrid antibody to be used for Cell-ELISA was prepared according to the above-mentioned method for expression of the reshaped human anti-HM 1.24 antibody.

4-5. Measurement of Antibody Concentration

Concentration of the antibody obtained was measured by ELISA. Each well of a 96-well ELISA plate (Maxisorp, manufactured by NUNC) was immobilized by adding 100 μl of goat anti-human IgG antibody (manufactured by BIO SOURCE) prepared to a concentration of 1 μg/ml with the coating buffer (0.1 M $NaHCO_3$, 0.02% $NaN_3$ pH 9.6) and incubating at room temperature for one hour. After blocking with 100 μl of the dilution buffer (50 mM Tris-HCl, 1 mM $MgCl_2$, 0.15 M NaCl, 0.05% Tween 20, 0.02% $NaN_3$, 1% bovine serum albumin (BSA), pH 8.1), 100 μl each of serial dilutions of the culture supernatant of cos-7 cells secrating the reshaped human anti-HM 1.24 antibody, the chimeric anti-HM 1.24 antibody, or the H chain hybrid antibody that were concentrated by ultrafiltration were added to each well and incubated at room temperature for one hour. Then after washing, 100 μl of alkaline phosphatase-labelled goat anti-human IgG antibody (manufactured by DAKO) was added.

After incubating at room temperature for one hour and washing, 100 μl of 1 μg/ml substrate solution (Sigma104, p-nitrophenyl phosphate, SIGMA) dissolved in the substrate buffer (50 mM $NaHCO_3$, 10 mM $MgCl_2$, pH 9.8) was added, and then the absorbance at 405 nm was measured using the MICROPLATE READER Model 3550 (manufactured by Bio Rad). As the standard for the measurement of concentration, human IgG1κ (manufactured by The binding Site) was used.

5. Establishment of the CHO Cell Line that Stably Produces the Reshaped Human Anti-HM 1.24 Antibody 5-1. Construction of the Expression Vector for the H Chain of the Reshaped Human Anti-HM 1.24 Antibody By digesting plasmid HEF-RVHr-AHM-gγ1 with the restriction enzymes PvuI and BamHI, an about 2.8 kbp fragment containing the DNA encoding the EF1 promoter and the V region of the H chain of the reshaped human anti-HM 1.24 antibody was purified using 1.5% low melting point agarose gel. Then, the above DNA fragment was inserted into an about 6 kbp fragment that was prepared by digesting the expression vector used for a human H chain expression vector, DHFR-ΔE-RVh-PM1f (International Application Publication No. WO 92-19759), containing the DHFR gene and the gene encoding the constant region of a human H chain with PvuI and BamHI to construct an expression vector, DHFR-ΔE-HEF-RVHr-AHM-gγ1, for the H chain of the reshaped anti-HM 1.24 antibody.

5-2. Gene Introduction into CHO Cells

In order to establish a stable production system of the reshaped human anti-HM 1.24 antibody, the genes of the above-mentioned expression vectors, DHFR-ΔE-HEF-RVHr-AHM-gγ1 and HEF-RVLa-AHM-gκ, that were linearized by digestion with PvuI were simultaneously introduced into the CHO cell DXB-11 by the electroporation method under the condition similar to the above-mentioned one (transfection into the above-mentioned COS-7 cells).

5-3. Gene Amplification by MTX

Among the gene-introduced CHO cells, only those CHO cells in which both of L chain and H chain expression vectors have been introduced can survive in the nucleoside-free α-MEM culture medium (manufactured by GIBCO-BRL) to which 500 μg/ml G418 (manufactured by GIBCO-BRL) and 10% fetal bovine serum were added, and so they were selected. Subsequently, 10 nM MTX (manufactured by Sigma) was added to the above culture medium. Among the clones that propagated, those that produce the reshaped human anti-HM 1.24 antibody in large amounts were selected. As a result, clone 1 that exhibits a production efficiency of about 3 μg/ml of the reshaped human anti-HM 1.24 antibody was obtained and termed the reshaped human anti-HM 1.24 antibody-producing cell line.

5-4. Construction of the Reshaped Human Anti-HM 1.24 Antibody

The reshaped anti-HM 1.24 antibody was constructed in the following method. The above CHO cells that produce the reshaped human anti-HM 1.24 antibody were cultured for 10 days using as the medium the nucleoside-free α-MEM culture medium (manufactured by GIBCO-BRL) to which 500 μg/ml G418 (manufactured by GIBCO-BRL) and 10% γ-free fetal bovine serum were added using the $CO_2$ incubator BNAS120D (manufactured by TABAI) under the condition of 37° C. and 5% $CO_2$. On day 8 and 10 after starting the culture the culture liquid was recovered, the cell debris were removed by centrifuging for 10 minutes at 2000 rpm using the centrifuge RL-500SP (manufactured by Tomy Seiko) equipped with the TS-9 rotor, and then filter-sterilized using a bottle top filter (manufactured by FALCON) having a membrane of 0.45 μm in diameter.

After an equal amount of PBS(−) was added to the culture liquid of the CHO cells that produce the reshaped human anti-HM 1.24 antibody, then the reshaped human anti-HM 1.24 antibody was affinity-purified using the high-speed antibody purification system ConSep LC100 (manufactured by MILLIPORE) and Hyper D Protein A column (manufactured by Nippon Gaishi) using PBS(−) as the absorption/wash buffer and 0.1 M sodium citrate buffer (pH 3) as the elution buffer according to the attached instructions. The eluted fractions were adjusted to about pH 7.4 by immediately adding 1 M Tris-HCl (pH 8.0) and then using the centrifuging ultrafiltration concentrator Centriprep-10 (manufactured by MILLIPORE), concentration and substitution to PBS(−) was carried out and filter-sterilized using a membrane filter MILLEX-GV (manufactured by MILLIPORE) with a pore size of 0.22 μm to obtain the purified reshaped human anti-HM 1.24 antibody. Antibody concentration was measured by absorbance at 280 nm and calculated with 1 mg/ml as 1.35 OD.

Example 11

Determination of Activity of the Reshaped Human Anti-HM 1.24 Antibody

The reshaped human anti-HM 1.24 antibody was evaluated for the following antigen binding activity and binding inhibition activity.

1. The Method of Measurement of Antigen Binding Activity and Binding Inhibition Activity 1-1. Measurement of Antigen Binding Activity Antigen binding activity was measured by the Cell-ELISA using WICH cells. Cell-ELISA plates were prepared as described in the above Example 7.1-2.

After blocking, 100 μl of serial dilutions of the reshaped human anti-HM 1.24 antibody that was obtained from the concentrate of the culture supernatant of COS-7 cells or purified from the culture supernatant of CHO cells was added to each well. After it was incubated for 2 hours at room temperature and washed, peroxidase-labelled rabbit anti-human IgG antibody (manufactured by DAKO) was added. After it was incubated for 1 hour at room temperature and washed, 100 μl of substrate solution was added in each well. After incubation, the reaction was stopped by 50 μl of 6N sulfuric acid, and absorbance at 490 nm was measured using the MICROPLATE READER Model 3550 (manufactured by Bio-Rad).

1-2. Measurement of Binding Inhibition Activity

The binding inhibition activity by the biotin-labelled mouse anti-HM 1.24 antibody was measured by the Cell-ELISA using WISH cells. Cell ELISA plates were prepared as described in the above Example 7. 1-2. After blocking, 50 μl of serial dilutions of the reshaped human anti-HM 1.24 antibody that was obtained from the concentrate of the culture supernatant of COS-7 cells or purified from the culture supernatant of CHO cells was added to each well, and 50 μl of the biotin-labelled mouse anti-HM 1.24 antibody was added simultaneously. After incubating at room temperature for two hours and washing, peroxidase-labelled streptavidin (manufactured by DAKO) was added. After incubating at room temperature for one hour and then washing, 100 μl of substrate solution was added in each well. After incubation, the reaction was stopped by 50 μl of 6N sulfuric acid, and absorbance at 490 nm was measured using the MICROPLATE READER Model 3550 (manufactured by Bio-Rad).

2. Evaluation of the Reshaped Human Anti-HM 1.24 Antibody 2-1. L Chain

Figure 8:
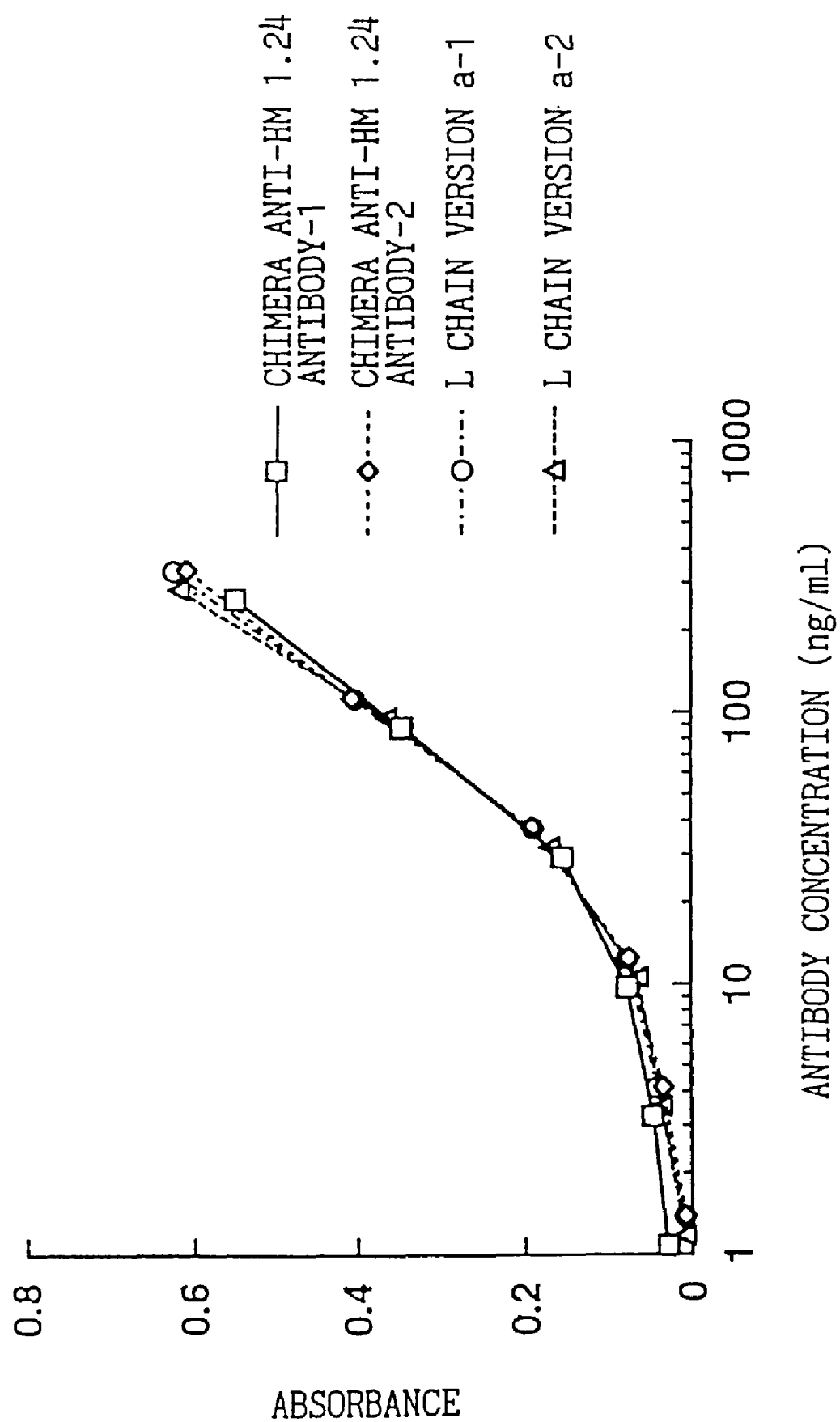
FIG. 8 is a graph showing that the version a of the L chain of a reshaped human anti-HM 1.24 antibody has an antigen biding activity equal to that of the chimeric anti-HM 1.24 antibody. -1 and -2 show that they are different lots.
Figure 9:
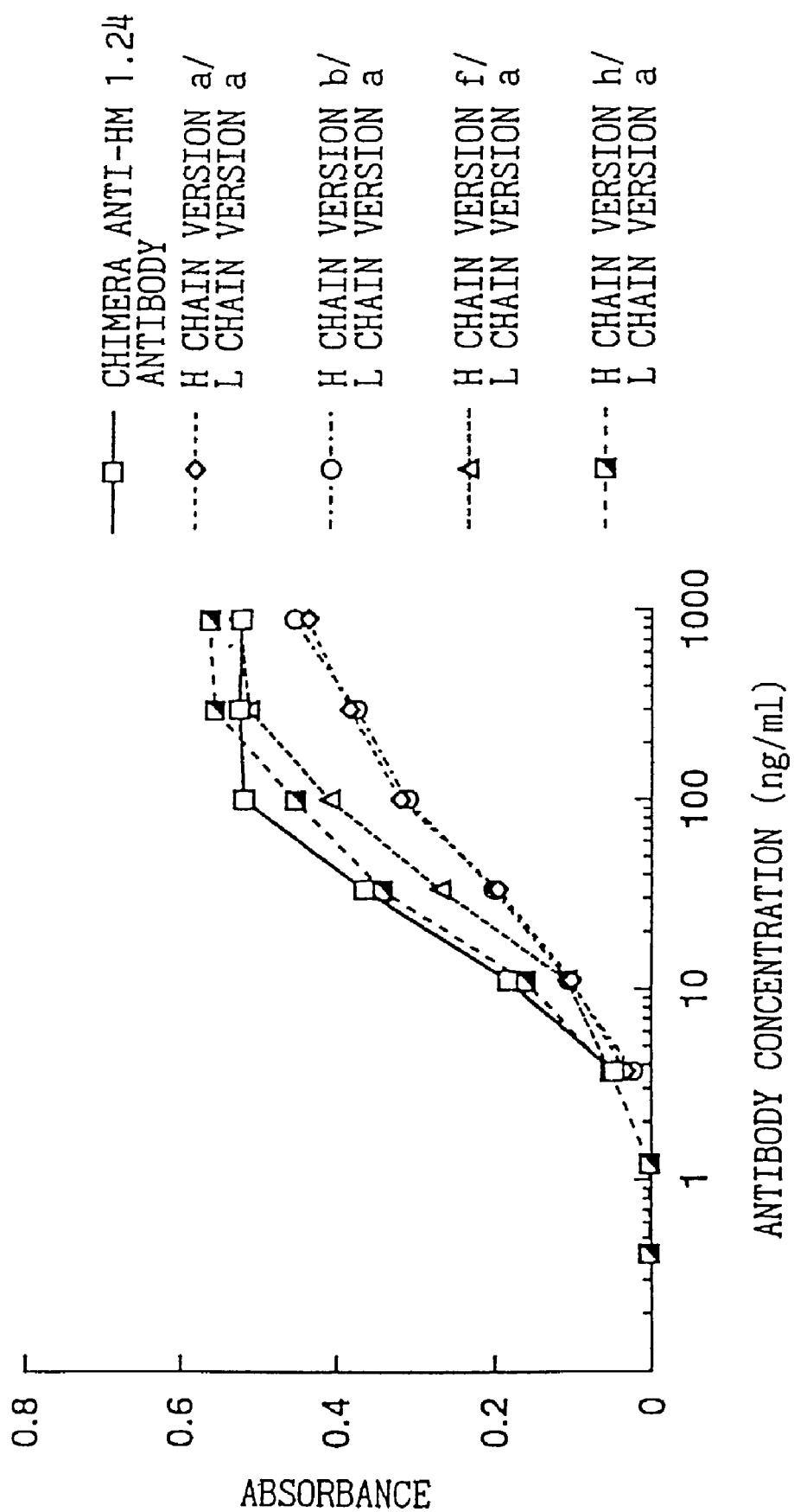
FIG. 9 is a graph showing the antigen binding activity of a reshaped human anti-HM 1.24 antibody in which the version a of the L chain and the version a, b, f, or h of the H chain have been combined, and a chimeric anti-HM 1.24 antibody.
Figure 10:
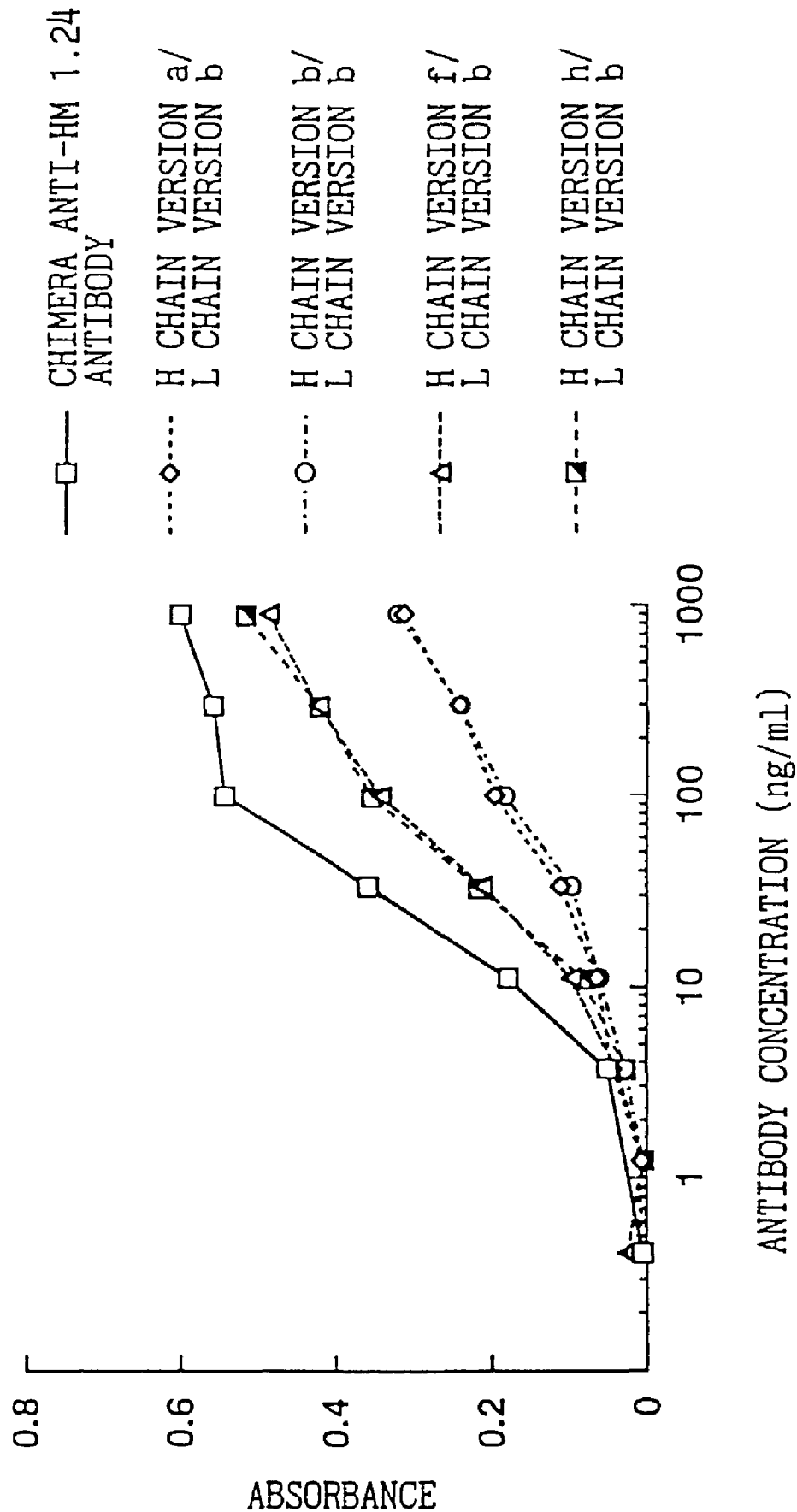
FIG. 10 is a graph showing the binding activity of a reshaped human anti-HM 1.24 antibody in which the version b of the L chain and the version a, b, f, or h of the H chain have been combined, and a chimeric anti-HM 1.24 antibody.
Figure 11:
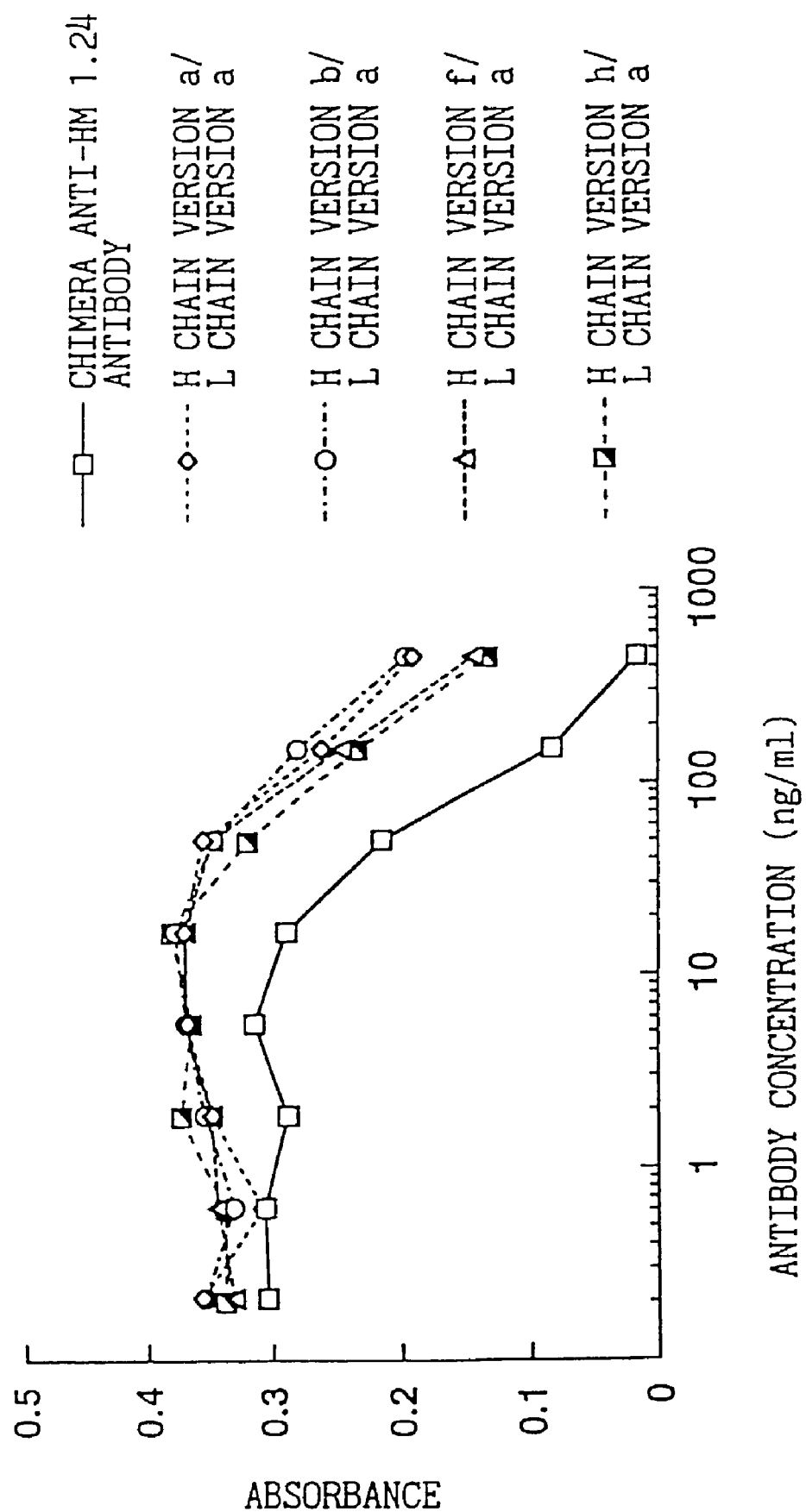
FIG. 11 is a graph showing the binding inhibition activity of a reshaped human anti-HM 1.24 antibody in which the version a of the L chain and H chain version a, b, f, or h have been combined, and a chimeric anti-HM 1.24 antibody.
Figure 12:
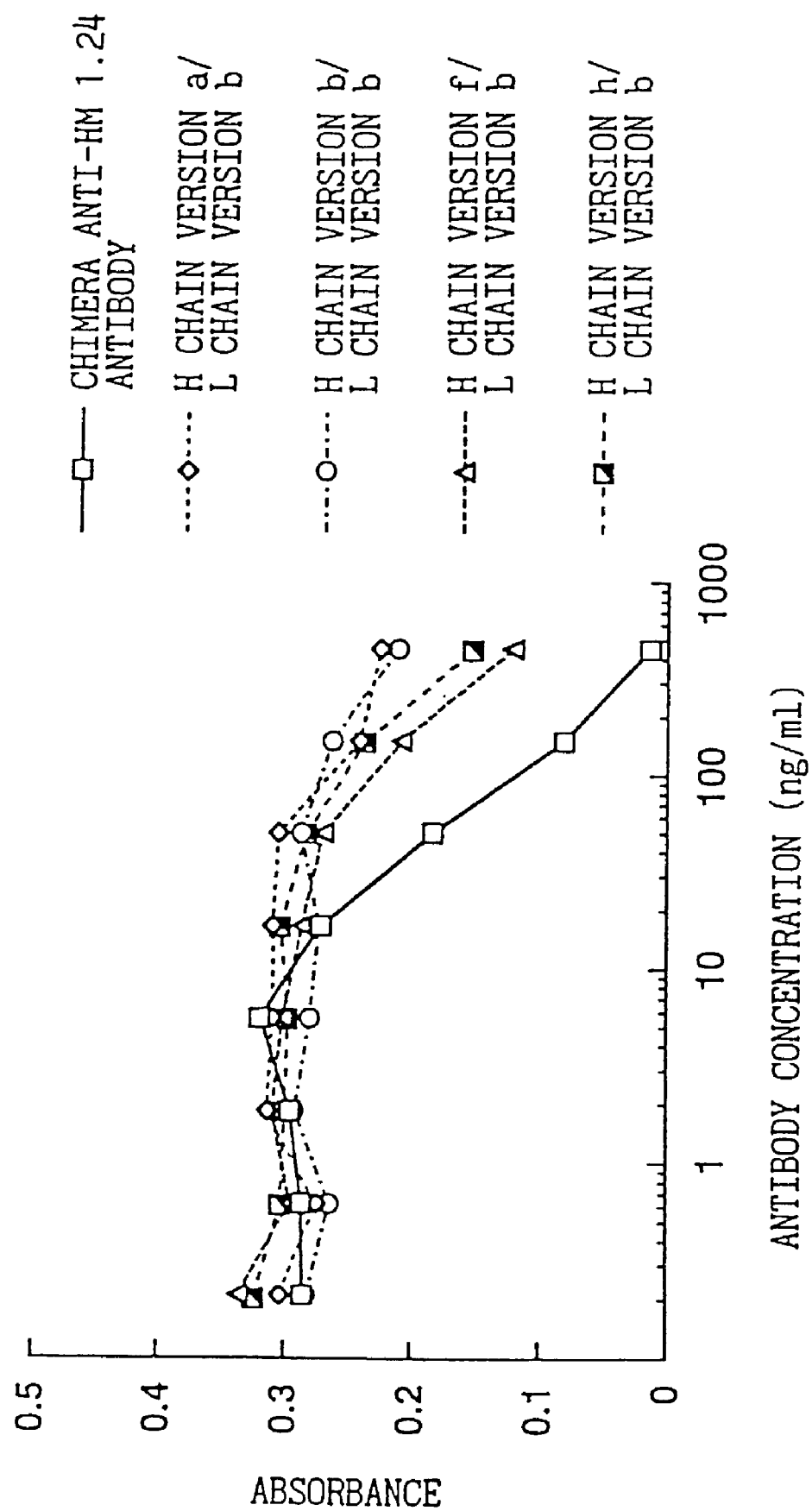
FIG. 12 is a graph showing the binding inhibition activity of a reshaped human anti-HM 1.24 antibody in which the version b of the L chain and the version a, b, f, or h of the H chain have been combined, and a chimeric anti-HM 1.24 antibody.
Figure 13:
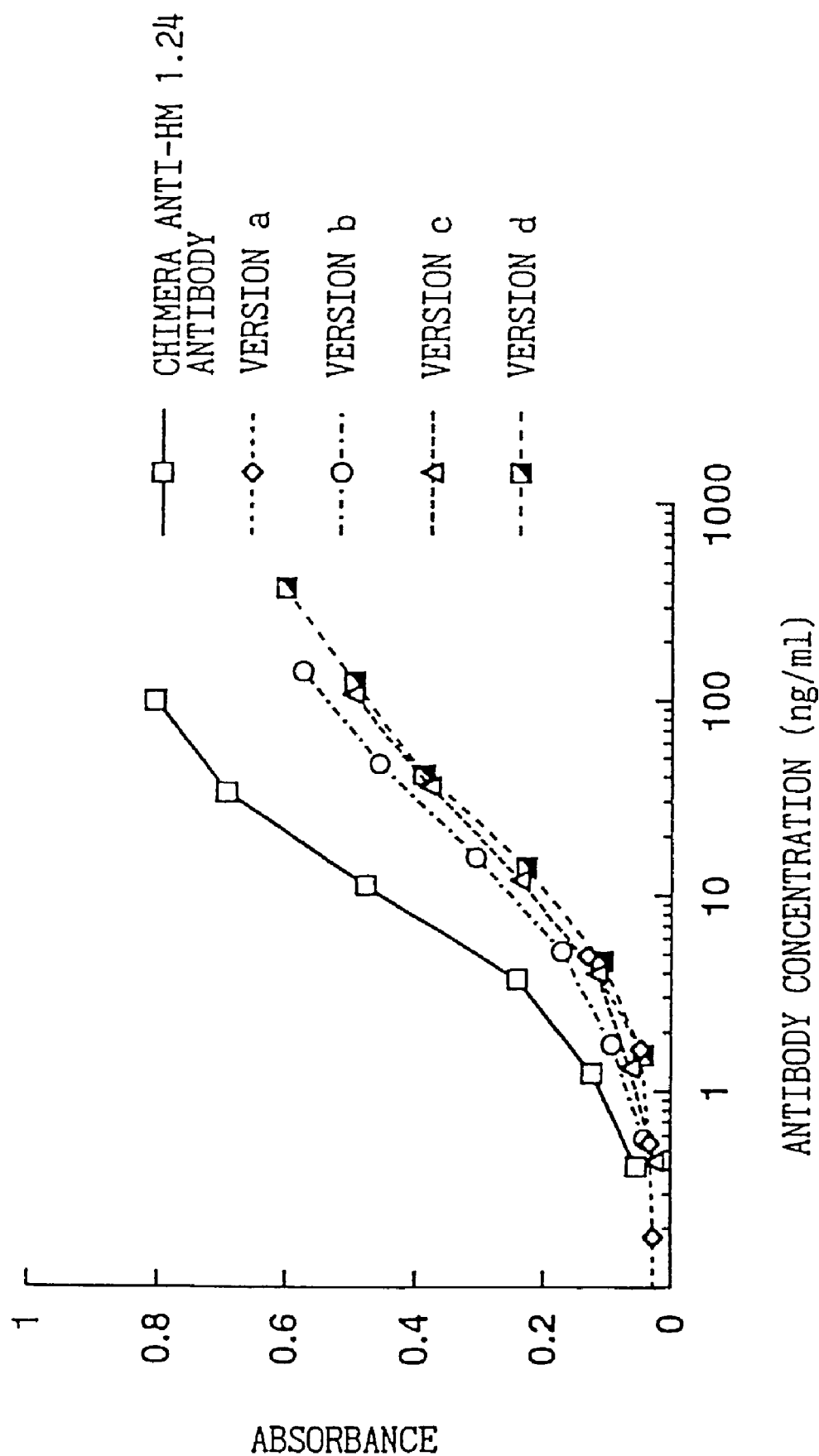
FIG. 13 is a graph showing the antigen binding activity of the versions a, b, c, and d of the H chain of a reshaped human anti-HM 1.24 antibody, and a chimeric anti-HM 1.24 antibody.
Figure 14:
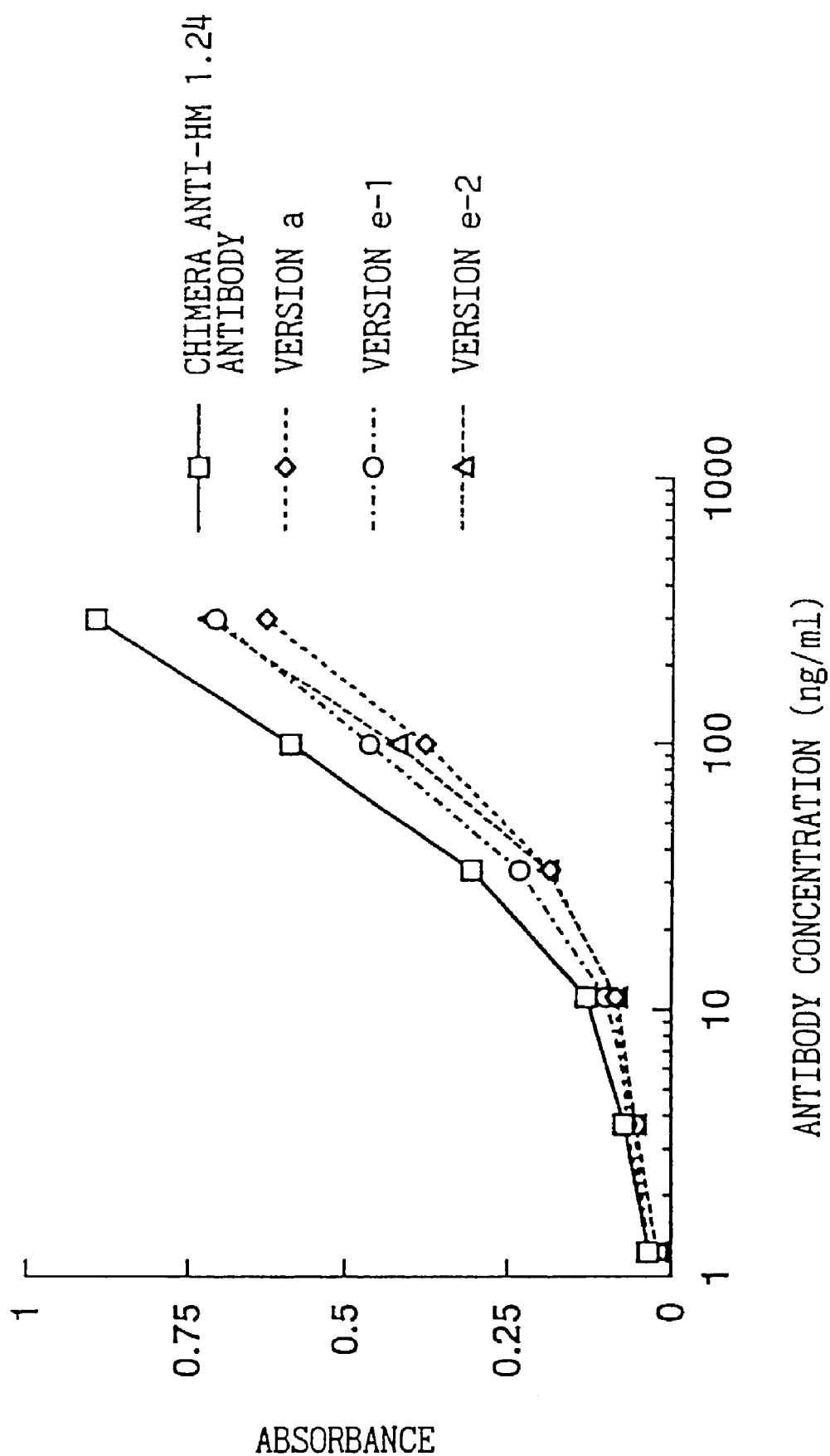
FIG. 14 is a graph showing the antigen binding activity of the versions a and e of the H chain of a reshaped human anti-HM 1.24 antibody, and a chimeric anti-HM 1.24 antibody. -1 and -2 show that they are different lots.

Version a of the L chain of the reshaped human anti-HM 1.24 antibody was evaluated as mentioned for measurement of antigen binding activity. As shown in FIG. 8, when version a of the L chain is expressed in combination with the chimeric H chain it has shown a similar level of antigen binding activity. However, in consideration of further increase in activity and of compatibility with the H chain, version b of the L chain was constructed. Versions a and b of the L chain were evaluated together for antigen binding activity and of binding inhibition activity when combined with versions a, b, f, or h of the H chain. As shown in FIGS. 9, 10, 11, and 12, version a of the L chain had a higher activity than version b in both activities in all versions a, b, f, and h of the H chain. Therefore, version a of the L chain of the reshaped human anti-HM 1.24 antibody was used for the following experiment.

2-2. H Chain Versions A to E

Versions a to e of the H chain of the reshaped human anti-HM 1.24 antibody were evaluated in combination with the version a of the L chain as mentioned for measurement of antigen binding activity and binding inhibition activity. The result, as shown in FIGS. 11, 13, 14, and 15, indicated that all versions were weaker in both activities as compared to the chimeric anti-HM 1.24 antibody, suggesting that further amino acid substitution is required.

2-3. The H Chain Hybrid Antibody

Figure 16:
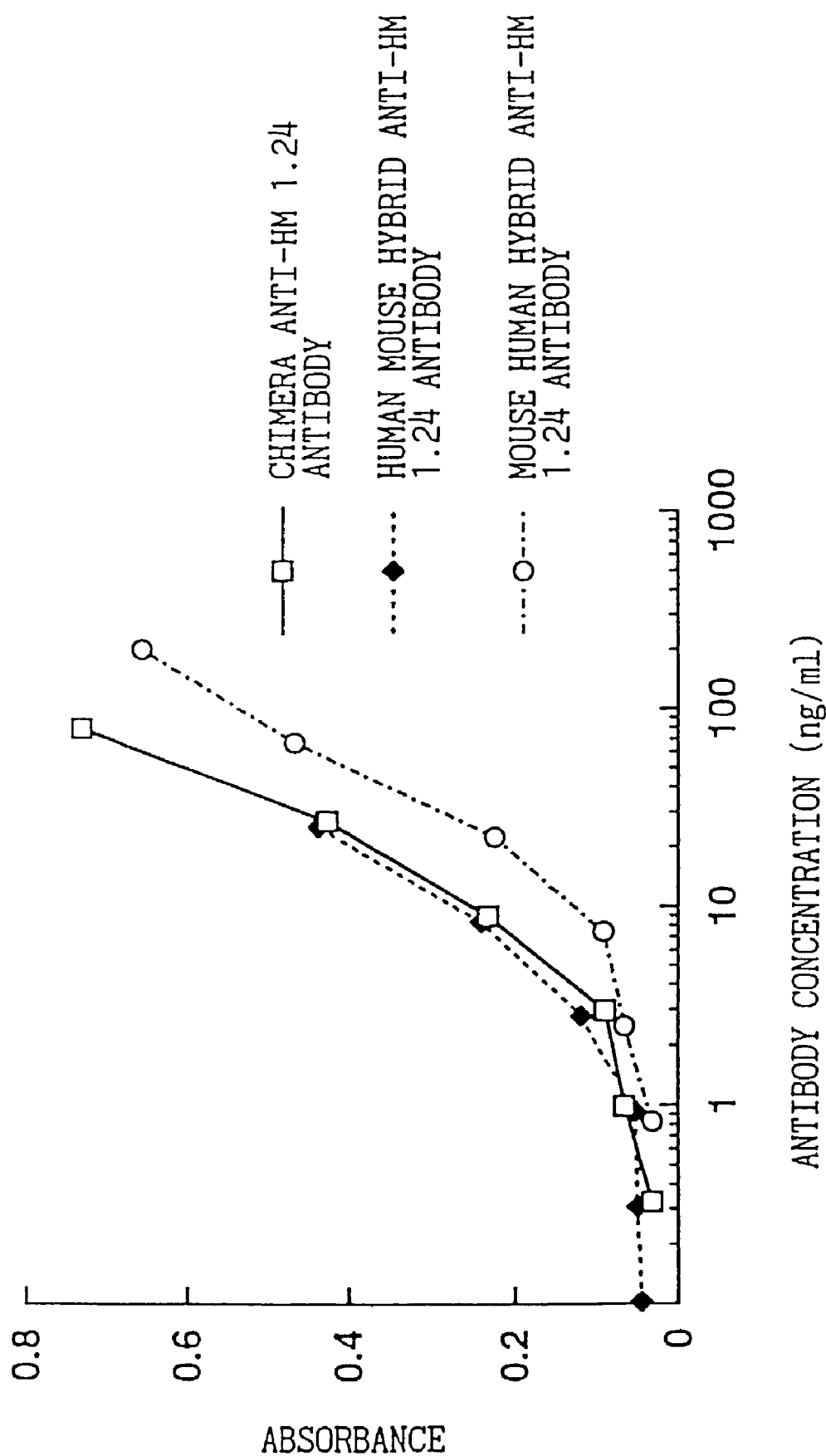
FIG. 16 is a graph showing the antigen binding activity of a human mouse hybrid anti-HM 1.24 antibody, a mouse human hybrid anti-HM 1.24 antibody, and a chimeric anti-HM 1.24 antibody.

The H chain hybrid antibody was evaluated as mentioned for measurement of antigen binding activity. The result, as shown in FIG. 16, indicated that the human-mouse hybrid anti-HM 1.24 antibody has shown a similar activity to that of the chimeric anti-HM 1.24 antibody for antigen binding activity, whereas the mouse human hybrid anti-HM 1.24 antibody had a weaker activity than the chimeric anti-HM 1.24 antibody. This indicated that in order to construct the reshaped human anti-HM 1.24 antibody having the antigen binding activity similar to that of the chimeric anti-HM 1.24 antibody, it is necessary to convert amino acids included in FR3 or FR4 among those contained the V region of the H chain.

2-4. Versions f to r of the H Chain

Figure 17:
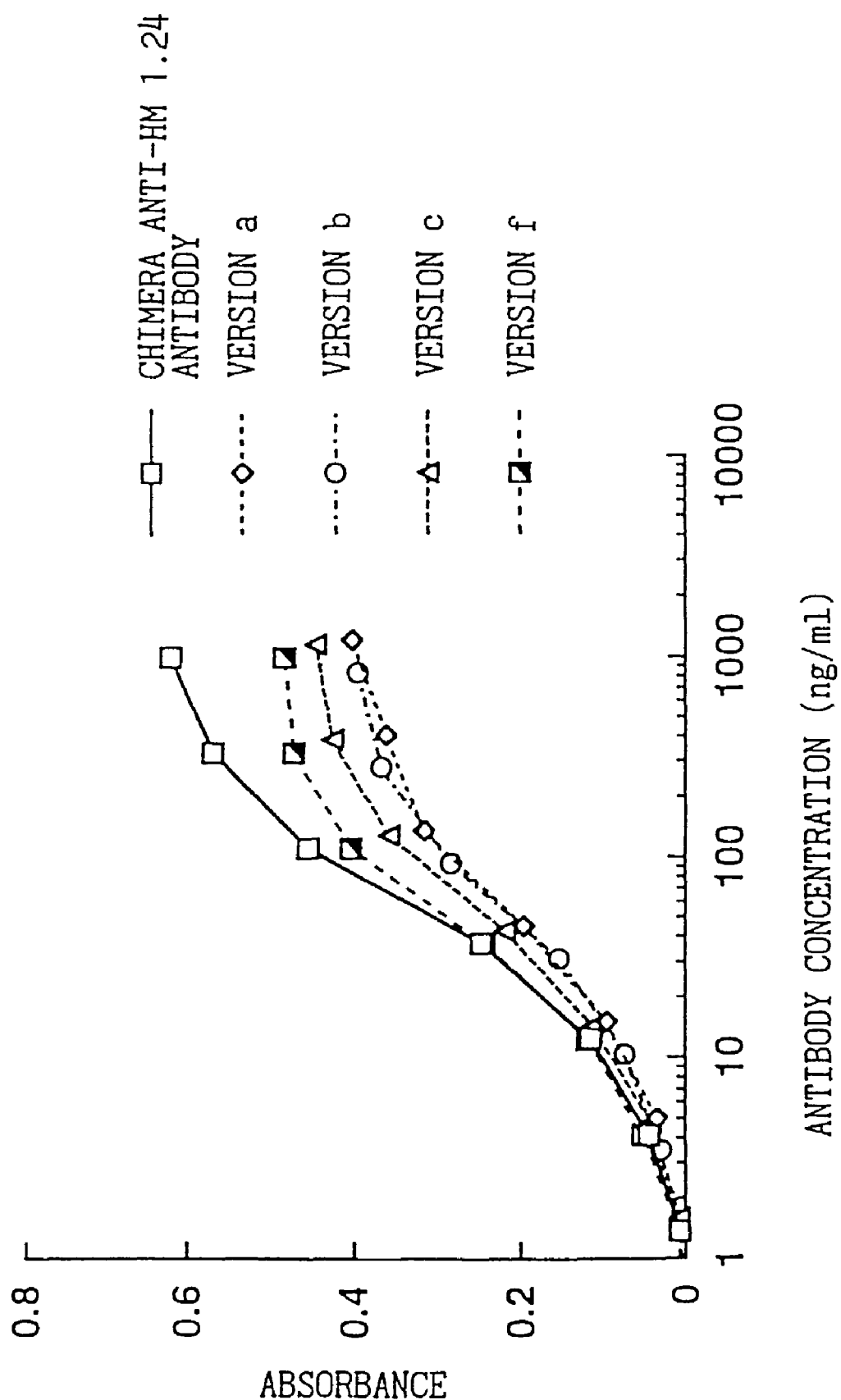
FIG. 17 is a graph showing the antigen binding activity of the versions a, b, c, and f of the H chain of a reshaped human anti-HM 1.24 antibody, and a chimeric anti-HM 1.24 antibody.

Version f of the H chain of the reshaped human anti-HM 1.24 antibody was evaluated as mentioned for measurement of antigen binding activity. The result, as shown in FIG. 17, indicated that its antigen binding activity is decreased as compared to the chimeric anti-HM 1.24 antibody, but is increased as compared to the above versions a to c, suggesting that any of the four amino acids at position 67, 69, 75, and 78 that were newly converted in this version is responsible for the activity of the reshaped human antibody.

Figure 18:
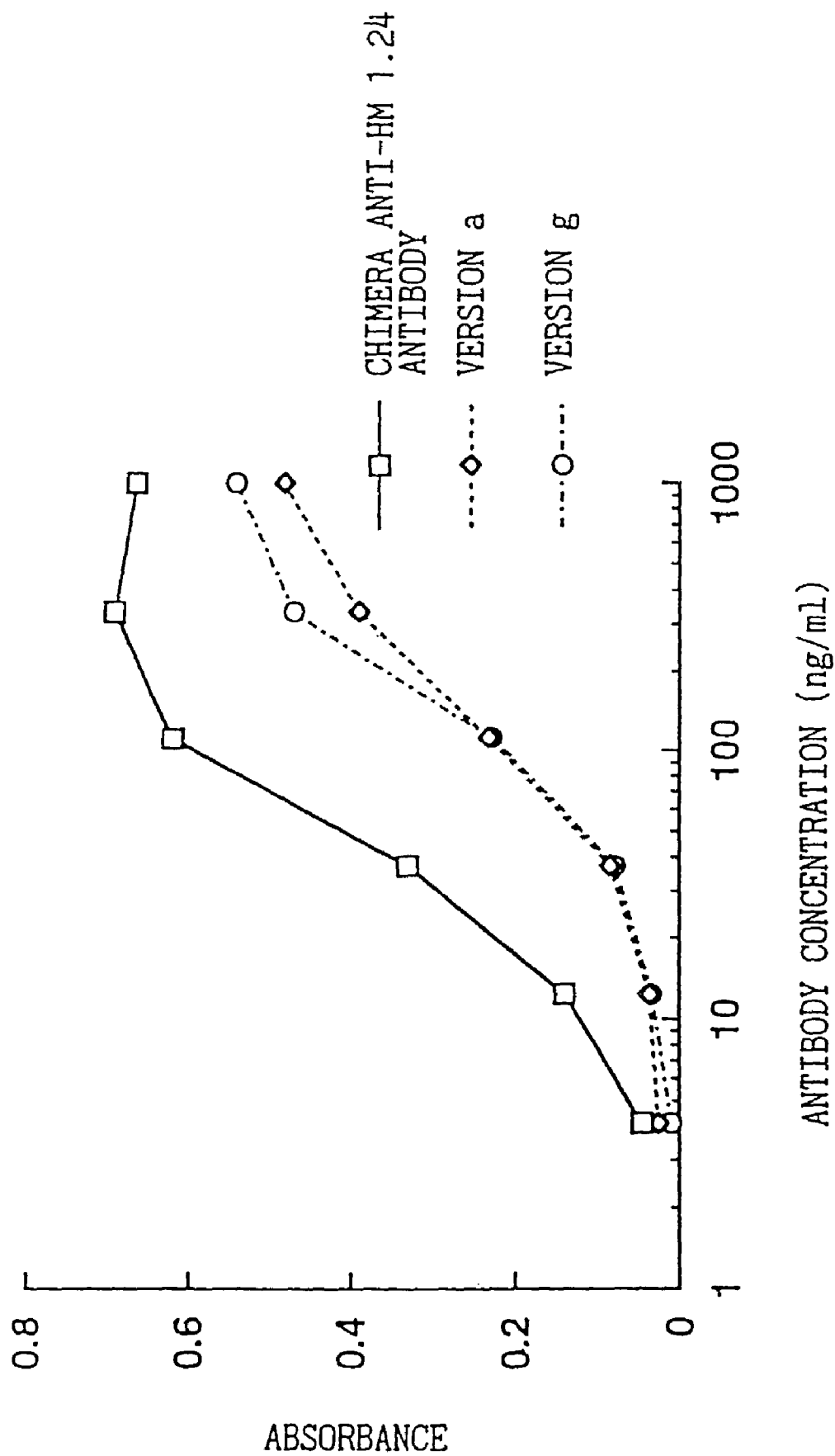
FIG. 18 is a graph showing the antigen binding activity of the versions a and g of the H chain of a reshaped human anti-HM 1.24 antibody and a chimeric anti-HM 1.24 antibody.
Figure 19:
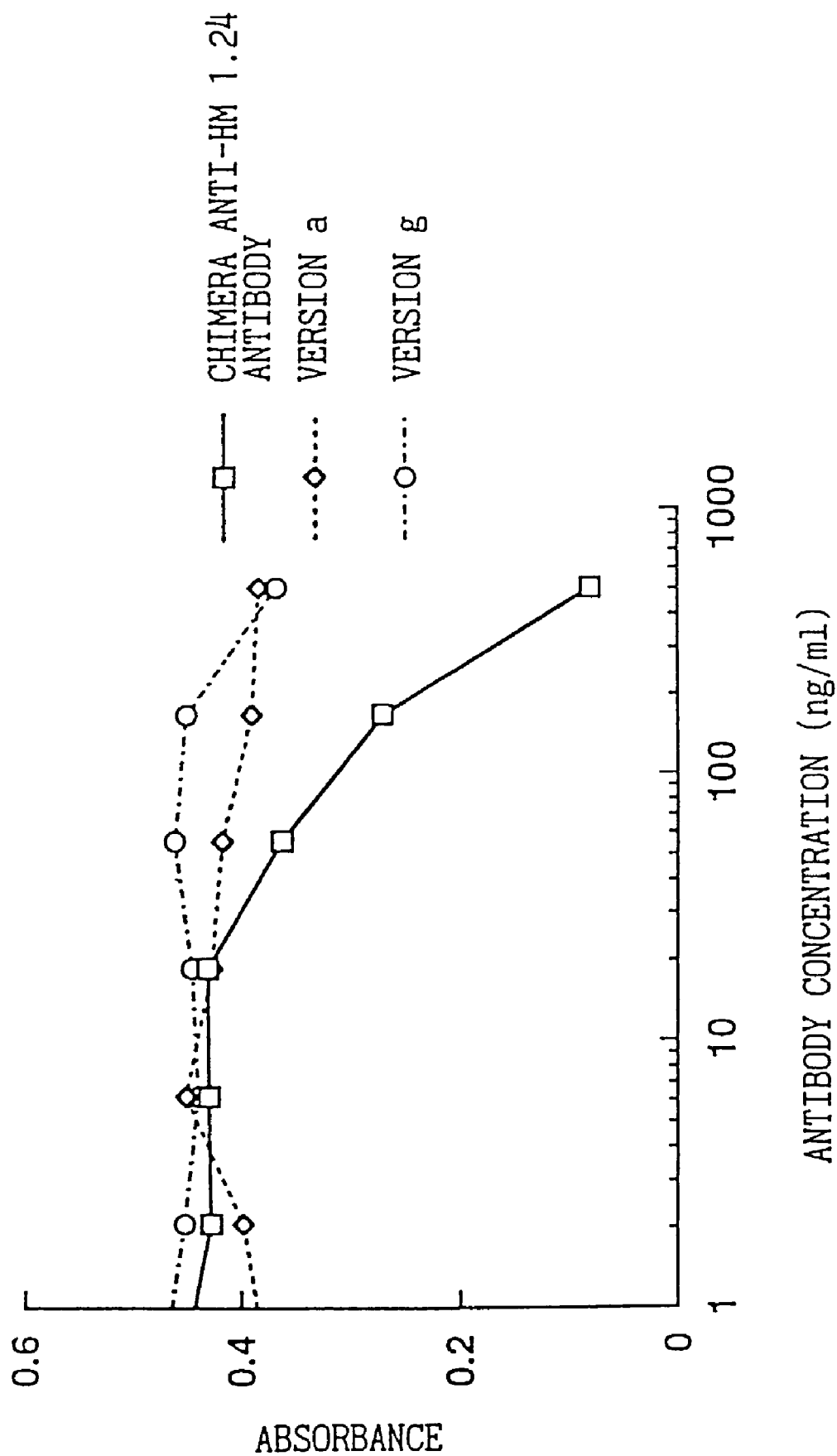
FIG. 19 is a graph showing the binding inhibition activity of the versions a and g of the H chain of a reshaped human anti-HM 1.24 antibody and a chimeric anti-HM 1.24 antibody.
Figure 20:
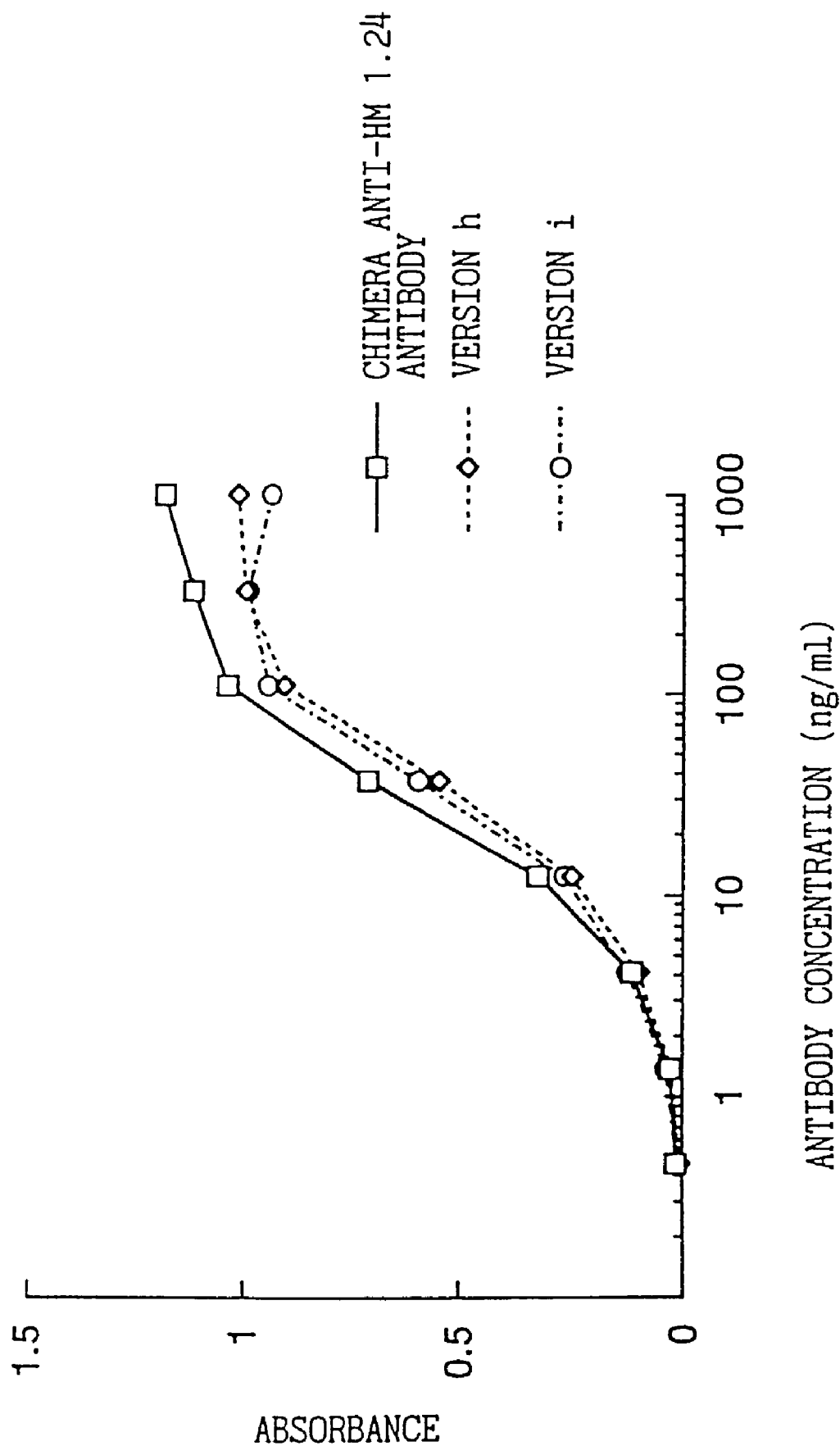
FIG. 20 is a graph showing the antigen binding activity of the versions h and i of the H chain of a reshaped human anti-HM 1.24 antibody and a chimeric anti-HM 1.24 antibody.
Figure 21:
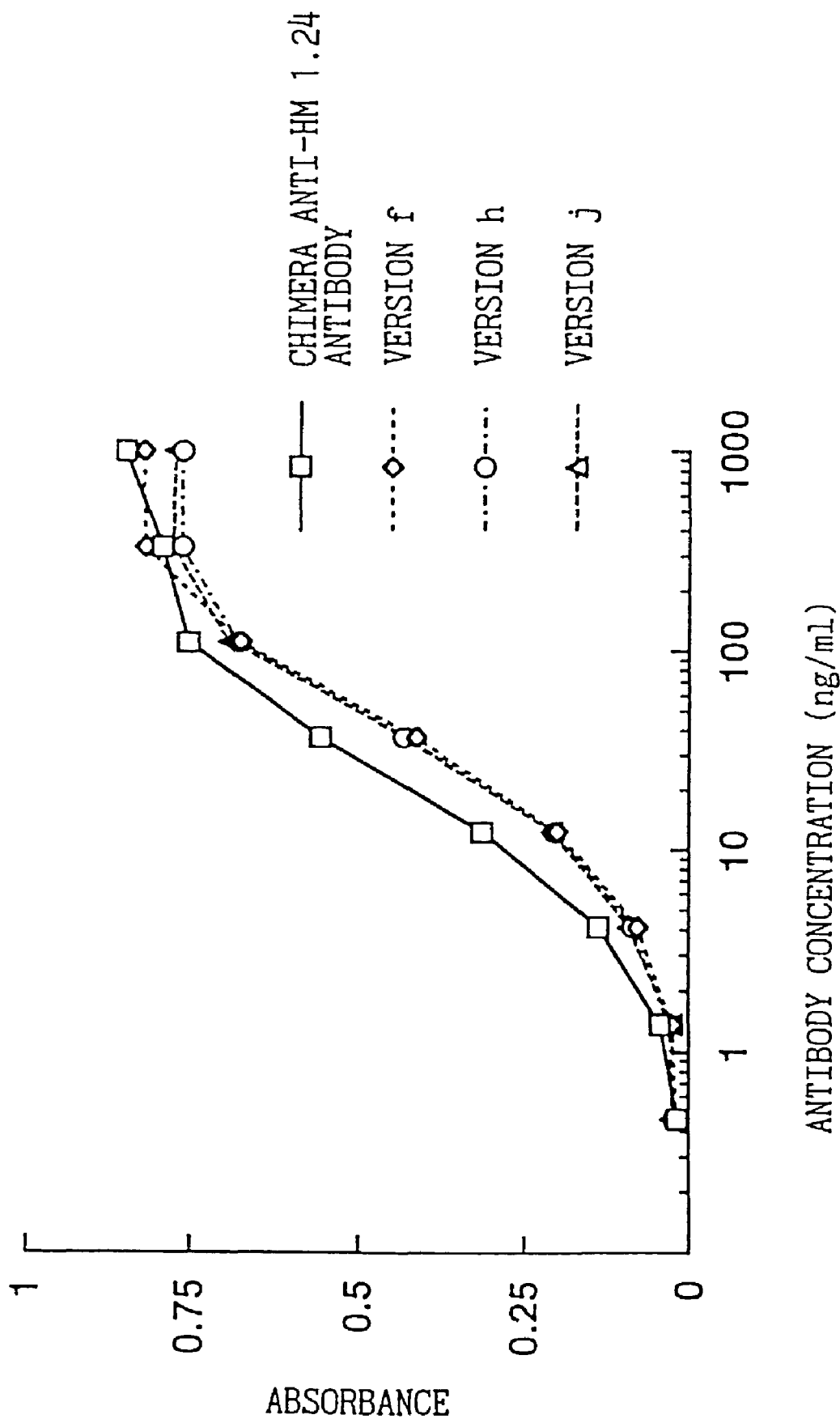
FIG. 21 is a graph showing the antigen binding activity of the versions f, h, and j of the H chain c reshaped human anti-HM 1.24 antibody and a chimeric anti-HM 1.24 antibody.
Figure 22:
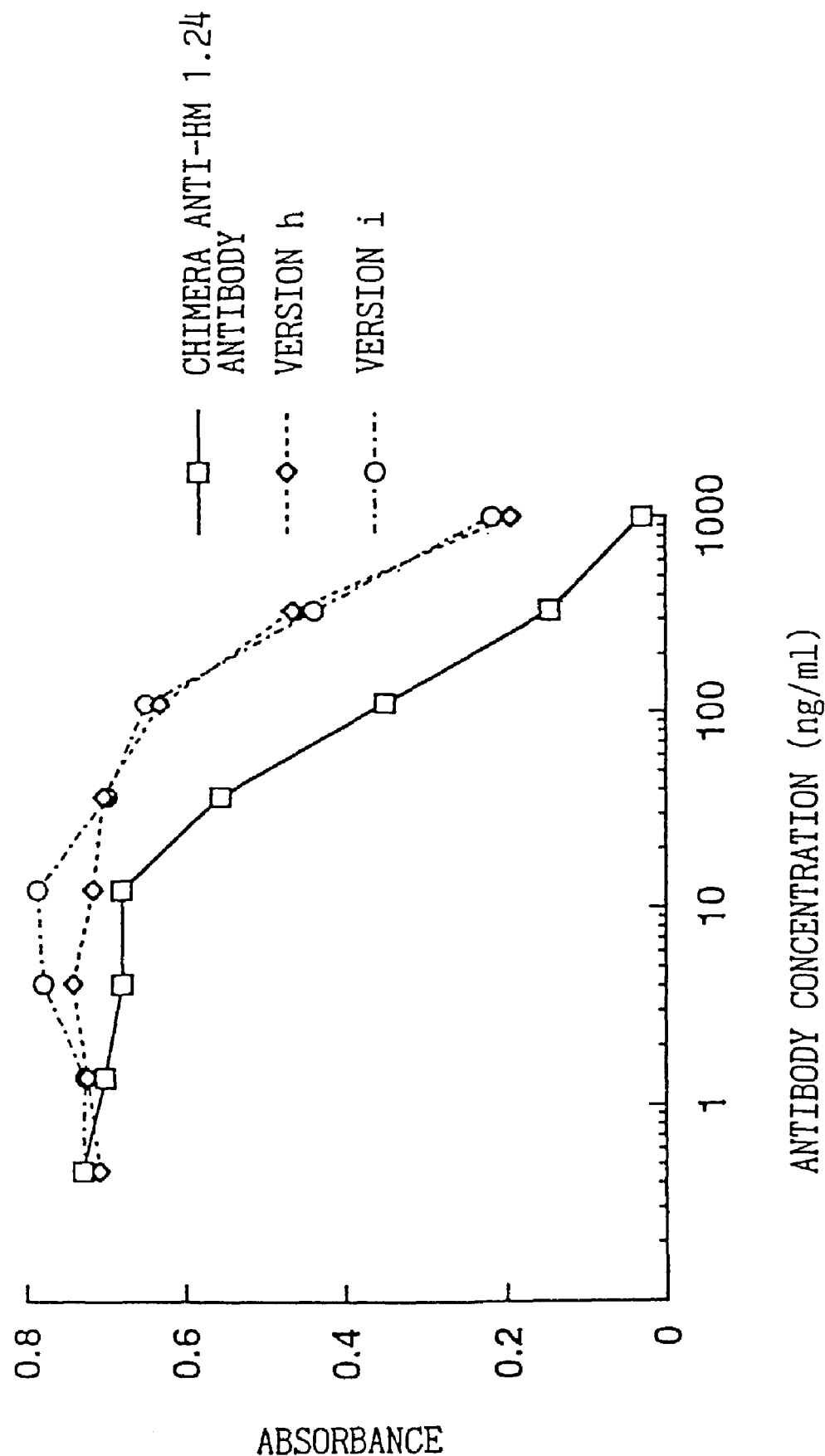
FIG. 22 is a graph showing the binding inhibition activity of the versions h and i of the H chain of a reshaped human anti-HM 1.24 antibody and a chimeric anti-HM 1.24 antibody.
Figure 23:
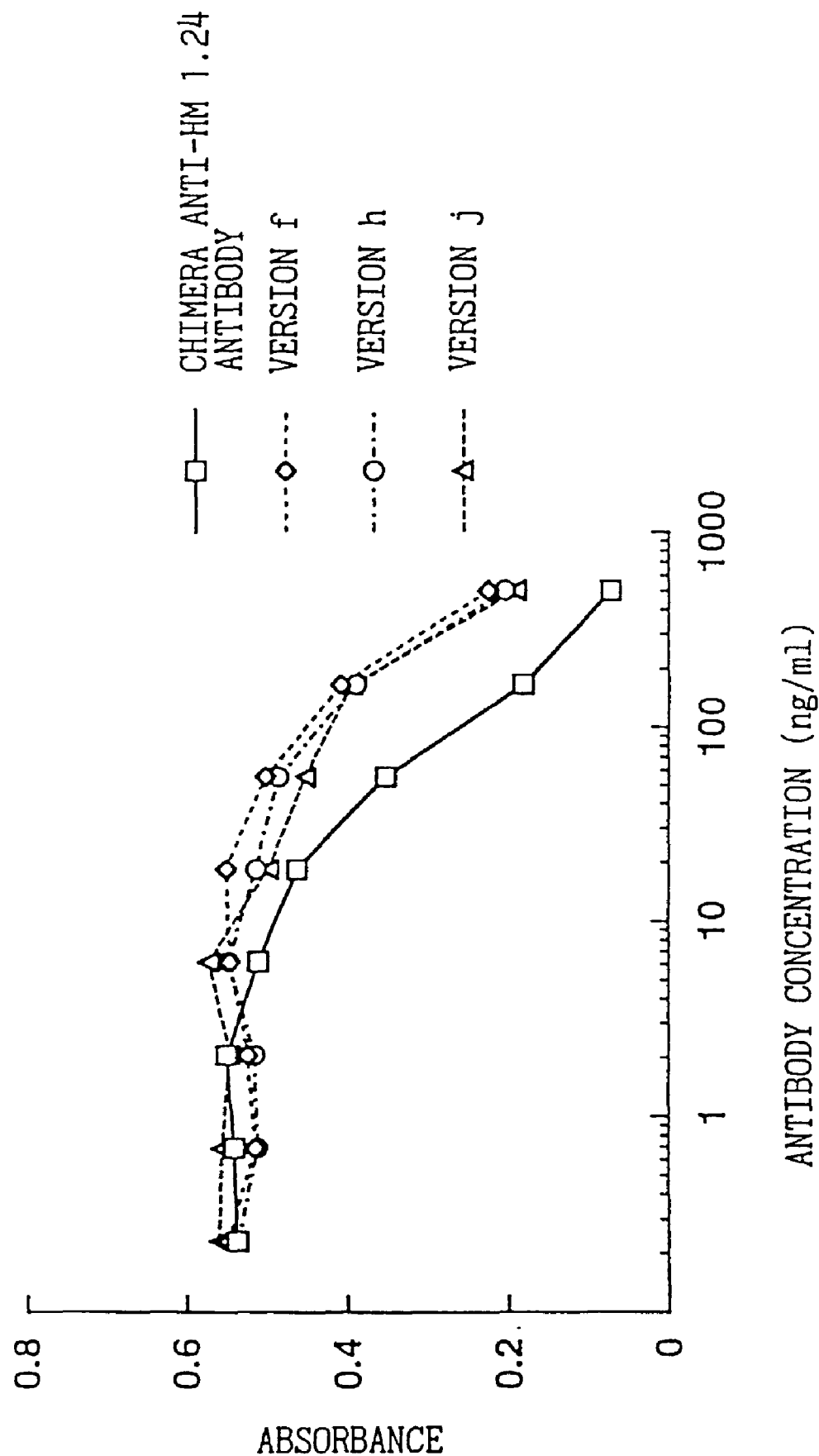
FIG. 23 is a graph showing the binding inhibition activity of the versions f, h, and j of the H chain of a reshaped human anti-HM 1.24 antibody and a chimeric anti-HM 1.24 antibody.
Figure 24:
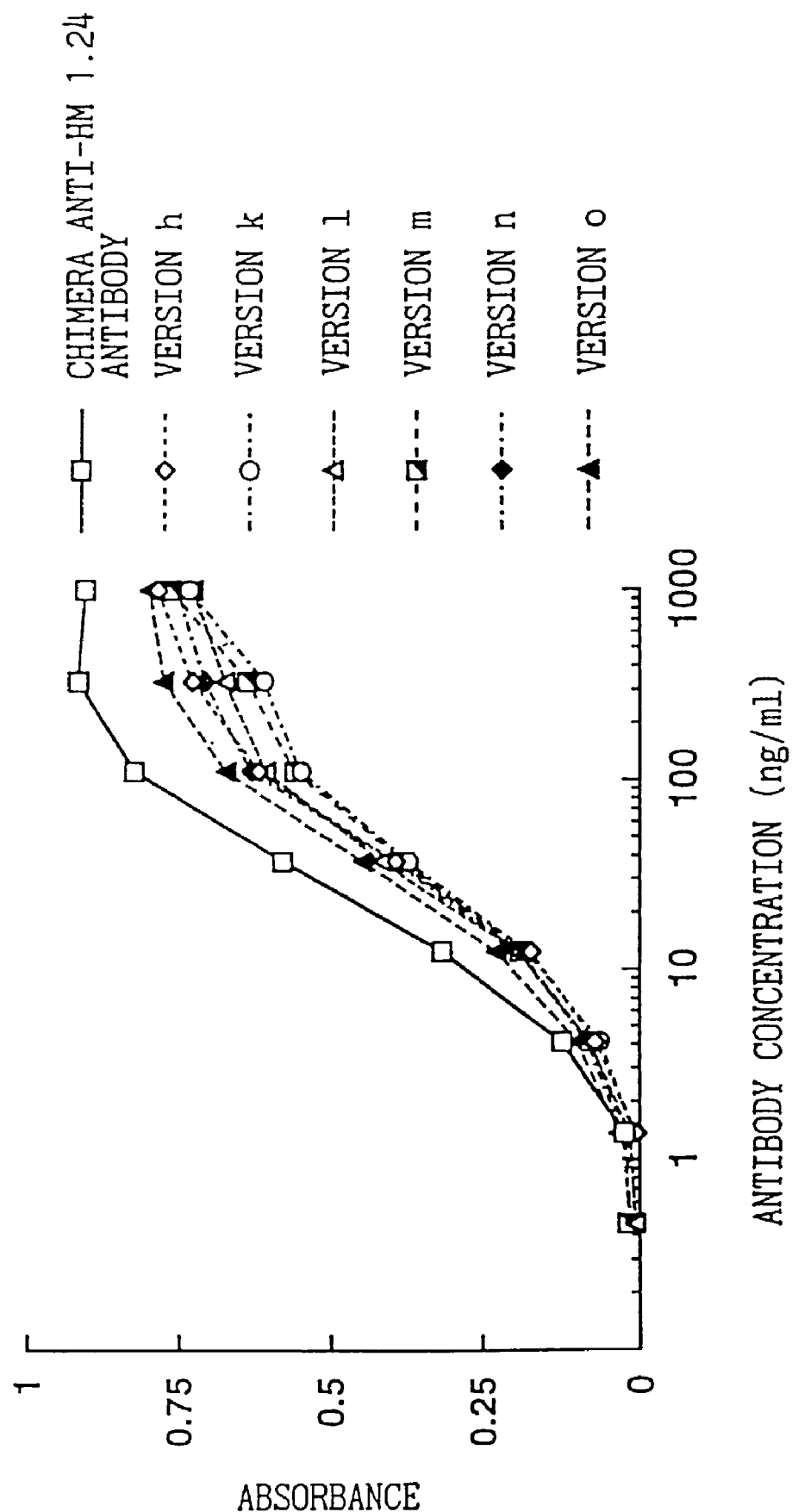
FIG. 24 is a graph showing the antigen binding activity of the versions h, k, l, m, n, and O of the H chain of a reshaped human anti-HM 1.24 antibody and a chimeric anti-HM 1.24 antibody.

Version g of the H chain of the reshaped human anti-HM 1.24 antibody was evaluated as mentioned for measurement of antigen binding activity. The result, as shown in FIGS. 18 and 19, indicated that this version has exhibited a similar level of activity to that of the above version a at most, revealing that, as shown for the above H chain human mouse hybrid antibody, the amino acid at position 40 that was converted in this version is not responsible for the increase in the activity of the reshaped human antibody.

Versions h to j of the H chain of the reshaped human anti-HM 1.24 antibody were evaluated as mentioned for measurement of antigen binding activity and binding inhibition activity. The result, as shown in FIGS. 20, 21, 22, and 23, indicated that all versions were weaker for both activities as compared to the chimeric anti-HM 1.24 antibody and were similar to the above-mentioned version f, suggesting that the amino acids at position 67 and 69 among the four amino acids that were newly converted in version f are not responsible for the increase in the activity of the reshaped human antibody.

Versions k to p of the H chain of the reshaped human anti-HM 1.24 antibody were evaluated as mentioned for measurement of antigen binding activity and binding inhibition activity. The result, as shown in FIGS. 24, 25, 26, and 27, indicated that all versions were weaker for both activities as compared to the chimeric anti-HM 1.24 antibody and were similar to the above-mentioned version h, suggesting that the amino acids at position 80 and after that were newly converted in these six versions are not responsible for the increase in the activity of the reshaped human antibody.

Figure 25:
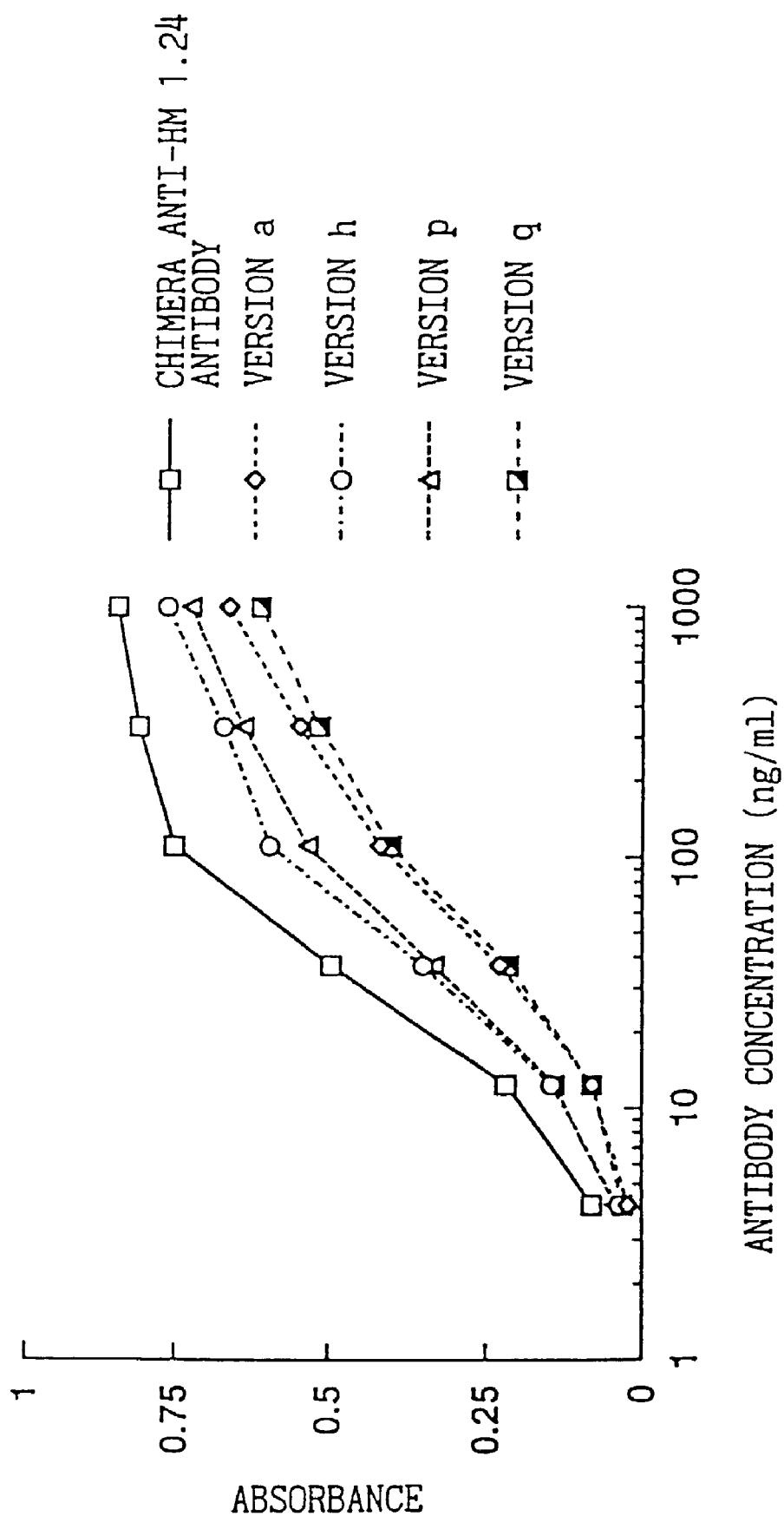
FIG. 25 is a graph showing the antigen binding activity of the versions a, h, p, and q of the H chain of a reshaped human anti-HM 1.24 antibody and a chimeric anti-HM 1.24 antibody.
Figure 26:
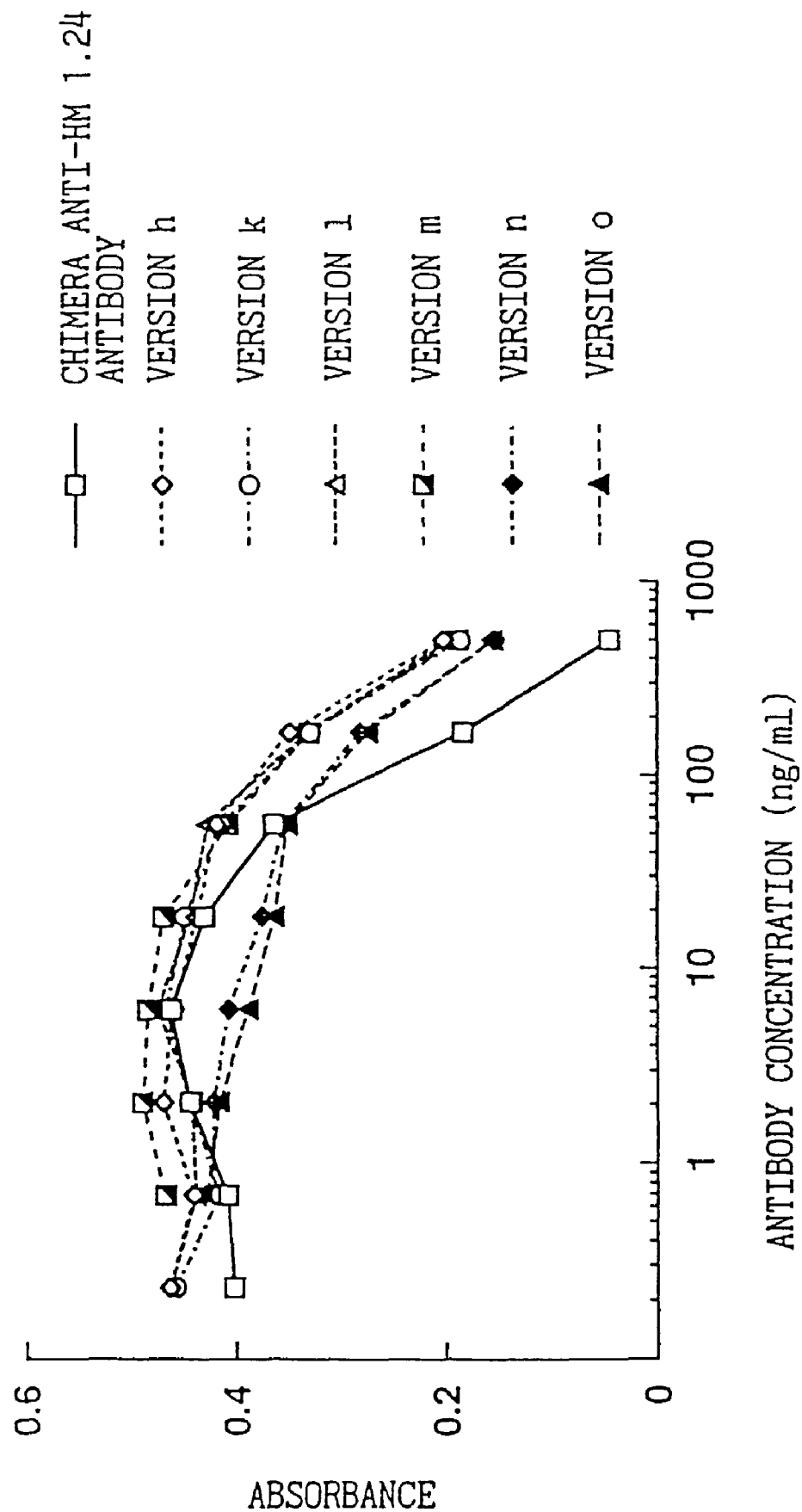
FIG. 26 is a graph showing the inhibition activity of binding to the WISH cell of the versions h, k, l, m, n, and o of the H chain of a reshaped human anti-HM 1.24 antibody and a chimeric anti-HM 1.24 antibody.
Figure 27:
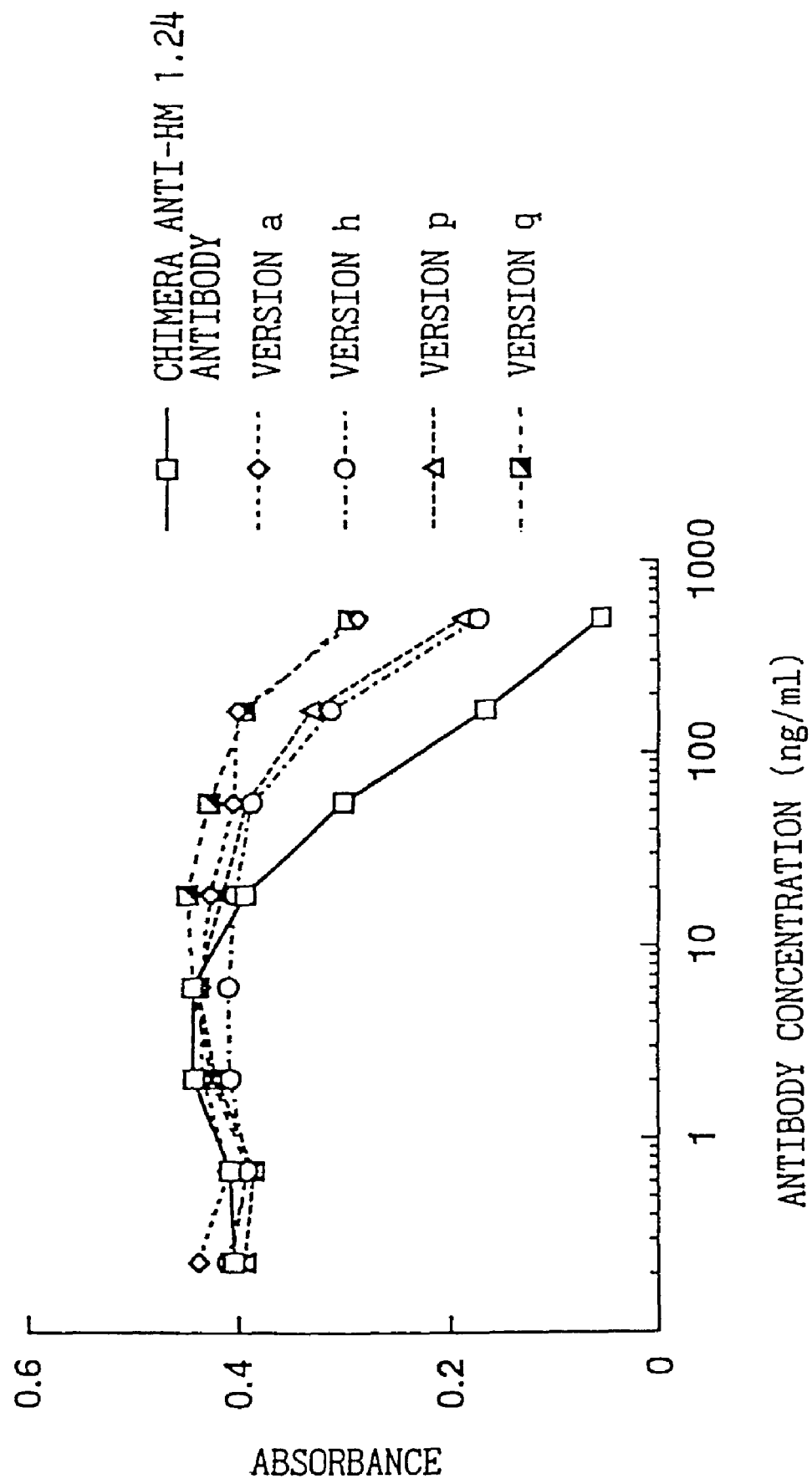
FIG. 27 is a graph showing the binding inhibition activity of the versions a, h, p, and q of the H chain Qf a reshaped human anti-HM 1.24 antibody and a chimeric anti-HM 1.24 antibody.

Version q of the H chain of the reshaped human anti-HM 1.24 antibody was evaluated as mentioned for measurement of antigen binding activity and binding inhibition activity. The result, as shown in FIGS. 25 and 27, indicated that this version was weaker for both activities as compared to the above version h or version p and was similar to that of the above-mentioned a, suggesting that substitution of the amino acid at position 78 is essential for the increase in the activity of the reshaped human antibody.

Figure 15:
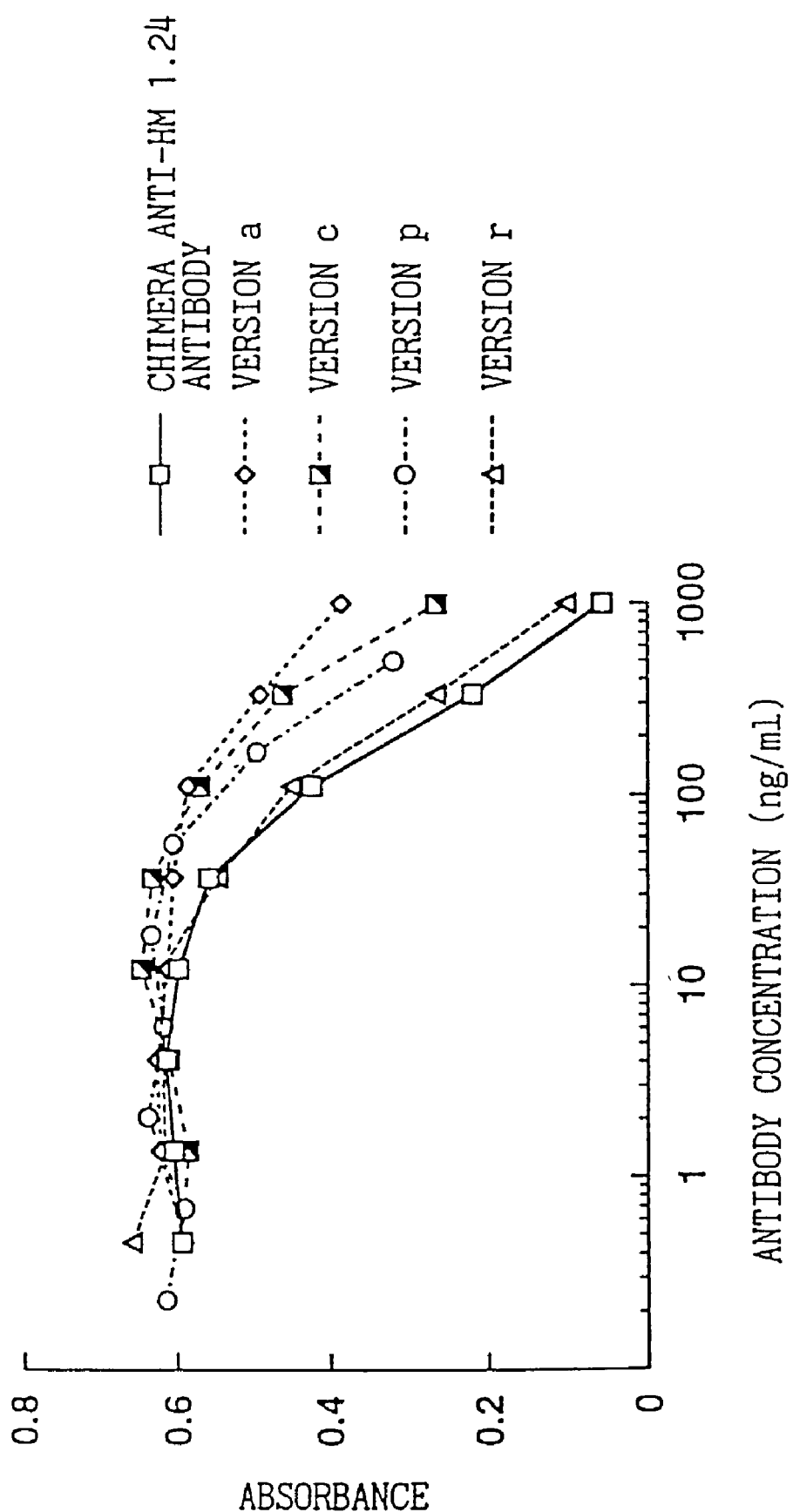
FIG. 15 is a graph showing the binding inhibition activity of the versions a, c, p, and r of the H chain of a reshaped human anti-HM 1.24 antibody, and a chimeric anti-HM 1.24 antibody.
Figure 28:
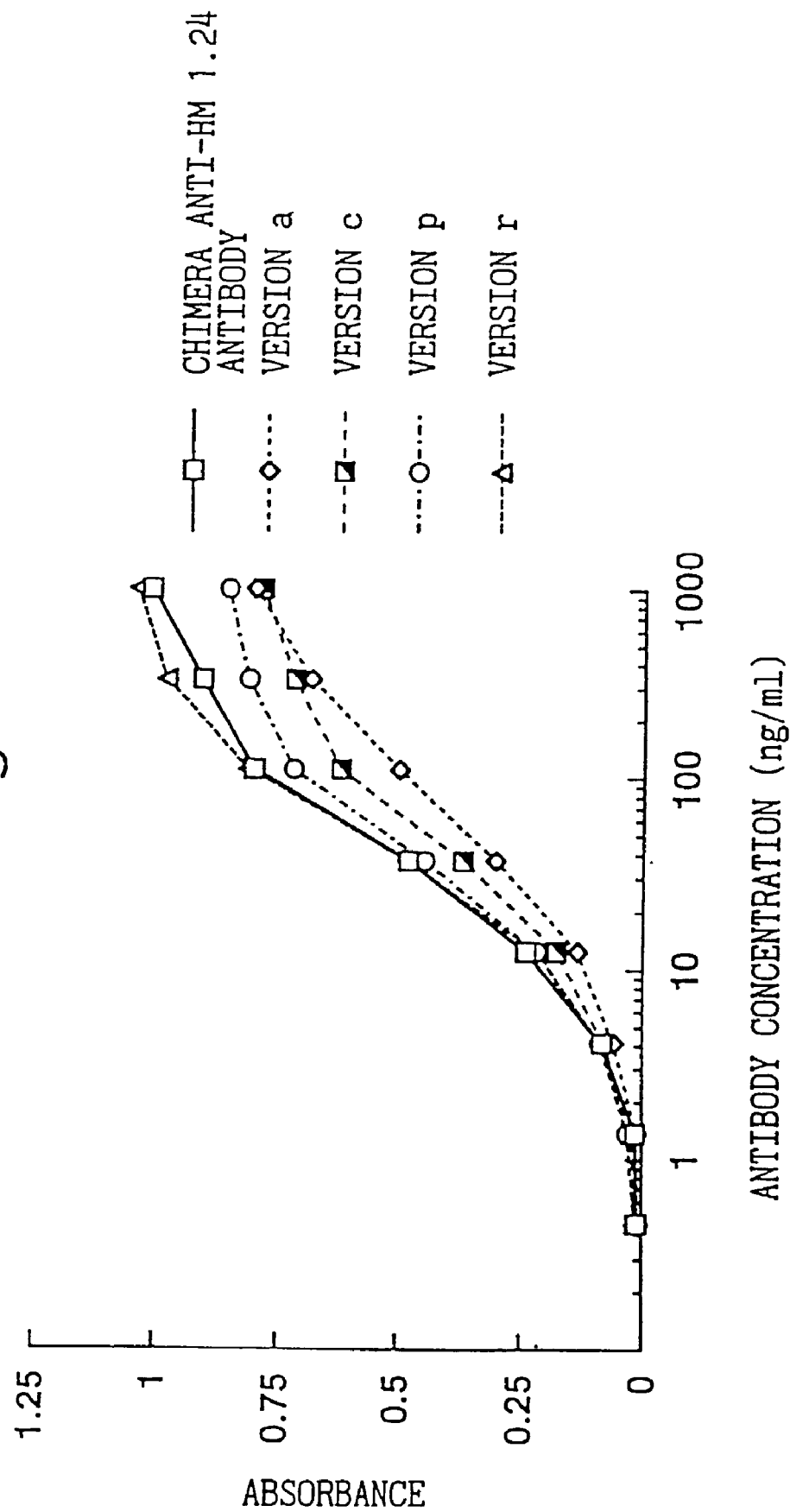
FIG. 28 is a graph showing the antigen binding activity of the versions a, c, p, and r of the H chain of a reshaped human anti-HM 1.24 antibody and a chimeric anti-HM 1.24 antibody.

Version r of the H chain of the reshaped human anti-HM 1.24 antibody were evaluated by the method mentioned above. The result, as shown in FIGS. 15 and 28, indicated that version r has a similar level of antigen binding activity and binding inhibition activity to that of the chimeric anti-HM 1.24 antibody.

The above results indicated that the minimum conversion required for the reshaped human anti-HM 1.24 antibody to have a similar level of antigen binding activity to that of the mouse anti-HM 1.24 antibody or the chimeric anti-HM 1.24 antibody is the amino acids at positions 30, 71, and 78, and furthermore 73.

The antigen binding activity and the binding inhibition activity for H chain versions a to r of the reshaped human anti-HM 1.24 antibody are summarized in Table 6.

TABLE 6

| H chain version | Antigen binding activity | Binding inhibition activity |
|---|---|---|
| a | + | + |
| b | + | + |
| c | + | + |
| d | + | not measured |
| e | + | nor measured |
| f | ++ | ++ |
| g | + | + |
| h | ++ | ++ |
| i | ++ | ++ |
| j | ++ | ++ |
| k | ++ | ++ |
| l | ++ | ++ |
| m | ++ | ++ |
| n | ++ | ++ |
| o | ++ | ++ |
| p | ++ | ++ |
| q | + | + |
| r | +++ | +++ |

2-5. Version s of the H Chain

Figure 29:
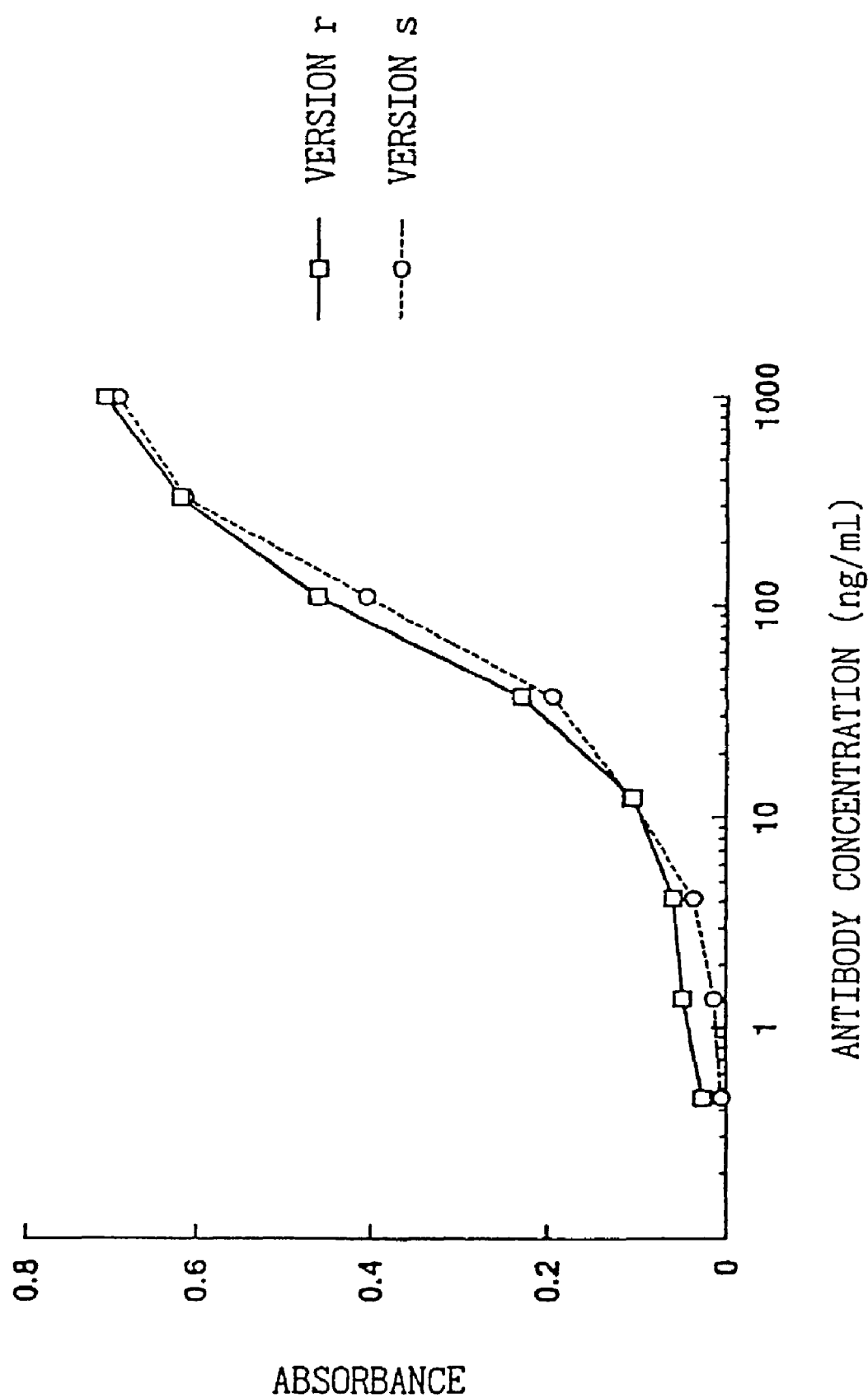
FIG. 29 is a graph showing that the version s of a reshaped human anti-HM 1.24 antibody has an antigen binding activity equal to that of the version r of the reshaped human anti-HM 1.24 antibody.
Figure 30:
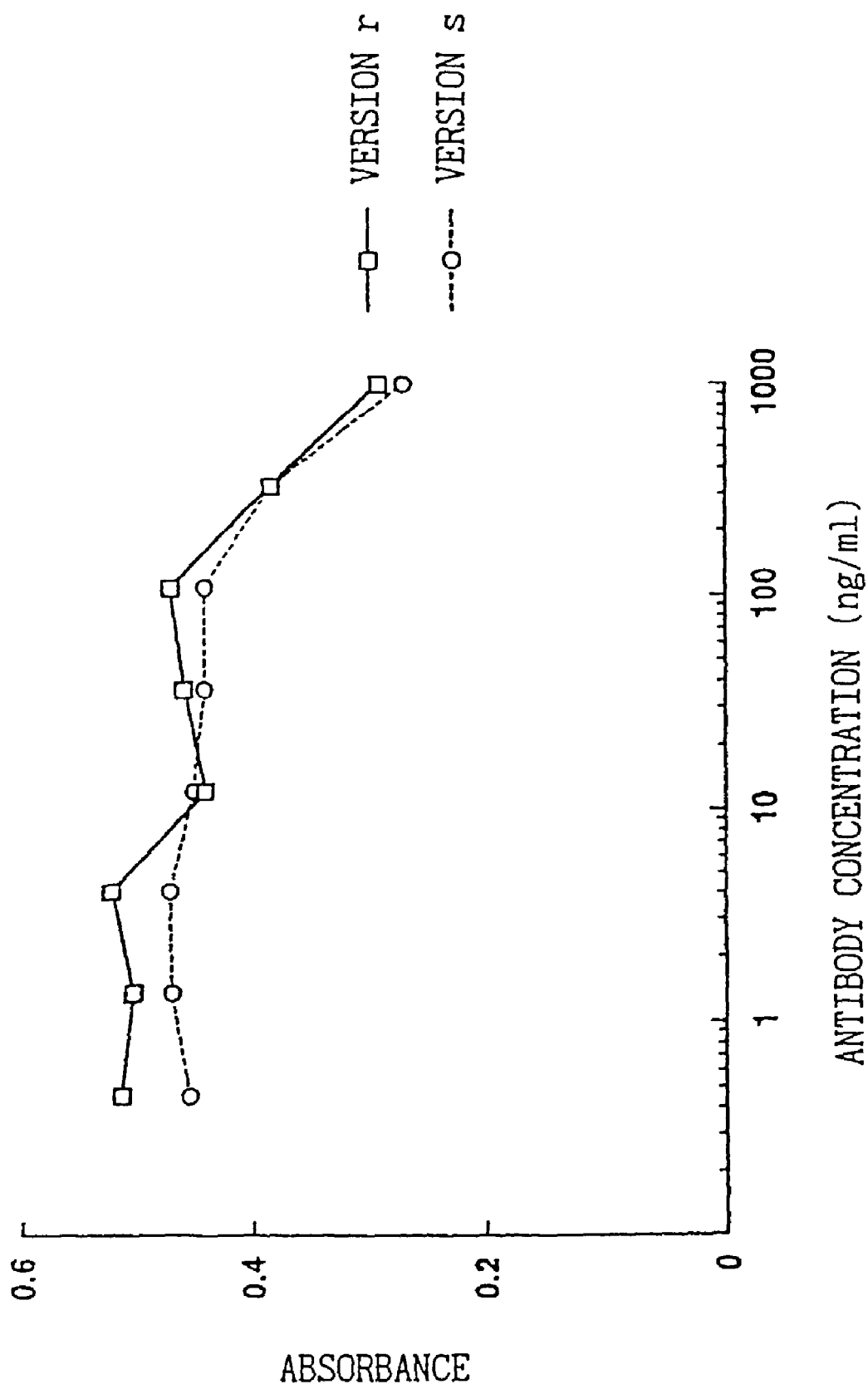
FIG. 30 is a graph showing that the version s of a reshaped human anti-HM 1.24 antibody has a binding inhibition activity equal to that of the version r of the reshaped human anti-HM 1.24 antibody.

Version s of the H chain of the reshaped human anti-HM 1.24 antibody was evaluated in combination with the above-mentioned version a of the L chain as mentioned for measurement of antigen binding activity and binding inhibition activity. The result, as shown in FIGS. 29 and 30, indicated that version s has a similar level of antigen binding activity and binding inhibition activity to that of version r.

As mentioned above, the reshaped human anti-HM 1.24 antibody of the present invention retains the ability of binding to antigen even after one or more amino acid residues have been replaced with other amino acids. Accordingly, the present invention includes the reshaped human anti-HM 1.24 antibody in which one or more amino acid residues have been replaced with other amino acids in the variable region of the H chain or the L chain as long as it retains the original properties.

3. Evaluation of the Purified Reshaped Human Anti-HM 1.24 Antibody

Figure 31:
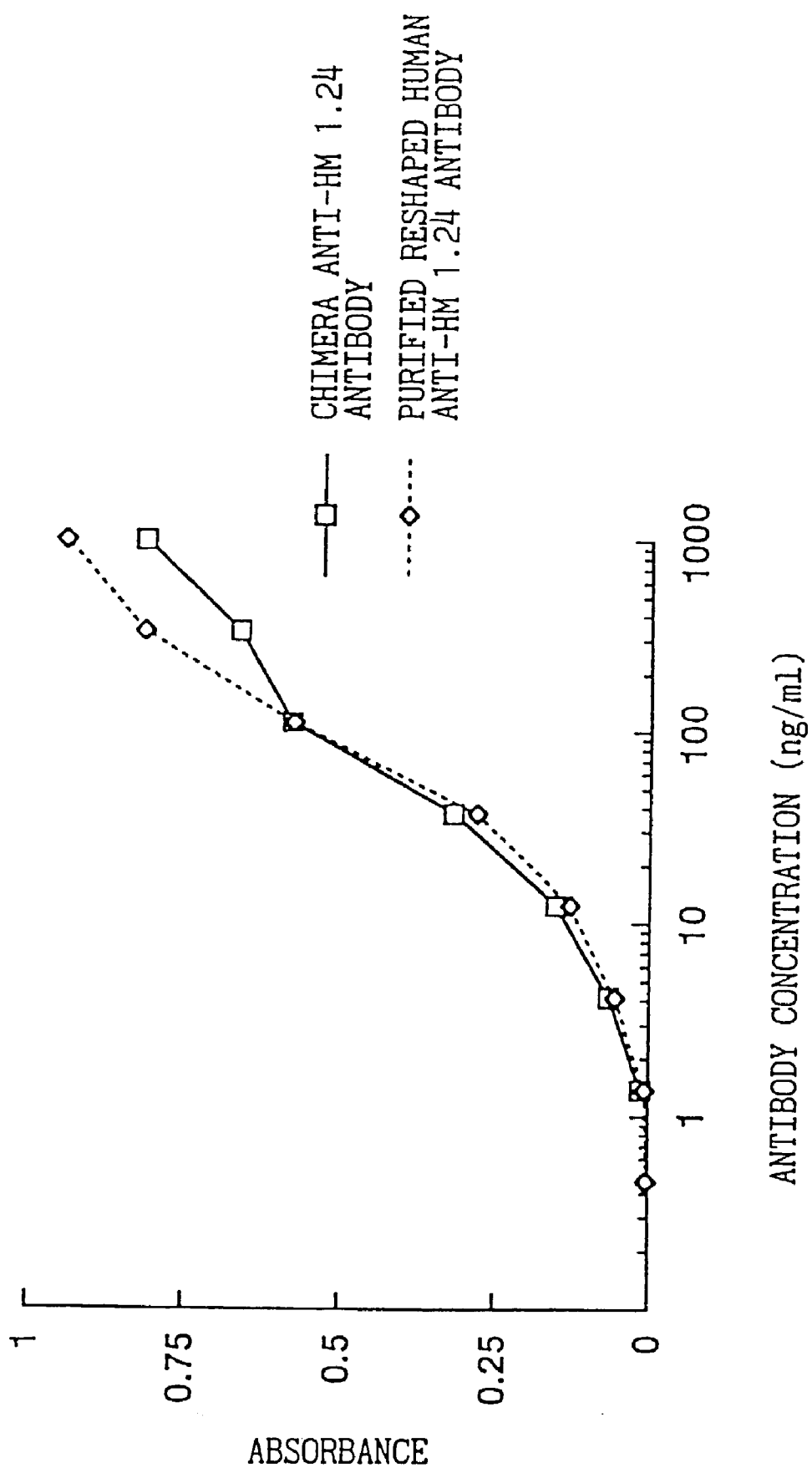
FIG. 31 is a graph showing that a purified reshaped human anti-HM 1.24 antibody has an antigen binding activity equal to that of a chimeric anti-HM 1.24 antibody.
Figure 32:
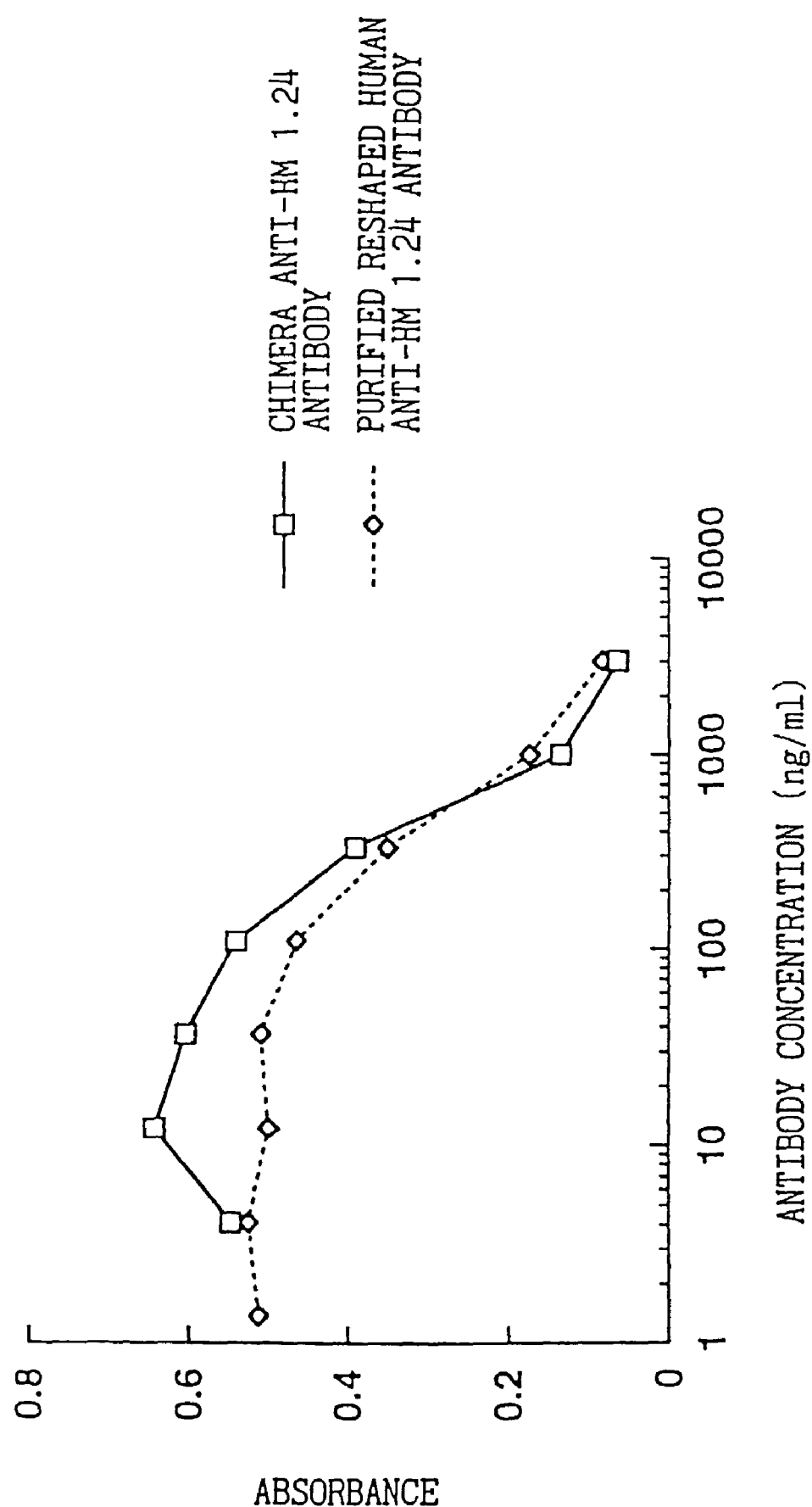
FIG. 32 is a graph showing that a purified reshaped human anti-HM 1.24 antibody has a binding inhibition activity equal to that of a chimeric anti-HM 1.24 antibody.

The purified reshaped human anti-HM 1.24 antibody was evaluated for the above-mentioned antigen binding activity and binding inhibition activity. The result, as shown in FIGS. 31 and 32, indicated that the reshaped human anti-HM 1.24 antibody has a similar level of antigen binding activity and binding inhibition activity to that of the chimeric anti-HM 1.24 antibody. This fact indicated that the reshaped human anti-HM 1.24 antibody has the same antigen binding activity as the mouse anti-HM 1.24 antibody.

Example 12

Anti-tumor Effect of the Chimeric Anti-HM 1.24 Antibody Against the Human Myeloma Mouse Model 1. Preparation of Antibody to be Administered 1-1. Preparation of the Chimeric Anti-HM 1.24 Antibody The purified chimeric anti-HM 1.24 antibody obtained in the above Example 6 was concentrated and the buffer solution was replaced by PBS(−) using the centrifuging ultrafiltration concentrator Centriprep 10 (manufactured by Amicon). This was filter-sterilized using the membrane filter MILLEX-GV (manufactured by MILLIPORE) with a pore size of 0.22 μm. This was prepared to a concentration of 200 μg/ml using the filter-sterilized PBS(−), which was used for the following experiments. The concentration of the antibody was measured by absorbance at 280 nm and calculated with 1 mg/ml as 1.35 OD.

1-2. Purification of the Control Human IgG1

Human IgG1 to be used as a control for the chimeric anti-HM 1.24 antibody was purified as follows. After an equal amount of PBS(−) was added to Hu IgG1 Kappa Purified (manufactured by BINDING SITE), it was affinity-purified using the high-speed antibody purification system ConSep LC100 (manufactured by MILLIPORE) and Hyper D Protein A column (manufactured by Nippon Gaishi) using PBS(−) as the absorption buffer and 0.1 M sodium citrate buffer (pH 3) as the elution buffer according to the attached instructions. The eluted fractions were adjusted to about pH 7.4 by immediately adding 1 M Tris-HCl (pH 8.0) and then using the centrifuging ultrafiltration concentrator Centriprep 10 (manufactured by Amicon) concentration and buffer substitution to PBS(−) was carried out, and filter-sterilized using the membrane filter MILLEX-GV (manufactured by MILLIPORE) with a pore size of 0.22 μm. This was adjusted to 200 μg/ml using the filter-sterilized PBS(−) and used for the following experiments. Antibody concentration was measured by absorbance at 280 nm and calculated with 1 mg/ml as 1.35 OD.

2. Method for Quantitating of Human Serum IgG in the Mouse Serum

Human IgG contained in the mouse serum was quantitated by the following ELISA. 100 μl of goat anti-human IgG diluted to 1 μg/ml with 0.1 M bicarbonate buffer (pH 9.6) was added to a 96-well plate (manufactured by NUNC) and incubated at 4° C. overnight to immobilize the antibody. After blocking, 100 μl of serially diluted mouse serum or human IgG as standard (manufactured by CAPPEL) was added and incubated at room temperature for one hour. After washing, 100 μl of 2000-fold diluted alkaline phosphatase-labelled anti-human IgG (manufactured by CAPPEL) was added and incubated at room temperature for one hour. After washing, the substrate solution was added and incubated, and then absorbance at 405 nm was measured using the MICROPLATE READER Model 3550 (manufactured by Bio-Rad).

3. Anti-tumor effect of the Chimeric Anti-HM 1.24 Antibody Against the Human Myeloma Cells-transplanted Mouse 3-1. Construction the Human Myeloma Cells-transplanted Mouse The human myeloma cells-transplanted mouse was constructed as follows. KPMM2 cells passaged in vivo using SCID mice (breeded by Nihon CLEA) were prepared at a concentration of $3 \times 10^7$ cells/ml with RPMI 1640 medium supplemented with 10% fetal bovine serum (manufactured by GIBCOBRL). Two hundred μl of the above KPMM2 cell suspension was injected via the tail vein to SCID mice (male, 8-weeks old breeded by Nihon CLEA) to which 100 μl of anti-asialo GM1 (manufactured by Wako Pure Chemical Industries Co., Ltd.) had been intraperitoneally given on the previous day.

3-2. Administration of Antibody

On day 12 after KPMM2 cell transplantation, serum was collected from the above human myeloma cells-transplanted mice, and human IgG in the serum was quantitated using the ELISA mentioned in the above 2. Take of KPMM2 cells in the bone marrow was confirmed by the increase of human IgG level in the serum. On day 14, 21, and 28 after KPMM2 cell transplantation, 100 μl each of the antibodies prepared in the above 1 was intraperitoneally given to these mice.

Figure 33:
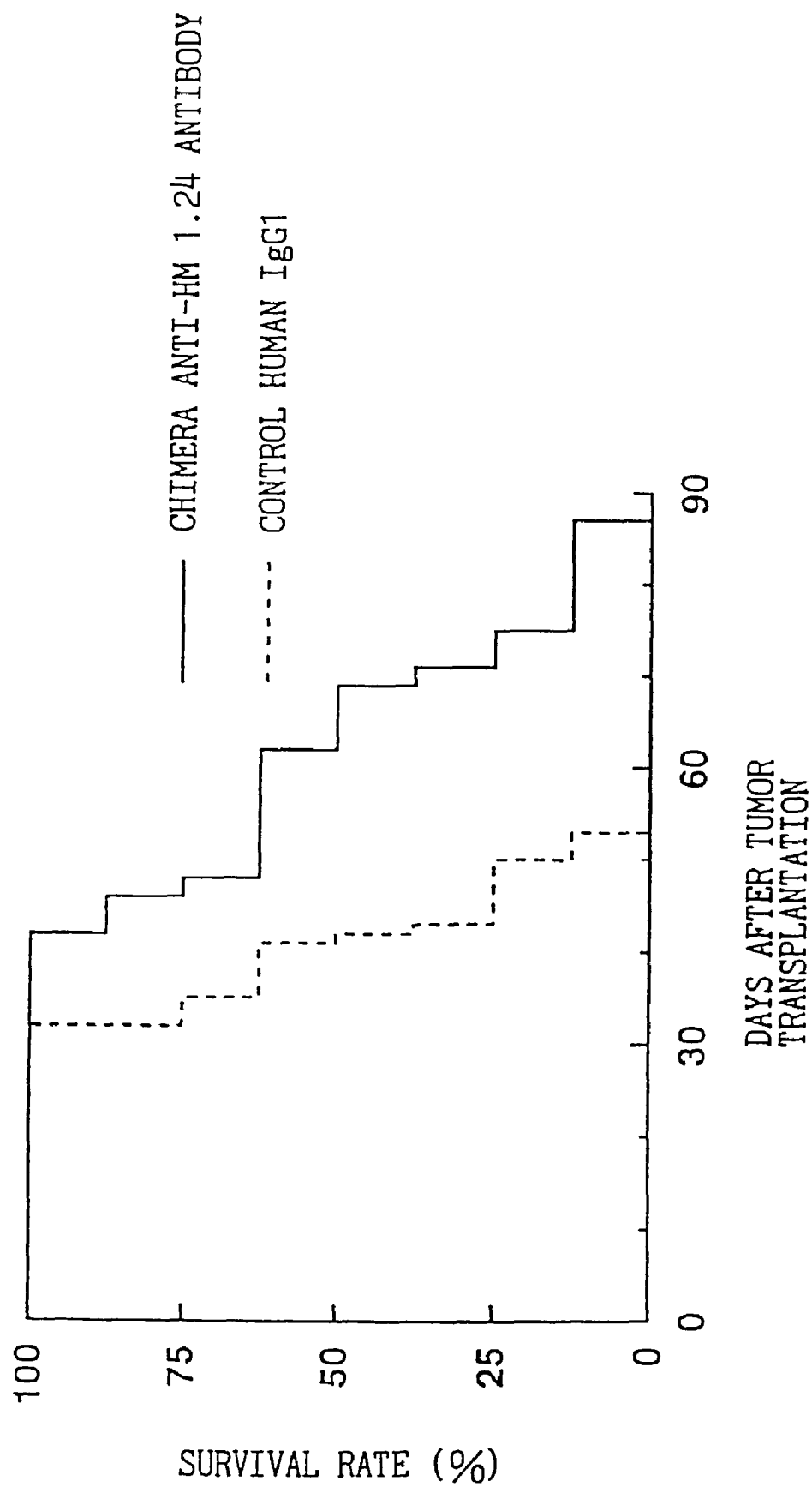
FIG. 33 is a graph showing that the administration of a chimeric anti-HM 1.24 antibody caused prolongation of the survival period as compared to the administration of the control human IgG1 in a human myeloma cells-transplanted mouse.

3-3. Evaluation of the Anti-tumor Effect of the Chimeric Anti-HM 1.24 Antibody Against the Human Myeloma Cells-transplanted Mouse The anti-tumor effect of the chimeric anti-HM 1.24 antibody was evaluated by the survival period of the mice. As shown in FIG. 33, the mice that were given the chimeric anti-HM 1.24 antibody showed a prolonged period of survival as compared to the mice that received control human IgG1. Thus, it was confirmed that the chimeric anti-HM 1.24 antibody has the anti-tumor effect against the human myeloma cells-transplanted mouse.

Example 13

Measurement of ADCC Activity of the Reshaded Human Anti-HM 1.24 Antibody

ADCC (Antibody-dependent Cellular Cytotoxicity) activity was measured according to the method as set forth in Current Protocols in Immunology, Chapter 7, Immunologic studies in humans, Editor, John E, Coligan et al., John Wiley & Sons, Inc., 1993.

1. Preparation of Effector Cells

Mononuclear cells were separated from the peripheral blood of healthy humans by the density centrifugation method. Thus, an equal amount of PBS(−) was added to the peripheral blood of healthy humans, which was layered on Ficoll-Paque PLUS (manufactured by Pharmacia), and was centrifuged at 400 g for 40 minutes. The mononuclear cells layer was collected, and washed four times with RPMI 1640 medium (manufactured by GIBCO BRL) supplemented with 10% fetal bovine serum (manufactured by GIBCO BRL), and prepared at a cell density of $5 \times 10^6$/ml with the same culture medium.

LAK (Limphokine Activated Killer Cell) was induced from the bone marrow cells of SCID mice (breeded by Nihon CLEA). Thus, bone marrow cells were isolated from the femoral bone of the mice and washed twice with RPMI1640 medium (manufactured by GIBCO BRL) supplemented with 10% fetal bovine serum (manufactured by GIBCO BRL), and prepared at a cell density of $2 \times 10^5$/ml with the same culture medium. This was incubated together with 50 ng/ml of recombinant human IL-2 (manufactured by R & D SYSTEMS) and 10 ng/ml of recombinant mouse GM-CSF (manufactured by R & D SYSTEMS) in the $CO_2$ incubator (manufactured by TABAI) for seven days. The cell number was adjusted to $2 \times 10^6$/ml with the same culture medium.

2. Preparation of Target Cells

The human myeloma cell line KPMM2 (Japanese Unexamined Patent Publication (Kokai) No. 7-236475) or plasma cell leukemia-derived ARH-77 (ATCC CCL-1621) was radiolabelled by incubating in the RPMI 1640 medium (manufactured by GIBCO BRL) supplemented with 10% fetal bovine serum (manufactured by GIBCO BRL) together with 0.1 mCi of 51Cr-sodium chromate (manufactured by ICN) at 37° C. for 60 minutes. After radiolabelling, the cells were washed three times with the same culture medium and adjusted to $2\times10^5$/ml.

3. ADCC Assay

Into a 96-well U-bottomed plate (manufactured by Becton Dickinson) were added 50 µl of $2\times10^5$ target cells/ml, 50 µl of the reshaped human anti-HM 1.24 antibody, the mouse anti-HM 1.24 antibody, control human IgG1 (manufactured by THE BINDING SITE) or control mouse IgG2a (UPC10, manufactured by CAPPEL), and reacted at 4° C. for 15 minutes.

Then, 100 µl of the effector cells was cultured in the $CO_2$ incubator for 4 hours, when the ratio (E:T) of the effector cells (E) to the target cells (T) was set at 0:1, 3.2:1, 8:1, 20:1, or 50:1.

One hundred µl of the supernatant was taken and the radioactivity released into the culture supernatant was measured by the gamma counter (ARC-300, manufactured by Aloka). For measurement of the maximum radioactivity, 1% NP-40 (manufactured by Nakalai) was used. Cytotoxicity (%) was calculated by $(A-C)/(B-C)\times100$, wherein A is radioactivity (cpm) released in the presence of antibody, B is radioactivity (cpm) released by NP-40, and C is radioactivity (cpm) released by the culture medium alone without antibody.

Figure 34:
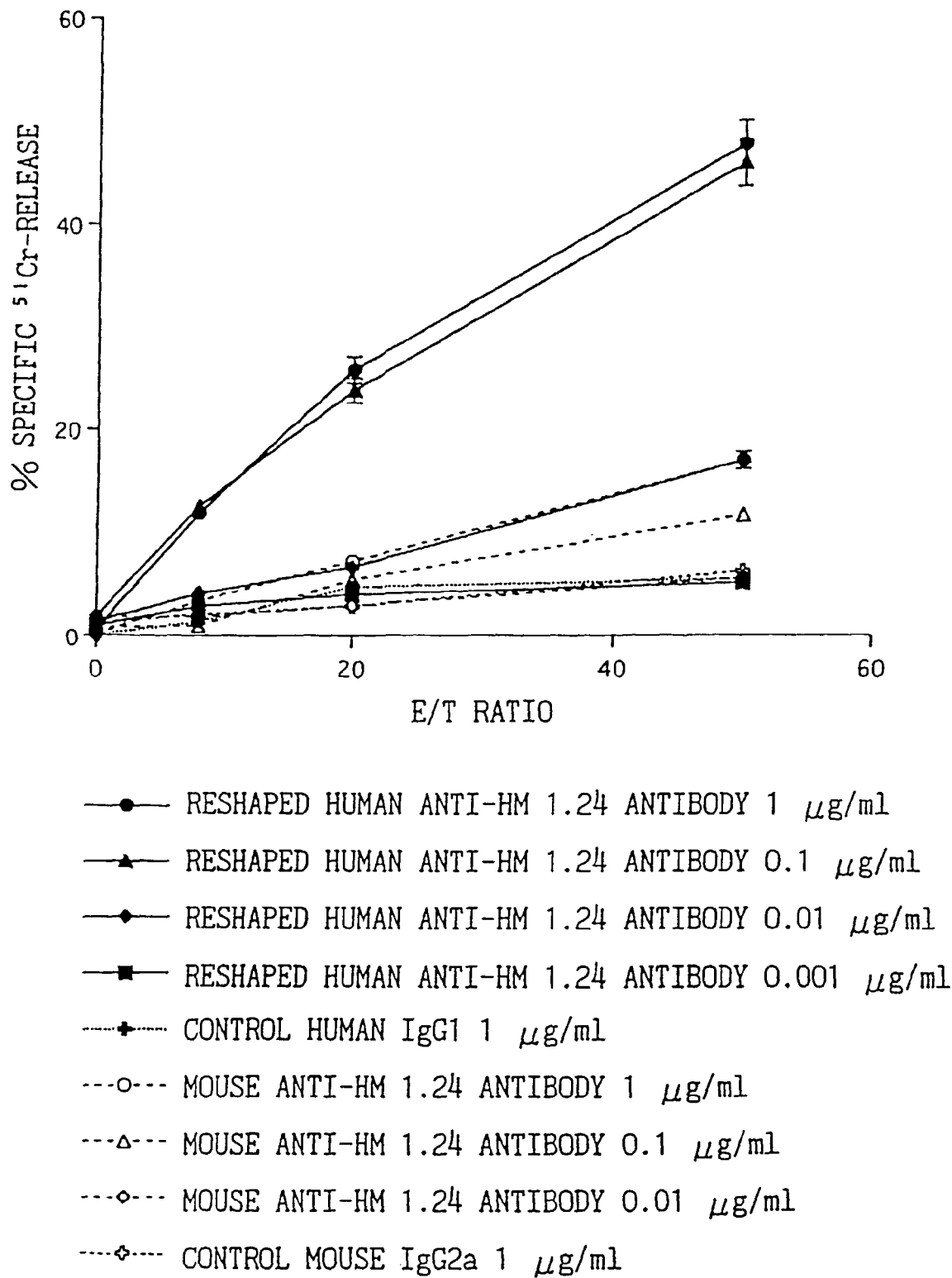
FIG. 34 is a graph showing that when cells derived from the peripheral blood of healthy human are used as a effector cell the control human IgG1 exhibits no cytotoxicity to the KPMM2 cells and a mouse anti-HM 1.24 antibody also has a weak cytotoxicity whereas a reshaped human anti-HM 1.24 antibody exhibits a strong cytotoxicity to the KPMM2 cells.
Figure 35:
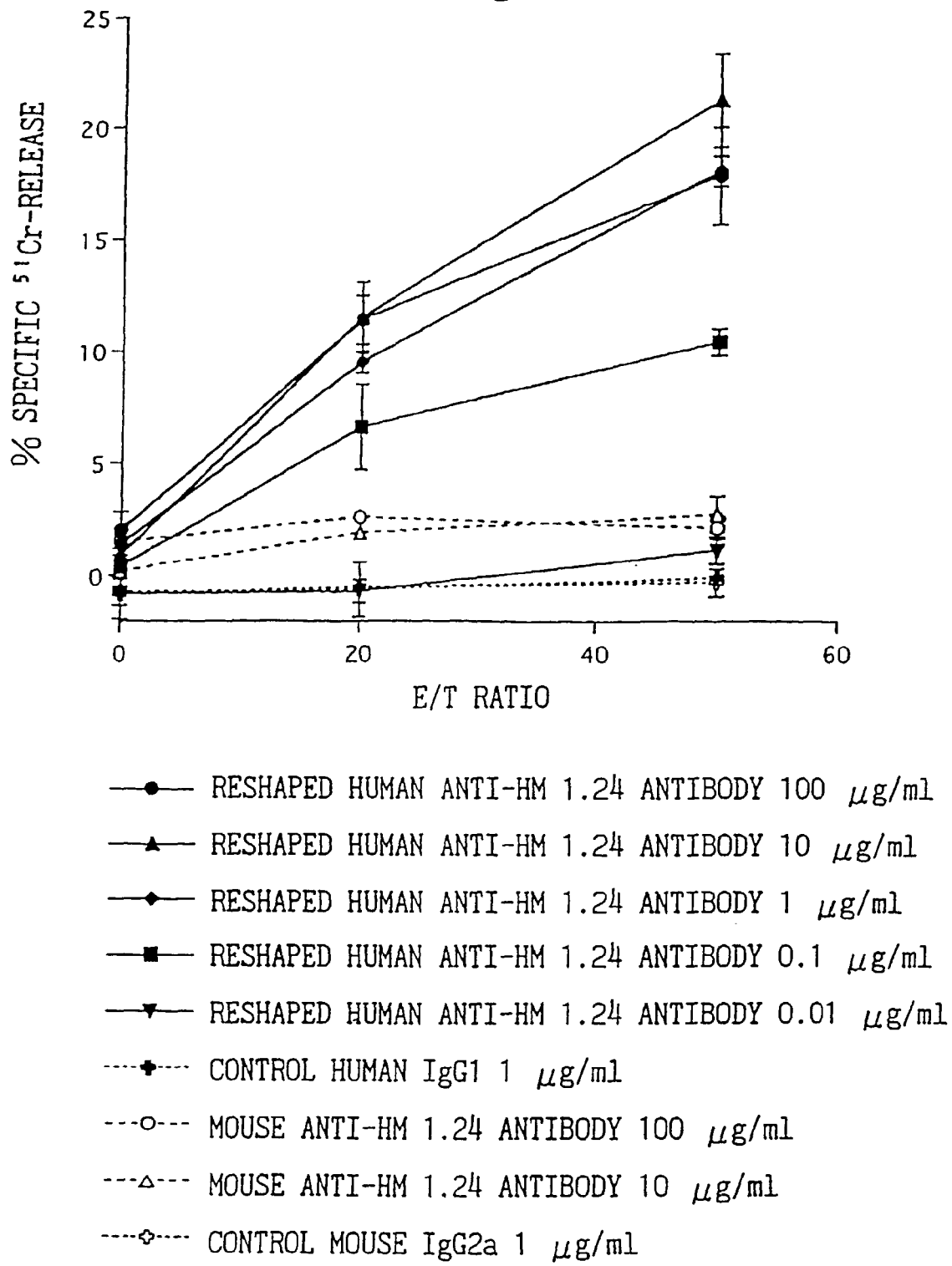
FIG. 35 is a graph showing that when cells derived from the peripheral blood of healthy human are used as a effector cell the control human IgG1 exhibits no cytotoxicity to the ARH-77 cells and a mouse anti-HM 1.24 antibody also has a weak cytotoxicity, whereas a reshaped human anti-HM 1.24 antibody exhibits a strong cytotoxicity to the ARH-77 cells.

FIG. 34 shows the result obtained when the cells prepared from the peripheral blood from the healthy human were used as the effector cell and KPMM2 cells were used as the target cell. FIG. 35 shows the result obtained when the cells prepared from the peripheral blood from the healthy human were used as the effector cell and ARH-77 was used as the target cell. When the reshaped human anti-HM 1.24 antibody was added, cytotoxicity increased with the increase in antibody concentration as compared to the control human IgG1, indicating that the reshaped human anti-HM 1.24 antibody has ADCC activity.

Furthermore, when the reshaped human anti-HM 1.24 antibody was added, cytotoxicity evidently increased as compared to the mouse anti-HM 1.24 antibody, indicating that the reshaped human anti-HM 1.24 antibody has higher ADCC activity than the mouse anti-HM 1.24 antibody. Furthermore, when KPMM2 was used as the target cell, the addition of the reshaped human anti-HM 1.24 antibody at a concentration of 0.1 µg/ml or higher caused no change in cytotoxicity, indicating that the concentration of 0.1 µg/ml or higher has sufficient ADCC activity. When ARH-77 was used as the target cell, the addition of the reshaped human anti-HM 1.24 antibody at a concentration of 1 µg/ml or higher caused no change in cytotoxicity, indicating that the concentration of 1 µg/ml or higher has sufficient ADCC activity.

Figure 36:
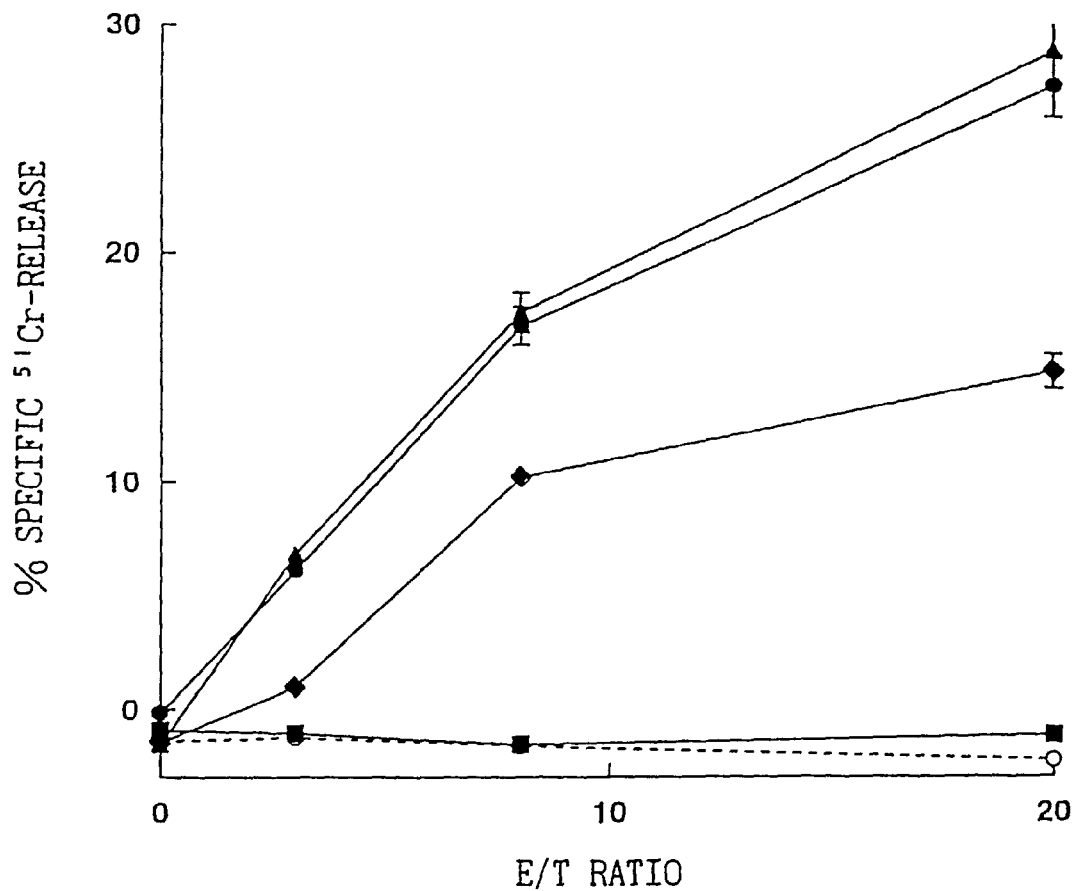
FIG. 36 is a graph showing that when cells derived from the bone marrow of SCID mice are used as a effector cell the control human IgG1 exhibits no cytotoxicity to the KPMM2 cells, whereas a reshaped human anti-HM 1.24 antibody exhibits an increased cytotoxicity to the KPMM2 cells with the increase in the antibody concentration.

FIG. 36 shows the result obtained when the cells prepared from the bone marrow of SCID mice were used as the effector cell. When the reshaped human anti-HM 1.24 antibody was added, cytotoxicity increased with the increase in antibody concentration as compared to the control human IgG1, indicating that the reshaped human anti-HM 1.24 antibody has ADCC activity. Furthermore, the addition of the reshaped human anti-HM 1.24 antibody at a concentration of 0.1 µg/ml or higher caused no change in cytotoxicity, indicating that the concentration of 0.1 µg/ml or higher has sufficient ADCC activity.

These results show that the reshaped human anti-HM 1.24 antibody has ADCC activity even when the effector cells used are derived from humans or mice.

Example 14

Anti-tumor Effect of the Reshaped Anti-HM 1.24 Antibody Against the Human Myeloma Mouse Model 1. Preparation of Antibody to be Administered The reshaped anti-HM 1.24 antibody obtained by introduction of plasmid HEF-RVLa-AHM-gκ and plasmid HEF-RVHr-AHM-gγ1 into CHO cells was prepared to a concentration of 40, 200, and 1000 µg/ml using the filter-sterilized PBS(−), and the control human IgG1 obtained in Example 12.1-2 was prepared to a concentration of 200 µg/ml using the filter-sterilized PBS(−), which were used as the antibodies to be administered.

2. Anti-tumor Effect of the Reshaped Anti-HM 1.24 Antibody Against the Human Myeloma Cells-transplanted Mouse 2-1. Construction of the Human Myeloma Cells-transplanted Mouse The human myeloma cells-transplanted mice were prepared according to Example 12.3-1. The mice used were SCID mice (five weeks old) (breeded by Nihon CLEA).

2-2. The Administration of Antibodies

On day 9 after KPMM2 cell transplantation, serum was collected from the above human myeloma cells-transplanted mice prepared in the above 2-1, and human IgG in the serum was quantitated using the ELISA mentioned in the above 12.2. Take of KPMM2 cells on the bone marrow was confirmed by the increase of human IgG level in the serum. On day 10 after KPMM2 cell transplantation, 100 µl each of the antibodies prepared in the above 1 was intravenously given to these mice.

2-3. Evaluation of the Anti-tumor Effect of the Reshaped Anti-HM 1.24 Antibody Against the Human Myeloma Cells-transplanted Mouse The anti-tumor effect of the reshaped anti-HM 1.24 antibody was evaluated by the change in the amount of human IgG in the mouse serum and in the survival period of mice.

Figure 37:
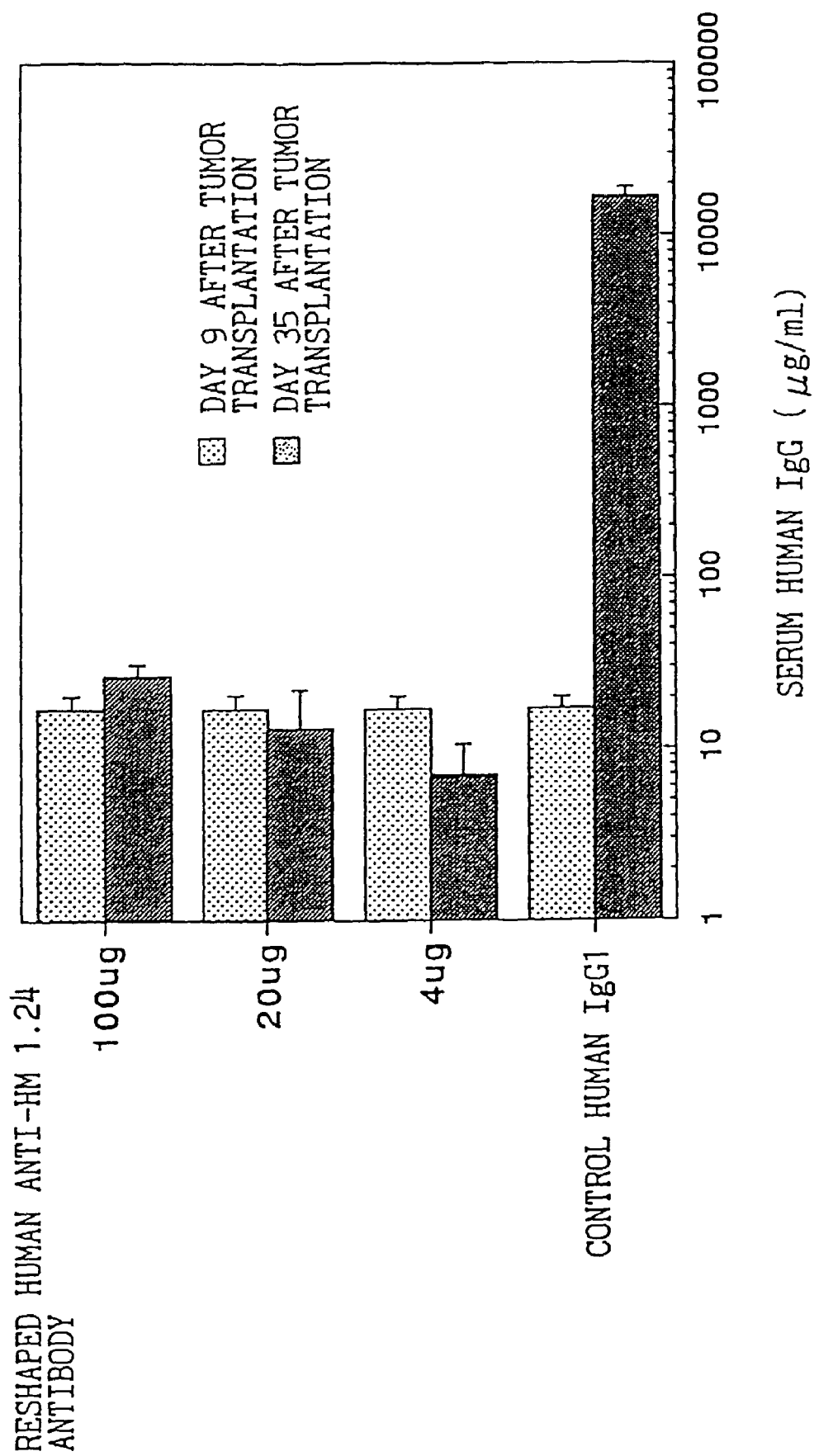
FIG. 37 is a graph showing that in a human myeloma cells-transplanted mouse the serum IgG human level is increased after the administration of the control human IgG1 as compared to the level before the administration, whereas the administration of a reshaped human anti-HM 1.24 antibody inhibits the increase in the serum human IgG level.
Figure 38:
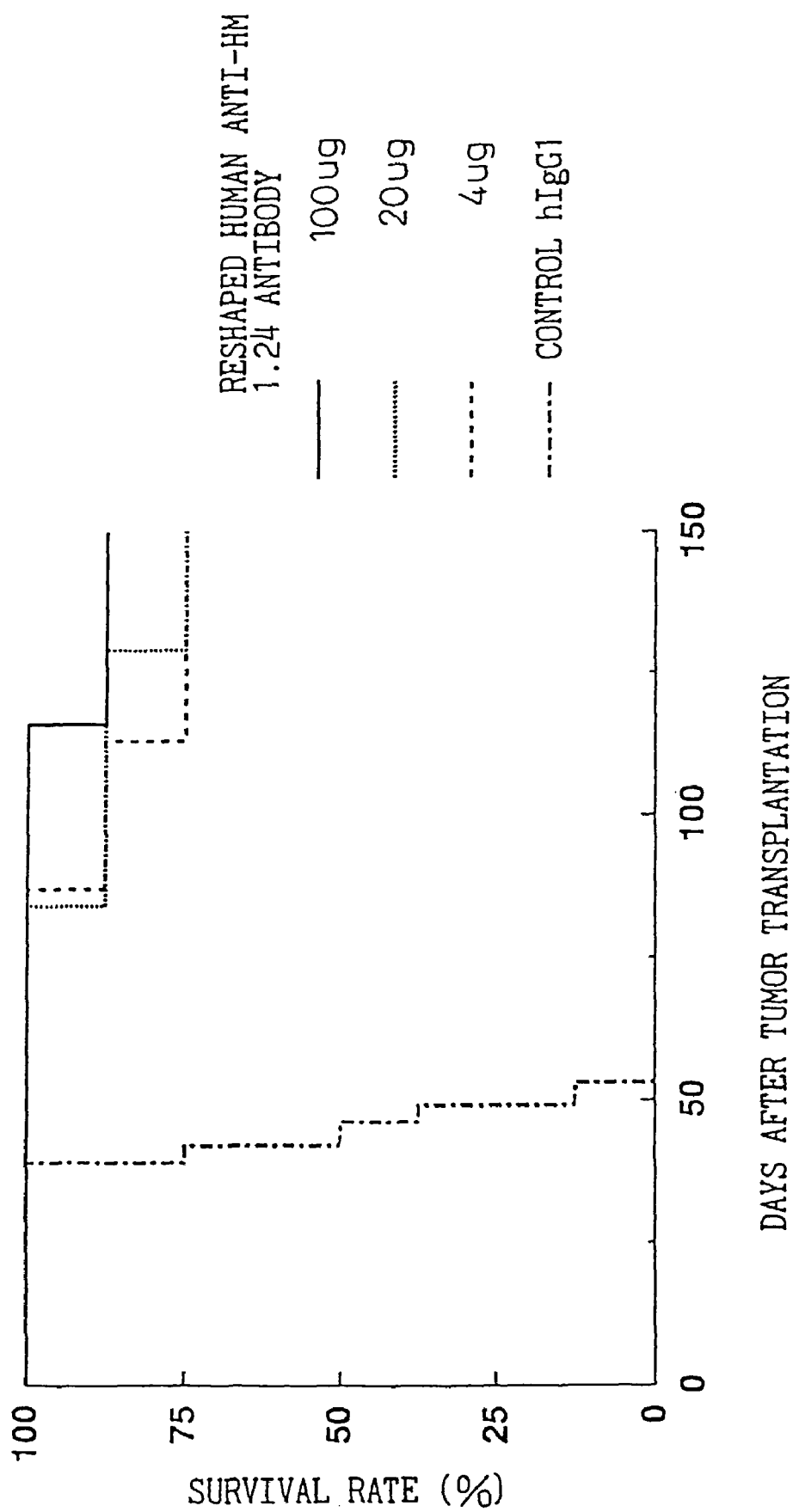
FIG. 38 is a graph showing that in a human myeloma cells-transplanted mouse the administration of a reshaped human anti-HM 1.24 antibody causes prolongation of the survival period as compared to the administration of the control human IgG1.

The change in the amount of human IgG in the mouse serum was quantitated for the serum collected on day 35 after the transplantation of KPMM2 cells by determining human IgG using the ELISA mentioned in Example 12.2. The result as shown in FIG. 37 revealed that in the control human IgG1-administration group the amount of human IgG in the serum on day 35 after the KPMM2 cell transplantation was increased by about 1000-fold as compared to that on day 9 (the day before antibody administration), whereas in the reshaped human anti-HM 1.24 antibody-administration group it was almost equal to or below that on day 9 for any dosage, indicating that the reshaped human anti-HM 1.24 antibody suppressed the growth of KPMM2 cells. On the other hand, for the survival period as shown in FIG. 38, prolongation was observed for the reshaped human anti-HM 1.24 antibody-administration group as compared to the control human IgG1-administration group. The foregoing shows that the reshaped human anti-HM 1.24 antibody has the anti-tumor effect against the human myeloma cells-transplanted mouse.

Example 15

Comparison of Anti-tumor Effect Between the Reshaped Human Anti-HM 1.24 Antibody and the Existing Drug Melphalan Against the Human Myeloma Mouse Model 1. Preparation of the Drugs to be Administered
1-1. Preparation of Antibodies to be Administered The reshaped human anti-HM 1.24 antibody obtained by the introduction of plasmid HEF-RVLa-AHM-gκ and plasmid HEF-RVHr-AHM-gγ1 into CHO cells was prepared to a concentration of 40 and 200 µg/ml using the filter-sterilized PBS(-), and the control human IgG1 obtained in Example 12.1-2 was prepared to a concentration of 200 µg/ml using the filter-sterilized PBS(-), which were used as the antibodies to be administered.

1-2. Preparation of Melphalan

Melphalan (manufactured by SIGMA) that is an existing drug for myeloma was prepared to a concentration of 0.1 mg/ml using 0.2% carboxymethyl cellulose (CMC) (manufactured by Daicel Chemical Industries, Ltd.).

2. The Anti-tumor Effect of the Reshaped Human Anti-HM 1.24 Antibody and Melphalan Against the Human Myeloma Cells-transplanted Mouse 2-1. Construction of Human Myeloma Cells-transplanted Mouse The human myeloma cells-transplanted mice were prepared according to Example 14.2-1.

2-2. The Administration of Drug

On day 9 after KPMM2 cells transplantation, serum was collected from the above human myeloma cells-transplanted mice prepared in the above 2-1, and human IgG in the serum was quantitated using the ELISA mentioned in the above 12.2. Take of KPMM2 cells on the bone marrow was confirmed by the increase of human IgG level in the serum. On day 10 after KPMM2 cell transplantation, 100 µl each of the antibodies prepared in the above 1-1 were intravenously given to these mice. Furthermore, 200 µl of 0.2% CMC solution was orally given once daily for five days from day 10 after transplantation. On the other hand, for the melphalan-administration group, the melphalan solution prepared in the above 1-2 was orally given at an amount of 100 µl per 10 g of body weight (1 mg/kg as melphalan) once daily for five days from day 10 after transplantation of KPMM2 cells.

2-3. Evaluation of the Anti-tumor Effect of the Reshaped Anti-HM 1.24 Antibody Against the Human Myeloma Cells-transplanted Mouse The anti-tumor effect of the reshaped anti-HM 1.24 antibody was evaluated by the change in the amount of human IgG in the mice serum and in the survival period of mice.

Figure 39:
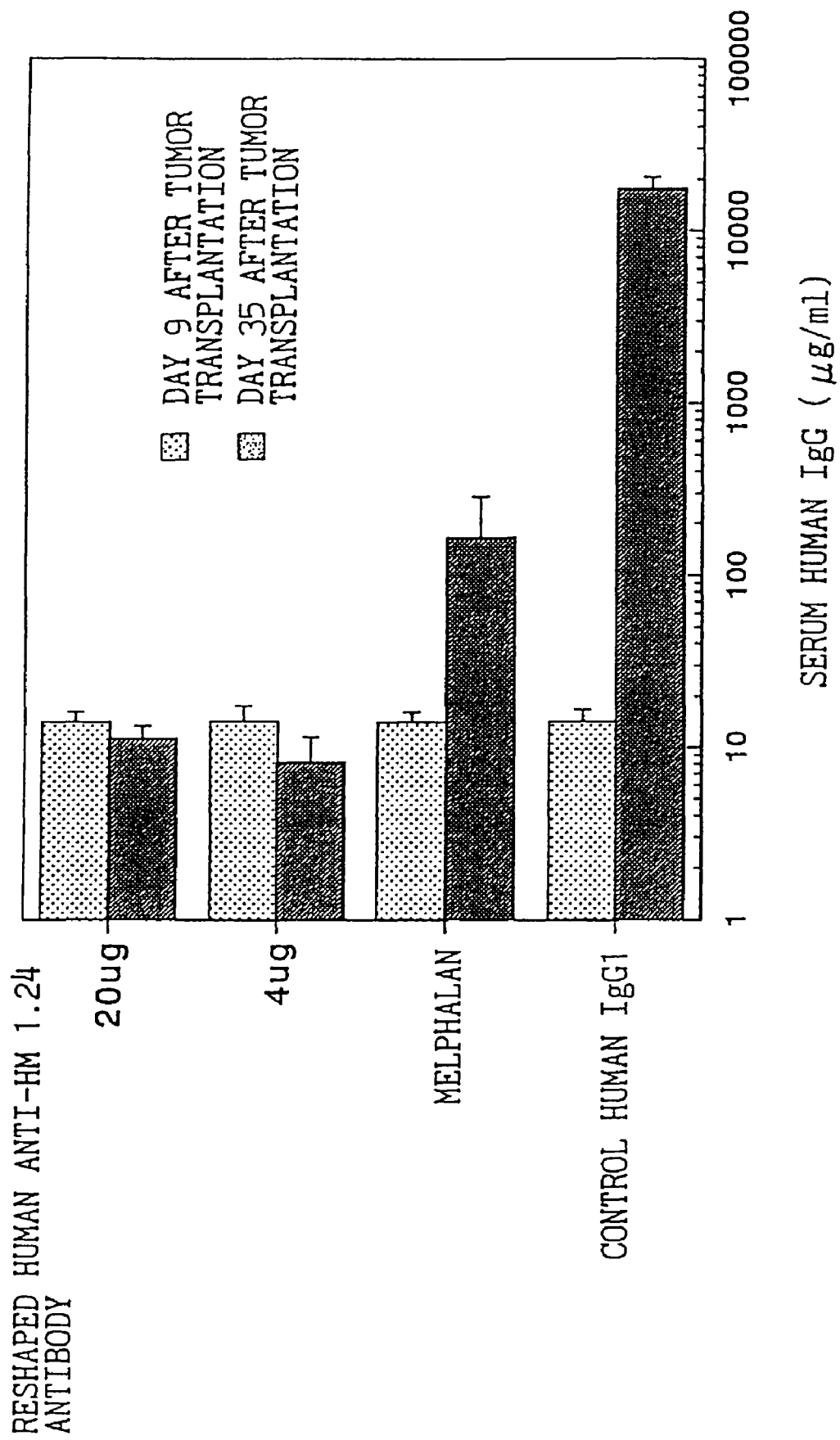
FIG. 39 is a graph showing that in a human myeloma cells-transplanted mouse the serum human IgG level is increased after the administration of melphalan and the control human IgG1 as compared to the level before the administration, whereas the administration of a reshaped human anti-HM 1.24 antibody inhibits the increase in the serum human IgG level.

The change in the amount of human IgG in the mice serum was quantitated for the serum collected on day 35 after the transplantation of KPMM2 cells by determining human IgG using the ELISA mentioned in Example 12.2. The result as shown in FIG. 39 revealed that in the control human IgG1-administration group the amount of human IgG in the serum on day 35 after the KPMM2 cell transplantation was increased by about 1000-fold as compared to that on day 9 (the day before antibody administration), whereas it seemed that KPMM2 cells grew in these mice. In the melphalan-administration group as well, the amount of serum human IgG was more increased than that before the drug administration, though not so high as in the control human IgG-administration group. This result indicates that administration of melphalan did not suppress the growth of KPMM2 cells perfectly. On the other hand, in the reshaped human anti-HM 1.24 antibody-administration group, the amount of serum human IgG at day was less than at day 9 after transplantation for any dosage, indicating that the reshaped human anti-HM 1.24 antibody suppressed the growth of KPMM2 cells.

On the other hand, for the survival period also as shown in FIG. 40, prolongation was observed for the reshaped human anti-HM 1.24 antibody-administration group as compared to the control human IgG1-administration group or melphalan-administration group. From the foregoing, it was shown that the reshaped human anti-HM 1.24 antibody has the anti-tumor effect against the human myeloma cells-transplanted mice and that the anti-tumor effect of the present antibody is stronger than the existing drug melphalan.

The above results indicated that when the human-derived effector cells were used, the mouse anti-HM 1.24 antibody had little cytotoxicity to human myeloma cells, whereas the reshaped human anti-HM 1.24 antibody and the chimeric anti-HM 1.24 antibody had strong cytotoxicity. This fact indicates the importance of humanizing antibody and provides hope on the usefulness of the reshaped human anti-HM 1.24 antibody in humans.

The reshaped human anti-HM 1.24 antibody have exhibited a very strong anti-tumor effect in the human myeloma cells-transplanted SCID mice. Since in humans the effector cells are derived from humans and lymphocytes are normally present, an even stronger anti-tumor effect of the reshaped human anti-HM 1.24 antibody is expected.

In the myeloma model, the reshaped human anti-HM 1.24 antibody have exhibited a strong anti-tumor effect as compared to the existing drug, and therefore, it is expected that the reshaped human anti-HM 1.24 antibody will make an epoch-making drug for treatment of myeloma.

Reference Example 1

Construction of the Hybridoma that Produces the Mouse Anti-HM 1.24 Monoclonal Antibody The hybridoma that produces the mouse anti-HM 1.24 monoclonal antibody was prepared according to the method described in Goto, T. et al., Blood (1994) 84, 1992-1930.

The Epstein-Barr virus nuclear antigen (EBNA)-negative plasma cell line KPC-32 ($1 \times 10^7$ cells) derived from the bone marrow of human patient with multiple myeloma (Goto, T. et al., Jpn. J. Clin. Hematol. (11991) 32, 1400) was intraperitoneally given twice to BALB/c mice (breeded by Charles River) every six weeks.

In order to further elevate the titer of antibody production, $1.5 \times 10^6$ KPC-32 cells were injected into the spleen of the mise three days before sacrificing the animals (Goto, T. et al., Tokushima J. Exp. Med. (1990) 37, 89). After sacrificing the mice, the spleen were removed, and the spleen cells removed according to the method of Groth, de St. & Schreidegger (Cancer Research (1981) 41, 3465) were subjected to cell fusion with the myeloma cells SP2/0.

Antibody in the supernatant of the hybridoma culture was screened by the ELISA (Posner, M. R. et al., J. Immunol. Methods (1982) 48, 23) using the KPC-32 cell-coated plates. $5 \times 10^4$ KPC-32 cells were suspended in 50 ml of PBS and aliquoted into 96-well plates (U-bottomed, Corning, manufactured by Iwaki). After blocking with PBS containing 1% bovine serum albumin (BSA), the supernatant of the hybridoma was added and incubated at 4° C. for 2 hours. Subsequently, it reacted with peroxidase-labelled goat anti-mouse IgG antibody (manufactured by Zymed) at 4° C. for 1 hour, washed once, and was reacted with o-phenylenediamine substrate solution (manufactured by Sumitomo Bakelite) at room temperature for 30 minutes.

After stopping the reaction with 2N sulfuric acid, absorbance at 492 nm was measured using the ELISA reader (manufactured by Bio-Rad). In order to remove the hybridoma that produces antibody against human immunoglobulin, the positive hybridoma culture supernatant had previously been adsorbed to human serum, and the reactivity to other sub-cellular components were screened. Positive hybridomas were selected and their reactivity to various cell lines and human samples were investigated using flow cytometry. The finally selected hybridoma clones were cloned twice, which were injected into the abdominal cavity of the pristane-treated BALB/c mice and then the ascitic fluid was obtained therefrom.

Monoclonal antibody was purified from the mouse ascites by ammonium sulfate precipitation and Protein A affinity chromatography kit (Ampure PA, manufactured by Amersham). The purified antibody was conjugated to fluorescein isothiocyanate (FITC) using the QuickTag FITC conjugation kit (manufactured by Boehringer Mannheim).

As a result, the monoclonal antibodies produced by 30 hybridoma clones reacted with KPC-32 and RPMI 8226 cells. After cloning, the reactivity of the supernatant of these hybridomas with other cell lines and peripheral blood-derived mononuclear cells was investigated.

Among them, three clones produced monoclonal antibodies that specifically react with plasma cells. Out of these three clones, the hybridoma clone that produce monocloned antibody that is most useful for flow cytometry analysis and that has complement-dependent cytotoxicity against RPUI 8226 cells was selected and termed HM1.24. The subclass of monoclonal antibody produced by this hybridoma was determined by the ELISA using subclass-specific rabbit anti-mouse antibody (manufactured by Zymed). Anti-HM 1.24 antibody had a subclass of IgG2a κ. The hybridoma that produces the anti-HM 1.24 antibody was internationally deposited on Sep. 14, 1995, with the National Institute of Bioscience and Human Technology, Agency of Industrial Science and Technology, MITI (Higashi 1-Chome 1-3, Tsukuba city, Ibalaki prefecture, Japan) under the accession number FERM BP-5233 under the provisions of the Budapest Treaty.

Reference Example 2

Cloning of cDNA Encoding the HM 1.24 Antigen Polypeptide

1. Construction of cDNA Library
1) Preparation of Total RNA

The cDNA that encodes the HM 1.24 antigen which is a polypeptide specifically recognized by mouse anti-HM1.24 monoclonal antibody was isolated as follows.

From the human multiple myeloma cell line KPMM2, total RNA was prepared according to the method of Chirgwin et al. (Biochemistry, 18, 5294 (1979)). Thus, $2.2 \times 10^8$ KPMM2 cells were completely homogenized in 20 ml of 4 M guanidine thiocyanate (manufactured by Nakalai tesque).

The homogenate was layered on 5.3 M cesium chloride layer in the centrifuge tube, which was then centrifuged using Beckman SW40 rotor at 31,000 rpm at 20° C. for 24 hours to precipitate RNA. The RNA precipitate was washed with 70% ethanol, and dissolved in 300 µl of 10 mM Tris-HCl (pH 7.4) containing 1 mM EDTA and 0.5% SDS. After adding Pronase (manufactured by Boehringer) thereto to a concentration of 0.5 mg/ml, it was incubated at 37° C. for 30 minutes. The mixture was extracted with phenol and chloroform to precipitate RNA. Then, the RNA precipitate was dissolved in 200 µl of 10 mM Tris-HCl (pH 7.4) containing 1 mM EDTA.

2) Preparation of Poly(A)+RNA

Using about 500 µg of the total RNA prepared as above as a raw material, poly(A)+RNA was purified using the Fast Track 2.0 m RNA Isolation Kit (manufactured by Invitrogen) according to the instructions attached to the kit.

3) Construction of cDNA Library

Using 10 µg of the above poly(A)+RNA as a raw material, double stranded cDNA was synthesized using the cDNA synthesizing kit TimeSaver cDNA Synthesis Kit (manufactured by Pharmacia) according to the instructions attached to the kit, and using the Directional Cloning Toolbox (manufactured by Pharmacia) EcoRI adapter was linked thereto according to the instructions attached to the kit. Kination and restriction enzyme NotI treatment of the EcoRI adapter were carried out according to the instructions attached to the kit. Furthermore, the adapter-attached double strand cDNA having a size of about 500 bp or higher was isolated and purified using 1.5% low melting point agarose gel (manufactured by SIGMA) to obtain about 40 µl of adapter-attached double strand cDNA.

The adapter-attached double strand cDNA thus prepared was linked to pCOS1 vector (Japanese Unexamined Patent Publication (Kokai) 8-255196) that had previously been treated with restriction enzymes EcoRI and NotI and alkaline phosphatase (manufactured by Takara Shuzo) using T4 to construct DNA ligase (manufactured by GIBCO BRL) to construct cDNA library. The constructed cDNA library was transduced into *Escherichia coli* strain DH5α (manufactured by GIBCO BRL) and the total size was estimated to be about $2.5 \times 10^6$ independent clones.

2. Cloning by Direct Expression
1) Transfection into COS-7 Cells cDNA was amplified by culturing about $5 \times 10^5$ clones of the above transduced *Escherichia coli* in the 2-YT medium (Molecular Cloning: A Laboratory Manual, Sambrook et al., Cold Spring Harbor Laboratory Press, (1989)) containing 50 µg/ml of ampicillin, and plasmid DNA was recovered from the *Escherichia coli* by the alkali method (Molecular Cloning: A Laboratory Manual, Sambrook et al., Cold Spring Harbor Laboratory Press, (1989)). The plasmid DNA obtained was transfected into COS-7 cells by electroporation using the Gene Pulser instrument (manufactured by BioRad).

Thus, 10 µg of the purified plasmid DNA was added to 0.8 ml of COS-7 cells that were suspended into PBS at a concentration of $1 \times 10^7$ cells/ml, and was subjected to pulses at 1500 V and a capacity of 25 µF. After 10 minutes of recovery period at room temperature, the electroporated cells were cultured in the DMEM (manufactured by GIBCO BRL) supplemented with 10% fetal bovine serum under the condition of 37° C. and 5% $CO_2$ for three days.

2) Preparation of the Panning Dish

A panning dish coated with the mouse anti-HM 1.24 antibody was prepared by the method of B. Seed et al. (Proc. Natl. Acad. Sci. USA, 84, 3365-3369 (1987)). Thus, the mouse anti-HM 1.24 antibody was added to 50 mM Tris-HCl, pH 9.5, to a concentration of 10 µg/ml. Three ml of the antibody solution thus prepared was added to a tissue culture plate with a diameter of 60 mm and incubated at room temperature for 2 hours. After washing three times with 0.15 M NaCl solution and blocking with PBS containing 5% fetal bovine serum, 1 mM EDTA, and 0.02% $NaN_3$, these plates used for the following cloning.

3) Cloning of cDNA Library

The COS-7 cells transfected as described above were detached by PBS containing 5 mM EDTA, and then washed once with PBS containing 5% fetal bovine serum. These cells were then suspended in PBS containing 5% fetal bovine serum and 0.02% NaN$_3$ to a concentration of about 1×10$^6$ cells/ml, which was added to the panning dish prepared as above and incubated at room temperature for 2 hours. After washing three times gently with PBS containing 5% fetal bovine serum and 0.02% NaN$_3$, plasmid DNA was recovered from the cells bound to the panning dish using a solution containing 0.6% SDS and 10 mM EDTA.

The recovered plasmid DNA was transduced again to *Escherichia coli* DH5α. After amplifying plasmid DNA as above, it was recovered by the alkali method. The recovered plasmid DNA was transfected into COS-7 cells by the electroporation method and plasmid DNA recovered from the bound cells as described above. The same procedure was repeated one more time, and the recovered plasmid DNA was digested with restriction enzymes EcoRI and NotI. As a result, concentration of the insert with a size of about 0.9 kbp was confirmed. *Escherichia coli* transduced with part of the recovered plasmid DNA was inoculated to the 2-YT agar plate containing 50 μg/ml of ampicillin. After culturing overnight, plasmid DNA was recovered from single colony. It was digested with restriction enzymes EcoRI and NotI and clone p3.19 having an insert of 0.9 kbp was obtained.

The base sequence of this clone was determined by reacting using PRISM, Dye Terminater Cycle Sequencing kit (manufactured by Perkin Elmer) according to the instructions attached to the kit and sequencing using ABI 373A DNA Sequencer (manufactured by Perkin Elmer). The amino acid sequence and the base sequence thereof are shown in SEQ ID NO: 103.

The cDNA encoding the polypeptide having the amino acid sequence as set forth in SEQ ID NO: 103 was inserted into the XbaI cleavage site of pUC19 vector, and has been prepared as plasmid pRS38-pUC19. The *Escherichia coli* that contains this plasmid pRS38-pUC19 has been internationally deposited on Oct. 5, 1993, as *Escherichia coli* DH5α (pRS38-pUC19), with the National Institute of Bioscience and Human-Technology, Agency of Industrial Science and Technology, MITI (Higashi 1-Chome 1-3, Tsukuba city, Ibalaki prefecture, Japan) under the accession number FERM BP-4434 under the provisions of the Budapest Treaty (see Japanese Unexamined Patent Publication (Kokai) No. 7-196694).

INDUSTRIAL APPLICABILITY

Since the chimeric anti-HM 1.24 antibody is composed of the variable region of the mouse anti-HM 1.24 antibody and the constant region of a human antibody, and the reshaped human anti-HM 1.24 antibody is composed of the complementarity determining region of the mouse anti-HM 1.24 antibody, the framework region of a human antibody, and the constant region of a human antibody, it has a low antigenicity against humans, and therefore, is expected to be used as a medical composition, especially for treatment of myeloma.

REFERENCE TO THE ORGANISMS DONATED

The International depository concerned

Title: the National Institute of Bioscience and Human-Technology, Agency of Industrial Science and Technology, MITI Address: Higashi 1-Chome 1-3, Tsukuba city, Ibalaki prefecture, Japan 1. *Escherichia coli* DH5α (pRS 38-pUC19) Accession No.: FERM BP-4434 Date of donation: Oct. 5, 1993
2. Mouse-mouse hybridoma HM1.24 Accession No.: FERM BP-5233 Date of donation: Apr. 27, 1995
3. *Escherichia coli* DH5α (pUC19-RVHr-AHM-gγ1) Accession No.: FERM BP-5643 Date of donation: Aug. 29, 1996
4. *Escherichia coli* DH5α (pUC19-1.24H-gγ1) Accession No.: FERM BP-5644 Date of donation: Aug. 29, 1996
5. *Escherichia coli* DH5α (pUC19-RVLa-AHM-gκ) Accession No.: FERM BP-5645 Date of donation: Aug. 29, 1996
6. *Escherichia coli* DH5α (pUC19-1.24L-gκ) Accession No.: FERM BP-5646 Date of donation: Aug. 29, 1996
7. *Escherichia coli* DH5α (pUC19-RVHs-AHM-gγ1) Accession No.: FERM BP-6127 Date of donation: Sep. 29, 1997

The invention claimed is:

1. An isolated or recombinant nucleic acid encoding an L chain and an H chain of an antibody, comprising a nucleotide sequence encoding a V region of the L chain
   comprising the amino acid sequence of SEQ ID NO:104, and
   a nucleotide sequence encoding a V region of the H chain comprising the amino acid sequence of SEQ ID NO:105.

2. The isolated or recombinant nucleic acid of claim 1 wherein the nucleotide sequence encoding said V region of the L chain comprises the nucleotide sequence of SEQ ID NO:1, and the nucleotide sequence encoding said V region of the H chain comprises the nucleotide sequence of SEQ ID NO:2.

3. The isolated or recombinant nucleic acid of claim 1, further comprising a nucleotide sequence encoding a C region of a human L chain and/or the C region of a human H chain.

4. An isolated or recombinant nucleic acid comprising:
   (A) a nucleotide sequence encoding a V region of a reshaped human L chain of an anti-HM 1.24 antibody comprising the amino acid sequence of SEQ ID NO:106 from position 1 to 107; and
   (B) a nucleotide sequence encoding a V region of a reshaped human H chain of an anti-HM 1.24 antibody comprising the amino acid sequence of SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125 or SEQ ID NO:128, from position 1 to position 120.

5. The isolated or recombinant nucleic acid of claim 4, wherein the nucleotide sequence encoding the V region of the reshaped human L chain comprises the nucleotide sequence of SEQ ID NO:9 from position 58 to 378.

6. The isolated or recombinant nucleic acid of claim 4, wherein the nucleotide sequence encoding the V region of the reshaped human H chain comprises the nucleotide sequence of SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:28 or SEQ ID NO:102, from position 58 to position 417.

7. The isolated or recombinant nucleic acid of claim 4 further comprising a nucleotide sequence encoding the C region of a human L chain; and/or the C region of a human H chain.

8. An isolated or recombinant nucleic acid, comprising:
   (A) a nucleotide sequence encoding a V region of a reshaped human L chain of an anti-HM 1.24 antibody comprising the amino acid sequence of SEQ ID NO:106; and
   (B) a nucleotide sequence encoding a V region of a reshaped human H chain on an anti-HM 1.24 antibody comprising the amino acid sequence of SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125 or SEQ ID NO:128.

9. An isolated vector comprising the nucleic acid of claim 3.

10. An isolated vector comprising the nucleic acid of claim 4.

11. An isolated vector comprising the nucleic acid of claim 7.

12. An isolated cell modified with the vector of claim 9.
13. An isolated cell modified with the vector of claim 10.
14. An isolated cell modified with the vector of claim 11.

15. A method for preparing an antibody, comprising:
   a cell modified with the vector of claim 9 under conditions wherein the antibody-encoding nucleic acid is expressed, and
   recovering said antibody from the culture.

16. A method for preparing an antibody, comprising:
   culturing a cell modified with the vector of claim 10 under conditions wherein the antibody-encoding nucleic acid is expressed, and
   recovering said antibody from the culture.

17. A method for preparing an antibody, comprising:
   culturing a cell modified with the vector of claim 11 under conditions wherein the antibody-encoding nucleic acid is expressed, and
   recovering said antibody from the culture.

18. An isolated or recombinant nucleic acid encoding an L chain and an H chain of an antibody, comprising:
   a nucleotide sequence encoding a V region of the L chain, wherein the nucleotide sequence comprises the amino acid sequence from position 1 to position 107 of SEQ ID NO:104, and
   a nucleotide sequence encoding a V region of the H chain, wherein the nucleotide sequence comprises the amino acid sequence from position 1 to position 120 of SEQ ID NO:105.

19. The isolated or recombinant nucleic acid of claim 18 wherein the nucleotide sequence encoding said V region of the L chain comprises the nucleotide sequence of position 73 to position 393 of SEQ ID NO:1, and the nucleotide sequence encoding said V region of the H chain comprises the nucleotide sequence of position 58 to position 417 of SEQ ID NO:2.

20. The isolated or recombinant nucleic acid of claim 19, further comprising a nucleotide sequence encoding a C region of a human L chain and/or the C region of a human H chain.

21. The isolated or recombinant nucleic acid of claim 8, wherein the nucleotide sequence encoding the V region of the reshaped human L chain comprises the nucleotide sequence of SEQ ID NO:9.

22. The isolated or recombinant nucleic acid of claim 8, wherein the nucleotide sequence encoding the V region of the reshaped human H chain comprises the nucleotide sequence of SEQ ID NO:16, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:28, or SEQ ID NO:102.

23. The isolated or recombinant nucleic acid of claim 8 further comprising a nucleotide sequence encoding the C region of a human L chain; and/or the C region of a human H chain.

24. An isolated vector comprising the nucleic acid of claim 1.

25. An isolated vector comprising the nucleic acid of claim 18.

26. An isolated vector comprising the nucleic acid of claim 20.

27. An isolated vector comprising the nucleic acid of claim 8.

28. An isolated vector comprising the nucleic acid of claim 23.

29. An isolated cell modified with the vector of claim 24.
30. An isolated cell modified with the vector of claim 25.
31. An isolated cell modified with the vector of claim 26.
32. An isolated cell modified with the vector of claim 27.
33. An isolated cell modified with the vector of claim 28.
34. The isolated cell of claim 29, where said cell is a mammalian cell.
35. The isolated cell of claim 12, where said cell is a mammalian cell.
36. The isolated cell of claim 30, where said cell is a mammalian cell.
37. The isolated cell of claim 31, where said cell is a mammalian cell.
38. The isolated cell of claim 13, where said cell is a mammalian cell.
39. The isolated cell of claim 14, where said cell is a mammalian cell.
40. The isolated cell of claim 32, where said cell is a mammalian cell.
41. The isolated cell of claim 33, where said cell is a mammalian cell.
42. A method for preparing an antibody which has the nucleotide sequence of claim 1, wherein the method comprises culturing the cells which are modified with a vector comprising said nucleotide sequence under conditions wherein said nucleic acid is expressed, and recovering said antibody from the culture.

43. A method for preparing an antibody which is encoded by the nucleotide sequence of claim 18, wherein the method comprises culturing the cells which are modified with a vector comprising said nucleotide sequence under conditions wherein said nucleic acid is expressed, and recovering said antibody from the culture.

44. A method for preparing an antibody which is encoded by the nucleotide sequence of claim 20, wherein the method comprises culturing the cells which are modified with a vector comprising said nucleotide sequence under conditions wherein said nucleic acid is expressed, and recovering said antibody from the culture.

45. A method for preparing an antibody which has the nucleotide sequence of claim 8, wherein the method comprises culturing the cells which are modified with a vector comprising said nucleotide sequence under conditions wherein said nucleic acid is expressed, and recovering said antibody from the culture.

46. A method for preparing an antibody which has the nucleotide sequence of claim 23, wherein the method comprises culturing the cells which are modified with a vector comprising said nucleotide sequence under conditions wherein said nucleic acid is expressed, and recovering said antibody from the culture.

* * * * *